US011608488B2

(12) United States Patent
Louis et al.

(10) Patent No.: US 11,608,488 B2
(45) Date of Patent: Mar. 21, 2023

(54) ENHANCED METABOLITE-PRODUCING YEAST

(71) Applicant: ADISSEO FRANCE S.A.S., Antony (FR)

(72) Inventors: Dominique Louis, Forges les Bains (FR); Karine Jaillardon, Saint Michel sur Orge (FR); Dominique Thomas, Gif sur Yvette (FR)

(73) Assignee: ADISSEO FRANCE S.A.S., Antony (FR)

( * ) Notice: Subject to any disclaimer, the term of this patent is extended or adjusted under 35 U.S.C. 154(b) by 319 days.

(21) Appl. No.: 16/628,338

(22) PCT Filed: Jul. 10, 2018

(86) PCT No.: PCT/EP2018/068717
§ 371 (c)(1),
(2) Date: Jan. 3, 2020

(87) PCT Pub. No.: WO2019/011945
PCT Pub. Date: Jan. 17, 2019

(65) Prior Publication Data
US 2020/0224150 A1 Jul. 16, 2020

(30) Foreign Application Priority Data

Jul. 11, 2017 (EP) .................................... 17305907

(51) Int. Cl.
*C12N 1/16* (2006.01)
*C12P 13/06* (2006.01)
*C12P 13/12* (2006.01)
*C12N 15/81* (2006.01)

(52) U.S. Cl.
CPC ............... *C12N 1/16* (2013.01); *C12N 15/81* (2013.01); *C12P 13/06* (2013.01); *C12P 13/12* (2013.01); *C12Y 101/01001* (2013.01); *C12Y 101/01037* (2013.01); *C12Y 102/0101* (2013.01); *C12Y 207/0104* (2013.01); *C12Y 401/01031* (2013.01)

(58) Field of Classification Search
None
See application file for complete search history.

(56) References Cited

U.S. PATENT DOCUMENTS

2013/0066035 A1  3/2013 Burgard et al.
2014/0127765 A1* 5/2014 Osterhout ................ C12N 9/13
                                                              435/157
2020/0224150 A1* 7/2020 Louis ...................... C12P 13/04

OTHER PUBLICATIONS

Becker, Judith et al. "Systems and synthetic metabolic engineering for amino acid production—the heartbeat of industrial strain development". Current Opinion in Biotechnology, vol. 23, pp. 718-726, 2012.

Halász, Anna et al. "Study of the Sulphur Metabolism of Methionine-Rich Yeasts". Periodica Polytechnica Ser. Chem. Engl., vol. 40 No. 1-2, pp. 53-78, 1996.

Park, SD et al. "Characteristics of methionine production by an engineered Corynebacterium gluctamicum strain". Metabolism English, vol. 9 No. 4, pp. 327-336, 2007.

Bachmair, Andreas et al. "In Vivo Half-Life of a Protein Is a Function of Its Amino-Terminal Residue". Science, vol. 234, pp. 179-186, 1986.

Bazaes, Sergio at al. "Comparative Kinetic Effects of Mn (II), Mg (II) and the ATP/ADP Ratio on Phosphoenolpyruvate Carboxykinases from Anaerobiospirillum succiniciproducens and *Saccharomyces cerevisiae*". The Protein Journal, vol. 26 No. 4, pp. 265-269, 2007.

Cho, Sungchan et al. "A degron created by SMN2 exon 7 skipping is a principal contributor to spinal muscular atrophy severity". Genes & Development, vol. 24, pp. 438-442, 2010.

Dicarlo, James E. et al. "Genome engineering in *Saccharomyces cerevisiae* using CRISPR-Cas systems". Nucleic Acids Research, vol. 41 No. 7, pp. 4336-4343, 2013.

Faehnle, Christopher R. et al. "A New Branch in the Family: Structure of Aspartate-β-semialdehyde Dehydrogenase from *Methanococcus jannaschii*". Journal of Molecular Biology, vol. 353, pp. 1055-1068, 2005.

Fischer, Baptiste et al. "Catalytic properties of a bacterial acylating acetaldehyde dehydrogenase: Evidence for several active oligomeric states and coenzyme A activation upon binding". Chemico-Biological Interactions, vol. 202, pp. 70-77, 2013.

Fortmann, Karen et al. "A regulated, ubiquitin-independent degron in IκBα". Journal of Molecular Biology, vol. 427, pp. 2748-2756, 2015.

(Continued)

*Primary Examiner* — Richard C Ekstrom
(74) *Attorney, Agent, or Firm* — Oliff PLC

(57) ABSTRACT

Metabolites produced by a microorganism using oxaloacetate, pyruvate and/or acetyl-CoA as substrate or co-substrate upstream in the biosynthesis pathway, and more particularly using oxaloacetate. There is indeed a need in the art for transformed, in particular recombinant, microorganisms having at least an increased ability to produce oxaloacetate, pyruvate and/or acetyl-CoA, and in particular oxaloacetate, thus allowing an increased capacity to produce metabolites produced using oxaloacetate, pyruvate and/or acetyl-CoA as substrate or co-substrate upstream in the biosynthesis pathway, and in particular amino acids and their derivatives thereof, fatty acids, derivatives from the mevalonate pathway (in particular farnesyl, squalene, lanosterol, cholesterol and derivatives, and dolichols), flavonoides and/or polyketides. The solution proposed is the use of a genetically modified yeast comprising many modifications as described in the present text.

21 Claims, No Drawings

Specification includes a Sequence Listing.

(56) References Cited

OTHER PUBLICATIONS

Ganzhorn, Axel et al. "Kinetic Characterization of Yeast Alcohol Dehydrogenases: Amino Acid Residue 294 and Substrate Specificity". The Journal of Biological Chemistry, vol. 262 No. 8, pp. 3754-3761, 1987.
Gerrard-Wheeler, Mariel C. et al., "Identification of domains involved in the allosteric regulation of cytosolic *Arabidopsis thaliana* NADP-malic enzymes". The FEBS Journal, vol. 276, pp. 5665-5677, 2009.
Gibbs, Daniel J. et al. "The eukaryotic N-end rule pathway: conserved mechanisms and diverse functions". Trends in Cell Biology, vol. 10, pp. 1-9, 2014.
He, Weiwei et al."Crystal structure of *Saccharomyces cerevisiae* 6-phosphogluconate dehydrogenase Gnd1". BMC Structural Biology, vol. 7 No. 38, pp. 1-9, 2007.
Hochstrasser, Mark. "Ubiquitin-Dependent Protein Degradation". Annual Review of Genetics, vol. 30, pp. 405-439, 1996.
Keren, Leeat et al. "Promoters maintain their relative activity levels under different growth conditions". Molecular Systems Biology, vol. 9 No. 701, pp. 1-17, 2013.
Koller, A. et al. "The CUP1 promoter of *Saccharomyces cerevisiae* is inducible by copper in Pichia pastoris". Yeast, vol. 16, pp. 651-656, 2000.
Kuby, Stephen A. et al. "Glucose 6-Phosphate Dehydrogenase (Crystalline) from Brewers' Yeast". Dehydrogenases and Oxidases Methods in Enzymology, vol. 9, pp. 116-125, 1966.
Loizeau, Karen et al. "Regulation of One-Carbon Metabolism in *Arabidopsis*: The N-Terminal Regulatory Domain of Cystathionine γ-Synthase Is Cleaved in Response to Folate Starvation". Plant Physiology, vol. 145, pp. 491-503, 2007.
De Felipe, F. Lopez et al. "Purification and characterisation of the water forming NADH-oxidase from Lactococcus lactis". International Daily Journal, vol. 11, pp. 37-44, 2001.
Mariët, J. Van der Werf et al. "Environmental and physiological factors affecting the succinate product ratio during carbohydrate fermentation by *Actinobacillus* sp. 130Z". Archives of Microbiology, vol. 167, pp. 332-342, 1997.
Onoue, Noriyuki et al. "S-Adenosyl-L-methionine Induces Compaction of Nascent Peptide Chain inside the Ribosomal Exit Tunnel upon Translation Arrest in the *Arabidopsis* CGS1 Gene". The Journal of Biological Chemistry, vol. 286 No. 17, pp. 14903-14912, 2011.
Peng, Bingyin et al., "Coupling gene regulatory patterns to bioprocess conditions to optimize synthetic metabolic modules for improved sesquiterpene production in yeast". Biotechnology for Biofuels. vol. 10 No. 43, pp. 1-16, 2017.
Ravid, Tommer et al. "Degradation signal diversity in the ubiquitin-proteasome system". Nature Reviews Molecular Cell Biology, vol. 9, pp. 1-24, 2008.
Sagers, Richard D. et al. "Acetate Formation in Clostridium Acidi-Urici: Acetokinase" Journal of Bacteriology, vol. 82, pp. 233-238, 1961.
Stadtman, E. R. et al. Feed-back Inhibition and Repression of Aspartokinase Activity in *Escherichia coli* and *Saccharomyces cerevisiae*. The Journal of Biological Chemistry, vol. 236 No. 7, pp. 2033-2038, 1961.
Velculescu, Victor E. et al. "Characterization of the Yeast Transcriptome". Cell, vol. 88, pp. 243-251, 1997.
Wang, Jue et al. "Consequences of a Modified Putative Substrate-Activation Site on Catalysis by Yeast Pyruvate Decarboxylase". Biochemistry, vol. 40, pp. 1755-1763, 2001.
Yagi, Toshiharu et al. "Aspartate: 2-Oxoglutarate Aminotransferase from Bakers' Yeast: Crystallization and Characterization". The Journal of Biochemistry, vol. 92, pp. 35-43, 1982.
Yamanishi, Mamoru et al. "A Genome-Wide Activity Assessment of Terminator Regions in *Saccharomyces cerevisiae* Provides a "Terminatome" Toolbox". ACS Synthetic Biology, vol. 2, pp. A-K, 2013.
Yu, Geng et al. "Pac-Man for biotechnology: co-opting degrons for targeted protein degradation to control and alter cell function". Current Opinion in Biotechnology, vol. 36, pp. 199-204, 2015.
Çelik, Eda et al. "Production of recombinant proteins by yeast cells". Biotechnology Advances, vol. 30, pp. 1108-1118, 2012.
Nielsen, Jens Christian et al. "Development of fungal cell factories for the production of secondary metabolites: Linking genomics and metabolism". Synthetic and Systems Biotechnology, vol. 2, pp. 5-12, 2017.
Kumar, Dharmendra et al. "Methionine production by fermentation". Biotechnology Advances, vol. 23, pp. 41-61, 2005.
Siddiqui, Michael S. et al. "Advancing secondary metabolite biosynthesis in yeast with synthetic biology tools". Federation of European Microbiological Societies, vol. 12, pp. 144-170, 2012.
Sep. 5, 2018 International Search Report issued in International Patent Application No. PCT/EP2018/068717.

\* cited by examiner

SEQUENCE LISTING

<160> NUMBER OF SEQ ID NOS: 124

<210> SEQ ID NO 1
<211> LENGTH: 1023
<212> TYPE: DNA
<213> ORGANISM: Saccharomyces cerevisiae
<220> FEATURE:
<223> OTHER INFORMATION: MALATE DEHYDROGENASE (MDH3)
<220> FEATURE:
<223> OTHER INFORMATION: MALATE DEHYDROGENASE (MDH3)

<400> SEQUENCE: 1

```
atggtcaaag tcgcaattct tggcgcttct ggtggcgtgg gacaaccgct atcattactg      60
ctaaaattaa gcccttacgt ttccgagctg gcgttgtacg atatccgagc tgcggaaggc     120
attggtaagg atttatctca catcaacacc aactcaagtt gtgtcggtta tgataaggat     180
agtattgaga cacccttgtc aaatgctcag gtggtgctaa taccggctgg tgttcccaga     240
aagcccggtt taactagaga tgatttgttc aagatgaacg ccggtattgt caaaagcctg     300
gtaaccgctg ttggaaagtt cgcaccaaat gcgaggattt agtcatttc aaaccctgta      360 aacagtttgg tccctattgc tgtggaaact ttgaagaaaa tgggtaagtt caaacctgga     420
aacgttatgg gtgtgacgaa ccttgacctg gtacgtgcag aaaccttttt ggtagattat     480
ttgatgctaa aaaccccaa aattggacaa gaacaagaca aaactacaat gcacagaaag      540
gtcactgtta ttggggggtca ttcaggggaa accattatcc aataatcac cgacaaatcg      600 ctggtatttc aacttgataa gcagtacgag cacttcattc atagggtcca gttcggaggt     660
gatgaaattg tcaaagctaa acagggcgcc ggttccgcca cgttgtccat ggcgttcgcg     720
ggggccaagt tgctgaaga gttttgagg agcttccata tgagaaacc agaaacggag        780 tcactttccg cattcgttta tttaccaggc ttaaaaaacg gtaagaaagc gcagcaatta     840
gttggcgaca actctattga gtattttcc ttgccaattg ttttgagaaa tggtagcgta      900
gtatccatcg ataccagtgt tctggaaaaa ctgtctccga gagaggaaca actcgttaat     960
actgcggtca agagctacg caagaatatt gaaaaggca agagtttcat cctagactct     1020
taa                                                                   1023
```

<210> SEQ ID NO 2
<211> LENGTH: 340
<212> TYPE: PRT
<213> ORGANISM: Saccharomyces cerevisiae
<220> FEATURE:
<223> OTHER INFORMATION: MALATE DEHYDROGENASE (MDH3)
<220> FEATURE:
<223> OTHER INFORMATION: MALATE DEHYDROGENASE (MDH3)

<400> SEQUENCE: 2

```
Met Val Lys Val Ala Ile Leu Gly Ala Ser Gly Gly Val Gly Gln Pro
1               5                   10                  15

Leu Ser Leu Leu Lys Leu Ser Pro Tyr Val Ser Glu Leu Ala Leu
            20                  25                  30

Tyr Asp Ile Arg Ala Ala Glu Gly Ile Gly Lys Asp Leu Ser His Ile
                35                  40                  45

Asn Thr Asn Ser Ser Cys Val Gly Tyr Asp Lys Asp Ser Ile Glu Asn
    50                  55                  60

Thr Leu Ser Asn Ala Gln Val Val Leu Ile Pro Ala Gly Val Pro Arg
65                  70                  75                  80

Lys Pro Gly Leu Thr Arg Asp Asp Leu Phe Lys Met Asn Ala Gly Ile
                85                  90                  95
```

Val Lys Ser Leu Val Thr Ala Val Gly Lys Phe Ala Pro Asn Ala Arg
            100                 105                 110

Ile Leu Val Ile Ser Asn Pro Val Asn Ser Leu Val Pro Ile Ala Val
            115                 120                 125

Glu Thr Leu Lys Lys Met Gly Lys Phe Lys Pro Gly Asn Val Met Gly
130                 135                 140

Val Thr Asn Leu Asp Leu Val Arg Ala Glu Thr Phe Leu Val Asp Tyr
145                 150                 155                 160

Leu Met Leu Lys Asn Pro Lys Ile Gly Gln Glu Asp Lys Thr Thr
            165                 170                 175

Met His Arg Lys Val Thr Val Ile Gly Gly His Ser Gly Glu Thr Ile
            180                 185                 190

Ile Pro Ile Ile Thr Asp Lys Ser Leu Val Phe Gln Leu Asp Lys Gln
            195                 200                 205

Tyr Glu His Phe Ile His Arg Val Gln Phe Gly Gly Asp Glu Ile Val
            210                 215                 220

Lys Ala Lys Gln Gly Ala Gly Ser Ala Thr Leu Ser Met Ala Phe Ala
225                 230                 235                 240

Gly Ala Lys Phe Ala Glu Glu Val Leu Arg Ser Phe His Asn Glu Lys
                245                 250                 255

Pro Glu Thr Glu Ser Leu Ser Ala Phe Val Tyr Leu Pro Gly Leu Lys
            260                 265                 270

Asn Gly Lys Lys Ala Gln Gln Leu Val Gly Asp Asn Ser Ile Glu Tyr
            275                 280                 285

Phe Ser Leu Pro Ile Val Leu Arg Asn Gly Ser Val Val Ser Ile Asp
            290                 295                 300

Thr Ser Val Leu Glu Lys Leu Ser Pro Arg Glu Glu Gln Leu Val Asn
305                 310                 315                 320

Thr Ala Val Lys Glu Leu Arg Lys Asn Ile Glu Lys Gly Lys Ser Phe
                325                 330                 335

Ile Leu Asp Ser
            340

<210> SEQ ID NO 3
<211> LENGTH: 1767
<212> TYPE: DNA
<213> ORGANISM: Arabidopsis thaliana
<220> FEATURE:
<223> OTHER INFORMATION: NADP-DEPENDENT MALIC ENZYME (ME3)
<220> FEATURE:
<223> OTHER INFORMATION: NADP-DEPENDENT MALIC ENZYME (ME3)

<400> SEQUENCE: 3
atggggacta tcaaaccca aataagtgat gaatacgtaa ctggtaactc atcaggggta      60
ggaggaggaa tatctgatgt gtacggcgaa gactctgcca cactcgatca attggttact     120
ccgtgggtca caagtgtagc ctcgggatat acgctaatga gggaccccag atataacaaa    180
ggcttagcgt tcaccgacaa agagagggat gcccactaca tcaccggcct gttgccccg     240 gtcgtactct cccaggatgt acaggaacgt aaggttatgc ataatttaag gcagtatacc    300
gttccacttc agagatatat ggcattaatg gatttacaag aaagaaatga agattgttt     360 tataagttgt tgatcgacaa tgttgaggag ttgttacccg ttgtctacac gccgacggtt    420
ggcgaggcgt gccaaaaata tggttccatc tacagacgcc cacagggtt atatatttca     480 cttaaggaga agggaaaat attagaagtg ctaaagaatt ggccccaaag aggaatacag    540

```
gttatcgtag tgaccgatgg agagcgaata ttggggctgg gcgatttggg ttgtcaggga      600
atgggtatcc ctgtcggcaa attgtctcta tacacagctt taggaggaat acgaccttcg      660
gcctgccttc caataaccat cgacgtgggc accaataatg agaaattact aaacaacgag      720
ttctacatcg ggttgaaaca gaagcgtgcg aatggtgaag agtatgccga attcttacaa      780
gagtttatgt gtgccgtcaa acaaaattat ggagaaaaag tcttggtaca atttgaagat      840
tttgccaacc accatgcgtt tgaattacta tcgaaatatt gtagtagtca cctggtatt      900 aatgacgaca tacaaggtac agcgtccgta gttctggctg gacttattgc cgctcaaaag      960
gtcttgggca agagcctggc cgaccatacg ttcctcttct taggtgccgg tgaagccggc     1020
acgggcattg cagaattaat tgctttgaaa atttcaaaag aaacaggtaa acctattgac     1080
gagacacgga agaagatatg gcttgttgat agtaaaggtc taatcgttag cgagagaaag     1140
gaatctctac aacatttcaa gcaaccatgg gctcatgatc ataagccagt caaagaacta     1200
ttagcagctg tgaatgctat taaacctact gtcttgatcg gtacttcagg tgtgggtaaa     1260
actttcacaa agaagttgt tgaagcaatg gcaacactca atgaaaaacc tcttatttta     1320
gcactttcaa accctacatc acaagcagaa tgtacagctg aagaagctta tacttggact     1380
aaaggtaggg ctattttgc tagcggtagc cctttcgatc ctgtacaata cgatggtaag     1440
aaatttactc caggtcaagc aaacaattgc tacattttc caggtctcgg tttgggttta     1500
attatgtctg tgcaattag ggttagagat gatatgttgt tagcagcttc cgaagctctt     1560
gcttctcaag ttactgaaga aaacttcgca aatggtttaa tttacccacc atttgctaac     1620
attcgtaaaa tttccgctaa tattgctgct tctgttggtg caaagactta tgaattgggt     1680
ttggcatcca acctaccaag accaaaggat ttggttaaga tggcagaatc ttgtatgtat     1740
tctccagttt atagaaactt tagataa                                         1767
```

<210> SEQ ID NO 4
<211> LENGTH: 588
<212> TYPE: PRT
<213> ORGANISM: Arabidopsis thaliana
<220> FEATURE:
<223> OTHER INFORMATION: NADP-DEPENDENT MALIC ENZYME (ME3)
<220> FEATURE:
<223> OTHER INFORMATION: NADP-DEPENDENT MALIC ENZYME (ME3)

<400> SEQUENCE: 4

Met Gly Thr Asn Gln Thr Gln Ile Ser Asp Glu Tyr Val Thr Gly Asn
1               5                   10                  15

Ser Ser Gly Val Gly Gly Gly Ile Ser Asp Val Tyr Gly Glu Asp Ser
            20                  25                  30

Ala Thr Leu Asp Gln Leu Val Thr Pro Trp Val Thr Ser Val Ala Ser
        35                  40                  45

Gly Tyr Thr Leu Met Arg Asp Pro Arg Tyr Asn Lys Gly Leu Ala Phe
    50                  55                  60

Thr Asp Lys Glu Arg Asp Ala His Tyr Ile Thr Gly Leu Leu Pro Pro
65                  70                  75                  80

Val Val Leu Ser Gln Asp Val Gln Glu Arg Lys Val Met His Asn Leu
                85                  90                  95

Arg Gln Tyr Thr Val Pro Leu Gln Arg Tyr Met Ala Leu Met Asp Leu
            100                 105                 110

Gln Glu Arg Asn Glu Arg Leu Phe Tyr Lys Leu Leu Ile Asp Asn Val
        115                 120                 125

Glu Glu Leu Leu Pro Val Val Tyr Thr Pro Thr Val Gly Glu Ala Cys

```
            130                 135                 140
Gln Lys Tyr Gly Ser Ile Tyr Arg Arg Pro Gln Gly Leu Tyr Ile Ser
145                 150                 155                 160

Leu Lys Glu Lys Gly Lys Ile Leu Glu Val Leu Lys Asn Trp Pro Gln
                165                 170                 175

Arg Gly Ile Gln Val Ile Val Thr Asp Gly Glu Arg Ile Leu Gly
            180                 185                 190

Leu Gly Asp Leu Gly Cys Gln Gly Met Gly Ile Pro Val Gly Lys Leu
                195                 200                 205

Ser Leu Tyr Thr Ala Leu Gly Gly Ile Arg Pro Ser Ala Cys Leu Pro
    210                 215                 220

Ile Thr Ile Asp Val Gly Thr Asn Asn Glu Lys Leu Leu Asn Asn Glu
225                 230                 235                 240

Phe Tyr Ile Gly Leu Lys Gln Lys Arg Ala Asn Gly Glu Glu Tyr Ala
                245                 250                 255

Glu Phe Leu Gln Glu Phe Met Cys Ala Val Lys Gln Asn Tyr Gly Glu
                260                 265                 270

Lys Val Leu Val Gln Phe Glu Asp Phe Ala Asn His Ala Phe Glu
    275                 280                 285

Leu Leu Ser Lys Tyr Cys Ser Ser His Leu Val Phe Asn Asp Asp Ile
    290                 295                 300

Gln Gly Thr Ala Ser Val Val Leu Ala Gly Leu Ile Ala Ala Gln Lys
305                 310                 315                 320

Val Leu Gly Lys Ser Leu Ala Asp His Thr Phe Leu Phe Leu Gly Ala
                325                 330                 335

Gly Glu Ala Gly Thr Gly Ile Ala Glu Leu Ile Ala Leu Lys Ile Ser
                340                 345                 350

Lys Glu Thr Gly Lys Pro Ile Asp Glu Thr Arg Lys Lys Ile Trp Leu
                355                 360                 365

Val Asp Ser Lys Gly Leu Ile Val Ser Glu Arg Lys Glu Ser Leu Gln
    370                 375                 380

His Phe Lys Gln Pro Trp Ala His Asp His Lys Pro Val Lys Glu Leu
385                 390                 395                 400

Leu Ala Ala Val Asn Ala Ile Lys Pro Thr Val Leu Ile Gly Thr Ser
                405                 410                 415

Gly Val Gly Lys Thr Phe Thr Lys Glu Val Val Glu Ala Met Ala Thr
                420                 425                 430

Leu Asn Glu Lys Pro Leu Ile Leu Ala Leu Ser Asn Pro Thr Ser Gln
                435                 440                 445

Ala Glu Cys Thr Ala Glu Glu Ala Tyr Thr Trp Thr Lys Gly Arg Ala
    450                 455                 460

Ile Phe Ala Ser Gly Ser Pro Phe Asp Pro Val Gln Tyr Asp Gly Lys
465                 470                 475                 480

Lys Phe Thr Pro Gly Gln Ala Asn Asn Cys Tyr Ile Phe Pro Gly Leu
                485                 490                 495

Gly Leu Gly Leu Ile Met Ser Gly Ala Ile Arg Val Arg Asp Asp Met
                500                 505                 510

Leu Leu Ala Ala Ser Glu Ala Leu Ala Ser Gln Val Thr Glu Glu Asn
    515                 520                 525

Phe Ala Asn Gly Leu Ile Tyr Pro Pro Phe Ala Asn Ile Arg Lys Ile
    530                 535                 540

Ser Ala Asn Ile Ala Ala Ser Val Gly Ala Lys Thr Tyr Glu Leu Gly
545                 550                 555                 560
```

```
Leu Ala Ser Asn Leu Pro Arg Pro Lys Asp Leu Val Lys Met Ala Glu
            565                 570                 575
Ser Cys Met Tyr Ser Pro Val Tyr Arg Asn Phe Arg
            580                 585

<210> SEQ ID NO 5
<211> LENGTH: 2652
<212> TYPE: DNA
<213> ORGANISM: Escherichia coli
<220> FEATURE:
<223> OTHER INFORMATION: PHOSPHOENOLPYRUVATE CARBOXYLASE (PPC/PEPC)
<220> FEATURE:
<223> OTHER INFORMATION: PHOSPHOENOLPYRUVATE CARBOXYLASE (PPC/PEPC)

<400> SEQUENCE: 5
atgaacgagc agtattccgc attgcgtagt aacgtgagta tgttaggaaa ggttcttggc      60
gagacgatta aggacgcgtt gggtgagcat atactagaga gagtggagac tatcagaaaa     120
ttatcaaagt caagtcgtgc cggtaatgac gccaacaggc aggagttgct taccactctt     180
caaaacctat cgaacgatga gctacttccg gtggcccgtg ccttctcgca attttttaaat    240
ctagctaata cggctgaaca atatcattct attagtccaa aggggaggc cgcctccaac      300
cctgaagtaa ttgcacgtac cttaagaaaa ttgaaaaacc aaccggagtt gtcagaggac     360
actattaaga aggctgttga agtttatca cttgagctag tattaaccgc gcatccgact      420
gaaattacac gtaggaccct aatccacaag atggtagagg taaatgcgtg tctgaaacaa     480
ttagacaata aggatatagc agactacgaa cataaccaac ttatgcgtag attgagacag     540
ctaattgctc agtcgtggca tacggatgag attcgtaagc ttagaccttc cccagtcgac     600
gaggctaagt ggggctttgc agtcgtggag aatagtttat ggcagggtgt accaaactac     660
ttgagggaat taatgagca attggaggaa aacctaggtt acaaattgcc agtagaattc      720
gtacccgtca ggtttacctc atggatgggg ggagacagag atggaaatcc taatgtaacc     780
gccgacatta ctcgtcatgt attgctgttg agcaggtgga aggcgaccga cctgtttctg     840
aaagacatac aagtactagt ctccgagctg agtatggtcg aggccactcc tgagttatta    900
gcgctggtgg gggaggaggg agctgctgag ccctatcgtt acctgatgaa gaacctgagg      960
agtcgtctaa tggccaccca ggcatggctg gaagctagac taaaaggaga gaattacct     1020
aagcccgaag ggctgcttac tcagaatgaa gaattgtggg aaccattgta tgcttgttac     1080
cagtcactgc aggcgtgcgg tatgggcatt atcgccaacg gcgatctgtt agacactttg     1140
agaagggtca agtgcttcgg cgtcccatta gttaggattg acataagaca ggaatccact     1200
aggcatacgg aagcgttagg ggaattgacg aggtatttag ggattggaga ttacgaatcg     1260
tggtcagaag ccgacaagca agcattcttg atccgcgaat gaatagtaa acgtccactt     1320
ttacctagaa attggcagcc atccgcagag accagggagg tgctcgatac atgtcaagtg     1380
atagctgaag caccccaagg atcaattgct gcctacgtaa taagcatggc gaaaccccct     1440
tcagacgtat tagcagttca tcttttgctg aaagaagcgg gcattggctt cgcaatgcca     1500
gtcgctccgt tatttgaaac gctggacgat ttgaataatg caaacgacgt tatgacacag     1560
ttattaaaca tcgattggta tagaggtcta atccaaggaa agcaaatggt tatgattggt     1620
tactcggatt ctgctaaaga tgcaggggtc atggctgctt cttgggctca gtatcaagcc     1680
caagatgcct tgattaagac ttgcgaaaag gccggaatcg aattgactct atttcacggt     1740
agaggggggtt ccataggtcg aggtggtgcc cctgctcacg cagctctttt atcccaacca     1800
```

```
cctggttctt taaaaggtgg ccttagggtg actgaacaag gcgaaatgat aagattcaaa    1860
tacggtttac cagaaatcac tgtgtcttcc ctttctcttt atactggtgc aattttggaa    1920
gcaaatttat tgccacctcc tgaaccaaaa gaaagctgga gaagaatcat ggatgaattg    1980
tctgttatta gctgcgatgt ttatagaggc tatgttagag aaaataaaga ttttgttcca    2040
tattttagat ctgctacacc tgaacaagaa ttgggtaaac taccattggg ttctagacca    2100
gctaaaagaa gacctactgg tggtgttgaa tcattgagag ctattccatg gatatttgct    2160
tggacacaaa acagattaat gctacctgct tggctaggtg caggtacagc tttacaaaaa    2220
gttgttgaag atggtaaaca atcagaattg gaagctatgt gtagagattg gcctttttt     2280 tctacaagat taggtatgtt agaaatggtt tttgcaaaag cagatttatg gctagctgaa    2340
tattatgatc aaagattggt tgataaagca ttgtggcctt taggtaaaga attgagaaat    2400
ttgcaagaag aagatataaa agttgtttta gcaatagcta atgattctca cttaatggct    2460
gatttaccat ggatagctga atctatccaa ttaagaaata tttatacaga tccattgaat    2520
gttttgcaag cagaattatt gcacagatct agacaagctg aaaaagaagg tcaagaacca    2580
gatccaagag ttgaacaagc attgatggtt acaattgctg gtatcgctgc aggtatgaga    2640
aatacaggtt aa                                                        2652

<210> SEQ ID NO 6
<211> LENGTH: 883
<212> TYPE: PRT
<213> ORGANISM: Escherichia coli
<220> FEATURE:
<223> OTHER INFORMATION: PHOSPHOENOLPYRUVATE CARBOXYLASE (PPC/PEPC)
<220> FEATURE:
<223> OTHER INFORMATION: PHOSPHOENOLPYRUVATE CARBOXYLASE (PPC/PEPC)

<400> SEQUENCE: 6

Met Asn Glu Gln Tyr Ser Ala Leu Arg Ser Asn Val Ser Met Leu Gly
1               5                   10                  15

Lys Val Leu Gly Glu Thr Ile Lys Asp Ala Leu Gly Glu His Ile Leu
            20                  25                  30

Glu Arg Val Glu Thr Ile Arg Lys Leu Ser Lys Ser Ser Arg Ala Gly
        35                  40                  45

Asn Asp Ala Asn Arg Gln Glu Leu Leu Thr Thr Leu Gln Asn Leu Ser
    50                  55                  60

Asn Asp Glu Leu Leu Pro Val Ala Arg Ala Phe Ser Gln Phe Leu Asn
65                  70                  75                  80

Leu Ala Asn Thr Ala Glu Gln Tyr His Ser Ile Ser Pro Lys Gly Glu
                85                  90                  95

Ala Ala Ser Asn Pro Glu Val Ile Ala Arg Thr Leu Arg Lys Leu Lys
            100                 105                 110

Asn Gln Pro Glu Leu Ser Glu Asp Thr Ile Lys Lys Ala Val Glu Ser
        115                 120                 125

Leu Ser Leu Glu Leu Val Leu Thr Ala His Pro Thr Glu Ile Thr Arg
    130                 135                 140

Arg Thr Leu Ile His Lys Met Val Glu Val Asn Ala Cys Leu Lys Gln
145                 150                 155                 160

Leu Asp Asn Lys Asp Ile Ala Asp Tyr Glu His Asn Gln Leu Met Arg
                165                 170                 175

Arg Leu Arg Gln Leu Ile Ala Gln Ser Trp His Thr Asp Glu Ile Arg
            180                 185                 190

Lys Leu Arg Pro Ser Pro Val Asp Glu Ala Lys Trp Gly Phe Ala Val
```

```
            195                 200                 205
Val Glu Asn Ser Leu Trp Gln Gly Val Pro Asn Tyr Leu Arg Glu Leu
210                 215                 220

Asn Glu Gln Leu Glu Glu Asn Leu Gly Tyr Lys Leu Pro Val Glu Phe
225                 230                 235                 240

Val Pro Val Arg Phe Thr Ser Trp Met Gly Gly Asp Arg Asp Gly Asn
                245                 250                 255

Pro Asn Val Thr Ala Asp Ile Thr Arg His Val Leu Leu Leu Ser Arg
                260                 265                 270

Trp Lys Ala Thr Asp Leu Phe Leu Lys Asp Ile Gln Val Leu Val Ser
                275                 280                 285

Glu Leu Ser Met Val Glu Ala Thr Pro Glu Leu Leu Ala Leu Val Gly
                290                 295                 300

Glu Glu Gly Ala Ala Glu Pro Tyr Arg Tyr Leu Met Lys Asn Leu Arg
305                 310                 315                 320

Ser Arg Leu Met Ala Thr Gln Ala Trp Leu Glu Ala Arg Leu Lys Gly
                325                 330                 335

Glu Glu Leu Pro Lys Pro Glu Gly Leu Leu Thr Gln Asn Glu Glu Leu
                340                 345                 350

Trp Glu Pro Leu Tyr Ala Cys Tyr Gln Ser Leu Gln Ala Cys Gly Met
                355                 360                 365

Gly Ile Ile Ala Asn Gly Asp Leu Leu Asp Thr Leu Arg Arg Val Lys
370                 375                 380

Cys Phe Gly Val Pro Leu Val Arg Ile Asp Ile Arg Gln Glu Ser Thr
385                 390                 395                 400

Arg His Thr Glu Ala Leu Gly Glu Leu Thr Arg Tyr Leu Gly Ile Gly
                405                 410                 415

Asp Tyr Glu Ser Trp Ser Glu Ala Asp Lys Gln Ala Phe Leu Ile Arg
                420                 425                 430

Glu Leu Asn Ser Lys Arg Pro Leu Leu Pro Arg Asn Trp Gln Pro Ser
                435                 440                 445

Ala Glu Thr Arg Glu Val Leu Asp Thr Cys Gln Val Ile Ala Glu Ala
                450                 455                 460

Pro Gln Gly Ser Ile Ala Ala Tyr Val Ile Ser Met Ala Lys Thr Pro
465                 470                 475                 480

Ser Asp Val Leu Ala Val His Leu Leu Leu Lys Glu Ala Gly Ile Gly
                485                 490                 495

Phe Ala Met Pro Val Ala Pro Leu Phe Glu Thr Leu Asp Asp Leu Asn
                500                 505                 510

Asn Ala Asn Asp Val Met Thr Gln Leu Leu Asn Ile Asp Trp Tyr Arg
                515                 520                 525

Gly Leu Ile Gln Gly Lys Gln Met Val Met Ile Gly Tyr Ser Asp Ser
                530                 535                 540

Ala Lys Asp Ala Gly Val Met Ala Ala Ser Trp Ala Gln Tyr Gln Ala
545                 550                 555                 560

Gln Asp Ala Leu Ile Lys Thr Cys Glu Lys Ala Gly Ile Glu Leu Thr
                565                 570                 575

Leu Phe His Gly Arg Gly Gly Ser Ile Gly Arg Gly Gly Ala Pro Ala
                580                 585                 590

His Ala Ala Leu Leu Ser Gln Pro Pro Gly Ser Leu Lys Gly Gly Leu
                595                 600                 605

Arg Val Thr Glu Gln Gly Glu Met Ile Arg Phe Lys Tyr Gly Leu Pro
                610                 615                 620
```

Glu Ile Thr Val Ser Ser Leu Ser Leu Tyr Thr Gly Ala Ile Leu Glu
625                 630                 635                 640

Ala Asn Leu Leu Pro Pro Glu Pro Lys Glu Ser Trp Arg Arg Ile
            645                 650                 655

Met Asp Glu Leu Ser Val Ile Ser Cys Asp Val Tyr Arg Gly Tyr Val
                660                 665                 670

Arg Glu Asn Lys Asp Phe Val Pro Tyr Phe Arg Ser Ala Thr Pro Glu
            675                 680                 685

Gln Glu Leu Gly Lys Leu Pro Leu Gly Ser Arg Pro Ala Lys Arg Arg
690                 695                 700

Pro Thr Gly Gly Val Glu Ser Leu Arg Ala Ile Pro Trp Ile Phe Ala
705                 710                 715                 720

Trp Thr Gln Asn Arg Leu Met Leu Pro Ala Trp Leu Gly Ala Gly Thr
                725                 730                 735

Ala Leu Gln Lys Val Val Glu Asp Gly Lys Gln Ser Glu Leu Glu Ala
            740                 745                 750

Met Cys Arg Asp Trp Pro Phe Phe Ser Thr Arg Leu Gly Met Leu Glu
            755                 760                 765

Met Val Phe Ala Lys Ala Asp Leu Trp Leu Ala Glu Tyr Tyr Asp Gln
770                 775                 780

Arg Leu Val Asp Lys Ala Leu Trp Pro Leu Gly Lys Glu Leu Arg Asn
785                 790                 795                 800

Leu Gln Glu Glu Asp Ile Lys Val Val Leu Ala Ile Ala Asn Asp Ser
                805                 810                 815

His Leu Met Ala Asp Leu Pro Trp Ile Ala Glu Ser Ile Gln Leu Arg
            820                 825                 830

Asn Ile Tyr Thr Asp Pro Leu Asn Val Leu Gln Ala Glu Leu Leu His
            835                 840                 845

Arg Ser Arg Gln Ala Glu Lys Glu Gly Gln Glu Pro Asp Pro Arg Val
850                 855                 860

Glu Gln Ala Leu Met Val Thr Ile Ala Gly Ile Ala Ala Gly Met Arg
865                 870                 875                 880

Asn Thr Gly

<210> SEQ ID NO 7
<211> LENGTH: 1623
<212> TYPE: DNA
<213> ORGANISM: Escherichia coli
<220> FEATURE:
<223> OTHER INFORMATION: PHOSPHOENOLPYRUVATE CARBOXYKINASE (PEPCK)
<220> FEATURE:
<223> OTHER INFORMATION: PHOSPHOENOLPYRUVATE CARBOXYKINASE (PEPCK)

<400> SEQUENCE: 7

```
atgagagtta acaatggttt gactccacaa gaattggaag cctacggtat ttctgatgtt      60
catgatatcg tttacaaccc atcctacgac ttgttgtacc aagaagaatt agatccatct     120
ttgaccggtt acgaaagagg tgttttgact aatttgggtg ctgttgctgt tgatactggt     180 attttttactg gtagatcccc aaaggataag tacatcgtta gagatgatac caccagagat     240 acttttttggt gggctgataa gggtaaaggt aagaatgata caagccattg tctccagaa     300 acctggcaac atttgaaagg tttggttacc agacaattga gtggtaagag attattcgtt     360
gttgatgctt tctgtggtgc taatccagat acaagattgt ccgttagatt cattactgaa     420
gttgcttggc aagcccattt cgtcaagaat atgtttatca gaccatccga tgaagaattg     480
```

```
gctggtttta agccagattt catcgttatg aatggtgcta agtgtaccaa cccacaatgg    540
aaagaacaag gtttgaacag tgaaaacttc gtcgctttca acttgaccga agaatgcaa     600
ttgattggtg gtacttggta tggtggtgaa atgaagaaag gtatgttctc catgatgaac    660
tacttgttgc cattgaaggg tattgcttct atgcattgct ctgctaatgt tggtgaaaaa    720
ggtgatgttg ccgttttctt tggtttatct ggtactggta agactacctt gtctactgat    780
cctaagagaa gattgatcgg tgatgatgaa catggttggg atgatgatgg tgtttttaac    840
tttgaaggtg gttgttacgc caagaccatc aagttgtcta aagaagctga accagaaatc    900
tacaacgcca ttagaagaga tgctttgttg gaaaacgtta ccgttagaga agatggtact    960
atcgatttcg atgatggttc taagactgaa acaccagag  tttcttaccc aatctaccac   1020
attgataaca tcgttaagcc tgtttctaaa gctggtcatg ctaccaaggt tattttcttg   1080
actgctgatg cttttggtgt tttgccacca gtttctagat taactgctga tcaaacccaa   1140
taccacttct tgtctggttt tactgctaaa ttggcaggta ctgaaagagg tattactgaa   1200
cctactccaa ctttctctgc ttgttttggt gctgcttttt tgtcattgca tccaactcaa   1260
tacgctgaag ttttggtcaa gagaatgcaa gctgctggtg ctcaagctta tttggttaat   1320
actggttgga atggtacagg taaaagaatc tccattaagg ataccagagc cattattgat   1380
gccatcttga atggttcttt ggataacgct gaaactttca ccttgccaat gttcaatttg   1440
gctattccaa ctgaattgcc aggtgttgac accaagattt tagatccaag aaacacttac   1500
gcctctccag aacaatggca agaaaaagct gaaacattgg ccaagttgtt catcgataac   1560
ttcgacaagt atactgatac tccagctggt gctgcattgg ttgctgctgg tccaaagttg   1620
taa                                                                 1623
```

<210> SEQ ID NO 8
<211> LENGTH: 540
<212> TYPE: PRT
<213> ORGANISM: Escherichia coli
<220> FEATURE:
<223> OTHER INFORMATION: PHOSPHOENOLPYRUVATE CARBOXYKINASE (PEPCK)
<220> FEATURE:
<223> OTHER INFORMATION: PHOSPHOENOLPYRUVATE CARBOXYKINASE (PEPCK)

<400> SEQUENCE: 8

```
Met Arg Val Asn Asn Gly Leu Thr Pro Gln Glu Leu Glu Ala Tyr Gly
1               5                   10                  15

Ile Ser Asp Val His Asp Ile Val Tyr Asn Pro Ser Tyr Asp Leu Leu
            20                  25                  30

Tyr Gln Glu Glu Leu Asp Pro Ser Leu Thr Gly Tyr Glu Arg Gly Val
        35                  40                  45

Leu Thr Asn Leu Gly Ala Val Ala Val Asp Thr Gly Ile Phe Thr Gly
    50                  55                  60

Arg Ser Pro Lys Asp Lys Tyr Ile Val Arg Asp Asp Thr Thr Arg Asp
65                  70                  75                  80

Thr Phe Trp Trp Ala Asp Lys Gly Lys Gly Lys Asn Asp Asn Lys Pro
                85                  90                  95

Leu Ser Pro Glu Thr Trp Gln His Leu Lys Gly Leu Val Thr Arg Gln
            100                 105                 110

Leu Ser Gly Lys Arg Leu Phe Val Val Asp Ala Phe Cys Gly Ala Asn
        115                 120                 125

Pro Asp Thr Arg Leu Ser Val Arg Phe Ile Thr Glu Val Ala Trp Gln
    130                 135                 140
```

Ala His Phe Val Lys Asn Met Phe Ile Arg Pro Ser Asp Glu Glu Leu
145                 150                 155                 160

Ala Gly Phe Lys Pro Asp Phe Ile Val Met Asn Gly Ala Lys Cys Thr
            165                 170                 175

Asn Pro Gln Trp Lys Glu Gln Gly Leu Asn Ser Glu Asn Phe Val Ala
        180                 185                 190

Phe Asn Leu Thr Glu Arg Met Gln Leu Ile Gly Gly Thr Trp Tyr Gly
    195                 200                 205

Gly Glu Met Lys Lys Gly Met Phe Ser Met Met Asn Tyr Leu Leu Pro
210                 215                 220

Leu Lys Gly Ile Ala Ser Met His Cys Ser Ala Asn Val Gly Glu Lys
225                 230                 235                 240

Gly Asp Val Ala Val Phe Phe Gly Leu Ser Gly Thr Gly Lys Thr Thr
            245                 250                 255

Leu Ser Thr Asp Pro Lys Arg Arg Leu Ile Gly Asp Asp Glu His Gly
        260                 265                 270

Trp Asp Asp Asp Gly Val Phe Asn Phe Glu Gly Gly Cys Tyr Ala Lys
    275                 280                 285

Thr Ile Lys Leu Ser Lys Glu Ala Glu Pro Glu Ile Tyr Asn Ala Ile
290                 295                 300

Arg Arg Asp Ala Leu Leu Glu Asn Val Thr Val Arg Glu Asp Gly Thr
305                 310                 315                 320

Ile Asp Phe Asp Asp Gly Ser Lys Thr Glu Asn Thr Arg Val Ser Tyr
            325                 330                 335

Pro Ile Tyr His Ile Asp Asn Ile Val Lys Pro Val Ser Lys Ala Gly
        340                 345                 350

His Ala Thr Lys Val Ile Phe Leu Thr Ala Asp Ala Phe Gly Val Leu
    355                 360                 365

Pro Pro Val Ser Arg Leu Thr Ala Asp Gln Thr Gln Tyr His Phe Leu
370                 375                 380

Ser Gly Phe Thr Ala Lys Leu Ala Gly Thr Glu Arg Gly Ile Thr Glu
385                 390                 395                 400

Pro Thr Pro Thr Phe Ser Ala Cys Phe Gly Ala Ala Phe Leu Ser Leu
            405                 410                 415

His Pro Thr Gln Tyr Ala Glu Val Leu Val Lys Arg Met Gln Ala Ala
        420                 425                 430

Gly Ala Gln Ala Tyr Leu Val Asn Thr Gly Trp Asn Gly Thr Gly Lys
    435                 440                 445

Arg Ile Ser Ile Lys Asp Thr Arg Ala Ile Asp Ala Ile Leu Asn
450                 455                 460

Gly Ser Leu Asp Asn Ala Glu Thr Phe Thr Leu Pro Met Phe Asn Leu
465                 470                 475                 480

Ala Ile Pro Thr Glu Leu Pro Gly Val Asp Thr Lys Ile Leu Asp Pro
            485                 490                 495

Arg Asn Thr Tyr Ala Ser Pro Glu Gln Trp Gln Glu Lys Ala Glu Thr
        500                 505                 510

Leu Ala Lys Leu Phe Ile Asp Asn Phe Asp Lys Tyr Thr Asp Thr Pro
    515                 520                 525

Ala Gly Ala Ala Leu Val Ala Gly Pro Lys Leu
530                 535                 540

<210> SEQ ID NO 9
<211> LENGTH: 951
<212> TYPE: DNA

<213> ORGANISM: Escherichia coli
<220> FEATURE:
<223> OTHER INFORMATION: ACETALDEHYDE-COA DEHYDROGENASE (MHPF)
<220> FEATURE:
<223> OTHER INFORMATION: ACETALDEHYDE-COA DEHYDROGENASE (MHPF)

<400> SEQUENCE: 9

```
atgagtaaac ggaaagtagc gatcatcggt tccgggaata ttgggacaga tttaatgata    60
aaaattctca ggcacggaca acatttagag atggctgtca tggttggcat agatcctcaa   120
agcgatggtt tagcgcgtgc tcgaaggatg ggcgtggcta ctacacacga gggtgttatc   180
ggacttatga atatgcccga attcgccgac atcgacatcg ttttgacgc gacatctgct   240
ggcgcacatg ttaagaacga tgccgcgctg cgtgaagcga agcctgatat tcgcttaatt   300
gacctaaccc ctgctgccat cggaccgtat tgtgttcctg tggtgaattt agaggcaaat   360
gtcgaccaat tgaacgttaa tatggtgaca tgcggaggtc aggctacaat acccatggtt   420
gctgctgtaa gccgagtcgc tagagttcat tacgcagaaa ttattgcctc gattgcctcg   480
aaatctgcag gcccgggcac tagagctaat attgacgaat ttaccgaaac cactagcaga   540
gcaatagagg tagttggtgg agcagccaaa ggaaaagcaa tcatagtctt aaatccagcc   600
gagccaccac taatgatgag agatactgtg tatgtattgt ccgatgaagc ctcacaggat   660
gatattgaag cttctatcaa cgaaatggca gaggccgttc aagcttacgt acctggttat   720
agactgaaac aaagagtcca gtttgaagtc ataccacaag ataagccagt gaacctacca   780
ggtgtgggtc aattcagtgg tcttaagacg gcagtatggc ttgaagttga aggtgccgct   840
cattacttgc cagcttatgc tggtaacttg gatataatga cttcatccgc attggcaacg   900
gcagaaaaga tggctcagtc attggcaaga aaggctggtg aagctgctta a            951
```

<210> SEQ ID NO 10
<211> LENGTH: 316
<212> TYPE: PRT
<213> ORGANISM: Escherichia coli
<220> FEATURE:
<223> OTHER INFORMATION: ACETALDEHYDE-COA DEHYDROGENASE (MHPF)
<220> FEATURE:
<223> OTHER INFORMATION: ACETALDEHYDE-COA DEHYDROGENASE (MHPF)

<400> SEQUENCE: 10

```
Met Ser Lys Arg Lys Val Ala Ile Ile Gly Ser Gly Asn Ile Gly Thr
1               5                   10                  15

Asp Leu Met Ile Lys Ile Leu Arg His Gly Gln His Leu Glu Met Ala
            20                  25                  30

Val Met Val Gly Ile Asp Pro Gln Ser Asp Gly Leu Ala Arg Ala Arg
        35                  40                  45

Arg Met Gly Val Ala Thr Thr His Glu Gly Val Ile Gly Leu Met Asn
    50                  55                  60

Met Pro Glu Phe Ala Asp Ile Asp Ile Val Phe Asp Ala Thr Ser Ala
65                  70                  75                  80

Gly Ala His Val Lys Asn Asp Ala Ala Leu Arg Glu Ala Lys Pro Asp
                85                  90                  95

Ile Arg Leu Ile Asp Leu Thr Pro Ala Ala Ile Gly Pro Tyr Cys Val
            100                 105                 110

Pro Val Val Asn Leu Glu Ala Asn Val Asp Gln Leu Asn Val Asn Met
        115                 120                 125

Val Thr Cys Gly Gly Gln Ala Thr Ile Pro Met Val Ala Ala Val Ser
    130                 135                 140
```

```
Arg Val Ala Arg Val His Tyr Ala Glu Ile Ile Ala Ser Ile Ala Ser
145                 150                 155                 160

Lys Ser Ala Gly Pro Gly Thr Arg Ala Asn Ile Asp Glu Phe Thr Glu
            165                 170                 175

Thr Thr Ser Arg Ala Ile Glu Val Val Gly Gly Ala Ala Lys Gly Lys
        180                 185                 190

Ala Ile Ile Val Leu Asn Pro Ala Glu Pro Pro Leu Met Met Arg Asp
        195                 200                 205

Thr Val Tyr Val Leu Ser Asp Glu Ala Ser Gln Asp Asp Ile Glu Ala
210                 215                 220

Ser Ile Asn Glu Met Ala Glu Ala Val Gln Ala Tyr Val Pro Gly Tyr
225                 230                 235                 240

Arg Leu Lys Gln Arg Val Gln Phe Glu Val Ile Pro Gln Asp Lys Pro
            245                 250                 255

Val Asn Leu Pro Gly Val Gly Gln Phe Ser Gly Leu Lys Thr Ala Val
            260                 265                 270

Trp Leu Glu Val Glu Gly Ala Ala His Tyr Leu Pro Ala Tyr Ala Gly
        275                 280                 285

Asn Leu Asp Ile Met Thr Ser Ser Ala Leu Ala Thr Ala Glu Lys Met
290                 295                 300

Ala Gln Ser Leu Ala Arg Lys Ala Gly Glu Ala Ala
305                 310                 315
```

```
<210> SEQ ID NO 11
<211> LENGTH: 1503
<212> TYPE: DNA
<213> ORGANISM: Saccharomyces cerevisiae
<220> FEATURE:
<223> OTHER INFORMATION: PYRUVATE KINASE 1 (PYK1)
<220> FEATURE:
<223> OTHER INFORMATION: PYRUVATE KINASE 1 (PYK1)

<400> SEQUENCE: 11
atgtctagat tagaaagatt gacctcatta aacgttgttg ctggttctga cttgagaaga      60
acctccatca ttggtaccat cggtccaaag accaacaacc cagaaacctt ggttgctttg     120
agaaaggctg gtttgaacat tgtccgtatg aacttctctc acggttctta cgaataccac     180
aagtctgtca ttgacaacgc cagaaagtcc gaagaattgt acccaggtag accattggcc     240
attgctttgg acaccaaggg tccagaaatc agaactggta ccaccaccaa cgatgttgac     300
tacccaatcc caccaaacca cgaaatgatc ttcaccaccg atgacaagta cgctaaggct     360
tgtgacgaca gatcatgtta cgttgactac aagaacatca ccaaggtcat ctccgctggt     420
agaatcatct acgttgatga tggtgttttg tctttccaag ttttggaagt cgttgacgac     480
aagactttga aggtcaaggc tttgaacgcc ggtaagatct gttccacaa gggtgtcaac     540 ttaccaggta ccgatgtcga tttgccagct tgtctgaaa aggacaagga agatttgaga     600
ttcggtgtca agaacggtgt ccacatggtc ttcgcttctt tcatcagaac cgccaacgat     660
gttttgacca tcagagaagt cttgggtgaa caaggtaagg acgtcaagat cattgtcaag     720
attgaaaacc aacaaggtgt taacaacttc gacgaaatct tgaaggtcac tgacggtgtt     780
atggttgcca gaggtgactt gggtattgaa atcccagccc agaagtctt ggctgtccaa     840 aagaaattga ttgctaagtc taacttggct ggtaagccag ttatctgtgc tacccaaatg     900
ttggaatcca tgacttacaa cccaagacca ccagagctg aagtttccga tgtcggtaac     960
gctatcttgg atggtgctga ctgtgttatg ttgtctggtg aaaccgccaa gggtaactac    1020
```

```
ccaatcaacg ccgttaccac tatggctgaa accgctgtca ttgctgaaca agctatcgct    1080
tacttgccaa actacgatga catgagaaac tgtactccaa agccaacctc caccaccgaa    1140
accgtcgctg cctccgctgt cgctgctgtt ttcgaacaaa aggccaaggc tatcattgtc    1200
ttgtccactt ccggtaccac cccaagattg gtttccaagt acagaccaaa ctgtccaatc    1260
atcttggtta ccagatgccc aagagctgct agattctctc acttgtacag aggtgtcttc    1320
ccattcgttt cgaaaaagga acctgtctct gactggactg atgatgttga agcccgtatc    1380
aacttcggta ttgaaaaggc taaggaattc ggtatcttga agaagggtga cacttacgtt    1440
tccatccaag gtttcaaggc cggtgctggt cactccaaca ctttgcaagt ctctaccgtt    1500
taa                                                                 1503
```

<210> SEQ ID NO 12
<211> LENGTH: 500
<212> TYPE: PRT
<213> ORGANISM: Saccharomyces cerevisiae
<220> FEATURE:
<223> OTHER INFORMATION: PYRUVATE KINASE 1 (PYK1)
<220> FEATURE:
<223> OTHER INFORMATION: PYRUVATE KINASE 1 (PYK1)

<400> SEQUENCE: 12

```
Met Ser Arg Leu Glu Arg Leu Thr Ser Leu Asn Val Val Ala Gly Ser
1               5                   10                  15

Asp Leu Arg Arg Thr Ser Ile Ile Gly Thr Ile Gly Pro Lys Thr Asn
            20                  25                  30

Asn Pro Glu Thr Leu Val Ala Leu Arg Lys Ala Gly Leu Asn Ile Val
        35                  40                  45

Arg Met Asn Phe Ser His Gly Ser Tyr Glu Tyr His Lys Ser Val Ile
    50                  55                  60

Asp Asn Ala Arg Lys Ser Glu Glu Leu Tyr Pro Gly Arg Pro Leu Ala
65                  70                  75                  80

Ile Ala Leu Asp Thr Lys Gly Pro Glu Ile Arg Thr Gly Thr Thr Thr
                85                  90                  95

Asn Asp Val Asp Tyr Pro Ile Pro Pro Asn His Glu Met Ile Phe Thr
            100                 105                 110

Thr Asp Asp Lys Tyr Ala Lys Ala Cys Asp Asp Lys Ile Met Tyr Val
        115                 120                 125

Asp Tyr Lys Asn Ile Thr Lys Val Ile Ser Ala Gly Arg Ile Ile Tyr
    130                 135                 140

Val Asp Asp Gly Val Leu Ser Phe Gln Val Leu Glu Val Val Asp Asp
145                 150                 155                 160

Lys Thr Leu Lys Val Lys Ala Leu Asn Ala Gly Lys Ile Cys Ser His
                165                 170                 175

Lys Gly Val Asn Leu Pro Gly Thr Asp Val Asp Leu Pro Ala Leu Ser
            180                 185                 190

Glu Lys Asp Lys Glu Asp Leu Arg Phe Gly Val Lys Asn Gly Val His
        195                 200                 205

Met Val Phe Ala Ser Phe Ile Arg Thr Ala Asn Asp Val Leu Thr Ile
    210                 215                 220

Arg Glu Val Leu Gly Glu Gln Gly Lys Asp Val Lys Ile Ile Val Lys
225                 230                 235                 240

Ile Glu Asn Gln Gln Gly Val Asn Asn Phe Asp Glu Ile Leu Lys Val
                245                 250                 255

Thr Asp Gly Val Met Val Ala Arg Gly Asp Leu Gly Ile Glu Ile Pro
```

260                 265                 270
Ala Pro Glu Val Leu Ala Val Gln Lys Lys Leu Ile Ala Lys Ser Asn
            275                 280                 285

Leu Ala Gly Lys Pro Val Ile Cys Ala Thr Gln Met Leu Glu Ser Met
        290                 295                 300

Thr Tyr Asn Pro Arg Pro Thr Arg Ala Glu Val Ser Asp Val Gly Asn
305                 310                 315                 320

Ala Ile Leu Asp Gly Ala Asp Cys Val Met Leu Ser Gly Glu Thr Ala
                325                 330                 335

Lys Gly Asn Tyr Pro Ile Asn Ala Val Thr Thr Met Ala Glu Thr Ala
            340                 345                 350

Val Ile Ala Glu Gln Ala Ile Ala Tyr Leu Pro Asn Tyr Asp Asp Met
        355                 360                 365

Arg Asn Cys Thr Pro Lys Pro Thr Ser Thr Thr Glu Thr Val Ala Ala
370                 375                 380

Ser Ala Val Ala Ala Val Phe Glu Gln Lys Ala Lys Ala Ile Ile Val
385                 390                 395                 400

Leu Ser Thr Ser Gly Thr Thr Pro Arg Leu Val Ser Lys Tyr Arg Pro
                405                 410                 415

Asn Cys Pro Ile Ile Leu Val Thr Arg Cys Pro Arg Ala Ala Arg Phe
            420                 425                 430

Ser His Leu Tyr Arg Gly Val Phe Pro Phe Val Phe Glu Lys Glu Pro
        435                 440                 445

Val Ser Asp Trp Thr Asp Asp Val Glu Ala Arg Ile Asn Phe Gly Ile
450                 455                 460

Glu Lys Ala Lys Glu Phe Gly Ile Leu Lys Lys Gly Asp Thr Tyr Val
465                 470                 475                 480

Ser Ile Gln Gly Phe Lys Ala Gly Ala Gly His Ser Asn Thr Leu Gln
                485                 490                 495

Val Ser Thr Val
            500

<210> SEQ ID NO 13
<211> LENGTH: 1521
<212> TYPE: DNA
<213> ORGANISM: Saccharomyces cerevisiae
<220> FEATURE:
<223> OTHER INFORMATION: PYRUVATE KINASE 2 (PYK2)
<220> FEATURE:
<223> OTHER INFORMATION: PYRUVATE KINASE 2 (PYK2)

<400> SEQUENCE: 13
atgccagagt ccagattgca gagactagct aatttgaaaa taggaactcc gcagcagctc      60
agacgcacct ccataatagg taccattggg cccaagacaa atagctgcga ggccattact     120
gctctgagaa agctggtttt gaacatcatt cgattgaact tttcccatgg ctcctacgaa     180
ttccatcaat cagtaatcga aaatgctgtg aaatcggaac agcaattccc tggcaggccg     240
ctcgccattg ccctggatac caagggtccc gagatcagaa caggtcgcac gttaaatgac     300
caagatcttt atatccccgt agaccaccaa atgatcttta ccactgacgc aagttttgca     360
aacacctcca tgataaaaat catgtatata gactatgcta acctgacaaa agttatcgtt     420
ccggggagat ttatatacgt ggacgacggg attctctctt ttaaagtgct ccaaatcatt     480
gacgaatcta atttaagggt gcaagcggta aactcgggtt atatcgcatc tcataaaggt     540
gttaatctgc ctaataccga cgttgatttg ccccccttgt ccgccaaaga catgaaggac     600

-continued

```
ttgcaattcg gagtccgcaa tggcattcac atcgtatttg cctctttcat aagaacttca    660
gaagatgtgt tgtctatcag aaaagcgttg ggttctgaag ggcaagatat caagattata    720
tccaagatag aaaaccagca agggttggat aattttgacg aaatcctgga agtcacggat    780
ggtgttatga tagcgagagg cgatttagga attgaaatcc tggcacctga agtattagcc    840
attcaaaaaa agctgattgc aaaatgtaat ttggcgggca aacctgtcat ttgcgcgact    900
cagatgctgg attcaatgac acacaatccg agaccgacaa gggctgaagt atcggatgtg    960
ggtaacgctg tgttggatgg tgctgattgt gttatgcttt ctggagaaac ggcgaagggt   1020
gattatccgg tgaatgcagt taatattatg gcggcgaccg ctctgattgc tgaaagtact   1080
atcgctcatt tggctctta tgacgatctc agagacgcca ctcccaaacc tacttccact   1140
acggaaactg tagcagctgc agctaccgca gcaatcttgg agcaagatgg taaggccatc   1200
gttgtattat ctactacagg gaacacggca aggctactgt cgaagtatag accaagctgc   1260
cctatcatat tagtaacaag acacgcaaga acggcaagaa ttgcgcattt gtatagaggt   1320
gttttcccat ttctgtatga accgaaacgc ctagacgact ggggtgagga tgttcatagg   1380
cgcctaaagt ttggtgttga atggcgagg tctttcggaa tggtggacaa cggtgatact   1440
gttgtttcca ttcaaggatt caaggagga gtcggccatt ccaataccctt acgcatttct   1500
actgttggtc aagaattcta g                                             1521
```

<210> SEQ ID NO 14
<211> LENGTH: 506
<212> TYPE: PRT
<213> ORGANISM: Saccharomyces cerevisiae
<220> FEATURE:
<223> OTHER INFORMATION: PYRUVATE KINASE 2 (PYK2)
<220> FEATURE:
<223> OTHER INFORMATION: PYRUVATE KINASE 2 (PYK2)

<400> SEQUENCE: 14

```
Met Pro Glu Ser Arg Leu Gln Arg Leu Ala Asn Leu Lys Ile Gly Thr
  1               5                  10                  15

Pro Gln Gln Leu Arg Arg Thr Ser Ile Ile Gly Thr Ile Gly Pro Lys
             20                  25                  30

Thr Asn Ser Cys Glu Ala Ile Thr Ala Leu Arg Lys Ala Gly Leu Asn
         35                  40                  45

Ile Ile Arg Leu Asn Phe Ser His Gly Ser Tyr Glu Phe His Gln Ser
     50                  55                  60

Val Ile Glu Asn Ala Val Lys Ser Glu Gln Gln Phe Pro Gly Arg Pro
 65                  70                  75                  80

Leu Ala Ile Ala Leu Asp Thr Lys Gly Pro Glu Ile Arg Thr Gly Arg
                 85                  90                  95

Thr Leu Asn Asp Gln Asp Leu Tyr Ile Pro Val Asp His Gln Met Ile
            100                 105                 110

Phe Thr Thr Asp Ala Ser Phe Ala Asn Thr Ser Asn Asp Lys Ile Met
        115                 120                 125

Tyr Ile Asp Tyr Ala Asn Leu Thr Lys Val Ile Val Pro Gly Arg Phe
    130                 135                 140

Ile Tyr Val Asp Asp Gly Ile Leu Ser Phe Lys Val Leu Gln Ile Ile
145                 150                 155                 160

Asp Glu Ser Asn Leu Arg Val Gln Ala Val Asn Ser Gly Tyr Ile Ala
                165                 170                 175

Ser His Lys Gly Val Asn Leu Pro Asn Thr Asp Val Asp Leu Pro Pro
            180                 185                 190
```

| | | | | | | | | | | | |
|---|---|---|---|---|---|---|---|---|---|---|---|
|Leu|Ser|Ala|Lys|Asp|Met|Lys|Asp|Leu|Gln|Phe|Gly|Val|Arg|Asn|Gly|
| |195| | | |200| | | |205| | |

Leu Ser Ala Lys Asp Met Lys Asp Leu Gln Phe Gly Val Arg Asn Gly
        195                 200                 205

Ile His Ile Val Phe Ala Ser Phe Ile Arg Thr Ser Glu Asp Val Leu
    210                 215                 220

Ser Ile Arg Lys Ala Leu Gly Ser Glu Gly Gln Asp Ile Lys Ile Ile
225                 230                 235                 240

Ser Lys Ile Glu Asn Gln Gln Gly Leu Asp Asn Phe Asp Glu Ile Leu
            245                 250                 255

Glu Val Thr Asp Gly Val Met Ile Ala Arg Gly Asp Leu Gly Ile Glu
        260                 265                 270

Ile Leu Ala Pro Glu Val Leu Ala Ile Gln Lys Lys Leu Ile Ala Lys
            275                 280                 285

Cys Asn Leu Ala Gly Lys Pro Val Ile Cys Ala Thr Gln Met Leu Asp
        290                 295                 300

Ser Met Thr His Asn Pro Arg Pro Thr Arg Ala Glu Val Ser Asp Val
305                 310                 315                 320

Gly Asn Ala Val Leu Asp Gly Ala Asp Cys Val Met Leu Ser Gly Glu
            325                 330                 335

Thr Ala Lys Gly Asp Tyr Pro Val Asn Ala Val Asn Ile Met Ala Ala
        340                 345                 350

Thr Ala Leu Ile Ala Glu Ser Thr Ile Ala His Leu Ala Leu Tyr Asp
        355                 360                 365

Asp Leu Arg Asp Ala Thr Pro Lys Pro Thr Ser Thr Thr Glu Thr Val
    370                 375                 380

Ala Ala Ala Ala Thr Ala Ile Leu Glu Gln Asp Gly Lys Ala Ile
385                 390                 395                 400

Val Val Leu Ser Thr Thr Gly Asn Thr Ala Arg Leu Leu Ser Lys Tyr
            405                 410                 415

Arg Pro Ser Cys Pro Ile Ile Leu Val Thr Arg His Ala Arg Thr Ala
        420                 425                 430

Arg Ile Ala His Leu Tyr Arg Gly Val Phe Pro Phe Leu Tyr Glu Pro
        435                 440                 445

Lys Arg Leu Asp Asp Trp Gly Glu Asp Val His Arg Arg Leu Lys Phe
450                 455                 460

Gly Val Glu Met Ala Arg Ser Phe Gly Met Val Asp Asn Gly Asp Thr
465                 470                 475                 480

Val Val Ser Ile Gln Gly Phe Lys Gly Val Gly His Ser Asn Thr
            485                 490                 495

Leu Arg Ile Ser Thr Val Gly Gln Glu Phe
            500                 505

<210> SEQ ID NO 15
<211> LENGTH: 1047
<212> TYPE: DNA
<213> ORGANISM: Saccharomyces cerevisiae
<220> FEATURE:
<223> OTHER INFORMATION: ALCOHOL DEHYDROGENASE 1 (ADH1)
<220> FEATURE:
<223> OTHER INFORMATION: ALCOHOL DEHYDROGENASE 1 (ADH1)

<400> SEQUENCE: 15
atgtctatcc cagaaactca aaaggtgtt atcttctacg aatcccacgg taagttggaa      60
tacaaagata ttccagttcc aaagccaaag gccaacgaat tgttgatcaa cgttaaatac     120
tctggtgtct gtcacactga cttgcacgct tggcacggtg actggccatt gccagttaag    180

```
ctaccattag tcggtggtca cgaaggtgcc ggtgtcgttg tcggcatggg tgaaaacgtt      240
aagggctgga agatcggtga ctacgccggt atcaaatggt tgaacggttc ttgtatggcc      300
tgtgaatact gtgaattggg taacgaatcc aactgtcctc acgctgactt gtctggttac      360
acccacgacg gttctttcca acaatacgct accgctgacg ctgttcaagc cgctcacatt      420
cctcaaggta ccgacttggc ccaagtcgcc cccatcttgt gtgctggtat caccgtctac      480
aaggctttga gtctgctaa cttgatggcc ggtcactggg ttgctatctc cggtgctgct       540
ggtggtctag gttctttggc tgttcaatac gccaaggcta tgggttacag agtcttgggt      600
attgacggtg gtgaaggtaa ggaagaatta ttcagatcca tcggtggtga agtcttcatt      660
gacttcacta aggaaaagga cattgtcggt gctgttctaa aggccactga cggtggtgct      720
cacggtgtca tcaacgtttc cgtttccgaa gccgctattg aagcttctac cagatacgtt      780
agagctaacg gtaccaccgt tttggtcggt atgccagctg gtgccaagtg ttgttctgat      840
gtcttcaacc aagtcgtcaa gtccatctct attgttggtt cttacgtcgg taacagagct      900
gacaccagag aagctttgga cttcttcgcc agaggtttgg tcaagtctcc aatcaaggtt      960
gtcggcttgt ctaccttgcc agaaatttac gaaaagatgg aaaagggtca aatcgttggt     1020
agatacgttg ttgacacttc taaataa                                          1047
```

<210> SEQ ID NO 16
<211> LENGTH: 348
<212> TYPE: PRT
<213> ORGANISM: Saccharomyces cerevisiae
<220> FEATURE:
<223> OTHER INFORMATION: ALCOHOL DEHYDROGENASE 1 (ADH1)
<220> FEATURE:
<223> OTHER INFORMATION: ALCOHOL DEHYDROGENASE 1 (ADH1)

<400> SEQUENCE: 16

```
Met Ser Ile Pro Glu Thr Gln Lys Gly Val Ile Phe Tyr Glu Ser His
1               5                   10                  15

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
```

```
                195                 200                 205
            Glu Leu Phe Arg Ser Ile Gly Gly Glu Val Phe Ile Asp Phe Thr Lys
                210                 215                 220

Glu Lys Asp Ile Val Gly Ala Val Leu Lys Ala Thr Asp Gly Gly Ala
            225                 230                 235                 240

His Gly Val Ile Asn Val Ser Val Ser Glu Ala Ile Glu Ala Ser
                            245                 250                 255

Thr Arg Tyr Val Arg Ala Asn Gly Thr Thr Val Leu Val Gly Met Pro
                        260                 265                 270

Ala Gly Ala Lys Cys Cys Ser Asp Val Phe Asn Gln Val Val Lys Ser
                        275                 280                 285

Ile Ser Ile Val Gly Ser Tyr Val Gly Asn Arg Ala Asp Thr Arg Glu
                        290                 295                 300

Ala Leu Asp Phe Phe Ala Arg Gly Leu Val Lys Ser Pro Ile Lys Val
            305                 310                 315                 320

Val Gly Leu Ser Thr Leu Pro Glu Ile Tyr Glu Lys Met Glu Lys Gly
                                325                 330                 335

Gln Ile Val Gly Arg Tyr Val Val Asp Thr Ser Lys
                        340                 345
```

<210> SEQ ID NO 17
<211> LENGTH: 3537
<212> TYPE: DNA
<213> ORGANISM: Saccharomyces cerevisiae
<220> FEATURE:
<223> OTHER INFORMATION: PYRUVATE CARBOXYLASE 1 (PYC1)
<220> FEATURE:
<223> OTHER INFORMATION: PYRUVATE CARBOXYLASE 1 (PYC1)

<400> SEQUENCE: 17

```
atgtcgcaaa gaaaattcgc cggcttgaga gataacttca atctcttggg tgaaaagaac    60
aaaatattgg tggctaatag aggagaaatt ccaatcagaa tttttcgtac cgctcatgaa   120
ctgtctatgc agacggtagc tatatattct catgaagatc gtctttcaac gcacaaacaa   180
aaggctgacg aagcatacgt cataggtgaa gtaggccaat ataccccgt cggcgcttat   240
ttggccattg acgaaatcat ttccattgcc caaaaacacc aggtagattt catccatcca   300
ggttatgggt tcttgtctga aaattcggaa tttgccgaca agtagtgaa ggccggtatc    360
acttggattg gccctccagc tgaagttatt gactccgtgg gtgataaggt ctcagctaga   420
aacctggcag caaaagctaa tgtgcccacc gttcctggta caccaggtcc tatagaaact   480
gtagaggaag cacttgactt cgtcaatgaa tacggctacc cggtgatcat taaggccgcc   540
tttggtggtg gtggtagagg tatgagagtc gttagagaag gtgacgacgt ggcagatgcc   600
ttcaacgtg ctacctccga agcccgtact gccttcggta atggtacctg ctttgtggaa   660
agattcttgg acaagccaaa gcatattgaa gttcaattgt tggccgataa ccacggaaac   720
gtggttcatc ttttcgaaag agactgttcc gtgcagagaa gacaccaaaa ggttgtcgaa   780
gtggccccag caaagacttt accccgtgaa gtccgtgacg ccattttgac agatgcagtt   840
aaattggcca agagtgtgg ctacagaaat gcgggtactg ctgaattctt ggttgataac   900
caaaatagac actatttcat tgaaattaat ccaagaatcc aagtggaaca taccatcaca   960
gaagaaatta ccggtataga tattgtggcg gctcagatcc aaattgcggc aggtgcctct  1020
ctaccccagc tgggcctatt ccaggacaaa attacgactc gtggctttgc cattcagtgc  1080
cgtattacca cggaagaccc tgctaagaac ttccaaccag ataccggtag aatagaagtg  1140
```

```
taccgttctg caggtggtaa tggtgttaga ctggatggtg gtaacgccta tgcaggaaca    1200
ataatctcac ctcattacga ctcaatgctg gtcaaatgct catgctccgg ttccacctac    1260
gaaatcgttc gtagaaaaat gattcgtgca ttaatcgagt tcagaattag aggtgtcaag    1320
accaacattc ccttcctatt gactcttttg accaatccag tatttattga gggtacatac    1380
tggacgactt ttattgacga caccccacaa ctgttccaaa tggtttcatc acaaaacaga    1440
gcccaaaaac ttttacatta cctcgccgac gtggcagtca atggttcatc tatcaagggt    1500
caaattggct tgccaaaatt aaaatcaaat ccaagtgtcc cccatttgca cgatgctcag    1560
ggcaatgtca tcaacgttac aaagtctgca ccaccatccg gatggaggca agtgctacta    1620 gaaaagggc cagctgaatt tgccagacaa gttagacagt tcaatggtac tttattgatg    1680
gacaccacct ggagagacgc tcatcaatct ctacttgcaa caagagtcag aacccacgat    1740
ttggctacaa tcgctccaac aaccgcacat gcccttgcag gtcgtttcgc cttagaatgt    1800
tggggtggtg ccacattcga tgttgcaatg agattttttgc atgaggatcc atgggaacgt    1860
ttgagaaaat taagatctct ggtgcctaat attccattcc aaatgttatt gcgtggtgcc    1920
aatggtgtgg cttattcttc attgcctgac aatgctattg accatttcgt caagcaagcc    1980
aaggataatg gtgttgatat atttagagtc tttgatgcct taaatgactt ggaacaattg    2040
aaggtcggtg tagatgctgt gaagaaggca ggtggtgttg tagaagccac tgtttgtttc    2100
tctggggata tgcttcagcc aggcaagaaa tacaatttgg attactactt ggaaattgct    2160
gaaaaaattg tccaaatggg cactcatatc ctgggtatca agatatggc aggtaccatg    2220 aagccagcag ctgccaaact actgattgga tctttgaggg ctaagtaccc tgatctccca    2280
atacatgttc acactcacga ttctgcaggt actgctgttg catcaatgac tgcgtgtgct    2340
ctggcgggcg ccgatgtcgt tgatgttgcc atcaactcaa tgtctggttt aacttcacaa    2400
ccatcaatca atgctctgtt ggcttcatta gaaggtaata ttgacactgg tattaacgtt    2460
gagcatgtcc gtgaactaga tgcatattgg gcagagatga gattgttata ctcttgtttc    2520
gaggctgact tgaagggccc agatccagaa gtttatcaac atgaaatccc aggtggtcaa    2580
ttgacaaact tgttgtttca gcccaacaa ttgggtcttg gagaacaatg gccgaaaca     2640 aaaagagctt acagagaagc caattattta ttgggtgata ttgtcaaagt taccccaact    2700
tcgaaggtcg ttggtgatct ggcacaattt atggtctcca ataaattaac ttccgatgat    2760
gtgagacgcc tggctaattc ttttggattc cctgactctg ttatggattt cttcgaaggc    2820
ttaatcggcc aaccatatgg tgggttccca gaaccattta gatcagacgt tttaaggaac    2880
aagagaagaa agttgacttg tcgtccaggc ctggaactag agccatttga tctcgaaaaa    2940
attagagaag acttgcagaa tagatttggt gatgttgatg agtgcgacgt tgcttccttat   3000 aacatgtacc aagagtttta tgaagacttc caaaagatga gagaaacgta tggtgattta    3060
tctgtattgc caacaagaag cttttttgtct ccactagaga ctgacgaaga aattgaagtt   3120
gtaatcgaac aaggtaaaac gctaattatc aagctacagg ctgtgggtga tttgaacaaa    3180
aagaccggtg aaagagaagt ttactttgat ttgaatggtg aaatgagaaa aattcgtgtt    3240
gctgacagat cacaaaaagt ggaaactgtt actaaatcca aagcagacat gcatgatcca    3300
ttacacattg gtgcaccaat ggcaggtgtc attgttgaag ttaaagttca taaggatca    3360 ctaataaaga agggccaacc tgtagccgta ttaagcgcca tgaaaatgga aatgattata    3420
tcttctccat ccgatggaca agttaaagaa gtgtttgtct ctgatggtga aaatgtggac    3480
tcttctgatt tattagttct attagaagac caagttcctg ttgaaactaa ggcatga      3537
```

<210> SEQ ID NO 18
<211> LENGTH: 1178
<212> TYPE: PRT
<213> ORGANISM: Saccharomyces cerevisiae
<220> FEATURE:
<223> OTHER INFORMATION: PYRUVATE CARBOXYLASE 1 (PYC1)
<220> FEATURE:
<223> OTHER INFORMATION: PYRUVATE CARBOXYLASE 1 (PYC1)

<400> SEQUENCE: 18

```
Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
            20                  25                  30

Arg Ile Phe Arg Thr Ala His Glu Leu Ser Met Gln Thr Val Ala Ile
        35                  40                  45

Tyr Ser His Glu Asp Arg Leu Ser Thr His Lys Gln Lys Ala Asp Glu
    50                  55                  60

Ala Tyr Val Ile Gly Glu Val Gly Gln Tyr Thr Pro Val Gly Ala Tyr
65                  70                  75                  80

Leu Ala Ile Asp Glu Ile Ile Ser Ile Ala Gln Lys His Gln Val Asp
                85                  90                  95

Phe Ile His Pro Gly Tyr Gly Phe Leu Ser Glu Asn Ser Glu Phe Ala
            100                 105                 110

Asp Lys Val Val Lys Ala Gly Ile Thr Trp Ile Gly Pro Pro Ala Glu
        115                 120                 125

Val Ile Asp Ser Val Gly Asp Lys Val Ser Ala Arg Asn Leu Ala Ala
    130                 135                 140

Lys Ala Asn Val Pro Thr Val Pro Gly Thr Pro Gly Pro Ile Glu Thr
145                 150                 155                 160

Val Glu Glu Ala Leu Asp Phe Val Asn Glu Tyr Gly Tyr Pro Val Ile
                165                 170                 175

Ile Lys Ala Ala Phe Gly Gly Gly Gly Arg Gly Met Arg Val Val Arg
            180                 185                 190

Glu Gly Asp Asp Val Ala Asp Ala Phe Gln Arg Ala Thr Ser Glu Ala
        195                 200                 205

Arg Thr Ala Phe Gly Asn Gly Thr Cys Phe Val Glu Arg Phe Leu Asp
    210                 215                 220

Lys Pro Lys His Ile Glu Val Gln Leu Leu Ala Asp Asn His Gly Asn
225                 230                 235                 240

Val Val His Leu Phe Glu Arg Asp Cys Ser Val Gln Arg Arg His Gln
                245                 250                 255

Lys Val Val Glu Val Ala Pro Ala Lys Thr Leu Pro Arg Glu Val Arg
            260                 265                 270

Asp Ala Ile Leu Thr Asp Ala Val Lys Leu Ala Lys Glu Cys Gly Tyr
        275                 280                 285

Arg Asn Ala Gly Thr Ala Glu Phe Leu Val Asp Asn Gln Asn Arg His
    290                 295                 300

Tyr Phe Ile Glu Ile Asn Pro Arg Ile Gln Val Glu His Thr Ile Thr
305                 310                 315                 320

Glu Glu Ile Thr Gly Ile Asp Ile Val Ala Ala Gln Ile Gln Ile Ala
                325                 330                 335

Ala Gly Ala Ser Leu Pro Gln Leu Gly Leu Phe Gln Asp Lys Ile Thr
            340                 345                 350
```

```
Thr Arg Gly Phe Ala Ile Gln Cys Arg Ile Thr Glu Asp Pro Ala
            355                 360                 365

Lys Asn Phe Gln Pro Asp Thr Gly Arg Ile Glu Val Tyr Arg Ser Ala
    370                 375                 380

Gly Gly Asn Gly Val Arg Leu Asp Gly Gly Asn Ala Tyr Ala Gly Thr
385                 390                 395                 400

Ile Ile Ser Pro His Tyr Asp Ser Met Leu Val Lys Cys Ser Cys Ser
                405                 410                 415

Gly Ser Thr Tyr Glu Ile Val Arg Arg Lys Met Ile Arg Ala Leu Ile
            420                 425                 430

Glu Phe Arg Ile Arg Gly Val Lys Thr Asn Ile Pro Phe Leu Leu Thr
        435                 440                 445

Leu Leu Thr Asn Pro Val Phe Ile Glu Gly Thr Tyr Trp Thr Thr Phe
    450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
            500                 505                 510

Val Pro His Leu His Asp Ala Gln Gly Asn Val Ile Asn Val Thr Lys
        515                 520                 525

Ser Ala Pro Pro Ser Gly Trp Arg Gln Val Leu Leu Glu Lys Gly Pro
    530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
            580                 585                 590

Ala Gly Arg Phe Ala Leu Glu Cys Trp Gly Gly Ala Thr Phe Asp Val
        595                 600                 605

Ala Met Arg Phe Leu His Glu Asp Pro Trp Glu Arg Leu Arg Lys Leu
    610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
            660                 665                 670

Ala Leu Asn Asp Leu Glu Gln Leu Lys Val Gly Val Asp Ala Val Lys
        675                 680                 685

Lys Ala Gly Gly Val Val Glu Ala Thr Val Cys Phe Ser Gly Asp Met
    690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Lys Leu Leu Ile Gly Ser Leu
            740                 745                 750

Arg Ala Lys Tyr Pro Asp Leu Pro Ile His Val His Thr His Asp Ser
        755                 760                 765

Ala Gly Thr Ala Val Ala Ser Met Thr Ala Cys Ala Leu Ala Gly Ala
```

```
              770                 775                 780
Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
                820                 825                 830

Met Arg Leu Leu Tyr Ser Cys Phe Glu Ala Asp Leu Lys Gly Pro Asp
                835                 840                 845

Pro Glu Val Tyr Gln His Glu Ile Pro Gly Gly Gln Leu Thr Asn Leu
                850                 855                 860

Leu Phe Gln Ala Gln Gln Leu Gly Leu Gly Glu Gln Trp Ala Glu Thr
865                 870                 875                 880

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
                900                 905                 910

Ser Asn Lys Leu Thr Ser Asp Val Arg Arg Leu Ala Asn Ser Leu
                915                 920                 925

Asp Phe Pro Asp Ser Val Met Asp Phe Glu Gly Leu Ile Gly Gln
                930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
                980                 985                 990

Asp Glu Cys Asp Val Ala Ser Tyr Asn Met Tyr Pro Arg Val Tyr Glu
                995                 1000                1005

Asp Phe Gln Lys Met Arg Glu Thr Tyr Gly Asp Leu Ser Val Leu Pro
                1010                1015                1020

Thr Arg Ser Phe Leu Ser Pro Leu Glu Thr Asp Glu Glu Ile Glu Val
1025                1030                1035                1040

Val Ile Glu Gln Gly Lys Thr Leu Ile Ile Lys Leu Gln Ala Val Gly
                1045                1050                1055

Asp Leu Asn Lys Lys Thr Gly Glu Arg Glu Val Tyr Phe Asp Leu Asn
                1060                1065                1070

Gly Glu Met Arg Lys Ile Arg Val Ala Asp Arg Ser Gln Lys Val Glu
                1075                1080                1085

Thr Val Thr Lys Ser Lys Ala Asp Met His Asp Pro Leu His Ile Gly
                1090                1095                1100

Ala Pro Met Ala Gly Val Ile Val Glu Val Lys Val His Lys Gly Ser
1105                1110                1115                1120

Leu Ile Lys Lys Gly Gln Pro Val Ala Val Leu Ser Ala Met Lys Met
                1125                1130                1135

Glu Met Ile Ile Ser Ser Pro Ser Asp Gly Gln Val Lys Glu Val Phe
                1140                1145                1150

Val Ser Asp Gly Glu Asn Val Asp Ser Ser Asp Leu Leu Val Leu Leu
                1155                1160                1165

Glu Asp Gln Val Pro Val Glu Thr Lys Ala
        1170                1175

<210> SEQ ID NO 19
```

<211> LENGTH: 3543
<212> TYPE: DNA
<213> ORGANISM: Saccharomyces cerevisiae
<220> FEATURE:
<223> OTHER INFORMATION: PYRUVATE CARBOXYLASE 2 (PYC2)
<220> FEATURE:
<223> OTHER INFORMATION: PYRUVATE CARBOXYLASE 2 (PYC2)

<400> SEQUENCE: 19

```
atgagcagta gcaagaaatt ggccggtctt agggacaatt tcagtttgct cggcgaaaag    60
aataagatct tggtcgccaa tagaggtgaa attccgatta gaattttag atctgctcat    120
gagctgtcta tgagaactat cgccatatac tcccacgagg accgtctttc aatgcatagg    180
ttgaaggcgg acgaagcgta tgttatcggg gaggagggcc agtatacacc tgtgggtgct    240
tacttggcaa tggacgagat catcgaaatt gcaagaagc ataaggtgga tttcatccat    300
ccaggttatg ggttcttgtc tgaaaattcg gaatttgccg acaaagtagt gaaggccggt    360
atcacttgga ttggccctcc agctgaagtt attgaatctg tgggtgacaa agtctctgcc    420
agacacttgg cagcaagagc taacgttcct accgttcccg gtactccagg acctatcgaa    480
actgtgcaag aggcacttga cttcgttaat gaatacggct acccggtgat cattaaggcc    540
gcctttggtg gtggtggtag aggtatgaga gtcgttagag aaggtgacga cgtggcagat    600
gcctttcaac gtgctacctc cgaagcccgt actgccttcg gtaatggtac ctgctttgtg    660
gaaagattct tggacaagcc aaagcatatt gaagttcaat tgttggctga taaccacgga    720
aacgtggttc atctttcga agagactgt tctgtgcaaa gaagacacca aaaagttgtc    780
gaagtcgctc cagcaaagac tttgccccgt gaagttcgtg acgctatttt gacagatgct    840
gttaaattag ctaaggtatg tggttacaga aacgcaggta ccgccgaatt cttggttgac    900
aaccaaaaca gacactattt cattgaaatt aatccaagaa ttcaagtgga gcataccatc    960
actgaagaaa tcaccggtat tgacattgtt tctgcccaaa tccagattgc cgcaggtgcc    1020
actttgactc aactaggtct attacaggat aaaatcacca cccgtgggtt ttccatccaa    1080
tgtcgtatta ccactgaaga tcctctaag aatttccaac cggataccgg tcgcctggag    1140
gtctatcgtt ctgccggtgg taatggtgtg agattggacg tggtaacgc ttatgcaggt    1200
gctactatct cgcctcacta cgactcaatg ctggtcaaat gttcatgctc tggttctact    1260
tatgaaatcg tccgtaggaa gatgattcgt gccctgatcg aattcagaat cagaggtgtt    1320
aagaccaaca ttccctttcct attgactctt ttgaccaatc cagtttttat tgagggtact    1380
tactggacga cttttattga cgacacccca caactgttcc aaatggtatc atcacaaaac    1440
agagcgcaaa aactgttaca ctatttggca gacttggcag ttaacggttc ttctattaag    1500
ggtcaaattg gcttgccaaa actaaaatca aatccaagtg tcccccattt gcacgatgct    1560
cagggcaatg tcatcaacgt tacaaagtct gcaccaccat ccggatggag acaagtgcta    1620
ctggaaaagg gaccatctga atttgccaag caagtcagac agttcaatgg tactctactg    1680
atggacacca cctggagaga cgctcatcaa tctctacttg caacaagagt cagaacccac    1740
gatttggcta caatcgctcc aacaaccgca catgcccttg caggtgcttt cgctttagaa    1800
tgttggggtg gtgctacatt cgacgttgca atgagattct gcatgagga tccatgggaa    1860
cgtctgagaa aattaagatc tctggtgcct aatattccat tccaaatgtt attacgtggt    1920
gccaacggtg tggcttactc ttcattacct gacaatgcta ttgaccattt tgtcaagcaa    1980
gccaaggata tggtgttga tatatttaga gtctttgatg ccttgaatga tttagaacaa    2040
ttaaaagttg gtgtgaatgc tgtcaagaag gccggtggtg ttgtcgaagc tactgtttgt    2100
```

```
tactctggtg acatgcttca gccaggtaag aaatacaact tagattacta cctagaagtt    2160
gttgaaaaaa tagttcaaat gggtacacat atcttgggta ttaaggatat ggcaggtact    2220
atgaaaccgg ccgctgccaa attattaatt ggctccctaa gaaccagata tccggattta    2280
ccaattcatg ttcacagtca tgactccgca ggtactgctg ttgcgtctat gactgcatgt    2340
gccctagcag gtgctgatgt tgtcgatgta gctatcaatt caatgtcggg cttaacttcc    2400
caaccatcaa ttaatgcact gttggcttca ttagaaggta acattgatac tgggattaac    2460
gttgagcatg ttcgtgaatt agatgcatac tgggccgaaa tgagactgtt gtattcttgt    2520
ttcgaggccg acttgaaggg accagatcca gaagtttacc aacatgaaat cccaggtggt    2580
caattgacta acttgttatt ccaagctcaa caactgggtc ttggtgaaca atgggctgaa    2640
actaaaagag cttacagaga agccaattac ctactgggag atattgttaa agttaccccca   2700
acttctaagg ttgtcggtga tttagctcaa ttcatggttt ctaacaaact gacttccgac    2760
gatattagac gtttagctaa ttcttttggac tttcctgact ctgttatgga cttttttgaa    2820
ggtttaattg gtcaaccata cggtgggttc ccagaaccat taagatctga tgtattgaga    2880
aacaagagaa gaaagttgac gtgccgtcca ggtttagaat tagaaccatt tgatctcgaa    2940
aaaattagag aagacttgca gaacagattc ggtgatattg atgaatgcga tgttgcttct    3000
tacaatatgt atccaagggt ctatgaagat ttccaaaaga tcagagaaac atacggtgat    3060
ttatcagttc taccaaccaa aaatttccta gcaccagcag aacctgatga gaaaatcgaa    3120
gtcaccatcg aacaaggtaa gactttgatt atcaaattgc aagctgttgg tgacttaaat    3180
aagaaaactg ggcaaagaga agtgtatttt gaattgaacg gtgaattaag aaagatcaga    3240
gttgcagaca gtcacaaaaa catacaatct gttgctaaac caaaggctga tgtccacgat    3300
actcaccaaa tcggtgcacc aatggctggt gttatcatag aagttaaagt acataaaggg    3360
tctttggtga aaaagggcga atcgattgct gttttgagtg ccatgaaaat ggaaatggtt    3420
gtctcttcac cagcagatgg tcaagttaaa gatgttttca ttagggatgg tgaaagtgtt    3480
gacgcatcag atttgttggt tgtcctagaa gaagaaaccc taccccccatc ccaaaaaaag   3540
taa                                                                   3543
```

<210> SEQ ID NO 20
<211> LENGTH: 1180
<212> TYPE: PRT
<213> ORGANISM: Saccharomyces cerevisiae
<220> FEATURE:
<223> OTHER INFORMATION: PYRUVATE CARBOXYLASE 2 (PYC2)
<220> FEATURE:
<223> OTHER INFORMATION: PYRUVATE CARBOXYLASE 2 (PYC2)

<400> SEQUENCE: 20

```
Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Glu Gly Gln Tyr Thr Pro Val Gly Ala
65                  70                  75                  80

Tyr Leu Ala Met Asp Glu Ile Ile Glu Ile Ala Lys Lys His Lys Val
```

```
                85                  90                  95
Asp Phe Ile His Pro Gly Tyr Gly Phe Leu Ser Glu Asn Ser Glu Phe
            100                 105                 110

Ala Asp Lys Val Val Lys Ala Gly Ile Thr Trp Ile Gly Pro Pro Ala
            115                 120                 125

Glu Val Ile Asp Ser Val Gly Asp Lys Val Ser Ala Arg His Leu Ala
            130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
                180                 185                 190

Arg Glu Gly Asp Asp Val Ala Asp Ala Phe Gln Arg Ala Thr Ser Glu
                195                 200                 205

Ala Arg Thr Ala Phe Gly Asn Gly Thr Cys Phe Val Glu Arg Phe Leu
            210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
            260                 265                 270

Arg Asp Ala Ile Leu Thr Asp Ala Val Lys Leu Ala Lys Val Cys Gly
            275                 280                 285

Tyr Arg Asn Ala Gly Thr Ala Glu Phe Leu Val Asp Asn Gln Asn Arg
            290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
            340                 345                 350

Thr Thr Arg Gly Phe Ser Ile Gln Cys Arg Ile Thr Thr Glu Asp Pro
            355                 360                 365

Ser Lys Asn Phe Gln Pro Asp Thr Gly Arg Leu Glu Val Tyr Arg Ser
            370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys
                405                 410                 415

Ser Gly Ser Thr Tyr Glu Ile Val Arg Arg Lys Met Ile Arg Ala Leu
            420                 425                 430

Ile Glu Phe Arg Ile Arg Gly Val Lys Thr Asn Ile Pro Phe Leu Leu
            435                 440                 445

Thr Leu Leu Thr Asn Pro Val Phe Ile Glu Gly Thr Tyr Trp Thr Thr
            450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
                485                 490                 495

Ser Ser Ile Lys Gly Gln Ile Gly Leu Pro Lys Leu Lys Ser Asn Pro
            500                 505                 510
```

-continued

Ser Val Pro His Leu His Asp Ala Gln Gly Asn Val Ile Asn Val Thr
            515                 520                 525

Lys Ser Ala Pro Pro Ser Gly Trp Arg Gln Val Leu Leu Glu Lys Gly
    530                 535                 540

Pro Ser Glu Phe Ala Lys Gln Val Arg Gln Phe Asn Gly Thr Leu Leu
545                 550                 555                 560

Met Asp Thr Thr Trp Arg Asp Ala His Gln Ser Leu Leu Ala Thr Arg
                565                 570                 575

Val Arg Thr His Asp Leu Ala Thr Ile Ala Pro Thr Thr Ala His Ala
            580                 585                 590

Leu Ala Gly Ala Phe Ala Leu Glu Cys Trp Gly Gly Ala Thr Phe Asp
            595                 600                 605

Val Ala Met Arg Phe Leu His Glu Asp Pro Trp Glu Arg Leu Arg Lys
            610                 615                 620

Leu Arg Ser Leu Val Pro Asn Ile Pro Phe Gln Met Leu Leu Arg Gly
625                 630                 635                 640

Ala Asn Gly Val Ala Tyr Ser Ser Leu Pro Asp Asn Ala Ile Asp His
                645                 650                 655

Phe Val Lys Gln Ala Lys Asp Asn Gly Val Asp Ile Phe Arg Val Phe
                660                 665                 670

Asp Ala Leu Asn Asp Leu Glu Gln Leu Lys Val Gly Val Asn Ala Val
            675                 680                 685

Lys Lys Ala Gly Gly Val Val Glu Ala Thr Val Cys Tyr Ser Gly Asp
    690                 695                 700

Met Leu Gln Pro Gly Lys Lys Tyr Asn Leu Asp Tyr Tyr Leu Glu Val
705                 710                 715                 720

Val Glu Lys Ile Val Gln Met Gly Thr His Ile Leu Gly Ile Lys Asp
                725                 730                 735

Met Ala Gly Thr Met Lys Pro Ala Ala Ala Lys Leu Leu Ile Gly Ser
                740                 745                 750

Leu Arg Thr Arg Tyr Pro Asp Leu Pro Ile His Val His Ser His Asp
            755                 760                 765

Ser Ala Gly Thr Ala Val Ala Ser Met Thr Ala Cys Ala Leu Ala Gly
            770                 775                 780

Ala Asp Val Val Asp Val Ala Ile Asn Ser Met Ser Gly Leu Thr Ser
785                 790                 795                 800

Gln Pro Ser Ile Asn Ala Leu Leu Ala Ser Leu Glu Gly Asn Ile Asp
                805                 810                 815

Thr Gly Ile Asn Val Glu His Val Arg Glu Leu Asp Ala Tyr Trp Ala
                820                 825                 830

Glu Met Arg Leu Leu Tyr Ser Cys Phe Glu Ala Asp Leu Lys Gly Pro
            835                 840                 845

Asp Pro Glu Val Tyr Gln His Glu Ile Pro Gly Gly Gln Leu Thr Asn
850                 855                 860

Leu Leu Phe Gln Ala Gln Leu Gly Leu Gly Glu Gln Trp Ala Glu
865                 870                 875                 880

Thr Lys Arg Ala Tyr Arg Glu Ala Asn Tyr Leu Leu Gly Asp Ile Val
                885                 890                 895

Lys Val Thr Pro Thr Ser Lys Val Val Gly Asp Leu Ala Gln Phe Met
            900                 905                 910

Val Ser Asn Lys Leu Thr Ser Asp Asp Ile Arg Arg Leu Ala Asn Ser
            915                 920                 925

Leu Asp Phe Pro Asp Ser Val Met Asp Phe Phe Glu Gly Leu Ile Gly
    930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
                965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
        995                 1000                1005

Glu Asp Phe Gln Lys Ile Arg Glu Thr Tyr Gly Asp Leu Ser Val Leu
    1010                1015                1020

Pro Thr Lys Asn Phe Leu Ala Pro Ala Glu Pro Asp Glu Glu Ile Glu
1025                1030                1035                1040

Val Thr Ile Glu Gln Gly Lys Thr Leu Ile Ile Lys Leu Gln Ala Val
                1045                1050                1055

Gly Asp Leu Asn Lys Lys Thr Gly Gln Arg Glu Val Tyr Phe Glu Leu
            1060                1065                1070

Asn Gly Glu Leu Arg Lys Ile Arg Val Ala Asp Lys Ser Gln Asn Ile
        1075                1080                1085

Gln Ser Val Ala Lys Pro Lys Ala Asp Val His Asp Thr His Gln Ile
    1090                1095                1100

Gly Ala Pro Met Ala Gly Val Ile Ile Glu Val Lys Val His Lys Gly
1105                1110                1115                1120

Ser Leu Val Lys Lys Gly Glu Ser Ile Ala Val Leu Ser Ala Met Lys
                1125                1130                1135

Met Glu Met Val Val Ser Ser Pro Ala Asp Gly Gln Val Lys Asp Val
            1140                1145                1150

Phe Ile Lys Asp Gly Glu Ser Val Asp Ala Ser Asp Leu Leu Val Val
        1155                1160                1165

Leu Glu Glu Glu Thr Leu Pro Pro Ser Gln Lys Lys
    1170                1175                1180

<210> SEQ ID NO 21
<211> LENGTH: 1128
<212> TYPE: DNA
<213> ORGANISM: Saccharomyces cerevisiae
<220> FEATURE:
<223> OTHER INFORMATION: ALCOHOL DEHYDROGENASE 3 (ADH3)
<220> FEATURE:
<223> OTHER INFORMATION: ALCOHOL DEHYDROGENASE 3 (ADH3)

<400> SEQUENCE: 21
atgttgagaa cgtcaacatt gttcaccagg cgtgtccaac caagcctatt ttctagaaac      60
attcttagat tgcaatccac agctgcaatc cctaagactc aaaaaggtgt catctttat     120 gagaataagg ggaagctgca ttacaaagat atccctgtcc ccgagcctaa gccaaatgaa    180
attttaatca acgttaaata ttctggtgta tgtcacaccg atttcatgc ttggcacggc     240 gattggccat tacctgttaa actaccatta gtaggtggtc atgaaggtgc tggtgtagtt    300
gtcaaactag gttccaatgt caagggctgg aaagtcggtg atttagcagg tatcaaatgg    360
ctgaacggtt cttgtatgac atgcgaattc tgtgaatcag gtcatgaatc aaattgtcca    420
gatgctgatt tatctggtta cactcatgat ggttctttcc aacaatttgc gaccgctgat    480
gctattcaag ccgccaaaat tcaacagggt accgacttgg ccgaagtagc cccaatatta    540
tgtgctggtg ttactgtata taagcactaa aaagaggcag acttgaaagc tggtgactgg    600

```
gttgccatct ctggtgctgc aggtggcttg ggttccttgg ccgttcaata tgcaactgcg    660
atgggttaca gagttctagg tattgatgca ggtgaggaaa aggaaaaact tttcaagaaa    720 ttgggggggtg aagtattcat cgactttact aaaacaaaga atatggtttc tgacattcaa   780
gaagctacca aaggtggccc tcatggtgtc attaacgttt ccgttctgaa gccgctatt    840 tctctatcta cggaatatgt tagaccatgt ggtaccgtcg ttttggttgg tttgcccgct    900
aacgcctacg ttaaatcaga ggtattctct catgtggtga agtccatcaa atcaagggt    960 tcttatgttg gtaacagagc tgatacgaga gaagccttag acttctttag cagaggtttg   1020
atcaaatcac caatcaaaat tgttggatta tctgaattac caaaggttta tgacttgatg   1080
gaaaagggca agattttggg tagatacgtc gtcgatacta gtaaataa                 1128
```

<210> SEQ ID NO 22
<211> LENGTH: 375
<212> TYPE: PRT
<213> ORGANISM: Saccharomyces cerevisiae
<220> FEATURE:
<223> OTHER INFORMATION: ALCOHOL DEHYDROGENASE 3 (ADH3)
<220> FEATURE:
<223> OTHER INFORMATION: ALCOHOL DEHYDROGENASE 3 (ADH3)

<400> SEQUENCE: 22

Met Leu Arg Thr Ser Thr Leu Phe Thr Arg Arg Val Gln Pro Ser Leu
1               5                   10                  15

Phe Ser Arg Asn Ile Leu Arg Leu Gln Ser Thr Ala Ala Ile Pro Lys
                20                  25                  30

Thr Gln Lys Gly Val Ile Phe Tyr Glu Asn Lys Gly Lys Leu His Tyr
            35                  40                  45

Lys Asp Ile Pro Val Pro Glu Pro Lys Pro Asn Glu Ile Leu Ile Asn
        50                  55                  60

Val Lys Tyr Ser Gly Val Cys His Thr Asp Leu His Ala Trp His Gly
65                  70                  75                  80

Asp Trp Pro Leu Pro Val Lys Leu Pro Leu Val Gly Gly His Glu Gly
                85                  90                  95

Ala Gly Val Val Val Lys Leu Gly Ser Asn Val Lys Gly Trp Lys Val
            100                 105                 110

Gly Asp Leu Ala Gly Ile Lys Trp Leu Asn Gly Ser Cys Met Thr Cys
        115                 120                 125

Glu Phe Cys Glu Ser Gly His Glu Ser Asn Cys Pro Asp Ala Asp Leu
    130                 135                 140

Ser Gly Tyr Thr His Asp Gly Ser Phe Gln Gln Phe Ala Thr Ala Asp
145                 150                 155                 160

Ala Ile Gln Ala Ala Lys Ile Gln Gln Gly Thr Asp Leu Ala Glu Val
                165                 170                 175

Ala Pro Ile Leu Cys Ala Gly Val Thr Val Tyr Lys Ala Leu Lys Glu
            180                 185                 190

Ala Asp Leu Lys Ala Gly Asp Trp Val Ala Ile Ser Gly Ala Ala Gly
        195                 200                 205

Gly Leu Gly Ser Leu Ala Val Gln Tyr Ala Thr Ala Met Gly Tyr Arg
    210                 215                 220

Val Leu Gly Ile Asp Ala Gly Glu Glu Lys Glu Lys Leu Phe Lys Lys
225                 230                 235                 240

Leu Gly Gly Glu Val Phe Ile Asp Phe Thr Lys Thr Lys Asn Met Val
                245                 250                 255

Ser Asp Ile Gln Glu Ala Thr Lys Gly Gly Pro His Gly Val Ile Asn
         260                 265                 270

Val Ser Val Ser Glu Ala Ala Ile Ser Leu Ser Thr Glu Tyr Val Arg
     275                 280                 285

Pro Cys Gly Thr Val Val Leu Val Gly Leu Pro Ala Asn Ala Tyr Val
 290                 295                 300

Lys Ser Glu Val Phe Ser His Val Val Lys Ser Ile Asn Ile Lys Gly
305                 310                 315                 320

Ser Tyr Val Gly Asn Arg Ala Asp Thr Arg Glu Ala Leu Asp Phe Phe
                 325                 330                 335

Ser Arg Gly Leu Ile Lys Ser Pro Ile Lys Ile Val Gly Leu Ser Glu
             340                 345                 350

Leu Pro Lys Val Tyr Asp Leu Met Glu Lys Gly Lys Ile Leu Gly Arg
         355                 360                 365

Tyr Val Val Asp Thr Ser Lys
 370                 375

```
<210> SEQ ID NO 23
<211> LENGTH: 1149
<212> TYPE: DNA
<213> ORGANISM: Saccharomyces cerevisiae
<220> FEATURE:
<223> OTHER INFORMATION: ALCOHOL DEHYDROGENASE 4 (ADH4)
<220> FEATURE:
<223> OTHER INFORMATION: ALCOHOL DEHYDROGENASE 4 (ADH4)

<400> SEQUENCE: 23
```

| | | | | | |
|---|---|---|---|---|---|
| atgtcttccg | ttactgggtt | ttacattcca | ccaatctctt | tctttggtga | aggtgcttta | 60 |
| gaagaaaccg | ctgattacat | caaaaacaag | gattacaaaa | aggctttgat | cgttactgat | 120 |
| cctggtattg | cagctattgg | tctctccggt | agagtccaaa | agatgttgga | agaacgtgac | 180 |
| ttaaacgttg | ctatctatga | caaaactcaa | ccaaacccaa | atattgccaa | tgtcacagct | 240 |
| ggtttgaagg | ttttgaagga | acaaaactct | gaaattgttg | tttccattgg | tggtggttct | 300 |
| gctcacgaca | atgctaaggc | cattgcttta | ttggctacta | cggtggggga | aatcggagac | 360 |
| tatgaaggtg | tcaatcaatc | taagaaggct | gctttaccac | tatttgccat | caacactact | 420 |
| gctggtactg | cttccgaaat | gaccagattc | actattatct | ctaatgaaga | aagaaaatc | 480 |
| aagatggcta | tcattgacaa | caacgtcact | ccagctgttg | ctgtcaacga | tccatctacc | 540 |
| atgtttggtt | tgccacctgc | tttgactgct | gctactggtc | tagatgcttt | gactcactgt | 600 |
| atcgaagctt | atgtttccac | cgcctctaac | ccaatcaccg | atgcctgtgc | tttgaagggt | 660 |
| attgatttga | tcaatgaaag | cttagtcgct | gcatacaaag | acggtaaaga | caagaaggcc | 720 |
| agaactgaca | tgtgttacgc | tgaatacttg | gcaggtatgg | cttcaacaa | tgcttctcta | 780 |
| ggttatgttc | atgcccttgc | tcatcaactt | ggtggtttct | accacttgcc | tcatggtgtt | 840 |
| tgtaacgctg | tcttgttgcc | tcatgttcaa | gaggccaaca | tgcaatgtcc | aaaggccaag | 900 |
| aagagattag | gtgaaattgc | tttgcatttc | ggtgcttctc | aagaagatcc | agaagaaacc | 960 |
| atcaaggctt | tgcacgtttt | aaacagaacc | atgaacattc | aagaaacttt | gaagaatta | 1020 |
| ggtgttaaaa | ccgaagattt | tgaaattttg | gctgaacacg | ccatgcatga | tgcctgccat | 1080 |
| ttgactaacc | cagttcaatt | caccaaagaa | caagtggttg | ccattatcaa | gaaagcctat | 1140 |
| gaatattaa | | | | | | 1149 |

```
<210> SEQ ID NO 24
<211> LENGTH: 382
```

```
<212> TYPE: PRT
<213> ORGANISM: Saccharomyces cerevisiae
<220> FEATURE:
<223> OTHER INFORMATION: ALCOHOL DEHYDROGENASE 4 (ADH4)
<220> FEATURE:
<223> OTHER INFORMATION: ALCOHOL DEHYDROGENASE 4 (ADH4)

<400> SEQUENCE: 24
```

| | | | | | | | | | | | | | | |
|---|---|---|---|---|---|---|---|---|---|---|---|---|---|---|
|Met|Ser|Ser|Val|Thr|Gly|Phe|Tyr|Ile|Pro|Pro|Ile|Ser|Phe|Phe|Gly
|1| | | |5| | | | |10| | | | |15

Met Ser Ser Val Thr Gly Phe Tyr Ile Pro Pro Ile Ser Phe Phe Gly
1               5                   10                  15

Glu Gly Ala Leu Glu Thr Ala Asp Tyr Ile Lys Asn Lys Asp Tyr
            20                  25                  30

Lys Lys Ala Leu Ile Val Thr Asp Pro Gly Ile Ala Ala Ile Gly Leu
            35                  40                  45

Ser Gly Arg Val Gln Lys Met Leu Glu Glu Arg Asp Leu Asn Val Ala
50                  55                  60

Ile Tyr Asp Lys Thr Gln Pro Asn Pro Asn Ile Ala Asn Val Thr Ala
65                  70                  75                  80

Gly Leu Lys Val Leu Lys Glu Gln Asn Ser Glu Ile Val Val Ser Ile
                85                  90                  95

Gly Gly Gly Ser Ala His Asp Asn Ala Lys Ala Ile Ala Leu Leu Ala
                100                 105                 110

Thr Asn Gly Gly Glu Ile Gly Asp Tyr Glu Gly Val Asn Gln Ser Lys
            115                 120                 125

Lys Ala Ala Leu Pro Leu Phe Ala Ile Asn Thr Thr Ala Gly Thr Ala
            130                 135                 140

Ser Glu Met Thr Arg Phe Thr Ile Ile Ser Asn Glu Glu Lys Lys Ile
145                 150                 155                 160

Lys Met Ala Ile Ile Asp Asn Asn Val Thr Pro Ala Val Ala Val Asn
                165                 170                 175

Asp Pro Ser Thr Met Phe Gly Leu Pro Pro Ala Leu Thr Ala Ala Thr
            180                 185                 190

Gly Leu Asp Ala Leu Thr His Cys Ile Glu Ala Tyr Val Ser Thr Ala
            195                 200                 205

Ser Asn Pro Ile Thr Asp Ala Cys Ala Leu Lys Gly Ile Asp Leu Ile
210                 215                 220

Asn Glu Ser Leu Val Ala Ala Tyr Lys Asp Gly Lys Asp Lys Lys Ala
225                 230                 235                 240

Arg Thr Asp Met Cys Tyr Ala Glu Tyr Leu Ala Gly Met Ala Phe Asn
                245                 250                 255

Asn Ala Ser Leu Gly Tyr Val His Ala Leu Ala His Gln Leu Gly Gly
            260                 265                 270

Phe Tyr His Leu Pro His Gly Val Cys Asn Ala Val Leu Leu Pro His
            275                 280                 285

Val Gln Glu Ala Asn Met Gln Cys Pro Lys Ala Lys Lys Arg Leu Gly
290                 295                 300

Glu Ile Ala Leu His Phe Gly Ala Ser Gln Glu Asp Pro Glu Glu Thr
305                 310                 315                 320

Ile Lys Ala Leu His Val Leu Asn Arg Thr Met Asn Ile Pro Arg Asn
                325                 330                 335

Leu Lys Glu Leu Gly Val Lys Thr Glu Asp Phe Glu Ile Leu Ala Glu
            340                 345                 350

His Ala Met His Asp Ala Cys His Leu Thr Asn Pro Val Gln Phe Thr
            355                 360                 365

Lys Glu Gln Val Val Ala Ile Ile Lys Lys Ala Tyr Glu Tyr

<210> SEQ ID NO 25
<211> LENGTH: 1056
<212> TYPE: DNA
<213> ORGANISM: Saccharomyces cerevisiae
<220> FEATURE:
<223> OTHER INFORMATION: ALCOHOL DEHYDROGENASE 5 (ADH5)
<220> FEATURE:
<223> OTHER INFORMATION: ALCOHOL DEHYDROGENASE 5 (ADH5)

<400> SEQUENCE: 25

```
atgccttcgc aagtcattcc tgaaaaacaa aaggctattg tcttttatga gacagatgga    60
aaattggaat ataaagacgt cacagttccg gaacctaagc ctaacgaaat tttagtccac   120
gttaaatatt ctggtgtttg tcatagtgac ttgcacgcgt ggcacggtga ttggccattt   180
caattgaaat ttccattaat cggtggtcac gaaggtgctg gtgttgttgt taagttggga   240
tctaacgtta agggctggaa agtcggtgat tttgcaggta taaatggtt gaatgggact    300
tgcatgtcct gtgaatattg tgaagtaggt aatgaatctc aatgtcctta tttggatggt   360
actggcttca cacatgatgg tacttttcaa gaatacgcaa ctgccgatgc cgttcaagct   420
gcccatattc caccaaacgt caatcttgct gaagttgccc caatcttgtg tgcaggtatc   480
actgttttata aggcgttgaa aagagccaat gtgataccag ccaatgggt cactatatcc    540
ggtgcatgcg gtggcttggg ttctctggca atccaatacg cccttgctat gggttacagg   600
gtcattggta tcgatggtgg taatgccaag cgaaagttat ttgaacaatt aggcggagaa   660
atattcatcg atttcacgga agaaaaagac attgttggtg ctataataaa ggccactaat   720
ggcggttctc atggagttat taatgtgtct gtttctgaag cagctatcga ggcttctacg   780
aggtattgta ggcccaatgg tactgtcgtc ctggttggta tgccagctca tgcttactgc   840
aattccgatg ttttcaatca agttgtaaaa tcaatctcca tcgttggatc ttgtgttgga   900
aatagagctg atacaaggga ggctttagat ttcttcgcca gaggtttgat caaatctccg   960
atccacttag ctggcctatc ggatgttcct gaaattttg caaagatgga aagggtgaa    1020
attgttggta gatatgttgt tgagacttct aaatga                            1056
```

<210> SEQ ID NO 26
<211> LENGTH: 351
<212> TYPE: PRT
<213> ORGANISM: Saccharomyces cerevisiae
<220> FEATURE:
<223> OTHER INFORMATION: ALCOHOL DEHYDROGENASE 5 (ADH5)
<220> FEATURE:
<223> OTHER INFORMATION: ALCOHOL DEHYDROGENASE 5 (ADH5)

<400> SEQUENCE: 26

```
Met Pro Ser Gln Val Ile Pro Glu Lys Gln Lys Ala Ile Val Phe Tyr
1               5                   10                  15
Glu Thr Asp Gly Lys Leu Glu Tyr Lys Asp Val Thr Val Pro Glu Pro
            20                  25                  30
Lys Pro Asn Glu Ile Leu Val His Val Lys Tyr Ser Gly Val Cys His
        35                  40                  45
Ser Asp Leu His Ala Trp His Gly Asp Trp Pro Phe Gln Leu Lys Phe
    50                  55                  60
Pro Leu Ile Gly Gly His Glu Gly Ala Gly Val Val Lys Leu Gly
65                  70                  75                  80
Ser Asn Val Lys Gly Trp Lys Val Gly Asp Phe Ala Gly Ile Lys Trp
                85                  90                  95
```

```
Leu Asn Gly Thr Cys Met Ser Cys Glu Tyr Cys Val Gly Asn Glu
            100                 105                 110

Ser Gln Cys Pro Tyr Leu Asp Gly Thr Gly Phe Thr His Asp Gly Thr
        115                 120                 125

Phe Gln Glu Tyr Ala Thr Ala Asp Ala Val Gln Ala Ala His Ile Pro
    130                 135                 140

Pro Asn Val Asn Leu Ala Glu Val Ala Pro Ile Leu Cys Ala Gly Ile
145                 150                 155                 160

Thr Val Tyr Lys Ala Leu Lys Arg Ala Asn Val Ile Pro Gly Gln Trp
                165                 170                 175

Val Thr Ile Ser Gly Ala Cys Gly Gly Leu Gly Ser Leu Ala Ile Gln
            180                 185                 190

Tyr Ala Leu Ala Met Gly Tyr Arg Val Ile Gly Ile Asp Gly Gly Asn
        195                 200                 205

Ala Lys Arg Lys Leu Phe Glu Gln Leu Gly Gly Glu Ile Phe Ile Asp
    210                 215                 220

Phe Thr Glu Glu Lys Asp Ile Val Gly Ala Ile Ile Lys Ala Thr Asn
225                 230                 235                 240

Gly Gly Ser His Gly Val Ile Asn Val Ser Val Ser Glu Ala Ala Ile
                245                 250                 255

Glu Ala Ser Thr Arg Tyr Cys Arg Pro Asn Gly Thr Val Val Leu Val
            260                 265                 270

Gly Met Pro Ala His Ala Tyr Cys Asn Ser Asp Val Phe Asn Gln Val
        275                 280                 285

Val Lys Ser Ile Ser Ile Val Gly Ser Cys Val Gly Asn Arg Ala Asp
    290                 295                 300

Thr Arg Glu Ala Leu Asp Phe Phe Ala Arg Gly Leu Ile Lys Ser Pro
305                 310                 315                 320

Ile His Leu Ala Gly Leu Ser Asp Val Pro Glu Ile Phe Ala Lys Met
                325                 330                 335

Glu Lys Gly Glu Ile Val Gly Arg Tyr Val Val Glu Thr Ser Lys
            340                 345                 350

<210> SEQ ID NO 27
<211> LENGTH: 554
<212> TYPE: DNA
<213> ORGANISM: Saccharomyces cerevisiae
<220> FEATURE:
<223> OTHER INFORMATION: pTDH3
<220> FEATURE:
<223> OTHER INFORMATION: pTDH3

<400> SEQUENCE: 27 ccaaatagg gggcgggtta cacagaatat ataacatcgt aggtgtctgg gtgaacagtt      60
tattcctggc atccactaaa tataatggag cccgcttttt aagctggcat ccagaaaaaa    120
aaagaatccc agcaccaaaa tattgttttc ttcaccaacc atcagttcat aggtccattc    180
tcttagcgca actacagaga acaggggcac aaacaggcaa aaacgggca  caacctcaat    240 ggagtgatgc aacctgcctg gagtaaatga tgacacaagg caattgaccc acgcatgtat    300
ctatctcatt ttcttacacc ttctattacc ttctgctctc tctgatttgg aaaaagctga    360
aaaaaaaggt tgaaccagt  tccctgaaat tattccccta cttgactaat aagtatataa    420
agacggtagg tattgattgt aattctgtaa atctatttct taaacttctt aaattctact    480
tttatagtta gtctttttttt tagttttaaa acaccaagaa cttagtttcg aataaacaca    540
```
cataaacaaa caaa 554

<210> SEQ ID NO 28
<211> LENGTH: 550
<212> TYPE: DNA
<213> ORGANISM: Saccharomyces cerevisiae
<220> FEATURE:
<223> OTHER INFORMATION: pENO2
<220> FEATURE:
<223> OTHER INFORMATION: pENO2

<400> SEQUENCE: 28

```
cgctcagcat ctgcttcttc ccaaagatga acgcggcgtt atgtcactaa cgacgtgcac      60
caacttgcgg aaagtggaat cccgttccaa aactggcatc cactaattga tacatctaca     120
caccgcacgc cttttttctg aagcccactt tcgtggactt tgccatatgc aaaattcatg     180
aagtgtgata ccaagtcagc atacacctca ctagggtagt ttctttggtt gtattgatca     240
tttggttcat cgtggttcat taattttttt tctccattgc tttctggctt tgatcttact     300
atcatttgga ttttgtcga aggttgtaga attgtatgtg acaagtggca ccaagcatat      360
ataaaaaaaa aaagcattat cttcctacca gagttgattg ttaaaaacgt atttatagca     420
aacgcaattg taattaattc ttattttgta tcttttcttc ccttgtctca atcttttatt     480
tttatttat ttttctttc ttagtttctt tcataacacc aagcaactaa tactataaca      540
tacaataata                                                            550
```

<210> SEQ ID NO 29
<211> LENGTH: 419
<212> TYPE: DNA
<213> ORGANISM: Saccharomyces cerevisiae
<220> FEATURE:
<223> OTHER INFORMATION: pTEF Kl
<220> FEATURE:
<223> OTHER INFORMATION: pTEF Kl

<400> SEQUENCE: 29

```
ctctctcgca ataacaatga acactgggtc aatcatagcc tacacaggtg aacagagtag      60
cgttatataca gggtttatac ggtgattcct acggcaaaaa ttttcatttt ctaaaaaaaa     120
aaagaaaaat ttttctttcc aacgctagaa ggaaagaaa atctaatta aattgatttg       180
gtgatttct gagagttccc ttttcatat atcgaattt gaatataaaa ggagatcgaa       240
aaaattttc tattcaatct gttttctggt tttatttgat agtttttttg tgtattatta      300
ttatggatta gtactggttt atatgggttt tctgtataa cttctttta ttttagttg       360
tttaatctta ttttgagtta cattatagtt ccctaactgc aagagaagta acattaaaa     419
```

<210> SEQ ID NO 30
<211> LENGTH: 598
<212> TYPE: DNA
<213> ORGANISM: Saccharomyces cerevisiae
<220> FEATURE:
<223> OTHER INFORMATION: pTEF3
<220> FEATURE:
<223> OTHER INFORMATION: pTEF3

<400> SEQUENCE: 30

```
ggctgataat agcgtataaa caatgcatac tttgtacgtt caaaatacaa tgcagtagat      60
atatttatgc atattacata taatacatat cacataggaa gcaacaggcg cgttggactt     120
ttaattttcg aggaccgcga atccttacat cacacccaat cccccacaag tgatccccca     180
cacaccatag cttcaaaatg tttctactcc ttttttactc ttccagattt tctcggactc     240
```

```
cgcgcatcgc cgtaccactt caaaacaccc aagcacagca tactaaattt cccctctttc    300
ttcctctagg gtgtcgttaa ttacccgtac taaaggtttg gaaaagaaaa aagagaccgc    360
ctcgtttctt tttcttcgtc gaaaaaggca ataaaaattt ttatcacgtt tcttttttctt   420 gaaaattttt ttttttgatt ttttttctctt tcgatgacct cccattgata tttaagttaa    480
taaacggtct tcaatttctc aagtttcagt ttcattttttc ttgttctatt acaacttttt    540
ttacttcttg ctcattagaa agaaagcata gcaatctaat ctaagtttta attacaaa      598
```

<210> SEQ ID NO 31
<211> LENGTH: 383
<212> TYPE: DNA
<213> ORGANISM: Saccharomyces cerevisiae
<220> FEATURE:
<223> OTHER INFORMATION: pTEF1
<220> FEATURE:
<223> OTHER INFORMATION: pTEF1

<400> SEQUENCE: 31

```
gtttagcttg cctcgtcccc gccgggtcac ccggccagcg acatggaggc ccagaatacc     60
ctccttgaca gtcttgacgt gcgcagctca ggggcatgat gtgactgtcg cccgtacatt    120
tagcccatac atccccatgt ataatcattt gcatccatac attttgatgg ccgcacggcg    180
cgaagcaaaa attacggctc ctcgctgcag acctgcgagc agggaaacgc tcccctcaca    240
gacgcgttga attgtcccca cgccgcgccc ctgtagagaa atataaaagg ttaggatttg    300
ccactgaggt tcttctttca tatacttcct tttaaaatct tgctacgata cagttctcac    360
atcacatccg aacataaaca acc                                           383
```

<210> SEQ ID NO 32
<211> LENGTH: 700
<212> TYPE: DNA
<213> ORGANISM: Saccharomyces cerevisiae
<220> FEATURE:
<223> OTHER INFORMATION: pADH1
<220> FEATURE:
<223> OTHER INFORMATION: pADH1

<400> SEQUENCE: 32

```
gggtgtacaa tatggacttc ctcttttctg gcaaccaaac ccatacatcg ggattcctat     60
aataccttcg ttggtctccc taacatgtag gtggcggagg ggagatatac aatagaacag    120
ataccagaca agacataatg ggctaaacaa gactacacca attacactgc ctcattgatg    180
gtggtacata acgaactaat actgtagccc tagacttgat agccatcatc atatcgaagt    240
ttcactaccc ttttttccatt tgccatctat tgaagtaata ataggcgcat gcaacttctt    300
ttcttttttt ttcttttctc tctccccccgt tgttgtctca ccatatccgc aatgacaaaa    360
aaatgatgga agacactaaa ggaaaaaatt aacgacaaag acagcaccaa cagatgtcgt    420
tgttccagag ctgatgaggg gtatctcgaa gcacacgaaa cttttttcctt ccttcattca    480 cgcacactac tctctaatga gcaacggtat acggccttcc ttccagttac ttgaatttga    540
aataaaaaaa agtttgctgt cttgctatca agtataaata gacctgcaat tattaatctt    600
ttgtttcctc gtcattgttc tcgttccctt tcttccttgt ttcttttttct gcacaatatt    660 tcaagctata ccaagcatac aatcaactat ctcatataca                          700
```

<210> SEQ ID NO 33
<211> LENGTH: 549
<212> TYPE: DNA

<213> ORGANISM: Saccharomyces cerevisiae
<220> FEATURE:
<223> OTHER INFORMATION: pGPM 1
<220> FEATURE:
<223> OTHER INFORMATION: pGPM 1

<400> SEQUENCE: 33

```
gccaaacttt tcggttaaca catgcagtga tgcacgcgcg atggtgctaa gttacatata      60
tatatatata tatatatata tatatatata gccatagtga tgtctaagta acctttatgg     120
tatatttctt aatgtggaaa gatactagcg cgcgcaccca cacacaagct tcgtcttttc     180
ttgaagaaaa gaggaagctc gctaaatggg attccacttt ccgttccctg ccagctgatg     240
gaaaaaggtt agtggaacga tgaagaataa aagagagat ccactgaggt gaaatttcag     300
ctgacagcga gtttcatgat cgtgatgaac aatggtaacg agttgtggct gttgccaggg     360
agggtggttc tcaacttta atgtatggcc aaatcgctac ttgggtttgt tatataacaa     420
agaagaaata atgaactgat tctcttcctc cttcttgtcc tttcttaatt ctgttgtaat     480
taccttcctt tgtaatttt tttgtaatta ttcttcttaa taatccaaac aaacacacat     540
attacaata                                                              549
```

<210> SEQ ID NO 34
<211> LENGTH: 650
<212> TYPE: DNA
<213> ORGANISM: Saccharomyces cerevisiae
<220> FEATURE:
<223> OTHER INFORMATION: pFBA1
<220> FEATURE:
<223> OTHER INFORMATION: pFBA1

<400> SEQUENCE: 34

```
acgcaagccc taagaaatga ataacaatac tgacagtact aaataattgc ctacttggct      60
tcacatacgt tgcatacgtc gatatagata ataatgataa tgacagcagg attatcgtaa     120
tacgtaatag ttgaaaatct caaaaatgtg tgggtcatta cgtaaataat gataggaatg     180
ggattcttct attttccctt tttccattct agcagccgtc gggaaaacgt ggcatcctct     240
ctttcgggct caattggagt cacgctgccg tgagcatcct ctctttccat atctaacaac     300
tgagcacgta accaatggaa aagcatgagc ttagcgttgc tccaaaaaag tattggatgg     360
ttaataccat ttgtctgttc tcttctgact ttgactcctc aaaaaaaaaa aatctacaat     420
caacagatcg cttcaattac gccctcacaa aaactttttt ccttcttctt cgcccacgtt     480
aaatttatc cctcatgttg tctaacggat ttctgcactt gatttattat aaaaagacaa     540
agacataata cttctctatc aatttcagtt attgttcttc cttgcgttat tcttctgttc     600
ttcttttct tttgtcatat ataaccataa ccaagtaata catattcaaa                 650
```

<210> SEQ ID NO 35
<211> LENGTH: 700
<212> TYPE: DNA
<213> ORGANISM: Saccharomyces cerevisiae
<220> FEATURE:
<223> OTHER INFORMATION: pPDC1
<220> FEATURE:
<223> OTHER INFORMATION: pPDC1

<400> SEQUENCE: 35

```
ttatttacct atctctaaac ttcaacacct tatatcataa ctaatatttc ttgagataag      60
cacactgcac ccataccttc cttaaaaacg tagcttccag ttttggtgg ttccggcttc     120
cttcccgatt ccgcccgcta aacgcatatt tttgttgcct ggtggcattt gcaaaatgca     180
```

```
taacctatgc atttaaaaga ttatgtatgc tcttctgact tttcgtgtga tgaggctcgt    240
ggaaaaaatg aataatttat gaatttgaga acaattttgt gttgttacgg tattttacta    300
tggaataatc aatcaattga ggattttatg caaatatcgt ttgaatattt ttccgaccct    360
ttgagtactt tcttcataa ttgcataata ttgtccgctg ccccttttc tgttagacgg     420 tgtcttgatc tacttgctat cgttcaacac caccttattt tctaactatt tttttttag    480 ctcatttgaa tcagcttatg gtgatggcac attttttgcat aaacctagct gtcctcgttg    540
aacataggaa aaaaaatat ataaacaagg ctctttcact ctccttgcaa tcagatttgg     600
gtttgttccc tttattttca tatttcttgt catattcctt tctcaattat tattttctac    660
tcataacctc acgcaaaata acacagtcaa atcaatcaaa                          700

<210> SEQ ID NO 36
<211> LENGTH: 998
<212> TYPE: DNA
<213> ORGANISM: Saccharomyces cerevisiae
<220> FEATURE:
<223> OTHER INFORMATION: pCCW12
<220> FEATURE:
<223> OTHER INFORMATION: pCCW12

<400> SEQUENCE: 36 aacccagggca aagcaaaata aaagaaactt aatacgttat gccgtaatga agggctacca     60
aaaacgataa tctcaactgt aaacaggtac aatgcggacc cttttgccac aaaacataca    120
tcattcattg ccggaaaaag aaagaagtga agacagcagt gcagccagcc atgttgcgcc    180
aatctaatta tagatgctgg tgccctgagg atgtatctgg agccagccat ggcatcatgc    240
gctaccgccg gatgtaaaat ccgacacgca aagaaaaacc ttcgaggttg cgcacttcgc    300
ccacccatga accacacggt tagtccaaaa ggggcagttc agattccaga tgcgggaatt    360
agcttgctgc cacccctcacc tcactaacgc tgcggtgtgc ggatacttca tgctatttat    420
agacgcgcgt gtcggaatca gcacgcgcaa gaaccaaatg ggaaaatcgg aatgggtcca    480
gaactgcttt gagtgctggc tattggcgtc tgatttccgt tttggaatc ctttgccgcg    540 cgcccctctc aaaactccgc acaagtccca gaaagcggga agaaataaa acgccaccaa    600 aaaaaaaaat aaaagccaat cctcgaagcg tgggtggtag gccctggatt atcccgtaca    660
agtatttctc aggagtaaaa aaaccgtttg ttttggaatt ccccatttcg cggccaccta    720
cgccgctatc tttgcaacaa ctatctgcga taactcagca aattttgcat attcgtgttg    780
cagtattgcg ataatgggag tcttacttcc aacataacgg cagaaagaaa tgtgagaaaa    840
ttttgcatcc tttgcctccg ttcaagtata taagtcggc atgcttgata atctttcttt    900
ccatcctaca ttgttctaat tattcttatt ctcctttatt ctttcctaac ataccaagaa    960
attaatcttc tgtcattcgc ttaaacacta tatcaata                            998

<210> SEQ ID NO 37
<211> LENGTH: 700
<212> TYPE: DNA
<213> ORGANISM: Saccharomyces cerevisiae
<220> FEATURE:
<223> OTHER INFORMATION: pGK1
<220> FEATURE:
<223> OTHER INFORMATION: pGK1

<400> SEQUENCE: 37
gtgagtaagg aaagagtgag gaactatcgc atacctgcat ttaaagatgc cgatttgggc     60
```

```
gcgaatcctt tattttggct tcaccctcat actattatca gggccagaaa aaggaagtgt        120
ttccctcctt cttgaattga tgttaccctc ataaagcacg tggcctctta tcgagaaaga        180
aattaccgtc gctcgtgatt tgtttgcaaa aagaacaaaa ctgaaaaaac ccagacacgc        240
tcgacttcct gtcttcctat tgattgcagc ttccaatttc gtcacacaac aaggtcctag        300
cgacggctca caggttttgt aacaagcaat cgaaggttct ggaatggcgg gaaagggttt        360
agtaccacat gctatgatgc ccactgtgat ctccagagca agttcgttc gatcgtactg         420 ttactctctc tctttcaaac agaattgtcc gaatcgtgtg acaacaacag cctgttctca        480
cacactcttt tcttctaacc aaggggtgg tttagtttag tagaacctcg tgaaacttac         540
atttacatat atataaactt gcataaattg gtcaatgcaa gaaatacata tttggtcttt        600
tctaattcgt agttttcaa gttcttagat gctttctttt tctcttttt acagatcatc          660 aaggaagtaa ttatctactt tttacaacaa atataaaaca                              700

<210> SEQ ID NO 38
<211> LENGTH: 913
<212> TYPE: DNA
<213> ORGANISM: Saccharomyces cerevisiae
<220> FEATURE:
<223> OTHER INFORMATION: pMDH2
<220> FEATURE:
<223> OTHER INFORMATION: pMDH2

<400> SEQUENCE: 38
ccttcgctaa ataataaacc tgaactgtac ttagcgaagc cttcatagca cctacgtaca         60
cgtatatata gacattttac gtaatgggaga aactgaggtt tttgttttca cttttttttct      120 ttcttttttca ctattgctcg aaccgcctgc gatgagctaa gaaaaaaaag tgaaagaaat       180
catagaaagc aaaaatgaga ttatatagcc cagagccctc ttctggcgcc tgtcccaagg        240
cggaccaaca acaacacttg cccaaaccta gaaaatccc ctcatacttt tccgtttgta         300
tctcctactt tcttacttcc tttttttctt ctttatttgc ttggtttacc attgaagtcc        360
atttttacta cagacaatag ctagtcattc gctatcttcc gtttgtcact ttttttcaaa       420
tttctcatct atatagcgaa gtacggaaaa gatgtcactt gccggcatct cggccttccc        480
cggccaaatg gactcatcat ctacgatacg gccccttta tccgcaatta ctttgcccat        540
tcggccgtag ccgttctaaa gccgccgtgc cttgccccca atactcccct aatgatccgg       600
gaagttccgg tttttttcct tgtttagtg gcattttgtg ttgcccaagg ttgggaaggt        660
ccgatttgac tttaaggaac tacggaaggt atctaaggtt tctaaaaaca atatacacgc      720
gcgtgcgtag atatataaag ataaagattt atcgatatga gataaagatt gctgcatgat     780
tctccttctg attcttttc cctgtatata ttttctcccc ttctgtataa atcgtacagt       840
cagaagtagt ccagaatata gtgctgcaga ctattacaaa agttcaatac aatatcataa       900
aagttatagt aac                                                          913

<210> SEQ ID NO 39
<211> LENGTH: 406
<212> TYPE: DNA
<213> ORGANISM: Saccharomyces cerevisiae
<220> FEATURE:
<223> OTHER INFORMATION: pURA3
<220> FEATURE:
<223> OTHER INFORMATION: pURA3

<400> SEQUENCE: 39
ggtacccaaa ccgaagttat ctgatgtaga aaaggattaa agatgctaag agatagtgat        60
```

```
gatatttcat aaataatgta attctatata tgttaattac cttttttgcg aggcatattt      120
atggtgaagg ataagttttg accatcaaag aaggttaatg tggctgtggt ttcagggtcc      180
ataaagcttt tcaattcatc tttttttttt ttgttctttt ttttgattcc ggtttctttg      240 aaatttttt gattcggtaa tctccgagca gaaggaagaa cgaaggaagg agcacagact       300
tagattggta tatatacgca tatgtggtgt tgaagaaaca tgaaattgcc cagtattctt      360
aacccaactg cacagaacaa aaacctgcag gaaacgaaga taaatc                    406

<210> SEQ ID NO 40
<211> LENGTH: 535
<212> TYPE: DNA
<213> ORGANISM: Saccharomyces cerevisiae
<220> FEATURE:
<223> OTHER INFORMATION: pRPLA1
<220> FEATURE:
<223> OTHER INFORMATION: pRPLA1

<400> SEQUENCE: 40
tcaagttgga tactgatctg atctctccgc cctactacca gggaccctca tgattaccgc       60
tcgaatgcga cgtttcctgc ctcataaaac tggcttgaaa atatttattc gctgaacagt      120
agcctagctt ataaaaattt catttaatta atgtaatatg aaaactcaca tgccttctgt      180
ttctaaaatt gtcacagcaa gaaataacat taccatacgt gatcttatta aactctagta     240
tcttgtctaa tacttcattt aaaagaagcc ttaaccctgt agcctcatct atgtctgcta      300
catatcgtga ggtacgaata tcgtaagatg ataccacgca actttgtaat gattttttt     360 ttttcatttt ttaaagaatg cctttacatg gtatttgaaa aaaatatctt tataaagttt      420
gcgatctctt ctgttctgaa taattttag taaaagaaat caaaagaata aagaaatagt      480
ccgctttgtc caatacaaca gcttaaaccg attatctcta aaataacaag aagaa          535

<210> SEQ ID NO 41
<211> LENGTH: 400
<212> TYPE: DNA
<213> ORGANISM: Saccharomyces cerevisiae
<220> FEATURE:
<223> OTHER INFORMATION: pSAM4
<220> FEATURE:
<223> OTHER INFORMATION: pSAM4

<400> SEQUENCE: 41
agattttggt gttagatggt actcttgcat atgtaacctt taataaattt tgcaaatcga       60
attcctttgt aacgtgcaaa gcattttata gcctggcgct cgcattgtta agcaacaggc      120
ggtgcggcaa cgttgaaatg tttcacgcag ggttttttac gtactgcacg gcattctgga      180
gtgaaaaaaa atgaaaagta cagctcgaag ttttttgtcc atcggttgta ctttgcagag     240
tattagtcat ttttgatatc agagtactac tatcgaagca ttttttacgct tgaataactt     300 gaatattatt gaaagcttag ttcaaccaag ctgaaaagaa ccattattca acataattgg      360
aaatcatttc gttactaaat cgtccgaaaa ttgcagaaaa                           400

<210> SEQ ID NO 42
<211> LENGTH: 505
<212> TYPE: DNA
<213> ORGANISM: Saccharomyces cerevisiae
<220> FEATURE:
<223> OTHER INFORMATION: pCUP1-1
<220> FEATURE:
<223> OTHER INFORMATION: pCUP1-1
```

<400> SEQUENCE: 42

```
cggcaaactt caacgatttc tatgatgcat tttataatta gtaagccgat cccattaccg      60
acatttgggc gctatacgtg catatgttca tgtatgtatc tgtatttaaa acacttttgt     120
attattttc ctcatatatg tgtataggtt tatacggatg atttaattat tacttcacca     180
ccctttattt caggctgata tcttagcctt gttactagtt agaaaagac attttttgctg    240
tcagtcactg tcaagagatt cttttgctgg catttcttcc agaagcaaaa agagcgatgc    300
gtcttttccg ctgaaccgtt ccagcaaaaa agactaccaa cgcaatatgg attgtcagaa    360
tcatataaaa gagaagcaaa taactccttg tcttgtatca attgcattat aatatcttct    420
tgttagtgca atatcatata gaagtcatcg aaatagatat taagaaaaac aaactgtaca    480
atcaatcaat caatcatcac ataaa                                          505
```

<210> SEQ ID NO 43
<211> LENGTH: 500
<212> TYPE: DNA
<213> ORGANISM: Candida glabrata
<220> FEATURE:
<223> OTHER INFORMATION: pCUP1.Cgla
<220> FEATURE:
<223> OTHER INFORMATION: pCUP1.Cgla

<400> SEQUENCE: 43

```
cacaccacac aaccgtcagc accccggctg tacgtctgtg aaggctgcgg tatagacacg      60
gactgcgata cagaactcat gacttatatc tgtagactcc tctgcttcaa tgcgaactcc    120
aggatcaccg aatagcatgc gatgagctgt tgattcttat atataattat ctattgcatt    180
ttttttttaa tgctgcatgg gggggcctag taaatcaccc gtacaagtca cgcgtgagag    240
aaagagaagg gccctttcgt cgtggaagcg tggatcgtga gcgacctgtt tctaaatata    300
gcttttgggt aggatattat attaagtgaa attttattag agggtaaatg tatgtgaaag    360
ttatgtataa tatgttgcta aattagcgat cgtgaatgca tagaatctaa tcgttataga    420
aaaccgcaac ttgtgctgtt ttgttgtgtt ttcttgtcgt ttttttatat tatttatcta    480
gtattttgct ttagttgtta                                                500
```

<210> SEQ ID NO 44
<211> LENGTH: 425
<212> TYPE: DNA
<213> ORGANISM: Saccharomyces bayanus
<220> FEATURE:
<223> OTHER INFORMATION: pCUP1.Sba
<220> FEATURE:
<223> OTHER INFORMATION: pCUP1.Sba

<400> SEQUENCE: 44

```
agaaggaggg gtcctattac caatacttgg acgctatacg tgcatatgta catgtacgta      60
tctgtattta aacactttg tattatttc tttatatg tgtataggtt tacatggttg       120
actttatca ttgtttgtgc acatttgcaa tggccatttt tttgttttg agaaaggtat     180
tattgctgtc actattcgag atgcttttgc tgacattcct cctagaagcc aaaaggccga    240
tgcgtttttt ccgctgagag gataccagca aaaaaagcta ccagtacaag atgggacggc    300
aaaagcgtat aaaagaagaa gcaaaatgac cagatatgct ttcaatttca tcaatgtttc    360
tttctcctg ttatgatcca gaagaataat caaaagcaaa acatctattc aatcaatctc    420
ataaa                                                                425
```

```
<210> SEQ ID NO 45
<211> LENGTH: 741
<212> TYPE: DNA
<213> ORGANISM: Artificial Sequence
<220> FEATURE:
<223> OTHER INFORMATION: pACU1
<220> FEATURE:
<223> OTHER INFORMATION: pACU1

<400> SEQUENCE: 45
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tcgaaaaaga cattttttgct gtcagtcact gtcaagagat tcttttgctg gcatttcttc     420
cagaagcaaa aagagcgatg cgtctttttcc gctgaaccgt tccagcaaaa aagactacca     480
acgaattcta attaagttag tcaaggcgcc atcctcatga aaactgtgta acataataac     540
cgaagtgtcg aaaaggtggc accttgtcca attgaacacg ctcgatgaaa aaataagat      600 atatataagg ttaagtaaag cgtctgttag aaaggaagtt tttcctttttt cttgctctct     660 tgtcttttca tctactattt ccttcgtgta atacagggtc gtcagataca tagatacaat     720
tctattaccc ccatccatac a                                                741

<210> SEQ ID NO 46
<211> LENGTH: 757
<212> TYPE: DNA
<213> ORGANISM: Artificial Sequence
<220> FEATURE:
<223> OTHER INFORMATION: pACU2
<220> FEATURE:
<223> OTHER INFORMATION: pACU2

<400> SEQUENCE: 46
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccgaatt cgaaaaagac attttttgctg tcagtcactg     360 tcaagagatt cttttgctgg catttcttcc agaagcaaaa agagcgatgc gtctttttccg     420 ctgaaccgtt ccagcaaaaa agactaccaa cgaattccac gtgaagctgt cgatattggg     480
gaactgtggt ggttggcaaa tgactaatta agttagtcaa ggcgccatcc tcatgaaaac     540
tgtgtaacat aataaccgaa gtgtcgaaaa ggtggcacct tgtccaattg aacacgctcg     600
atgaaaaaaa taagatatat ataaggttaa gtaaagcgtc tgttagaaag gaagtttttc     660
ctttttcttg ctctcttgtc ttttcatcta ctatttcctt cgtgtaatac agggtcgtca     720
gatacataga tacaattcta ttaccccccat ccataca                              757

<210> SEQ ID NO 47
<211> LENGTH: 498
<212> TYPE: DNA
```

<210> SEQ ID NO 47
<211> LENGTH: 498
<212> TYPE: DNA
<213> ORGANISM: Artificial Sequence
<220> FEATURE:
<223> OTHER INFORMATION: pACU3p
<220> FEATURE:
<223> OTHER INFORMATION: pACU3p

<400> SEQUENCE: 47

```
ttatattgaa ttttcaaaaa ttcttacttt tttttggat  ggacgcaaag aagtttaata    60
atcatattac atggcattac caccatatac atatccatat ctaatcttac ttatatgttg   120
tggaaatgta aagagcccga attcgaaaaa gacattttg  ctgtcagtca ctgtcaagag   180
attcttttgc tggcatttct tccagaagca aaaagagcga tgcgtctttt ccgctgaacc   240
gttccagcaa aaaagactac caacgaattc ggatgataat gcgattagtt ttttagcctt   300
atttctgggg taattaatca gcgaagcgat gattttgat  ctattaacag atatataaat   360
ggaaaagctg cataaccact ttaactaata ctttcaacat tttcagtttg tattacttct   420
tattcaaatg tcataaaagt atcaacaaaa aattgttaat atacctctat actttaacgt   480
caaggagaaa aaactata                                                 498
```

<210> SEQ ID NO 48
<211> LENGTH: 498
<212> TYPE: DNA
<213> ORGANISM: Artificial Sequence
<220> FEATURE:
<223> OTHER INFORMATION: pACU4p
<220> FEATURE:
<223> OTHER INFORMATION: pACU4p

<400> SEQUENCE: 48

```
ttatattgaa ttttcaaaaa ttcttacttt tttttggat  ggacgcaaag aagtttaata    60
atcatattac atggcattac caccatatac atatccatat ctaatcttac ttatatgttg   120
tggaaatgta aagagcccga attcgttggt agtcttttt  gctggaacgg ttcagcggaa   180
aagacgcatc gctctttttg cttctggaag aaatgccagc aaaagaatct cttgacagtg   240
actgacagca aaatgtctt  tttcgaattc ggatgataat gcgattagtt ttttagcctt   300
atttctgggg taattaatca gcgaagcgat gattttgat  ctattaacag atatataaat   360
ggaaaagctg cataaccact ttaactaata ctttcaacat tttcagtttg tattacttct   420
tattcaaatg tcataaaagt atcaacaaaa aattgttaat atacctctat actttaacgt   480
caaggagaaa aaactata                                                 498
```

<210> SEQ ID NO 49
<211> LENGTH: 530
<212> TYPE: DNA
<213> ORGANISM: Artificial Sequence
<220> FEATURE:
<223> OTHER INFORMATION: pACU5
<220> FEATURE:
<223> OTHER INFORMATION: pACU5

<400> SEQUENCE: 49

```
ggaggacgaa acaaaaaagt gaaaaaaaat gaaaattttt ttggaaaacc aagaaatgaa    60
ttatatttcc gtgtgagacg acatcgtcga atatgattca gggtaacagt attgatgtaa   120
tcaatttcct acctgaatct aaaattcccg gaattcgaaa aagacatttt tgctgtcagt   180
cactgtcaag agattctttt gctggcattt cttccagaag caaaaagagc gatgcgtctt   240
ttccgctgaa ccgttccagc aaaaaagact accaacgaat tccgagcaga tccgccaggc   300
gtgtatatat agcgtggatg gccaggcaac tttagtgctg acacatacag gcatatatat   360
```

| | |
|---|---|
| atgtgtgcga cgacacatga tcatatggca tgcatgtgct ctgtatgtat ataaaactct | 420 |
| tgttttcttc ttttctctaa atattctttc cttatacatt aggacctttg cagcataaat | 480 |
| tactatactt ctatagacac acaaacacaa atacacacac taaattaata | 530 |

<210> SEQ ID NO 50
<211> LENGTH: 867
<212> TYPE: DNA
<213> ORGANISM: Artificial Sequence
<220> FEATURE:
<223> OTHER INFORMATION: pACU6
<220> FEATURE:
<223> OTHER INFORMATION: pACU6

<400> SEQUENCE: 50

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataaattc gccatttctt gaatgtattt | 180 |
| aaagatattt aatgctataa tagacattta atccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgaaaaaga cattttttgct gtcagtcact gtcaagagat tcttttgctg gcatttcttc | 420 |
| cagaagcaaa aagagcgatg cgtctttttcc gctgaaccgt tccagcaaaa aagactacca | 480 |
| acgaattcga aaaagacatt tttgctgtca gtcactgtca agagattctt ttgctggcat | 540 |
| tcttccaga agcaaaaaga gcgatgcgtc ttttccgctg aaccgttcca gcaaaaaga | 600 |
| ctaccaacga attctaatta agttagtcaa ggcgccatcc tcatgaaaac tgtgtaacat | 660 |
| aataaccgaa gtgtcgaaaa ggtggcacct tgtccaattg aacacgctcg atgaaaaaaa | 720 |
| taagatatat ataaggttaa gtaaagcgtc tgttagaaag gaagttttc cttttttcttg | 780 |
| ctctcttgtc ttttcatcta ctatttcctt cgtgtaaatac agggtcgtca gatacataga | 840 |
| tacaattcta ttacccccat ccataca | 867 |

<210> SEQ ID NO 51
<211> LENGTH: 867
<212> TYPE: DNA
<213> ORGANISM: Artificial Sequence
<220> FEATURE:
<223> OTHER INFORMATION: pACU7
<220> FEATURE:
<223> OTHER INFORMATION: pACU7

<400> SEQUENCE: 51

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataaattc gccatttctt gaatgtattt | 180 |
| aaagatattt aatgctataa tagacattta atccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgttggtag tctttttttgc tggaacggtt cagcggaaaa gacgcatcgc tcttttttgct | 420 |
| tctggaagaa atgccagcaa aagaatctct tgacagtgac tgcagcaaa aatgtctttt | 480 |
| tcgaattcgt tggtagtctt ttttgctgga acggttcagc ggaaaagacg catcgctctt | 540 |

| | |
|---|---|
| tttgcttctg gaagaaatgc cagcaaaaga atctcttgac agtgactgac agcaaaaatg | 600 |
| tcttttcga attctaatta agttagtcaa ggcgccatcc tcatgaaaac tgtgtaacat | 660 |
| aataaccgaa gtgtcgaaaa ggtggcacct tgtccaattg aacacgctcg atgaaaaaaa | 720 |
| taagatatat ataaggttaa gtaaagcgtc tgttagaaag gaagttttc cttttcttg | 780 |
| ctctcttgtc ttttcatcta ctatttcctt cgtgtaatac agggtcgtca gatacataga | 840 |
| tacaattcta ttaccccat ccataca | 867 |

```
<210> SEQ ID NO 52
<211> LENGTH: 1119
<212> TYPE: DNA
<213> ORGANISM: Artificial Sequence
<220> FEATURE:
<223> OTHER INFORMATION: pACU8
<220> FEATURE:
<223> OTHER INFORMATION: pACU8

<400> SEQUENCE: 52
```

| | |
|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataaatttc gccatttctt gaatgtattt | 180 |
| aaagatattt aatgctataa tagacattta aatccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tcgaaaaaga cattttgct gtcagtcact gtcaagagat tcttttgctg gcatttcttc | 420 |
| cagaagcaaa aagagcgatg cgtctttcc gctgaaccgt tccagcaaaa aagactacca | 480 |
| acgaattcga aaaagacatt ttgctgtca gtcactgtca agagattctt ttgctggcat | 540 |
| ttcttccaga agcaaaaaga gcgatgcgtc ttttccgctg aaccgttcca gcaaaaaaga | 600 |
| ctaccaacga attcgaaaaa gacattttg ctgtcagtca ctgtcaagag attcttttgc | 660 |
| tggcatttct tccagaagca aaaagagcga tgcgtctttt ccgctgaacc gttccagcaa | 720 |
| aaagactac caacgaattc gaaaagaca ttttgctgt cagtcactgt caagagattc | 780 |
| ttttgctggc atttcttcca gaagcaaaaa gagcgatgcg tcttttccgc tgaaccgttc | 840 |
| cagcaaaaaa gactaccaac gaattctaat taagttagtc aaggcgccat cctcatgaaa | 900 |
| actgtgtaac ataataaccg aagtgtcgaa aaggtggcac cttgtccaat gaacacgct | 960 |
| cgatgaaaaa aataagatat ataaggtt aagtaaagcg tctgttagaa aggaagttt | 1020 |
| tccttttct tgctctcttg tcttttcatc tactatttcc ttcgtgtaat acagggtcgt | 1080 |
| cagatacata gatacaattc tattaccccc atccataca | 1119 |

```
<210> SEQ ID NO 53
<211> LENGTH: 624
<212> TYPE: DNA
<213> ORGANISM: Artificial Sequence
<220> FEATURE:
<223> OTHER INFORMATION: pACU9
<220> FEATURE:
<223> OTHER INFORMATION: pACU9

<400> SEQUENCE: 53
```

| | |
|---|---|
| tatagttttt tctccttgac gttaaagtat agaggtatat taacaatttt tgttgatac | 60 |
| ttttatgaca tttgaataag aagtaataca aactgaaaat gttgaaagta ttagttaaag | 120 |
| tggttatgca gcttttccat ttatatatct gttaatagat caaaaatcat cgcttcgctg | 180 |

| | | |
|---|---|---|
| attaattacc ccagaaataa ggctaaaaaa ctaatcgcat tatcatccga attcgaaaaa | 240 | |
| gacattttg ctgtcagtca ctgtcaagag attcttttgc tggcatttct tccagaagca | 300 | |
| aaaagagcga tgcgtctttt ccgctgaacc gttccagcaa aaagactac caacgaattc | 360 | |
| gaaaagaca tttttgctgt cagtcactgt caagagattt ttttgctggc atttcttcca | 420 | |
| gaagcaaaaa gagcgatgcg tcttttccgc tgaaccgttc cagcaaaaaa gactaccaac | 480 | |
| gaattcgggc tctttacatt tccacaacat ataagtaaga ttagatatgg atatgtatat | 540 | |
| ggtggtaatg ccatgtaata tgattattaa acttctttgc gtccatccaa aaaaaaagta | 600 | |
| agaattttg aaaattcaat ataa | 624 | |

<210> SEQ ID NO 54
<211> LENGTH: 876
<212> TYPE: DNA
<213> ORGANISM: Artificial Sequence
<220> FEATURE:
<223> OTHER INFORMATION: pACU10p
<220> FEATURE:
<223> OTHER INFORMATION: pACU10p

<400> SEQUENCE: 54

| | | |
|---|---|---|
| ttatattgaa ttttcaaaaa ttcttacttt ttttttggat ggacgcaaag aagtttaata | 60 | |
| atcatattac atggcattac caccatatac atatccatat ctaatcttac ttatatgttg | 120 | |
| tggaaatgta agagcccga attggttggt agtctttttt gctggaacgg ttcagcggaa | 180 | |
| aagacgcatc gctcttttg cttctggaag aaatgccagc aaaagaatct cttgacagtg | 240 | |
| actgacagca aaaatgtctt tttcgaattc gttggtagtc tttttgctg gaacggttca | 300 | |
| gcggaaaaga cgcatcgctc ttttgcttc tggaagaaat gccagcaaaa gaatctcttg | 360 | |
| acagtgactg acagcaaaaa tgtcttttc gaattcgttg gtagtctttt tgctggaac | 420 | |
| ggttcagcgg aaaagacgca tcgctctttt gcttctgga agaaatgcca gcaaaagaat | 480 | |
| ctcttgacag tgactgacag caaaaatgtc tttttcgaat tcgttggtag tctttttgc | 540 | |
| tggaacggtt cagcggaaaa gacgcatcgc tcttttgct tctggaagaa atgccagcaa | 600 | |
| aagaatctct tgacagtgac tgacagcaaa aatgtctttt tccaattcgg atgataatgc | 660 | |
| gattagtttt ttagccttat ttctggggta attaatcagc gaagcgatga ttttgatct | 720 | |
| attaacagat atataaatgg aaaagctgca taaccacttt aactaatact ttcaacattt | 780 | |
| tcagtttgta ttacttctta ttcaaatgtc ataaagtat caacaaaaaa ttgttaatat | 840 | |
| acctctatac tttaacgtca aggagaaaaa actata | 876 | |

<210> SEQ ID NO 55
<211> LENGTH: 633
<212> TYPE: DNA
<213> ORGANISM: Artificial Sequence
<220> FEATURE:
<223> OTHER INFORMATION: pACU11
<220> FEATURE:
<223> OTHER INFORMATION: pACU11

<400> SEQUENCE: 55

| | | |
|---|---|---|
| gctcagcatc tgcttcttcc caaagatgaa cgcggcgtta tgtcactaac gacgtgcacc | 60 | |
| aacttgcggg aattcgaaaa agacattttt gctgtcagtc actgtcaaga gattcttttg | 120 | |
| ctggcatttc ttccagaagc aaaaagagcg atgcgtcttt tccgctgaac cgttccagca | 180 | |
| aaaaagacta ccaacgaatt ccaccgcacg cctttttct gaagcccact ttcgtggact | 240 | |

```
ttgccatata tgcaaaattc atgaagtgtg ataccaagtc agcatacacc tcactagggt    300
agtttctttg gttgtattga tcatttggtt catcgtggtt cattaatttt ttttctccat    360
tgctttctgg ctttgatctt actatcattt ggattttgt cgaaggttgt agaattgtat     420
gtgacaagtg gcaccaagca tatataaaaa aaaaaagcat tatcttccta ccagagttga    480
ttgttaaaaa cgtatttata gcaaacgcaa ttgtaattaa ttcttatttt gtatcttttc    540
ttcccttgtc tcaatctttt attttatt tattttcttt ttcttagttt ctttcataac      600
accaagcaac taatactata acatacaata ata                                 633
```

<210> SEQ ID NO 56
<211> LENGTH: 1119
<212> TYPE: DNA
<213> ORGANISM: Artificial Sequence
<220> FEATURE:
<223> OTHER INFORMATION: pACU12
<220> FEATURE:
<223> OTHER INFORMATION: pACU12

<400> SEQUENCE: 56

```
ttacattatc aatccttgcg tttcagcttc cactaattta gatgactatt tctcatcatt    60
tgcgtcatct tctaacaccg tatatgataa tatactagta acgtaaatac tagttagtag    120
atgatagttg attttattc caacactaag aaataatttc gccatttctt gaatgtattt     180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tggttggtag tctttttgc tggaacggtt cagcggaaaa gacgcatcgc tcttttttgct   420 tctggaagaa atgccagcaa aagaatctct tgacagtgac tgacagcaaa aatgtctttt    480
tcgaattcgt tggtagtctt ttttgctgga acggttcagc ggaaaagacg catcgctctt    540
tttgcttctg gaagaaatgc cagcaaaaga atctcttgac agtgactgac agcaaaaatg    600 tcttttcga attcgttggt agtcttttt gctggaacgg ttcagcggaa aagacgcatc       660
gctctttttg cttctggaag aaatgccagc aaaagaatct cttgacagtg actgacagca    720
aaaatgtctt tttcgaattc gttggtagtc ttttttgctg gaacggttca gcggaaaaga    780
cgcatcgctc ttttttgcttc tggaagaaat gccagcaaaa gaatctcttg acagtgactg    840
acagcaaaaa tgtctttttc caattctaat taagttagtc aaggcgccat cctcatgaaa    900
actgtgtaac ataataaccg aagtgtcgaa aaggtggcac cttgtccaat tgaacacgct    960
cgatgaaaaa aataagatat atataaggtt aagtaaagcg tctgttagaa aggaagtttt    1020 tccttttttct tgctctcttg tcttttcatc tactatttcc ttcgtgtaat acagggtcgt   1080
cagatacata gatacaattc tattaccccc atccataca                            1119
```

<210> SEQ ID NO 57
<211> LENGTH: 1497
<212> TYPE: DNA
<213> ORGANISM: Artificial Sequence
<220> FEATURE:
<223> OTHER INFORMATION: pACU13
<220> FEATURE:
<223> OTHER INFORMATION: pACU13

<400> SEQUENCE: 57

```
ttacattatc aatccttgcg tttcagcttc cactaattta gatgactatt tctcatcatt    60
tgcgtcatct tctaacaccg tatatgataa tatactagta acgtaaatac tagttagtag    120
```

```
atgatagttg attttattc caacactaag aaataatttc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tggttggtag tcttttttgc tggaacggtt cagcggaaaa gacgcatcgc tcttttttgct  420
tctggaagaa atgccagcaa aagaatctct tgacagtgac tgacagcaaa aatgtctttt   480
tcgaattcgt tggtagtctt ttttgctgga acggttcagc ggaaaagacg catcgctctt   540
tttgcttctg gaagaaatgc cagcaaaaga atctcttgac agtgactgac agcaaaaatg   600
tcttttttcga attcgttggt agtcttttt gctggaacgg ttcagcggaa agacgcatc    660
gctcttttg cttctggaag aaatgccagc aaaagaatct cttgacagtg actgacagca    720
aaaatgtctt tttcgaattc gttggtagtc ttttttgctg gaacggttca gcggaaaaga   780
cgcatcgctc ttttgcttc tggaagaaat gccagcaaaa gaatctcttg acagtgactg    840
acagcaaaaa tgtctttttc gaattcgttg gtagtctttt ttgctggaac ggttcagcgg   900
aaaagacgca tcgctctttt tgcttctgga gaaatgccag caaagaat ctcttgacag     960
tgactgacag caaaatgtc ttttttcgaat tcgttggtag tcttttttgc tggaacggtt  1020
cagcggaaaa gacgcatcgc tcttttgct tctggaagaa atgccagcaa agaatctct   1080
tgacagtgac tgacagcaaa aatgtctttt tcgaattcgt tggtagtctt ttttgctgga  1140
acggttcagc ggaaaagacg catcgctctt tttgcttctg gaagaaatgc cagcaaaaga  1200
atctcttgac agtgactgac agcaaaaatg tcttttttcca attctaatta agttagtcaa  1260
ggcgccatcc tcatgaaaac tgtgtaacat aataaccgaa gtgtcgaaaa ggtggcacct   1320
tgtccaattg aacacgctcg atgaaaaaaa taagatatat ataaggttaa gtaaagcgtc   1380
tgttagaaag gaagttttc ctttttcttg ctctcttgtc ttttcatcta ctatttcctt    1440
cgtgtaatac agggtcgtca gatacataga tacaattcta ttacccccat ccataca     1497
```

<210> SEQ ID NO 58
<211> LENGTH: 1011
<212> TYPE: DNA
<213> ORGANISM: Artificial Sequence
<220> FEATURE:
<223> OTHER INFORMATION: pACU14
<220> FEATURE:
<223> OTHER INFORMATION: pACU14

<400> SEQUENCE: 58

```
gctcagcatc tgcttcttcc caaagatgaa cgcggcgtta tgtcactaac gacgtgcacc     60
aacttgcggg aattggaaaa agacatttt gctgtcagtc actgtcaaga gattcttttg    120
ctggcatttc ttccagaagc aaaaagagcg atgcgtcttt ccgctgaac cgttccagca    180
aaaaagacta ccaacgaatt cgaaaaagac attttttgctg tcagtcactg tcaagagatt  240
cttttgctgg catttcttcc agaagcaaaa agagcgatgc gtcttttccg ctgaaccgtt   300
ccagcaaaaa agactaccaa cgaattcgaa aagacatttt tgctgtcag tcactgtcaa    360
gagattcttt tgctggcatt tcttccagaa gcaaaaagag cgatgcgtct tttccgctga   420
accgttccag caaaaagac taccaacgaa ttcgaaaaag acattttttgc tgtcagtcac   480
tgtcaagaga ttcttttgct ggcatttctt ccagaagcaa aaagagcgat gcgtcttttc   540
cgctgaaccg ttccagcaaa aaagactacc aaccaattcc accgcacgcc ttttttctga   600
```

-continued

| | |
|---|---|
| agcccacttt cgtggacttt gccatatatg caaaattcat gaagtgtgat accaagtcag | 660 |
| catacacctc actagggtag tttctttggt tgtattgatc atttggttca tcgtggttca | 720 |
| ttaattttt ttctccattg ctttctggct tgatcttac tatcatttgg attttgtcg | 780 |
| aaggttgtag aattgtatgt gacaagtggc accaagcata tataaaaaaa aaaagcatta | 840 |
| tcttcctacc agagttgatt gttaaaaacg tatttatagc aaacgcaatt gtaattaatt | 900 |
| cttatttgt atcttttctt cccttgtctc aatctttat ttttattta ttttctttt | 960 |
| cttagtttct ttcataacac caagcaacta atactataac atacaataat a | 1011 |

<210> SEQ ID NO 59
<211> LENGTH: 398
<212> TYPE: DNA
<213> ORGANISM: Artificial Sequence
<220> FEATURE:
<223> OTHER INFORMATION: pACU15
<220> FEATURE:
<223> OTHER INFORMATION: pACU15

<400> SEQUENCE: 59

| | |
|---|---|
| tatagtttt tctccttgac gttaaagtat agaggtatat taacaatttt ttgttgatac | 60 |
| ttttatgaca tttgaataag aagtaataca aactgaaaat gttgaaagta ttagttaaag | 120 |
| tggttatgca gcttttccat ttatatatct gttaatagat caaaaatcat cgcttcgctg | 180 |
| attaattacc ccagaaataa ggctaaaaaa ctaatcgcat tatcatccga attcgttggt | 240 |
| agtctttttt gctggaacgg ttcagcggaa aagacgcatc gctcttttg cttctggaag | 300 |
| aaatgccagc aaaagaatct cttgacagtg actgacagca aaaatgtctt tttcgaattc | 360 |
| gggctcttta catttccaca acatataagt aagattag | 398 |

<210> SEQ ID NO 60
<211> LENGTH: 428
<212> TYPE: DNA
<213> ORGANISM: Artificial Sequence
<220> FEATURE:
<223> OTHER INFORMATION: pGAL/CUP1p
<220> FEATURE:
<223> OTHER INFORMATION: pGAL/CUP1p

<400> SEQUENCE: 60

| | |
|---|---|
| ttatattgaa ttttcaaaaa ttcttacttt tttttggat ggacgcaaag aagtttaata | 60 |
| atcatattac atggcattac caccatatac atatccatat ctaatcttac ttatatgttg | 120 |
| tggaaatgta aagagcccga attcgaaaaa gacattttg ctgtcagtca ctgtcaagag | 180 |
| attcttttgc tggcatttct tccagaagca aaaagagcga tgcgtctttt ccgctgaacc | 240 |
| gttccagcaa aaaagactac caacgcaata tggattgtca gaatcatata aaagagaagc | 300 |
| aaataactcc ttgtcttgta tcaattgcat tataatatct tcttgttagt gcaatatcat | 360 |
| atagaagtca tcgaaataga tattaagaaa aacaaactgt acaatcaatc aatcaatcat | 420 |
| cacataaa | 428 |

<210> SEQ ID NO 61
<211> LENGTH: 518
<212> TYPE: DNA
<213> ORGANISM: Saccharomyces cerevisiae
<220> FEATURE:
<223> OTHER INFORMATION: pCRS5
<220> FEATURE:
<223> OTHER INFORMATION: pCRS5

<400> SEQUENCE: 61

```
gtggacgaaa agacataact gcagaagtac agctgccttt atttcttgtg gtcatttatt      60
gcttttattt tcaagtcaga tatacaagaa atcaaatcc catcgtcaac gtcacgtata      120
aacgattaat ttacagtaat accatactct accaacatta ttttagtccg acgttcagtc    180
ctgtaggtgt tccaaatcct tctggcattg acttctgtgc agaaacccctt caaaatgagt    240 tccactttac gtcagatcgc ataacaaccg tcatatatt ttttctttt gctaaacccc      300 ctactgcaag cacttttaag aaaaagaaca ataaatgcgt ctttattgct gtgtggaagt    360 gattttttgtc tttcggacaa aaaaaggata gggatgcgag agggctgtga agtagtgatc    420
aagcggggcc tatataagaa gggcgcacat cgtcccccct aagaatagcg aagcgatatt    480
acactgaaca ctacaatgtc aaatagtact caataaat                            518

<210> SEQ ID NO 62
<211> LENGTH: 510
<212> TYPE: DNA
<213> ORGANISM: Saccharomyces cerevisiae
<220> FEATURE:
<223> OTHER INFORMATION: pCHA1
<220> FEATURE:
<223> OTHER INFORMATION: pCHA1

<400> SEQUENCE: 62
gatctctgct gacgttgtat ccacagatct aattgcaaga tagcctcttg cgaccttatt    60
aaaagcctct ccgtgatatc ctctagggct tgggttgcca ttaatcgatg tgtccttgtt    120
tccttatgcg agctgtttct tatctatctt atggtcccat tctttactgc actgtttaca    180
ttttgatcaa ttgcgaaatg ttcctactat ttttctttt ctcttttcgc gagtactaat    240
caccgcgaac ggaaactaat gagtcctctg cgcggagaca tgattccgca tgggcggctc    300
ctgttaagcc ccagcggaaa tgtaattcca ctgagtgtca ttaaatagtg ccaaagcttt    360
atcaaattgt ttgcgatgag ataagataaa agggacaata tgaggaggaa cacaggtata    420
taaatatcgc caaataaaag gaaaatgttt atacagtttt ctctttttta agtgctggat    480
agacaagaga caggaaaatt aaccagcgag                                      510

<210> SEQ ID NO 63
<211> LENGTH: 601
<212> TYPE: DNA
<213> ORGANISM: Saccharomyces cerevisiae
<220> FEATURE:
<223> OTHER INFORMATION: pCTR1
<220> FEATURE:
<223> OTHER INFORMATION: pCTR1

<400> SEQUENCE: 63
caagtccgat tgttcctctt caggagcttc ctgaaccaaa cttttttccgc aaggccgcat    60 tttgaaccgt atttttgctcg ttccagcctt tccacgtttt tgttatctaa gcaacttggc    120
acatttccct actatactac aaaccgatac gtaaatactc ccctaaatag catatgaatt    180
attcagtaat ttttaaggat cgaaactgca cctcaactat tcgttactgt ggttatgttc    240
tcatgtattg atgcaaatca tgggatattt gctcaagacg acggtaaaat gagcaaaaat    300
ggcacgatcc tgaaaagagc acttttcaag attcgggcta caaaatgcaa cataaaaaat    360
gttgtattgt catctcgaca gggtcttgta tgttttattc ctcttatgat tagttcacat    420
tagtaaaaca gatacgcagt gtgctcttaa taaacaacta ctccatagct ttatttgcat    480
aacaaaactt ttaagcacaa acttaaacag gtggagtaat agttcggcgg cgactcaaat    540
```

```
tacatttgtt ggaagaatcg aatagaaaat aaaaaaaagt gtattatatt tgacattcaa    600
a                                                                   601

<210> SEQ ID NO 64
<211> LENGTH: 522
<212> TYPE: DNA
<213> ORGANISM: Saccharomyces cerevisiae
<220> FEATURE:
<223> OTHER INFORMATION: pCTR3
<220> FEATURE:
<223> OTHER INFORMATION: pCTR3

<400> SEQUENCE: 64
gatgtgatga caaaacctct tccgataaaa acatttaaac tattaacaaa caaatggatt     60
cattagatct attacattat gggtggtatg ttggaataaa aatcaactat catctactaa    120
ctagtattta cgttactagt atattatcat atacggtgtt agaagatgac gcaaatgatg    180
agaaatagtc atctaaatta gtggaagctg aaacgcaagg attgataatg taataggatc    240
aatgaatatt aacatataaa acgatgataa taatatttat agaattgtgt agaattgcag    300
attccctttt atggattcct aaatcctcca ggagaacttc tagtatatct acatacctaa    360
tattattgcc ttattaaaaa tggaatccca acaattacat caaaatccac attctcttca    420
cttctccgat agacttgtaa tttatcttat ttcatttcct aacactttga tcgaagaaga    480
gggataacaa cagacgaaaa cacatttaag ggctatacaa ag                       522

<210> SEQ ID NO 65
<211> LENGTH: 675
<212> TYPE: DNA
<213> ORGANISM: Artificial Sequence
<220> FEATURE:
<223> OTHER INFORMATION: pCUR1
<220> FEATURE:
<223> OTHER INFORMATION: pCUR1

<400> SEQUENCE: 65
ttacattatc aatccttgcg tttcagcttc cactaattta gatgactatt tctcatcatt     60
tgcgtcatct tctaacaccg tatatgataa tatactagta acgtaaatac tagttagtag    120
atgatagttg attttttattc caacactaag aaataaattc gccatttctt gaatgtattt    180
aaagatattt aatgctataa tagacattta aatccaattc ttccaacata caatgggagt    240
ttggccgagt ggtttaaggc gtcagattta ggtggattta acctctaaaa tctctgatat    300
cttcggatgc aagggttcga atcccttagc tctcattatt ttttgctttt tctcttgaat    360
tgtcatggga tatttgctca agacgacggt aaaatgagca aatatggcac gatcctcaat    420
tctaattaag ttagtcaagg cgccatcctc atgaaaactg tgtaacataa taaccgaagt    480
gtcgaaaagg tggcaccttg tccaattgaa cacgctcgat gaaaaaaata agatatatat    540
aaggttaagt aaagcgtctg ttagaaagga agttttttcct ttttcttgct ctcttgtctt    600
ttcatctact atttccttcg tgtaatacag ggtcgtcaga tacatagata caattctatt    660
accccccatcc ataca                                                    675

<210> SEQ ID NO 66
<211> LENGTH: 674
<212> TYPE: DNA
<213> ORGANISM: Artificial Sequence
<220> FEATURE:
<223> OTHER INFORMATION: pCUR2
<220> FEATURE:
<223> OTHER INFORMATION: pCUR2
```

```
<400> SEQUENCE: 66
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgatt   360
gaggatcgtg ccatatttgc tcattttacc gtcgtcttga gcaaatatcc catgacaatt   420
ctaattaagt tagtcaaggc gccatcctca tgaaaactgt gtaacataat aaccgaagtg   480
tcgaaaaggt ggcaccttgt ccaattgaac acgctcgatg aaaaaaataa gatatatata   540
aggttaagta aagcgtctgt tagaaaggaa gttttccctt tttcttgctc tcttgtcttt   600
tcatctacta tttccttcgt gtaatacagg gtcgtcagat acatagatac aattctatta   660
cccccatcca taca                                                     674

<210> SEQ ID NO 67
<211> LENGTH: 794
<212> TYPE: DNA
<213> ORGANISM: Artificial Sequence
<220> FEATURE:
<223> OTHER INFORMATION: pCUR3
<220> FEATURE:
<223> OTHER INFORMATION: pCUR3

<400> SEQUENCE: 67
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg atttttattc caacactaag aaataaattc gccatttctt gaatgtattt   180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
taggatcgtg ccatatttgc tcattttacc gtcgtcttga gcaaatatcc catgacaatt   420
gaggatcgtg ccatatttgc tcattttacc gtcgtcttga gcaaatatcc catgacaatt   480
gaggatcgtg ccatatttgc tcattttacc gtcgtcttga gcaaatatcc catgacaatt   540
ctaattaagt tagtcaaggc gccatcctca tgaaaactgt gtaacataat aaccgaagtg   600
tcgaaaaggt ggcaccttgt ccaattgaac acgctcgatg aaaaaaataa gatatatata   660
aggttaagta aagcgtctgt tagaaaggaa gttttccctt tttcttgctc tcttgtcttt   720
tcatctacta tttccttcgt gtaatacagg gtcgtcagat acatagatac aattctatta   780
cccccatcca taca                                                     794

<210> SEQ ID NO 68
<211> LENGTH: 850
<212> TYPE: DNA
<213> ORGANISM: Artificial Sequence
<220> FEATURE:
<223> OTHER INFORMATION: pCUR4
<220> FEATURE:
<223> OTHER INFORMATION: pCUR4

<400> SEQUENCE: 68
```

```
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgaat     360
tgtcatggga tatttgctca agacgacggt aaaatgagca aatatggcac gatcctcaat     420
tgtcatggga tatttgctca agacgacggt aaaatgagca aatatggcac gatcctcaat     480
gtcatgggat atttgctcaa gacgacggta aaatgagcaa atatggcacg atcctcaatt     540
gtcatgggat atttgctcaa gacgacggta aaatgagcaa atatcccatg acaattctaa     600
ttaagttagt caaggcgcca tcctcatgaa aactgtgtaa cataataacc gaagtgtcga     660
aaaggtggca ccttgtccaa ttgaacacgc tcgatgaaaa aataagata tatataaggt     720 taagtaaagc gtctgttaga aaggaagttt tccttttttc ttgctctctt gtcttttcat     780
ctactatttc cttcgtgtaa tacagggtcg tcagatacat agatacaatt ctattacccc     840
catccataca                                                            850

<210> SEQ ID NO 69
<211> LENGTH: 491
<212> TYPE: DNA
<213> ORGANISM: Artificial Sequence
<220> FEATURE:
<223> OTHER INFORMATION: pCUR5p
<220> FEATURE:
<223> OTHER INFORMATION: pCUR5p

<400> SEQUENCE: 69
ttatattgaa ttttcaaaaa ttcttacttt ttttttggat ggacgcaaag aagtttaata      60
atcatattac atggcattac caccatatac atatccatat ctaatcttac ttatatgttg    120
tggaaatgta aagagcccga attgtcatgg gatatttgct caagacgacg gtaaaatgag    180
caaatatggc acgatcctca attgtcatgg gatatttgct caagacgacg gtaaaatgag    240
caaatatggc acgatcccaa ttcggatgat aatgcgatta gttttttagc cttatttctg    300
gggtaattaa tcagcgaagc gatgatttt gatctattaa cagatatata aatggaaaag    360
ctgcataacc acttttaacta atactttcaa cattttcagt ttgtattact tcttattcaa    420
atgtcataaa agtatcaaca aaaaattgtt aatatacctc tatactttaa cgtcaaggag    480
aaaaaactat a                                                          491

<210> SEQ ID NO 70
<211> LENGTH: 833
<212> TYPE: DNA
<213> ORGANISM: Artificial Sequence
<220> FEATURE:
<223> OTHER INFORMATION: pCUR6
<220> FEATURE:
<223> OTHER INFORMATION: pCUR6

<400> SEQUENCE: 70
ttacattatc aatccttgcg tttcagcttc cactaattta gatgactatt tctcatcatt      60
tgcgtcatct tctaacaccg tatatgataa tatactagta acgtaaatac tagttagtag    120
atgatagttg atttttattc caacactaag aaataaattc gccatttctt gaatgtattt    180
aaagatattt aatgctataa tagacattta aatccaattc ttccaacata caatgggagt    240
```

```
ttggccgagt ggtttaaggc gtcagattta ggtggattta acctctaaaa tctctgatat    300
cttcggatgc aagggttcga atcccgaatt gaggatcgtg ccatatttgc tcattttacc    360
gtcgtcttga gcaaatatcc catgacaatt gaggatcgtg ccatatttgc tcattttacc    420
gtcgtcttga gcaaatatcc catgacaatt gaggatcgtg ccatatttgc tcattttacc    480
gtcgtcttga gcaaatatcc catgacaatt catgatcgca aaatggcaaa tggcacgtga    540
agctgtcgat attggggaac tgtggtggtt ggcaaatgac taattaagtt agtcaaggcg    600
ccatcctcat gaaaactgtg taacataata accgaagtgt cgaaaaggtg caccttgtc     660 caattgaaca cgctcgatga aaaaaataag atatatataa ggttaagtaa agcgtctgtt    720
agaaaggaag ttttcctttt tcttgctctc ttgtcttttt catctactat ttccttcgtg    780
taatacaggg tcgtcagata catagataca attctattac ccccatccat aca           833

<210> SEQ ID NO 71
<211> LENGTH: 803
<212> TYPE: DNA
<213> ORGANISM: Artificial Sequence
<220> FEATURE:
<223> OTHER INFORMATION: pCUR7
<220> FEATURE:
<223> OTHER INFORMATION: pCUR7

<400> SEQUENCE: 71
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gagaattctt cctgtcttcc   360
tattgattgc agcttccaat ttcgtcacac aacaaggtcc tagcgacggc tcacaggttt   420
tgtaacaagc aatcgaaggt tctggaatgg cgggaaaggg tttagtacca catgctatga   480
tgcccactgt gatctccaga gcaaagttcg ttcgatcgta ctgttactct ctctctttca   540
aacagaattg tccgaatcgt gtgacaacaa cagcctgttc tcacacactc ttttcttcta   600
accaaggggg tggtttagtt tagtagaacc tcgtgaaact acatttaca tatatataaa    660 cttgcataaa ttggtcaatg caagaaatac atatttggtc ttttctaatt cgtagttttt   720
caagttctta gatgctttct ttttctcttt tttacagatc atcaaggaag taattatcta   780 cttttttacaa caaatataaa aca                                          803

<210> SEQ ID NO 72
<211> LENGTH: 863
<212> TYPE: DNA
<213> ORGANISM: Artificial Sequence
<220> FEATURE:
<223> OTHER INFORMATION: pCUR8
<220> FEATURE:
<223> OTHER INFORMATION: pCUR8

<400> SEQUENCE: 72
gtgagtaagg aaagagtgag gaactatcgc atacctgcat ttaaagatgc cgatttgggc     60
gcgaatcctt tatttggct tcaccctcat actattatca gggccagaaa aaggaagtgt    120
ttccctcctt cttgaattga tgttaccctc ataaagcacg tggcctctta tcgagaaaga   180
```

```
aattaccgtc gctcgtgatt tgtttgcaaa aagaacaaaa ctgaattcag gatcgtgcca    240
tatttgctca ttttaccgtc gtcttgagca aatatcccat gacaattgag gatcgtgcca    300
tatttgctca ttttaccgtc gtcttgagca aatatcccat gacaattgag gatcgtgcca    360
tatttgctca ttttaccgtc gtcttgagca aatatcccat gagaattctt cctgtcttcc    420
tattgattgc agcttccaat ttcgtcacac aacaaggtcc tagcgacggc tcacaggttt    480
tgtaacaagc aatcgaaggt tctggaatgg cgggaaaggg tttagtacca catgctatga    540
tgcccactgt gatctccaga gcaaagttcg ttcgatcgta ctgttactct ctctctttca    600
aacagaattg tccgaatcgt gtgacaacaa cagcctgttc tcacacactc ttttcttcta    660
accaaggggg tggtttagtt tagtagaacc tcgtgaaact tacatttaca tatatataaa    720
cttgcataaa ttggtcaatg caagaaatac atatttggtc ttttctaatt cgtagttttt    780
caagttctta gatgctttct ttttctcttt tttacagatc atcaaggaag taattatcta    840 cttttttacaa caaatataaa aca                                           863
```

<210> SEQ ID NO 73
<211> LENGTH: 863
<212> TYPE: DNA
<213> ORGANISM: Artificial Sequence
<220> FEATURE:
<223> OTHER INFORMATION: pCUR9
<220> FEATURE:
<223> OTHER INFORMATION: pCUR9

<400> SEQUENCE: 73

```
gtgagtaagg aaagagtgag gaactatcgc ataccctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaga   180 aattaccgtc gctcgtgatt tgtttgcaaa aagaacaaaa ctgaattctc atgggatatt   240
tgctcaagac gacggtaaaa tgagcaaata tggcacgatc ctcaattgtc atgggatatt   300
tgctcaagac gacggtaaaa tgagcaaata tggcacgatc ctcaattgtc atgggatatt   360
tgctcaagac gacggtaaaa tgagcaaata tggcacgatc ctgaattctt cctgtcttcc   420
tattgattgc agcttccaat ttcgtcacac aacaaggtcc tagcgacggc tcacaggttt   480
tgtaacaagc aatcgaaggt tctggaatgg cgggaaaggg tttagtacca catgctatga   540
tgcccactgt gatctccaga gcaaagttcg ttcgatcgta ctgttactct ctctctttca   600
aacagaattg tccgaatcgt gtgacaacaa cagcctgttc tcacacactc ttttcttcta   660
accaaggggg tggtttagtt tagtagaacc tcgtgaaact tacatttaca tatatataaa   720
cttgcataaa ttggtcaatg caagaaatac atatttggtc ttttctaatt cgtagttttt   780
caagttctta gatgctttct ttttctcttt tttacagatc atcaaggaag taattatcta   840 cttttttacaa caaatataaa aca                                           863
```

<210> SEQ ID NO 74
<211> LENGTH: 923
<212> TYPE: DNA
<213> ORGANISM: Artificial Sequence
<220> FEATURE:
<223> OTHER INFORMATION: pCUR10
<220> FEATURE:
<223> OTHER INFORMATION: pCUR10

<400> SEQUENCE: 74

```
gtgagtaagg aaagagtgag gaactatcgc ataccctgcat ttaaagatgc cgatttgggc    60
```

```
gcgaatcctt tattttggct tcaccctcat actattatca gggccagaaa aaggaagtgt      120
ttccctcctt cttgaattga tgttaccctc ataaagcacg tggcctctta tcgagaaaga      180
aattaccgtc gctcgtgatt tgtttgcaaa aagaacaaaa ctgaattctc atgggatatt      240
tgctcaagac gacggtaaaa tgagcaaata tggcacgatc ctcaattgtc atgggatatt      300
tgctcaagac gacggtaaaa tgagcaaata tggcacgatc ctcaattgtc atgggatatt      360
tgctcaagac gacggtaaaa tgagcaaata tggcacgatc ctcaattgtc atgggatatt      420
tgctcaagac gacggtaaaa tgagcaaata tggcacgatc ctgaattctt cctgtcttcc      480
tattgattgc agcttccaat ttcgtcacac aacaaggtcc tagcgacggc tcacaggttt      540
tgtaacaagc aatcgaaggt tctggaatgg cgggaaaggg tttagtacca catgctatga      600
tgcccactgt gatctccaga gcaaagttcg ttcgatcgta ctgttactct ctctctttca      660
aacagaattg tccgaatcgt gtgacaacaa cagcctgttc tcacacactc ttttcttcta      720
accaaggggg tggtttagtt tagtagaacc tcgtgaaact tacatttaca tatatataaa      780
cttgcataaa ttggtcaatg caagaaatac atatttggtc ttttctaatt cgtagttttt      840
caagttctta gatgctttct ttttctcttt tttacagatc atcaaggaag taattatcta      900 cttttttacaa caaatataaa aca                                            923
```

<210> SEQ ID NO 75
<211> LENGTH: 983
<212> TYPE: DNA
<213> ORGANISM: Artificial Sequence
<220> FEATURE:
<223> OTHER INFORMATION: pCUR11
<220> FEATURE:
<223> OTHER INFORMATION: pCUR11

<400> SEQUENCE: 75

```
gtgagtaagg aaagagtgag gaactatcgc ataccctgcat ttaaagatgc cgatttgggc       60
gcgaatcctt tattttggct tcaccctcat actattatca gggccagaaa aaggaagtgt      120
ttccctcctt cttgaattga tgttaccctc ataaagcacg tggcctctta tcgagaaaga      180
aattaccgtc gctcgtgatt tgtttgcaaa aagaacaaaa ctgaattctc atgggatatt      240
tgctcaagac gacggtaaaa tgagcaaata tggcacgatc ctcaattgtc atgggatatt      300
tgctcaagac gacggtaaaa tgagcaaata tggcacgatc ctcaattgtc atgggatatt      360
tgctcaagac gacggtaaaa tgagcaaata tggcacgatc ctcaattgtc atgggatatt      420
tgctcaagac gacggtaaaa tgagcaaata tggcacgatc ctcaattgtc atgggatatt      480
tgctcaagac gacggtaaaa tgagcaaata tggcacgatc ctgaattctt cctgtcttcc      540
tattgattgc agcttccaat ttcgtcacac aacaaggtcc tagcgacggc tcacaggttt      600
tgtaacaagc aatcgaaggt tctggaatgg cgggaaaggg tttagtacca catgctatga      660
tgcccactgt gatctccaga gcaaagttcg ttcgatcgta ctgttactct ctctctttca      720
aacagaattg tccgaatcgt gtgacaacaa cagcctgttc tcacacactc ttttcttcta      780
accaaggggg tggtttagtt tagtagaacc tcgtgaaact tacatttaca tatatataaa      840
cttgcataaa ttggtcaatg caagaaatac atatttggtc ttttctaatt cgtagttttt      900
caagttctta gatgctttct ttttctcttt tttacagatc atcaaggaag taattatcta      960 cttttttacaa caaatataaa aca                                            983
```

<210> SEQ ID NO 76

```
<211> LENGTH: 1043
<212> TYPE: DNA
<213> ORGANISM: Artificial Sequence
<220> FEATURE:
<223> OTHER INFORMATION: pCUR12
<220> FEATURE:
<223> OTHER INFORMATION: pCUR12

<400> SEQUENCE: 76
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattcag gatcgtgcca   240
tatttgctca ttttaccgtc gtcttgagca aatatcccat gacaattgag gatcgtgcca   300
tatttgctca ttttaccgtc gtcttgagca aatatcccat gacaattgag gatcgtgcca   360
tatttgctca ttttaccgtc gtcttgagca aatatcccat gagaattcag gatcgtgcca   420
tatttgctca ttttaccgtc gtcttgagca aatatcccat gacaattgag gatcgtgcca   480
tatttgctca ttttaccgtc gtcttgagca aatatcccat gacaattgag gatcgtgcca   540
tatttgctca ttttaccgtc gtcttgagca aatatcccat gagaattctt cctgtcttcc   600
tattgattgc agcttccaat ttcgtcacac aacaaggtcc tagcgacggc tcacaggttt   660
tgtaacaagc aatcgaaggt tctggaatgg cgggaaaggg tttagtacca catgctatga   720
tgcccactgt gatctccaga gcaaagttcg ttcgatcgta ctgttactct ctctctttca   780
aacagaattg tccgaatcgt gtgacaacaa cagcctgttc tcacacactc ttttcttcta   840
accaagggggg tggtttagtt tagtagaacc tcgtgaaact tacatttaca tatatataaa   900
cttgcataaa ttggtcaatg caagaaatac atatttggtc ttttctaatt cgtagttttt   960
caagttctta gatgctttct ttttctcttt tttacagatc atcaaggaag taattatcta  1020
cttttttacaa caaatataaa aca                                          1043

<210> SEQ ID NO 77
<211> LENGTH: 1043
<212> TYPE: DNA
<213> ORGANISM: Artificial Sequence
<220> FEATURE:
<223> OTHER INFORMATION: pCUR13
<220> FEATURE:
<223> OTHER INFORMATION: pCUR13

<400> SEQUENCE: 77
gtgagtaagg aaagagtgag gaactatcgc atacctgcat ttaaagatgc cgatttgggc    60
gcgaatcctt tattttggct tcaccctcat actattatca gggccagaaa aaggaagtgt   120
ttccctcctt cttgaattga tgttaccctc ataaagcacg tggcctctta tcgagaaaga   180
aattaccgtc gctcgtgatt tgtttgcaaa aagaacaaaa ctgaattctc atgggatatt   240
tgctcaagac gacggtaaaa tgagcaaata tggcacgatc ctcaattgtc atgggatatt   300
tgctcaagac gacggtaaaa tgagcaaata tggcacgatc ctcaattgtc atgggatatt   360
tgctcaagac gacggtaaaa tgagcaaata tggcacgatc ctgaattctc atgggatatt   420
tgctcaagac gacggtaaaa tgagcaaata tggcacgatc ctcaattgtc atgggatatt   480
tgctcaagac gacggtaaaa tgagcaaata tggcacgatc ctcaattgtc atgggatatt   540
tgctcaagac gacggtaaaa tgagcaaata tggcacgatc ctgaattctt cctgtcttcc   600
tattgattgc agcttccaat ttcgtcacac aacaaggtcc tagcgacggc tcacaggttt   660
```

-continued

```
tgtaacaagc aatcgaaggt tctggaatgg cgggaaaggg tttagtacca catgctatga      720
tgcccactgt gatctccaga gcaaagttcg ttcgatcgta ctgttactct ctctctttca      780
aacagaattg tccgaatcgt gtgacaacaa cagcctgttc tcacacactc ttttcttcta      840
accaaggggg tggtttagtt tagtagaacc tcgtgaaact tacatttaca tatatataaa      900
cttgcataaa ttggtcaatg caagaaatac atatttggtc ttttctaatt cgtagttttt      960
caagttctta gatgctttct ttttctcttt tttacagatc atcaaggaag taattatcta     1020 cttttttacaa caaatataaa aca                                            1043
```

<210> SEQ ID NO 78
<211> LENGTH: 1223
<212> TYPE: DNA
<213> ORGANISM: Artificial Sequence
<220> FEATURE:
<223> OTHER INFORMATION: pCUR14
<220> FEATURE:
<223> OTHER INFORMATION: pCUR14

<400> SEQUENCE: 78

```
gtgagtaagg aaagagtgag gaactatcgc atacctgcat ttaaagatgc cgatttgggc       60
gcgaatcctt tattttggct tcaccctcat actattatca gggccagaaa aaggaagtgt      120
ttccctcctt cttgaattga tgttaccctc ataaagcacg tggcctctta tcgagaaaga      180
aattaccgtc gctcgtgatt tgtttgcaaa aagaacaaaa ctgaattctc atgggatatt      240
tgctcaagac gacggtaaaa tgagcaaata tggcacgatc ctcaattgtc atgggatatt      300
tgctcaagac gacggtaaaa tgagcaaata tggcacgatc ctcaattgtc atgggatatt      360
tgctcaagac gacggtaaaa tgagcaaata tggcacgatc ctgaattctc atgggatatt      420
tgctcaagac gacggtaaaa tgagcaaata tggcacgatc ctcaattgtc atgggatatt      480
tgctcaagac gacggtaaaa tgagcaaata tggcacgatc ctcaattgtc atgggatatt      540
tgctcaagac gacggtaaaa tgagcaaata tggcacgatc ctgaattctc atgggatatt      600
tgctcaagac gacggtaaaa tgagcaaata tggcacgatc ctcaattgtc atgggatatt      660
tgctcaagac gacggtaaaa tgagcaaata tggcacgatc ctcaattgtc atgggatatt      720
tgctcaagac gacggtaaaa tgagcaaata tggcacgatc ctgaattctt cctgtcttcc      780
tattgattgc agcttccaat ttcgtcacac aacaaggtcc tagcgacggc tcacaggttt      840
tgtaacaagc aatcgaaggt tctggaatgg cgggaaaggg tttagtacca catgctatga      900
tgcccactgt gatctccaga gcaaagttcg ttcgatcgta ctgttactct ctctctttca      960
aacagaattg tccgaatcgt gtgacaacaa cagcctgttc tcacacactc ttttcttcta     1020
accaaggggg tggtttagtt tagtagaacc tcgtgaaact tacatttaca tatatataaa     1080
cttgcataaa ttggtcaatg caagaaatac atatttggtc ttttctaatt cgtagttttt     1140
caagttctta gatgctttct ttttctcttt tttacagatc atcaaggaag taattatcta     1200 cttttttacaa caaatataaa aca                                            1223
```

<210> SEQ ID NO 79
<211> LENGTH: 1283
<212> TYPE: DNA
<213> ORGANISM: Artificial Sequence
<220> FEATURE:
<223> OTHER INFORMATION: pCUR15
<220> FEATURE:
<223> OTHER INFORMATION: pCUR15

<400> SEQUENCE: 79

```
gtgagtaagg aaagagtgag gaactatcgc atacctgcat ttaaagatgc cgatttgggc      60
gcgaatcctt tattttggct tcaccctcat actattatca gggccagaaa aaggaagtgt     120
ttccctcctt cttgaattga tgttaccctc ataaagcacg tggcctctta tcgagaaaga     180
aattaccgtc gctcgtgatt tgtttgcaaa aagaacaaaa ctgaattcag gatcgtgcca     240
tatttgctca ttttaccgtc gtcttgagca aatatcccat gacaattgag gatcgtgcca     300
tatttgctca ttttaccgtc gtcttgagca aatatcccat gacaattgag gatcgtgcca     360
tatttgctca ttttaccgtc gtcttgagca aatatcccat gacaattgag gatcgtgcca     420
tatttgctca ttttaccgtc gtcttgagca aatatcccat gagaattcag gatcgtgcca     480
tatttgctca ttttaccgtc gtcttgagca aatatcccat gacaattgag gatcgtgcca     540
tatttgctca ttttaccgtc gtcttgagca aatatcccat gacaattgag gatcgtgcca     600
tatttgctca ttttaccgtc gtcttgagca aatatcccat gagaattcag gatcgtgcca     660
tatttgctca ttttaccgtc gtcttgagca aatatcccat gacaattgag gatcgtgcca     720
tatttgctca ttttaccgtc gtcttgagca aatatcccat gacaattgag gatcgtgcca     780
tatttgctca ttttaccgtc gtcttgagca aatatcccat gagaattctt cctgtcttcc     840
tattgattgc agcttccaat ttcgtcacac aacaaggtcc tagcgacggc tcacaggttt     900
tgtaacaagc aatcgaaggt tctggaatgg cgggaaaggg tttagtacca catgctatga     960
tgcccactgt gatctccaga gcaaagttcg ttcgatcgta ctgttactct ctctctttca    1020
aacagaattg tccgaatcgt gtgacaacaa cagcctgttc tcacacactc ttttcttcta    1080
accaagggggg tggtttagtt tagtagaacc tcgtgaaact tacatttaca tatatataaa   1140
cttgcataaa ttggtcaatg caagaaatac atatttggtc ttttctaatt cgtagttttt    1200
caagttctta gatgctttct ttttctcttt tttacagatc atcaaggaag taattatcta    1260
cttttttacaa caaatataaa aca                                          1283
```

<210> SEQ ID NO 80
<211> LENGTH: 686
<212> TYPE: DNA
<213> ORGANISM: Artificial Sequence
<220> FEATURE:
<223> OTHER INFORMATION: pCUR16
<220> FEATURE:
<223> OTHER INFORMATION: pCUR16

<400> SEQUENCE: 80

```
gctcagcatc tgcttcttcc caaagatgaa cgcggcgtta tgtcactaac gacgtgcacc      60
aacttgcggg aattctcatg ggatatttgc tcaagacgac ggtaaaatga gcaaatatgg     120
cacgatcctc aattgtcatg ggatatttgc tcaagacgac ggtaaaatga gcaaatatgg     180
cacgatcctc aatgtcatgg gatatttgct caagacgacg gtaaaatgag caaatatggc     240
acgatcctga attccaccgc acgcctttttt tctgaagccc actttcgtgg actttgccat     300
atatgcaaaa ttcatgaagt gtgataccaa gtcagcatac acctcactag ggtagtttct     360
ttggttgtat tgatcatttg gttcatcgtg gttcattaat ttttttttctc cattgctttc     420
tggctttgat cttactatca tttggatttt tgtcgaaggt tgtagaattg tatgtgacaa     480
gtggcaccaa gcatatataa aaaaaaaaag cattatcttc ctaccagagt tgattgttaa     540
aaacgtattt atagcaaacg caattgtaat taattccttat tttgtatctt tcttcccctt    600
gtctcaatct tttatttttta ttttatttttt cttttcttag tttctttcat aacaccaagc   660
```
aactaatact ataacataca ataata                                          686

<210> SEQ ID NO 81
<211> LENGTH: 747
<212> TYPE: DNA
<213> ORGANISM: Artificial Sequence
<220> FEATURE:
<223> OTHER INFORMATION: pCUR17
<220> FEATURE:
<223> OTHER INFORMATION: pCUR17

<400> SEQUENCE: 81
gctcagcatc tgcttcttcc caaagatgaa cgcggcgtta tgtcactaac gacgtgcacc      60
aacttgcggg aattctcatg ggatatttgc tcaagacgac ggtaaaatga gcaaatatgg     120
cacgatcctc aattgtcatg ggatatttgc tcaagacgac ggtaaaatga gcaaatatgg     180
cacgatcctc aattctcatg ggatatttgc tcaagacgac ggtaaaatga gcaaatatgg     240
cacgatcctc aattctcatg ggatatttgc tcaagacgac ggtaaaatga gcaaatatgg     300
cacgatcctg aattccaccg cacgcctttt ttctgaagcc cactttcgtg gactttgcca     360
tatatgcaaa attcatgaag tgtgatacca agtcagcata cacctcacta gggtagtttc     420
tttggttgta ttgatcattt ggttcatcgt ggttcattaa ttttttttct ccattgcttt     480
ctggctttga tcttactatc atttggattt tgtcgaagg ttgtagaatt gtatgtgaca      540
agtggcacca agcatatata aaaaaaaaaa gcattatctt cctaccagag ttgattgtta     600
aaaacgtatt tatagcaaac gcaattgtaa ttaattctta ttttgtatct tttcttccct     660
tgtctcaatc ttttattttt attttatttt tcttttctta gtttctttca taacaccaag     720
caactaatac tataacatac aataata                                         747

<210> SEQ ID NO 82
<211> LENGTH: 500
<212> TYPE: DNA
<213> ORGANISM: Saccharomyces cerevisiae
<220> FEATURE:
<223> OTHER INFORMATION: pLYS1
<220> FEATURE:
<223> OTHER INFORMATION: pLYS1

<400> SEQUENCE: 82
gcaagttaac attagggaga acgtggggcc ttcctccatg agtgcagagc aattgaagat      60
gtttagaggt ttaaaggaga ataaccagtt gctggatagc tctgtgccag ctacagttta    120
tgccaaattg gcccttcatg gtattcctga cggtgttaat ggacagtact tgagctataa    180
tgaccctgcc ttggcggact ttatgccttg aggatagcag gtacatataa attgttacat    240
actaagtcga tgagtcaaaa aagactctta tacatttata catttttgcat tattattttt   300 tttttccagc ggaatttgga attccgctct caaccgccaa aattcccctg cgatttcagc    360
gacaaagagt cataaagtca tcctcgagaa accacgatga aatatataaa aagcccatct    420
tccctgacgg aaactggtat tttaggaggc ataccataag ataacaacga aaacgcttta    480
tttttcacac aaccgcaaaa                                                500

<210> SEQ ID NO 83
<211> LENGTH: 650
<212> TYPE: DNA
<213> ORGANISM: Saccharomyces cerevisiae
<220> FEATURE:
<223> OTHER INFORMATION: pLYS4
<220> FEATURE:

<223> OTHER INFORMATION: pLYS4

<400> SEQUENCE: 83

```
ttgaaaaatg cgaagttgaa gtgccataga agagaaacag cccacacagg ggagaagccc      60
actggaaagg gggcactgac caactttaaa taggaaacag aagataccac aagccagcga     120
tacaacagca ccaaacaccg aaaagaatag ccaaagctgt cctctggtgt tggaaaaact     180
ggaaaaaacg caactgcgtt ggctgctacg gtgaaaaatt ttcctatgac ttttttcact     240
gcttgttcgt gcgaaattac cgcaaacccg gtaaaatgta cacgtatcaa gtgataaaca     300
atttcgtgtc aagtgagcag aatggagcga tttggaaaaa aaaattttt attgttttt      360
cccccgggat tttgctcgag atgactgaaa ttttgtaatc gatgagtcta taccagaggc     420
agcaaatatc accaacatac acaggtatac acaatctcat gtccacacac acgtacagac     480
acgcacatat atatatatat atatatatcc ccataggtat ttatatatac aaaagaatcc     540
tcgtgtgttt gtgtgtgcaa tagctagttt tgcgctgcct cttatagtag acaatatcac     600
tttttcaata aaatagaact tgcaaggaaa caaaattgta tcgcttcaag              650
```

<210> SEQ ID NO 84
<211> LENGTH: 500
<212> TYPE: DNA
<213> ORGANISM: Saccharomyces cerevisiae
<220> FEATURE:
<223> OTHER INFORMATION: pLYS9
<220> FEATURE:
<223> OTHER INFORMATION: pLYS9

<400> SEQUENCE: 84

```
acatatgcaa gagtcttatg tatcgtatct aagtgccacg taggggattc ccatcatttg      60
atgatttcca atataatac ctgtagagag cggtggagca aaagtcaaat tttaatcgca     120
actgcagaca agtcaagctg aggaaattgt ggatgatctc ttgtttcttt tgatattcac     180
cacaacagaa gtgaagagtg tgattgcggt tactactgac cacgaagcaa tgcgtttagt     240
agtgaaaaga attactcata ctctggaatc gaaattccgt tggaaaaatt cgctttgtag     300
tgaaaaataa agatgtcaat aaagggtatt gagaatttcc aatggaatta tcagcaatag     360
atgatagaaa gtagcacaga atttggctta atggtatata aaccgtaggg tcctggtaaa     420
attacatggg aaggatcctt aggcagtagg gaaaacttat caggacaatt gagttatatt     480
aacgtattat atattttaat                                                500
```

<210> SEQ ID NO 85
<211> LENGTH: 494
<212> TYPE: DNA
<213> ORGANISM: Artificial Sequence
<220> FEATURE:
<223> OTHER INFORMATION: pLYR1p
<220> FEATURE:
<223> OTHER INFORMATION: pLYR1p

<400> SEQUENCE: 85

```
ttatattgaa ttttcaaaaa ttcttacttt ttttttggat ggacgcaaag aagtttaata      60
atcatattac atggcattac caccatatac atatccatat ctaatcttac ttatatgttg     120
tggaaatgta aagagcccga attcctcata ctctggaatc gaaattccgt tggaaaaatt     180
cgctttgtag tgaaaaataa agatgtcaat aaagggtatt gagaatttcc aatggaatta     240
tcagcaatag atgatagaaa gaattcggat gataatgcga ttgtttttt agccttattt     300
ctggggtaat taatcagcga agcgatgatt tttgatctat taacagatat ataaatggaa     360
```

```
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                      494
```

<210> SEQ ID NO 86
<211> LENGTH: 494
<212> TYPE: DNA
<213> ORGANISM: Artificial Sequence
<220> FEATURE:
<223> OTHER INFORMATION: pLYR2p
<220> FEATURE:
<223> OTHER INFORMATION: pLYR2p

<400> SEQUENCE: 86

```
ttatattgaa ttttcaaaaa ttcttacttt ttttttggat ggacgcaaag aagtttaata     60
atcatattac atggcattac caccatatac atatccatat ctaatcttac ttatatgttg    120
tggaaatgta aagagcccga attcttcta tcatctattg ctgataattc cattggaaat     180
tctcaatacc ctttattgac atctttattt ttcactacaa agcgaatttt tccaacggaa    240
tttcgattcc agagtatgag gaattcggat gataatgcga ttagtttttt agccttattt    300
ctggggtaat taatcagcga agcgatgatt tttgatctat taacagatat ataaatggaa    360
aagctgcata accactttaa ctaatacttt caacattttc agtttgtatt acttcttatt    420
caaatgtcat aaaagtatca acaaaaaatt gttaatatac ctctatactt taacgtcaag    480
gagaaaaaac tata                                                      494
```

<210> SEQ ID NO 87
<211> LENGTH: 616
<212> TYPE: DNA
<213> ORGANISM: Artificial Sequence
<220> FEATURE:
<223> OTHER INFORMATION: pLYR3p
<220> FEATURE:
<223> OTHER INFORMATION: pLYR3p

<400> SEQUENCE: 87

```
ttatattgaa ttttcaaaaa ttcttacttt ttttttggat ggacgcaaag aagtttaata     60
atcatattac atggcattac caccatatac atatccatat ctaatcttac ttatatgttg    120
tggaaatgta aagagcccga attcctcata ctctggaatc gaaattccgt tggaaaaatt    180
cgctttgtag tgaaaaataa agatgtcaat aaagggtatt gagaatttcc aatggaatta    240
tcagcaatag atgatagaaa gaattcctca tactctggaa tcgaattcc gttggaaaaa     300 ttcgctttgt agtgaaaaat aaagatgtca ataaagggta ttgagaattt ccaatggaat    360
tatcagcaat agatgataga agaattcgg atgataatgc gattagtttt ttagccttat     420
ttctggggta attaatcagc gaagcgatga ttttgatct attaacagat atataaatgg     480
aaaagctgca taaccacttt aactaatact ttcaacattt tcagtttgta ttacttctta    540
ttcaaatgtc ataaaagtat caacaaaaaa ttgttaatat acctctatac tttaacgtca    600
aggagaaaaa actata                                                    616
```

<210> SEQ ID NO 88
<211> LENGTH: 616
<212> TYPE: DNA
<213> ORGANISM: Artificial Sequence
<220> FEATURE:
<223> OTHER INFORMATION: pLYR4p
<220> FEATURE:

<223> OTHER INFORMATION: pLYR4p

<400> SEQUENCE: 88

```
ttatattgaa ttttcaaaaa ttcttacttt tttttggat ggacgcaaag aagtttaata      60
atcatattac atggcattac caccatatac atatccatat ctaatcttac ttatatgttg     120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattctttc tatcatctat tgctgataat tccattggaa    300
attctcaata ccctttattg acatctttat ttttcactac aaagcgaatt tttccaacgg    360
aatttcgatt ccagagtatg aggaattcgg atgataatgc gattagtttt ttagccttat    420
ttctggggta attaatcagc gaagcgatga ttttgatct attaacagat atataaatgg     480
aaaagctgca taaccacttt aactaatact ttcaacattt tcagtttgta ttacttctta    540
ttcaaatgtc ataaaagtat caacaaaaaa ttgttaatat acctctatac tttaacgtca    600
aggagaaaaa actata                                                     616
```

<210> SEQ ID NO 89
<211> LENGTH: 738
<212> TYPE: DNA
<213> ORGANISM: Artificial Sequence
<220> FEATURE:
<223> OTHER INFORMATION: pLYR5p
<220> FEATURE:
<223> OTHER INFORMATION: pLYR5p

<400> SEQUENCE: 89

```
ttatattgaa ttttcaaaaa ttcttacttt tttttggat ggacgcaaag aagtttaata      60
atcatattac atggcattac caccatatac atatccatat ctaatcttac ttatatgttg    120
tggaaatgta aagagcccga attctttcta tcatctattg ctgataattc cattggaaat    180
tctcaatacc ctttattgac atctttattt ttcactacaa agcgaatttt tccaacggaa    240
tttcgattcc agagtatgag gaattctttc tatcatctat tgctgataat tccattggaa    300
attctcaata ccctttattg acatctttat ttttcactac aaagcgaatt tttccaacgg    360
aatttcgatt ccagagtatg aggaattctt tctatcatct attgctgata attccattgg    420
aaattctcaa tacccttttat tgacatcttt atttttcact acaaagcgaa tttttccaac    480
ggaatttcga ttccagagta tgaggaattc ggatgataat gcgattagtt ttttagcctt    540
atttctgggg taattaatca gcgaagcgat gattttgat ctattaacag atatataaat     600
ggaaaagctg cataaccact ttaactaata ctttcaacat tttcagtttg tattacttct    660
tattcaaatg tcataaaagt atcaacaaaa aattgttaat atacctctat actttaacgt    720
caaggagaaa aaactata                                                   738
```

<210> SEQ ID NO 90
<211> LENGTH: 1104
<212> TYPE: DNA
<213> ORGANISM: Artificial Sequence
<220> FEATURE:
<223> OTHER INFORMATION: pLYR6p
<220> FEATURE:
<223> OTHER INFORMATION: pLYR6p

<400> SEQUENCE: 90

```
ttatattgaa ttttcaaaaa ttcttacttt tttttggat ggacgcaaag aagtttaata      60
atcatattac atggcattac caccatatac atatccatat ctaatcttac ttatatgttg    120
```

```
tggaaatgta aagagcccga attgctcata ctctggaatc gaaattccgt tggaaaaatt      180
cgctttgtag tgaaaaataa agatgtcaat aaagggtatt gagaatttcc aatggaatta      240
tcagcaatag atgatagaaa gaattcctca tactctggaa tcgaaattcc gttggaaaaa      300
ttcgctttgt agtgaaaaat aaagatgtca ataagggtta ttgagaattt ccaatggaat      360
tatcagcaat agatgataga agaattcctc atactctgg aatcgaaatt ccgttggaaa       420
aattcgcttt gtagtgaaaa ataaagatgt caataaaggg tattgagaat ttccaatgga      480
attatcagca atagatgata gaaacaattg ctcatactct ggaatcgaaa ttccgttgga      540
aaaattcgct ttgtagtgaa aataaagat gtcaataaag ggtattgaga atttccaatg       600
gaattatcag caatagatga tagaaagaat tcctcatact ctggaatcga attccgttg       660 gaaaaattcg ctttgtagtg aaaaataaag atgtcaataa agggtattga aatttccaa       720 tggaattatc agcaatagat gatagaaaga attcctcata ctctggaatc gaaattccgt      780
tggaaaaatt cgctttgtag tgaaaaataa agatgtcaat aaagggtatt gagaatttcc      840
aatggaatta tcagcaatag atgatagaaa caattcggat gataatgcga ttagtttttt      900
agccttattt ctggggtaat taatcagcga agcgatgatt tttgatctat aacagatat      960 ataaatggaa aagctgcata accactttaa ctaatacttt caacattttc agtttgtatt     1020
acttcttatt caaatgtcat aaaagtatca acaaaaaatt gttaatatac ctctatactt     1080
taacgtcaag gagaaaaaac tata                                            1104

<210> SEQ ID NO 91
<211> LENGTH: 1836
<212> TYPE: DNA
<213> ORGANISM: Artificial Sequence
<220> FEATURE:
<223> OTHER INFORMATION: pLYR7p
<220> FEATURE:
<223> OTHER INFORMATION: pLYR7p

<400> SEQUENCE: 91
ttatattgaa ttttcaaaaa ttcttacttt ttttttggat ggacgcaaag aagtttaata       60
atcatattac atggcattac caccatatac atatccatat ctaatcttac ttatatgttg      120
tggaaatgta aagagcccga attgtttcta tcatctattg ctgataattc cattggaaat      180
tctcaatacc cttattgac atctttattt ttcactacaa agcgaatttt tccaacggaa       240
tttcgattcc agagtatgag gaattctttc tatcatctat tgctgataat tccattggaa      300
attctcaata cccttttattg acatctttat ttttcactac aaagcgaatt tttccaacgg      360
aatttcgatt ccagagtatg aggaattctt tctatcatct attgctgata attccattgg      420
aaattctcaa tacccttttat tgacatcttt attttttcact acaaagcgaa ttttttccaac     480 ggaatttcga ttccagagta tgagcaattg tttctatcat ctattgctga taattccatt      540
ggaaattctc ataccctttt attgacatct ttattttttca ctacaaagcg aattttttcca     600 acggaatttc gattccagag tatgaggaat tctttctatc atctattgct gataattcca      660
ttggaaattc tcaataccct ttattgacat ctttattttt cactacaaag cgaatttttc      720
caacggaatt tcgattccag agtatgagga attcttttcta tcatctattg ctgataattc     780
cattggaaat tctcaatacc ctttattgac atctttattt ttcactacaa agcgaatttt      840
tccaacggaa tttcgattcc agagtatgag caattgtttc tatcatctat tgctgataat      900
tccattggaa attctcaata cccttttattg acatctttat ttttcactac aaagcgaatt     960
```

-continued

| | | |
|---|---|---|
| tttccaacgg aatttcgatt ccagagtatg aggaattctt tctatcatct attgctgata | 1020 |
| attccattgg aaattctcaa taccctttat tgacatcttt attttcact acaaagcgaa | 1080 |
| tttttccaac ggaatttcga ttccagagta tgaggaattc tttctatcat ctattgctga | 1140 |
| taattccatt ggaaattctc aatacccttt attgacatct ttatttttca ctacaaagcg | 1200 |
| aattttccaa cggaatttcg attccagagt atgagcaatg tttctatc atctattgct | 1260 |
| gataattcca ttggaaattc tcaataccct ttattgacat ctttatttt cactacaaag | 1320 |
| cgaattttc aacggaatt tcgattccag agtatgagga attctttcta tcatctattg | 1380 |
| ctgataattc cattggaaat tctcaatacc cttattgac atctttattt ttcactacaa | 1440 |
| agcgaatttt tccaacggaa tttcgattcc agagtatgag gaattctttc tatcatctat | 1500 |
| tgctgataat tccattggaa attctcaata cctttattg acatctttat tttcactac | 1560 |
| aaagcgaatt tttccaacgg aatttcgatt ccagagtatg agcaattcgg atgataatgc | 1620 |
| gattagtttt ttagccttat ttctggggta attaatcagc gaagcgatga tttttgatct | 1680 |
| attaacagat atataaatgg aaaagctgca taaccacttt aactaatact ttcaacattt | 1740 |
| tcagtttgta ttacttctta ttcaaatgtc ataaaagtat caacaaaaaa ttgttaatat | 1800 |
| acctctatac tttaacgtca aggagaaaaa actata | 1836 |

<210> SEQ ID NO 92
<211> LENGTH: 981
<212> TYPE: DNA
<213> ORGANISM: Artificial Sequence
<220> FEATURE:
<223> OTHER INFORMATION: pLYR8
<220> FEATURE:
<223> OTHER INFORMATION: pLYR8

<400> SEQUENCE: 92

| | | |
|---|---|---|
| ttacattatc aatccttgcg tttcagcttc cactaattta gatgactatt tctcatcatt | 60 |
| tgcgtcatct tctaacaccg tatatgataa tatactagta acgtaaatac tagttagtag | 120 |
| atgatagttg atttttattc caacactaag aaataattc gccatttctt gaatgtattt | 180 |
| aaagatattt aatgctataa tagacatta aatccaattc ttccaacata caatgggagt | 240 |
| ttggccgagt ggtttaaggc gtcagattta ggtggattta acctctaaaa tctctgatat | 300 |
| cttcggatgc aagggttcga atcccttagc tctcattatt ttttgctttt tctcttgaat | 360 |
| tgctcatact ctggaatcga aattccgttg gaaaaattcg ctttgtagtg aaaaataaag | 420 |
| atgtcaataa agggtattga gaatttccaa tggaattatc agcaatagat gatagaaaga | 480 |
| attcctcata ctctggaatc gaaattccgt tggaaaaatt cgctttgtag tgaaaaataa | 540 |
| agatgtcaat aaagggtatt gagaatttcc aatggaatta tcagcaatag atgatagaaa | 600 |
| gaattcctca tactctggaa tcgaaattcc gttggaaaaa ttcgctttgt agtgaaaaat | 660 |
| aaagatgtca ataaagggta ttgagaattt ccaatggaat tatcagcaat agatgataga | 720 |
| aacaattcta attaagttag tcaaggcgcc atcctcatga aaactgtgta acataataac | 780 |
| cgaagtgtcg aaaaggtggc accttgtcca attgaacacg ctcgatgaaa aaataagat | 840 |
| atatataagg ttaagtaaag cgtctgttag aaaggaagtt tttcctttttt cttgctctct | 900 |
| tgtcttttca tctactattt ccttcgtgta atacagggtc gtcagataca tagatacaat | 960 |
| tctattaccc ccatccatac a | 981 |

<210> SEQ ID NO 93
<211> LENGTH: 981

```
<212> TYPE: DNA
<213> ORGANISM: Artificial Sequence
<220> FEATURE:
<223> OTHER INFORMATION: pLYR9
<220> FEATURE:
<223> OTHER INFORMATION: pLYR9

<400> SEQUENCE: 93
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtttctatc atctattgct gataattcca ttggaaattc tcaatacct ttattgacat    420
ctttatttt cactacaaag cgaattttc caacggaatt tcgattccag agtatgagga    480
attctttcta tcatctattg ctgataattc cattggaaat tctcaatacc ctttattgac   540
atctttattt tcactacaa agcgaattttt tccaacggaa tttcgattcc agagtatgag   600
gaattctttc tatcatctat tgctgataat tccattggaa attctcaata ccctttattg   660
acatctttat ttttcactac aaagcgaatt tttccaacgg aatttcgatt ccagagtatg   720
agcaattcta attaagttag tcaaggcgcc atcctcatga aaactgtgta acataataac   780
cgaagtgtcg aaaaggtggc accttgtcca attgaacacg ctcgatgaaa aaataagat    840
atatataagg ttaagtaaag cgtctgttag aaaggaagtt tttcctttt cttgctctct    900
tgtcttttca tctactatt ccttcgtgta atacagggtc gtcagataca tagatacaat    960
tctattaccc ccatccatac a                                            981

<210> SEQ ID NO 94
<211> LENGTH: 1225
<212> TYPE: DNA
<213> ORGANISM: Artificial Sequence
<220> FEATURE:
<223> OTHER INFORMATION: pLYR10
<220> FEATURE:
<223> OTHER INFORMATION: pLYR10

<400> SEQUENCE: 94
ttacattatc aatccttgcg tttcagcttc cactaattta gatgactatt tctcatcatt    60
tgcgtcatct tctaacaccg tatatgataa tatactagta acgtaaatac tagttagtag   120
atgatagttg attttattc caacactaag aaataattc gccatttctt gaatgtattt    180
aaagatattt aatgctataa tagacattta aatccaattc ttccaacata caatgggagt   240
ttggccgagt ggtttaaggc gtcagattta ggtggattta acctctaaaa tctctgatat   300
cttcggatgc aagggttcga atcccttagc tctcattatt ttttgctttt tctcttgaat   360
tgtttctatc atctattgct gataattcca ttggaaattc tcaatacct ttattgacat    420
ctttatttt cactacaaag cgaattttc caacggaatt tcgattccag agtatgagga    480
attctttcta tcatctattg ctgataattc cattggaaat tctcaatacc ctttattgac   540
atctttattt tcactacaa agcgaattttt tccaacggaa tttcgattcc agagtatgag   600
gaattctttc tatcatctat tgctgataat tccattggaa attctcaata ccctttattg   660
acatctttat ttttcactac aaagcgaatt tttccaacgg aatttcgatt ccagagtatg   720
```

```
aggaattctt tctatcatct attgctgata attccattgg aaattctcaa tacccttat      780 tgacatcttt attttcact acaaagcgaa ttttccaac ggaatttcga ttccagagta      840
tgaggaattc tttctatcat ctattgctga taattccatt ggaaattctc aatacccttt      900
attgacatct ttatttttca ctacaaagcg aattttccca acggaatttc gattccagag      960
tatgagcaat tctaattaag ttagtcaagg cgccatcctc atgaaaactg tgtaacataa     1020
taaccgaagt gtcgaaaagg tggcaccttg tccaattgaa cacgctcgat gaaaaaaata     1080
agatatatat aaggttaagt aaagcgtctg ttagaaagga agtttttcct ttttcttgct     1140
ctcttgtctt ttcatctact atttccttcg tgtaatacag ggtcgtcaga tacatagata     1200
caattctatt accccatcc ataca                                           1225
```

<210> SEQ ID NO 95
<211> LENGTH: 1347
<212> TYPE: DNA
<213> ORGANISM: Artificial Sequence
<220> FEATURE:
<223> OTHER INFORMATION: pLYR11
<220> FEATURE:
<223> OTHER INFORMATION: pLYR11

<400> SEQUENCE: 95

```
ttacattatc aatccttgcg tttcagcttc cactaattta gatgactatt tctcatcatt       60
tgcgtcatct tctaacaccg tatatgataa tatactagta acgtaaatac tagttagtag      120
atgatagttg attttttattc caacactaag aaataaattc gccatttctt gaatgtattt      180
aaagatattt aatgctataa tagacattta aatccaattc ttccaacata caatgggagt      240
ttggccgagt ggtttaaggc gtcagattta ggtggattta acctctaaaa tctctgatat      300
cttcggatgc aagggttcga atcccttagc tctcattatt ttttgctttt tctcttgaat      360
tgctcatact ctggaatcga aattccgttg gaaaaattcg ctttgtagtg aaaaataaag      420
atgtcaataa agggtattga gaatttccaa tggaattatc agcaatagat gatagaaaga      480
attcctcata ctctggaatc gaaattccgt tggaaaaatt cgctttgtag tgaaaaataa      540
agatgtcaat aaagggtatt gagaatttcc aatggaatta tcagcaatag atgatagaaa      600
gaattcctca tactctggaa tcgaaattcc gttggaaaaa ttcgctttgt agtgaaaaat      660
aaagatgtca ataagggta ttgagaattt ccaatggaat tatcagcaat agatgataga      720
aagaattcct catactctgg aatcgaaatt ccgttggaaa aattcgcttt gtagtgaaaa      780
ataaagatgt caataaaggg tattgagaat ttccaatgga attatcagca atagatgata      840
gaaagaattc ctcatactct ggaatcgaaa ttccgttgga aaaattcgct ttgtagtgaa      900
aaataaagat gtcaataaag ggtattgaga atttccaatg gaattatcag caatagatga      960
tagaaagaat tcctcatact ctggaatcga aattccgttg gaaaaattcg ctttgtagtg     1020
aaaaataaag atgtcaataa agggtattga gaatttccaa tggaattatc agcaatagat     1080
gatagaaaca attctaatta agttagtcaa ggcgccatcc tcatgaaaac tgtgtaacat     1140
aataaccgaa gtgtcgaaaa ggtggcacct tgtccaattg aacacgctcg atgaaaaaaa     1200
taagatatat ataaggttaa gtaaagcgtc tgttagaaag gaagttttc ctttttcttg     1260 ctctcttgtc ttttcatcta ctatttcctt cgtgtaatac agggtcgtca gatacataga     1320
tacaattcta ttaccccat ccataca                                         1347
```

<210> SEQ ID NO 96
<211> LENGTH: 686

```
<212> TYPE: DNA
<213> ORGANISM: Saccharomyces cerevisiae
<220> FEATURE:
<223> OTHER INFORMATION: pMET17
<220> FEATURE:
<223> OTHER INFORMATION: pMET17

<400> SEQUENCE: 96
ttacattatc aatccttgcg tttcagcttc cactaattta gatgactatt tctcatcatt      60
tgcgtcatct tctaacaccg tatatgataa tatactagta acgtaaatac tagttagtag     120
atgatagttg atttttattc caacactaag aaataaattc gccatttctt gaatgtattt     180
aaagatattt aatgctataa tagacattta aatccaattc ttccaacata caatgggagt     240
ttggccgagt ggtttaaggc gtcagattta ggtggattta acctctaaaa tctctgatat     300
cttcggatgc aagggttcga atcccttagc tctcattatt ttttgctttt tctcttgagg     360
tcacatgatc gcaaaatggc aaatggcacg tgaagctgtc gatattgggg aactgtggtg     420
gttggcaaat gactaattaa gttagtcaag gcgccatcct catgaaaact gtgtaacata     480
ataaccgaag tgtcgaaaag gtggcacctt gtccaattga acacgctcga tgaaaaaaat     540
aagatatata taaggttaag taaagcgtct gttagaaagg aagttttttcc tttttcttgc    600 tctcttgtct tttcatctac tatttccttc gtgtaataca gggtcgtcag atacatagat     660
acaattctat taccccatc cataca                                           686

<210> SEQ ID NO 97
<211> LENGTH: 510
<212> TYPE: DNA
<213> ORGANISM: Saccharomyces cerevisiae
<220> FEATURE:
<223> OTHER INFORMATION: pMET6
<220> FEATURE:
<223> OTHER INFORMATION: pMET6

<400> SEQUENCE: 97
ccacaggaaa tatttcacgt gacttacaaa cagagtcgta cgtcaggacc ggagtcaggt      60
gaaaaaatgt gggccggtaa agggaaaaaa ccagaaacgg gactactatc gaactcgttt     120
agtcgcgaac gtgcaaaagg ccaatatttt tcgctagagt catcgcagtc atggcagctc     180
tttcgctcta tctcccggtc gcaaaactgt ggtagtcata gctcgttctg ctcaattgag     240
aactgtgaat gtgaatatgg aacaaatgcg atagatgcac taatttaagg gaagctagct     300
agttttccca actgcgaaag aaaaaaagga aagaaaaaaa aattctatat aagtgataga     360
tatttccatc tttactagca ttagtttctc ttttacgtat tcaatatttt tgttaaactc     420
ttcctttatc ataaaaagc aagcatctaa gagcattgac aacactctaa gaaacaaaat     480
accaatataa tttcaaagta catatcaaaa                                      510

<210> SEQ ID NO 98
<211> LENGTH: 508
<212> TYPE: DNA
<213> ORGANISM: Saccharomyces cerevisiae
<220> FEATURE:
<223> OTHER INFORMATION: pMET14
<220> FEATURE:
<223> OTHER INFORMATION: pMET14

<400> SEQUENCE: 98
cctatgcatg tttagagcaa gcgcctttgt gagccctccc ggttacgacg ccttggcaat      60
gtagcagata actctgcact tctagaatca ttccactacg acatttggct catcaccagc     120
```

```
tcgcgagaaa tgtaaataag ccaacaacca agaatgcgta acattaaaga atacagttgc    180
tttcatttcg gcgtgatggt acggcaccca cggttcctta cattattctc gaaaaatagc    240
tgcacgcttt tccaggaata aaagaccgtg ccactaattt cacgtgatca atatatttac    300
aagccacctc aaaaaatgtg gcaatggaga agaggatgaa cgactcaata tgacttcaac    360
ttcatgaatt tgtcaaaata tctatataag atgcaaaatt tctatacaac atcagttgcg    420
tatccgttaa tgtcgttcat tttctctctt tgttcgaact tgacatcaag aaaagttgga    480
attatttctc caagcacact gtacacca                                       508

<210> SEQ ID NO 99
<211> LENGTH: 552
<212> TYPE: DNA
<213> ORGANISM: Saccharomyces cerevisiae
<220> FEATURE:
<223> OTHER INFORMATION: pMET3
<220> FEATURE:
<223> OTHER INFORMATION: pMET3

<400> SEQUENCE: 99
aacgatatgt acgtagtggt ataaggtgag ggggtccaca gatataacat cgtttaattt    60
agtactaaca gagactttg tcacaactac atataagtgt acaaatatag tacagatatg     120
acacacttgt agcgccaacg cgcatcctac ggattgctga cagaaaaaaa ggtcacgtga    180
ccagaaaagt cacgtgtaat tttgtaactc accgcattct agcggtccct gtcgtgcaca    240
ctgcactcaa caccataaac cttagcaacc tccaaggaa atcaccgtat aacaaagcca     300
cagttttaca acttagtctc ttatgaagtt acttaccaat gagaaataga ggctcttct    360 cgacaaatat gaatatggat atatatatat atatatat atatatat atatatatgt       420 aaacttggtt ctttttttagc ttgtgatctc tagcttgggc ctctctctgt cgtaacagtt    480
gtgatatcgt ttcttaacaa ttgaaaagga actaagaaag tataataata acaagaataa    540
agtataatta ac                                                         552

<210> SEQ ID NO 100
<211> LENGTH: 363
<212> TYPE: DNA
<213> ORGANISM: Saccharomyces cerevisiae
<220> FEATURE:
<223> OTHER INFORMATION: pSAM1
<220> FEATURE:
<223> OTHER INFORMATION: pSAM1

<400> SEQUENCE: 100
gaaacggacg taagacggaa atagaatttg aagataaagt tatatatcac tacacacgaa    60
tactttcttt ttttttttc acaggaaaac tgtggtggcg cccttgccta ctagtgcatt    120 tctttttcg ggttcttgtc tcgacgaaat tttagcctca tcgtagtttt tcactctggt     180
atcgatgaaa aagggaagag taaaaagttt tccgtttagt acttaatggg attggtttgg    240
gacgtatata tcgactggtg ttgtctgtta ttcatcgttg tttttcggtt agcttcgaaa    300
aaaaaataga gtaaaaacca ggaatttacc ctaaaaacaa gaaaaaataa gataaacgaa    360
aat                                                                   363

<210> SEQ ID NO 101
<211> LENGTH: 500
<212> TYPE: DNA
<213> ORGANISM: Saccharomyces cerevisiae
<220> FEATURE:
<223> OTHER INFORMATION: pSAM2
```

<220> FEATURE:
<223> OTHER INFORMATION: pSAM2

<400> SEQUENCE: 101

| | | | | | |
|---|---|---|---|---|---|
| gagctttgct | ctattatata | agataaaata | tgcactaaaa | gtttgcattt | ctttacataa | 60 |
| ctaaaactaa | gacattatgc | atagcttacc | tgatcaaaaa | gtatgtaaac | ttgttaacat | 120 |
| cttcacatgt | gattcatctg | gtcgtacttt | cttgcggtgc | agtgtaatat | ttctacccac | 180 |
| gtgactataa | ttgagcttga | aaactgtggc | gttttccac | cgatgggtcc | acgccagata | 240 |
| ttaaccgaag | ccaaaatacc | gatgaaattt | ctgagatagc | tcttgtaaac | gacgtcaaat | 300 |
| cttcatatgc | aaggagatct | tgatttcttt | ttggtagtca | tctgtcgtct | tgaggcgtat | 360 |
| aagaaggagg | ttatatctgt | cctttctaca | aagtattttc | gagaatcttg | cttctgcccc | 420 |
| tttttctt | ttttaaaagg | tttaaaaaac | ataactgtct | tcaatatatc | cagtatttac | 480 |
| gacaatatac | aaacataatc | | | | | 500 |

<210> SEQ ID NO 102
<211> LENGTH: 300
<212> TYPE: DNA
<213> ORGANISM: Saccharomyces cerevisiae
<220> FEATURE:
<223> OTHER INFORMATION: tTDH2
<220> FEATURE:
<223> OTHER INFORMATION: tTHD2

<400> SEQUENCE: 102

| | | | | | |
|---|---|---|---|---|---|
| atttaactcc | ttaagttact | ttaatgattt | agtttttatt | attaataatt | catgctcatg | 60 |
| acatctcata | tacacgttta | taaaacttaa | atagattgaa | aatgtattaa | agattcctca | 120 |
| gggattcgat | ttttttggaa | gttttgtgtt | ttttttcctt | gagatgctgt | agtatttggg | 180 |
| aacaattata | caatcgaaag | atatatgctt | acattcgacc | gttttagccg | tgatcattat | 240 |
| cctatagtaa | cataacctga | agcataactg | acactactat | catcaatact | tgtcacatga | 300 |

<210> SEQ ID NO 103
<211> LENGTH: 300
<212> TYPE: DNA
<213> ORGANISM: Saccharomyces cerevisiae
<220> FEATURE:
<223> OTHER INFORMATION: tCYC1
<220> FEATURE:
<223> OTHER INFORMATION: tCYC1

<400> SEQUENCE: 103

| | | | | | |
|---|---|---|---|---|---|
| acaggccct | tttcctttgt | cgatatcatg | taattagtta | tgtcacgctt | acattcacgc | 60 |
| cctcctccca | catccgctct | aaccgaaaag | gaaggagtta | gacaacctga | agtctaggtc | 120 |
| cctatttatt | tttttaata | gttatgttag | tattaagaac | gttatttata | tttcaaattt | 180 |
| ttcttttttt | tctgtacaaa | cgcgtgtacg | catgtaacat | tatactgaaa | accttgcttg | 240 |
| agaaggtttt | gggacgctcg | aaggctttaa | tttgcaagct | tcgcagttta | cactctcatc | 300 |

<210> SEQ ID NO 104
<211> LENGTH: 300
<212> TYPE: DNA
<213> ORGANISM: Saccharomyces cerevisiae
<220> FEATURE:
<223> OTHER INFORMATION: tTDH3
<220> FEATURE:
<223> OTHER INFORMATION: tTDH3

<400> SEQUENCE: 104

```
gtgaatttac tttaaatctt gcatttaaat aaattttctt tttatagctt tatgacttag    60
tttcaattta tatactattt taatgacatt ttcgattcat tgattgaaag ctttgtgttt   120
tttcttgatg cgctattgca ttgttcttgt ctttttcgcc acatgtaata tctgtagtag   180
atacctgata cattgtggat gctgagtgaa attttagtta ataatggagg cgctcttaat   240
aattttgggg atattggctt tttttttttaa agtttacaaa tgaattttttt ccgccaggat   300
```

<210> SEQ ID NO 105
<211> LENGTH: 354
<212> TYPE: DNA
<213> ORGANISM: Saccharomyces cerevisiae
<220> FEATURE:
<223> OTHER INFORMATION: tADH1
<220> FEATURE:
<223> OTHER INFORMATION: tADH1

<400> SEQUENCE: 105

```
actagttcta gagcggccgc caccgcggtg gcgaatttc ttatgattta tgatttttat    60
tattaaataa gttataaaaa aataagtgt atacaaattt taaagtgact cttaggtttt   120
aaaacgaaaa ttcttattct tgagtaactc tttcctgtag gtcaggttgc tttctcaggt   180
atagcatgag gtcgctctta ttgaccacac ctctaccggc atgccagcaa atgcctgca   240 aatcgctccc catttcaccc aattgtagat atgctaactc cagcaatgag ttgatgaatc   300
tcggtgtgta ttttatgtcc tcagaggaca acacctgttg taatcgttct tcca         354
```

<210> SEQ ID NO 106
<211> LENGTH: 301
<212> TYPE: DNA
<213> ORGANISM: Saccharomyces cerevisiae
<220> FEATURE:
<223> OTHER INFORMATION: tADH2
<220> FEATURE:
<223> OTHER INFORMATION: tADH2

<400> SEQUENCE: 106

```
gcggatctct tatgtcttta cgatttatag ttttcattat caagtatgcc tatattagta    60
tatagcatct ttagatgaca gtgttcgaag tttcacgaat aaaagataat attctacttt   120
ttgctcccac cgcgtttgct agcacgagtg aacaccatcc ctcgcctgtg agttgtaccc   180
attcctctaa actgtagaca tggtagcttc agcagtgttc gttatgtacg gcatcctcca   240
acaaacagtc ggttatagtt tgtcctgctc ctctgaatcg tctccctcga tatttctcat   300
t                                                                    301
```

<210> SEQ ID NO 107
<211> LENGTH: 299
<212> TYPE: DNA
<213> ORGANISM: Saccharomyces cerevisiae
<220> FEATURE:
<223> OTHER INFORMATION: tTPI1
<220> FEATURE:
<223> OTHER INFORMATION: tTPI1

<400> SEQUENCE: 107

```
gattaatata attatataaa aatattatct tcttttctttt atatctagtg ttatgtaaaa    60
taaattgatg actacggaaa gcttttttat attgtttctt tttcattctg agccacttaa   120
atttcgtgaa tgttcttgta agggacggta gatttacaag tgatacaaca aaaagcaagg   180 cgcttttttct aataaaaaga agaaaagcat ttaacaattg aacacctcta tatcaacgaa   240
gaatattact ttgtctctaa atccttgtaa aatgtgtacg atctctatat gggttactc    299
```

<210> SEQ ID NO 108
<211> LENGTH: 299
<212> TYPE: DNA
<213> ORGANISM: Saccharomyces cerevisiae
<220> FEATURE:
<223> OTHER INFORMATION: tMET17
<220> FEATURE:
<223> OTHER INFORMATION: tMET17

<400> SEQUENCE: 108

```
gtgtgcgtaa tgagttgtaa aattatgtat aaacctactt tctctcacaa gtactatact    60
tttataaaac gaactttatt gaaatgaata tcctttttt cccttgttac atgtcgtgac   120
tcgtactttg aacctaaatt gttctaacat caaagaacag tgttaattcg cagtcgagaa   180
gaaaaatatg gtgaacaaga ctcatctact tcatgagact actttacgcc tcctataaag   240
ctgtcacact ggataaattt attgtaggac caagttacaa agaggatga tggaggttt     299
```

<210> SEQ ID NO 109
<211> LENGTH: 305
<212> TYPE: DNA
<213> ORGANISM: Saccharomyces cerevisiae
<220> FEATURE:
<223> OTHER INFORMATION: tENO2
<220> FEATURE:
<223> OTHER INFORMATION: tENO2

<400> SEQUENCE: 109

```
ggatcctaaa gtgctttaa ctaagaatta ttagtctttt ctgcttattt tttcatcata    60
gtttagaaca ctttatatta acgaatagtt tatgaatcta tttaggttta aaaattgata   120
cagttttata agttactttt tcaaagactc gtgctgtcta ttgcataatg cactggaagg   180
ggaaaaaaaa ggtgcacacg cgtggctttt tcttgaattt gcagtttgaa aataactac   240
atggatgata agaaaacatg gagtacagtc actttgagaa ccttcaatca gctggtaacg   300
tcttc                                                              305
```

<210> SEQ ID NO 110
<211> LENGTH: 300
<212> TYPE: DNA
<213> ORGANISM: Saccharomyces cerevisiae
<220> FEATURE:
<223> OTHER INFORMATION: tMET3
<220> FEATURE:
<223> OTHER INFORMATION: tMET3

<400> SEQUENCE: 110

```
tcgtcataaa atgctcccat ctcaaaagta gggcaaaatt catgatcgac cgcgcaaaat    60
aaatagattt gcaaataagt tttgtatgta catttattaa tatatataat atatcaaaag   120
aaaaaaatca aaaaaaaaaa aaaaaaaaa ttgcactctt attcagtcat caattacaaa   180
acctagagat agcgatggtg catattcaat aaaaaactcc ttatactgtc gagaaagctt   240
attattggta cttctcgaag atactaaaaa aggttaattt ttggagacgg aggcaatagc   300
```

<210> SEQ ID NO 111
<211> LENGTH: 301
<212> TYPE: DNA
<213> ORGANISM: Saccharomyces cerevisiae
<220> FEATURE:
<223> OTHER INFORMATION: tPGK1
<220> FEATURE:
<223> OTHER INFORMATION: tPGK1

<400> SEQUENCE: 111

```
attgaattga attgaaatcg atagatcaat ttttttcttt tctctttccc catcctttac      60
gctaaaataa tagtttattt tatttttga atatttttta tttatatacg tatatataga      120
ctattattta tcttttaatg attattaaga tttttattaa aaaaaaattc gctcctcttt     180
taatgccttt atgcagtttt tttttcccat tcgatatttc tatgttcggg ttcagcgtat     240
tttaagttta ataactcgaa aattctgcgt tcgttaaagc tttcgagaag gatattattt     300
a                                                                     301
```

<210> SEQ ID NO 112
<211> LENGTH: 300
<212> TYPE: DNA
<213> ORGANISM: Saccharomyces cerevisiae
<220> FEATURE:
<223> OTHER INFORMATION: tDIT1
<220> FEATURE:
<223> OTHER INFORMATION: tDIT1

<400> SEQUENCE: 112

```
taaagtaaga gcgctacatt ggtctaccct tttgttcttt tacttaaaca ttagttagtt      60
cgttttcttt ttctcatttt tttatgtttc cccccaaag ttctgatttt ataatatttt      120
atttcacaca attccattta acagaggggg aatagattct ttagcttaga aaattagtga     180
tcaatatata tttgcctttc ttttcatctt ttcagtgata ttaatggttt cgagacactg     240
caatggccct agttgtctaa gaggatagat gttactgtca aagatgatat tttgaatttc     300
```

<210> SEQ ID NO 113
<211> LENGTH: 300
<212> TYPE: DNA
<213> ORGANISM: Saccharomyces cerevisiae
<220> FEATURE:
<223> OTHER INFORMATION: tRPL3
<220> FEATURE:
<223> OTHER INFORMATION: tRPL3

<400> SEQUENCE: 113

```
gaagttttgt tagaaaataa atcatttttt aattgagcat tcttattcct attttattta      60
aatagtttta tgtattgtta gctacataca acagtttaaa tcaaattttc ttttccccaa     120
gtccaaaatg gaggtttatt ttgatgaccc gcatgcgatt atgttttgaa agtataagac     180
tacatacatg tacatatatt taaacatgta aacccgtcca ttatattgct tactttcttc     240
tttttttgccg ttttgacttg gacctctggt ttgctatttc cttacaatct ttgctacaat     300
```

<210> SEQ ID NO 114
<211> LENGTH: 300
<212> TYPE: DNA
<213> ORGANISM: Saccharomyces cerevisiae
<220> FEATURE:
<223> OTHER INFORMATION: tRPL41B
<220> FEATURE:
<223> OTHER INFORMATION: tRPL41B

<400> SEQUENCE: 114

```
gcggattgag agcaaatcgt taagttcagg tcaagtaaaa attgatttcg aaaactaatt      60
tctcttatac aatcctttga ttggaccgtc atcctttcga atataagatt tgttaagaa      120
tattttagac agagatctac tttatattta atatctagat attacataat ttcctctcta     180
ataaatatc attaataaaa taaaatgaa gcgatttgat tttgtgttgt caacttagtt       240
tgccgctatg cctcttgggt aatgctatta ttgaatcgaa gggctttatt atattaccct     300
```

<210> SEQ ID NO 115
<211> LENGTH: 300
<212> TYPE: DNA
<213> ORGANISM: Saccharomyces cerevisiae
<220> FEATURE:
<223> OTHER INFORMATION: tRPL15A
<220> FEATURE:
<223> OTHER INFORMATION: tRPL15A

<400> SEQUENCE: 115

```
gctggttgat ggaaaatata attttattgg caaactttt gtttatctga tgtgttttat      60
actattatct ttttaattaa tgattctata tacaaacctg tatattttt ctttaaccaa     120 tttttttttt tatagaccta gagctgtact tttattctgc tatcaagcaa acccctaccc    180
cctcttctca atcctcccct caggcagaac ttatctacct gtatcaagga gcggacgagg    240
gagtcctaat tgttctacgt ataccaatgc tagcagctta cataggtggt ggcactacca    300
```

<210> SEQ ID NO 116
<211> LENGTH: 300
<212> TYPE: DNA
<213> ORGANISM: Saccharomyces cerevisiae
<220> FEATURE:
<223> OTHER INFORMATION: tIDP1
<220> FEATURE:
<223> OTHER INFORMATION: tIDP1

<400> SEQUENCE: 116

```
tcgaatttac gtagcccaat ctaccacttt ttttttttcat ttttaaagt gttatactta     60 gttatgctct aggataatga actactttt ttttttttt tttactgtta tcataaatat    120 atataccta ttgttgtttg caaccgtcgg ttaattcctt atcaaggttc cccaagttcg    180
gatcattacc atcaatttcc aacatttttca tgagttcttc ttcttcatta ccgtgtttta    240
gggggctgtt cgcacttcta atagggctat caccaagctg ttctaattcg tccaaaagtt    300
```

<210> SEQ ID NO 117
<211> LENGTH: 1089
<212> TYPE: DNA
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 117

```
atgtctaaga atatcgttgt cctaccgggt gatcacgtcg gtaaagaagt tactgacgaa     60
gctattaagg tcttgaatgc cattgctgaa gtccgtccag aaattaagtt caatttccaa    120
catcacttga tcgggggtgc tgccatcgat gccactggca ctcctttacc agatgaagct    180
ctagaagcct ctaagaaagc cgatgctgtc ttactaggtg ctgttggtgg tccaaaatgg    240
ggtacgggcg cagttagacc agaacaaggt ctattgaaga tcagaaagga ttgggtcta    300 tacgccaact tgagaccatg taactttgct tctgattctt tactagatct ttctcctttg    360
aagcctgaat atgcaaaggg taccgattte gtcgtcgtta gagaattggt tggtggtatc    420
tactttggtg aaagaaaaga agatgaaggt gacggagttg cttgggactc tgagaaatac    480
agtgttcctg aagttcaaag aattacaaga atggctgctt tcttggcatt gcaacaaaac    540
ccaccattac caatctggtc tcttgacaag gctaacgtgc ttgcctcttc cagattgtgg    600
agaaagactg ttgaagaaac catcaagact gagttccac aattaactgt tcagcaccaa    660
```

-continued

```
ttgatcgact ctgctgctat gattttggtt aaatcaccaa ctaagctaaa cggtgttgtt    720
attaccaaca acatgtttgg tgatattatc tccgatgaag cctctgttat tccaggttct    780
ttgggtttat taccttctgc atctctagct tccctacctg acactaacaa ggcattcggt    840
ttgtacgaac catgtcatgg ttctgcccca gatttaccag caaacaaggt taacccaatt    900
gctaccatct tatctgcagc tatgatgttg aagttatcct ggatttggt tgaagaaggt     960 agggctcttg aagaagctgt tagaaatgtc ttggatgcag gtgtcagaac cggtgaccttt  1020 ggtggttcta actctaccac tgaggttggc gatgctatcg ccaaggctgt caaggaaatc   1080
ttggcttaa                                                           1089
```

```
<210> SEQ ID NO 118
<211> LENGTH: 362
<212> TYPE: PRT
<213> ORGANISM: Kluveromyces lactis
<220> FEATURE:
<223> OTHER INFORMATION: Leu2
<220> FEATURE:
<223> OTHER INFORMATION: Leu2

<400> SEQUENCE: 118
```

```
Met Ser Lys Asn Ile Val Val Leu Pro Gly Asp His Val Gly Lys Glu
1               5                   10                  15

Val Thr Asp Glu Ala Ile Lys Val Leu Asn Ala Ile Ala Glu Val Arg
            20                  25                  30

Pro Glu Ile Lys Phe Asn Phe Gln His His Leu Ile Gly Gly Ala Ala
        35                  40                  45

Ile Asp Ala Thr Gly Thr Pro Leu Pro Asp Glu Ala Leu Glu Ala Ser
    50                  55                  60

Lys Lys Ala Asp Ala Val Leu Leu Gly Ala Val Gly Gly Pro Lys Trp
65                  70                  75                  80

Gly Thr Gly Ala Val Arg Pro Glu Gln Gly Leu Leu Lys Ile Arg Lys
                85                  90                  95

Glu Leu Gly Leu Tyr Ala Asn Leu Arg Pro Cys Asn Phe Ala Ser Asp
            100                 105                 110

Ser Leu Leu Asp Leu Ser Pro Leu Lys Pro Glu Tyr Ala Lys Gly Thr
        115                 120                 125

Asp Phe Val Val Val Arg Glu Leu Val Gly Gly Ile Tyr Phe Gly Glu
    130                 135                 140

Arg Lys Glu Asp Glu Gly Asp Gly Val Ala Trp Asp Ser Glu Lys Tyr
145                 150                 155                 160

Ser Val Pro Glu Val Gln Arg Ile Thr Arg Met Ala Ala Phe Leu Ala
                165                 170                 175

Leu Gln Gln Asn Pro Pro Leu Pro Ile Trp Ser Leu Asp Lys Ala Asn
            180                 185                 190

Val Leu Ala Ser Ser Arg Leu Trp Arg Lys Thr Val Glu Glu Thr Ile
        195                 200                 205

Lys Thr Glu Phe Pro Gln Leu Thr Val Gln His Gln Leu Ile Asp Ser
    210                 215                 220

Ala Ala Met Ile Leu Val Lys Ser Pro Thr Lys Leu Asn Gly Val Val
225                 230                 235                 240

Ile Thr Asn Asn Met Phe Gly Asp Ile Ile Ser Asp Glu Ala Ser Val
                245                 250                 255

Ile Pro Gly Ser Leu Gly Leu Leu Pro Ser Ala Ser Leu Ala Ser Leu
            260                 265                 270
```

```
Pro Asp Thr Asn Lys Ala Phe Gly Leu Tyr Glu Pro Cys His Gly Ser
            275                 280                 285

Ala Pro Asp Leu Pro Ala Asn Lys Val Asn Pro Ile Ala Thr Ile Leu
290                 295                 300

Ser Ala Ala Met Met Leu Lys Leu Ser Leu Asp Leu Val Glu Glu Gly
305                 310                 315                 320

Arg Ala Leu Glu Glu Ala Val Arg Asn Val Leu Asp Ala Gly Val Arg
                325                 330                 335

Thr Gly Asp Leu Gly Gly Ser Asn Ser Thr Thr Glu Val Gly Asp Ala
            340                 345                 350

Ile Ala Lys Ala Val Lys Glu Ile Leu Ala
            355                 360

<210> SEQ ID NO 119
<211> LENGTH: 499
<212> TYPE: DNA
<213> ORGANISM: Saccharomyces cerevisiae
<220> FEATURE:
<223> OTHER INFORMATION: pNUP57
<220> FEATURE:
<223> OTHER INFORMATION: pNUP57

<400> SEQUENCE: 119
tcatctgcgc aatgactatc aagaccttct gcaagaattt caaatctcac tgaaaatctt      60
gaccgaaaag tgtcttgaaa acccatcaag cctgcaaaac ctatctttga cattagtctc     120
cattataaaa acggcatagt tgggagaaaa cttttcatac ttcaattgtg gactgatata     180
agtattttgg ttttgcccgc atgatcatcc cacatggcta cagcagttct ctcataggaa     240
atagtacaat agctacgtga tataatctaa ataattgttg ccaatgtgta attatatcat     300
tttgaacgtt cgcgaaatgg attattttca aaaattttgt ttcttgaaat gagtaaaagc     360
aaaagtccaa ctctccaagt cgatgtaaac aacttttgc caagggact gaaagactaa      420 atcgaggatt atcccgttca aactattcca gaaacgctcg ttagtaacaa aagacatacc     480
ttgttgacca attgatcac                                                  499

<210> SEQ ID NO 120
<211> LENGTH: 451
<212> TYPE: DNA
<213> ORGANISM: Saccharomyces cerevisiae
<220> FEATURE:
<223> OTHER INFORMATION: pGAP1
<220> FEATURE:
<223> OTHER INFORMATION: pGAP1

<400> SEQUENCE: 120
cactttcacc agatcccaaa tgtcccgccc ctattcccgt gttccatcac gtaccataac      60
ttaccatttc atcacgttct ctatggcaca ctggtactgc ttcgactgct ttgcttcatc     120
ttctctatgg gccaatgagc taatgagcac aatgtgctgc gaaataaagg gatatctaat     180
ttatattatt acattataat atgtactagt gtggttattg gtaattgtac ttaattttga     240
tatataaagg gtggatcttt ttcatttga atcagaattg gaattgcaac ttgtctcttg     300
tcactattac ttaatagtaa ttatatttct tattaacctt ttttttaagt caaaacacca     360
aggacaagaa ctactcttca aaggtatttc aagttatcat acgtctcaca cacgcttcac     420
agtttcaagt aaaaaaaaag aatattacac a                                    451

<210> SEQ ID NO 121
<211> LENGTH: 998
```

```
<212> TYPE: DNA
<213> ORGANISM: Saccharomyces cerevisiae
<220> FEATURE:
<223> OTHER INFORMATION: pJEN1
<220> FEATURE:
<223> OTHER INFORMATION: pJEN1

<400> SEQUENCE: 121
aatgtgttta taaattattt ttttgctgg tagcaaaatc aactcattgt cttccattca     60
gagtctaatc gaacgttatc gcaatgcttg cacactttta aacaatacga tttagtttaa   120
gtggatggac ccccacgctt agtgttccac aggtttgtcc ccactgtttt tacattccac   180
tgtacatttt tgcaatagaa ggtcattgta tgctaccttg ggcggctaag aatacctgta   240
aaaatttgga gaaattagat tcgtaaagaa tgactcgcaa cgactccaat gatttcttct   300
tttcacccctt tgaacggccg atatccgcgc gggatcctga ccccgcaatt tactccacta  360
gaccggcgtg tttctctttt tccttttcct ggggttagag cccaagagct aatagccgac   420
aaacggactc caaaaaaaaa aggaggcaca ggacaaacgc agcacctgcg tcattcacgc   480
tgaagcggca gcaagcattt tcgatcagct ccaattaaat gaagactatt cgccgtaccg   540
ttcccagatg ggtgcgaaag tcagtgatcg aggaagttat tgagcgcgcg gcttgaaact   600
atttctccat ctcagagccg ccaagcctac cattattctc caccaggaag ttagtttgta   660
agcttctgca caccatccgg acgtccataa ttcttcactt aacggtcttt tgccccccct   720
tctactataa tgcattagaa cgttacctgg tcatttggat ggagatctaa gtaacactta   780
ctatctccta tggtactatc ctttaccaaa aaaaaaaaa aaaaaaaaa aaaaaatcag     840
caaagtgaag taccctcttg atgtataaat acattgcaca tcattgttga gaaatagttt   900
tggaagttgt ctagtccttc tcccttagat ctaaaaggaa gaagagtaac agtttcaaaa   960
gttttccctc aaagagatta aatactgcta ctgaaaat                           998

<210> SEQ ID NO 122
<211> LENGTH: 450
<212> TYPE: DNA
<213> ORGANISM: Saccharomyces cerevisiae
<220> FEATURE:
<223> OTHER INFORMATION: pICL1
<220> FEATURE:
<223> OTHER INFORMATION: pICL1

<400> SEQUENCE: 122
ttttgctact cgtcatccga tgagaaaaac tgttcccttt tgccccaggt ttccattcat     60
ccgagcgatc acttatctga cttcgtcact tttcatttc atccgaaaca atcaaaactg    120
aagccaatca ccacaaaatt aacactcaac gtcatctttc actacccttt acagaagaaa   180
atatccatag tccggactag catcccagta tgtgactcaa tattggtgca aaagagaaaa   240
gcataagtca gtccaaagtc cgcccttaac caggcacatc ggaattcaca aaacgtttct   300
ttattatata aaggagctgc ttcactggca aaattcttat tatttgtctt ggcttgctaa   360
tttcatctta tccttttttt ctttttcacac ccaaatacct aacaattgag agaaaactct   420
tagcataaca taacaaaaag tcaacgaaaa                                     450

<210> SEQ ID NO 123
<211> LENGTH: 598
<212> TYPE: DNA
<213> ORGANISM: Saccharomyces cerevisiae
<220> FEATURE:
<223> OTHER INFORMATION: pADH2
<220> FEATURE:
```

<223> OTHER INFORMATION: pADH2

<400> SEQUENCE: 123

```
tatcttaact gatagtttga tcaaaggggc aaaacgtagg ggcaaacaaa cggaaaaatc      60
gtttctcaaa ttttctgatg ccaagaactc taaccagtct tatctaaaaa ttgccttatg     120
atccgtctct ccggttacag cctgtgtaac tgattaatcc tgcctttcta atcaccattc     180
taatgtttta attaagggat tttgtcttca ttaacggctt tcgctcataa aaatgttatg     240
acgttttgcc cgcaggcggg aaaccatcca cttcacgaga ctgatctcct ctgccggaac     300
accgggcatc tccaacttat aagttggaga aataagagaa tttcagattg agagaatgaa     360
aaaaaaaaaa aaaaaaggca gaggagagca tagaaatggg gttcactttt tggtaaagct     420
atagcatgcc tatcacatat aaatagagtg ccagtagcga cttttttcac actcgaaata     480
ctcttactac tgctctcttg ttgtttttat cacttcttgt ttcttcttgg taaatagaat     540
atcaagctac aaaaagcata caatcaacta tcaactatta actatatcgt aatacaca      598
```

<210> SEQ ID NO 124
<211> LENGTH: 793
<212> TYPE: DNA
<213> ORGANISM: Saccharomyces cerevisiae
<220> FEATURE:
<223> OTHER INFORMATION: pMLS1
<220> FEATURE:
<223> OTHER INFORMATION: pMLS1

<400> SEQUENCE: 124

```
tgtctaatgc gaaggtactt ttattttttt cagattcaaa gcaatattat ttagacaatt      60
gatactaagt gagcttaagg aggattaaac aactgtggaa tccttcacaa ggattcaata     120
tttgtttttc ctggttattt tgccatcatt caactttcct cagacgtaaa attcgtgctt     180
agtgatgtct caatattccc gcagggtaat aaaattcaat aactatcact atatacgcaa     240
cagtattacc ctacattgct atcggctcaa tggaaatccc catatcatag cttccattgg     300
gccgatgaag ttagtcgacg gatagaagcg gttgtcccct ttcccggcga gccggcagtc     360
gggccgaggt tcggataaat tttgtattgt gttttgattc tgtcatgagt attacttatg     420
ttctctttag gtaaccccag gttaatcaat cacagtttca taccggctag tattcaaatt     480
atgacttttc ttctgcagtg tcagccttac gacgattatc tatgagcttt gaatatagtt     540
tgccgtgatt cgtatcttta attggataat aaaatgcgaa ggatcgatga cccttattat     600
tattttctta cactggctac cgatttaact catcttcttg aaagtatata agtaacagta     660
aaatataccg tacttctgct aatgttattt gtcccttatt tttcttttct tgtcttatgc     720
tatagtacct aagaataacg actattgttt tgaactaaac aaagtagtaa aagcacataa     780
aagaattaag aaa                                                       793
```

ENHANCED METABOLITE-PRODUCING YEAST

The present application contains a Sequence Listing that has been submitted electronically in ASCII format and is hereby incorporated by reference in its entirety. The ASCII copy, created on Mar. 20, 2020, is named Sequence_Listing.txt and is 197,933 bytes in size.

FIELD OF THE INVENTION

The present invention relates to the field of bio-production of metabolites, and in particular of metabolites produced by a microorganism using oxaloacetate, pyruvate and/or acetyl-CoA as substrate or co-substrate upstream in the biosynthesis pathway, and more particularly using oxaloacetate. Said metabolites are preferably amino acids and amino acids derivatives.

BACKGROUND OF THE INVENTION

Amino acids and fatty acids support an industry worth billions of dollars worldwide. All twenty amino acids are sold and of interest in different fields such as animal feed additives, as for example lysine, methionine and threonine, as specialty nutrients in the medical field and as flavor enhancers, as for example monosodium glutamic, serine and aspartic acid. Fatty acids also are of interest and can be used in order to produce solvents, plastisicer and/or biodiesel. Amino acids, their derivatives and fatty acids are moreover important precursors in the pharmaceutical industry. Concerning in particular the production of amino acids, there are three general approaches used today for making them: direct chemical synthesis, bioconversion using enzymes and fermentation. Choosing between these processes depends on available technology, costs of raw material, market prices and sizes, as well as cost of running fermentation versus synthesis reactions, and the environmental impact of the process itself. It is also important to determine which method allows for the better production yield.

Because the precursors are often chemically synthesized or have to be produced in a first step by fermentation, there is no real industrial or financial advantage over the processes of amino acids chemical synthesis.

Production of amino acids by fermentation from natural sources is of course one of the preferred method of producing amino acids. There are indeed numerous bacteria and yeasts which are able to overproduce amino acids under adequate conditions. However, because of the very complex regulation of many of the amino acids syntheses, only a few strains are able to produce relevant amounts of amino acids.

In natural amino acid biosynthesis the amino acid aspartate serves as the precursor for the production of other amino acids, such as lysine, threonine, isoleucine and methionine. Aspartate is produced from oxaloacetate, which is a central metabolite of the citric acid cycle.

A strong production of oxaloacetate is a prerequisite for the industrial production of oxaloacetate-derived amino acids and amino acid derivatives, here-after named oxaloacetate derivatives.

In all cases, candidate oxaloacetate derivatives producer microorganisms have to undergo numerous rounds of mutation and selection before being retained as relevant producers. Illustrative embodiments of candidate methionine-producing microorganisms selected after spontaneous mutation or chemically-induced mutagenesis are disclosed in the U.S. Pat. No. 4,439,525 as well as in Halasz et al. (1996, Periodica Polytechnica Ser. Chem. Engl., Vol. 40(1-2): 53-78).

The production of essential amino acids and their derivatives through the biosynthetic pathways of bacteria and yeasts requires an important amount of reducing power in the form of NADPH. However, the main pathway for the metabolisation of glucose in these microorganisms, and in particular in yeasts, is glycolysis followed by fermentation which only produces NADH. Maintaining an appropriate NADPH/NADH balance within the microorganism, albeit complex, is therefore essential to optimize bio-production of the amino acids and amino acids derivatives of interest while obtaining a viable recombinant microorganism.

The major known bacterial amino acid producer is *C. glutanicum*, a gram-positive, facultative anaerobic, non-pathogenic soil bacterium. *C. glutanicum* is used for the large-scale industrial production of the flavor enhancer L-glutamate as well as of the food additive L-lysine.

There is still a need in the art for transformed, in particular recombinant, microorganisms having at least an increased ability to produce oxaloacetate, pyruvate and/or acetyl-CoA, and in particular oxaloacetate, thus allowing an increased capacity to produce metabolites produced using oxaloacetate, pyruvate and/or acetyl-CoA as substrate or co-substrate upstream in the biosynthesis pathway, and in particular amino acids and their derivatives thereof, fatty acids, derivatives from the mevalonate pathway (in particular farnesyl, squalene, lanosterol, cholesterol and derivatives, and dolichols), flavonoides and/or polyketides.

There is in particular a need for transformed, in particular recombinant, microorganisms having at least an increased ability to produce oxaloacetate, as well as an increased production of pyruvate and/or of acetyl coenzyme A (Acetyl-CoA).

There is more particularly a need in the art for transformed, in particular recombinant, microorganisms having at least an increased ability to produce oxaloacetate, thus allowing an increased ability to produce oxaloacetate-derived amino acids and amino acid derivatives, said oxaloacetate-derived amino acids and amino acid derivatives being termed in the present text oxaloacetate derivatives.

Finally, there is a need for (i) an over-production of NADPH, (ii) a controlled and balanced conversion of phosphoenol pyruvate into oxaloacetate and pyruvate, respectively, (iii) a reduced conversion of pyruvate into ethanol and (iv) a redirection towards conversion of phosphoenol pyruvate into oxaloacetate and/or pyruvate, in particular into oxaloacetate.

SUMMARY OF THE INVENTION

The present invention accordingly relates to a recombinant yeast, in the genome of which:

(A) (i) at least one nucleic acid encoding a malate dehydrogenase is overexpressed and/or is under the control of an inducible or repressible promoter, and
  (ii) at least one, preferably all, the nucleic acid encoding a malate dehydrogenase does not contain the Peroxisome Targeting Sequence thereof;

(B) at least one nucleic acid encoding a NADP-dependent malic enzyme is overexpressed and/or is under the control of an inducible or repressible promoter;

(C) (i) at least one nucleic acid encoding a phosphoenolpyruvate carboxylase that converts phosphoenol pyruvate into oxaloacetate is overexpressed and/or is under the control of an inducible or repressible promoter; and/or (ii) at least one nucleic acid encoding a phosphoenolpyruvate carboxykinase that converts phosphoenol pyruvate into oxaloacetate is overexpressed and/or is under the control of an inducible or repressible promoter;

(D) at least one nucleic acid encoding an acetaldehyde-CoA dehydrogenase is overexpressed and/or is under the control of an inducible or repressible promoter; and (E) (i) at least one, preferably all, nucleic acid encoding a pyruvate kinase 1 has been deleted, and/or (ii) at least one, preferably all, nucleic acid encoding a pyruvate kinase 1 is independently under the control of an inducible or repressible promoter, under the control of a weak promoter, and/or in a destabilized form.

As illustrated in the enclosed examples, the recombinant yeasts of the invention have an increased ability to produce at least oxaloacetate which leads to an improved ability to produce oxaloacetate-derived amino acids and amino acid derivatives.

Said advantageous property can be further increased by also recombining the yeast with additional modifications described here-after.

A recombinant yeast of the invention can be an oxaloacetate, pyruvate and/or acetyl-CoA derivatives-producing recombinant yeast.

Accordingly, the present invention in particular relates to a method for producing at least one oxaloacetate derivative, pyruvate derivative and/or acetyl-CoA derivative, and in particular at least one oxaloacetate derivative, said method comprising the steps of:

(a) culturing a recombinant yeast of the invention in a culture medium; and (b) recovering the oxaloacetate derivative, pyruvate derivative and/or acetyl-CoA derivative from said culture medium.

In a particular embodiment, the culture medium comprises at least one carbon source, preferably a carbon source selected from the group consisting of glucose and sucrose.

The invention further relates to the use of a recombinant yeast of the invention for the production of at least one oxaloacetate derivative, pyruvate derivative and/or acetyl-CoA derivative, in particular of at least one oxaloacetate derivative.

A recombinant yeast of the invention is in particular at least an oxaloacetate derivative-producing recombinant yeast.

An oxaloacetate derivative-producing recombinant yeast of the invention can consequently advantageously be used in a method for producing an oxaloacetate derivative, in particular oxaloacetate-derived amino acids and amino acid derivatives as described here-after or be used for the production of an oxaloacetate derivative, in particular of oxaloacetate-derived amino acids and amino acid derivatives.

In a method and use according to the invention, the at least one oxaloacetate derivative can be selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine, and ethyl-homoserine.

DETAILED DESCRIPTION OF THE INVENTION

The inventors have conceived genetically modified microorganisms, and especially genetically modified yeasts, having a controlled ability to balance pyruvate/oxaloacetate/Acetyl-CoA production allowing a controlled ability, and advantageously an increased ability, to obtain metabolites such as those described here-above originating from pyruvate, oxaloacetate and/or acetyl-CoA, and in particular originating from oxaloacetate.

More particularly, the genetically modified yeasts of the invention conceived by the inventors advantageously have a controlled ability, and preferably an increased ability, to produce oxaloacetate, i.e. oxaloacetate derivatives, and in particular oxaloacetate-derived amino acids and amino acid derivatives, as compared to the parent microorganisms, and especially as compared to the parent yeasts.

Another advantage of the genetically modified yeasts of the invention is their ability to produce more reductive power in the form of NADPH instead of NADH as compared to the parent microorganisms, and especially as compared to the parent yeasts. These genetically modified microorganisms, including these genetically modified yeasts, are described throughout the present specification.

Definitions

As already indicated here-above, an oxaloacetate derivative according to the invention is a metabolite, in particular an amino acid or amino acid derivative, that can be obtained from oxaloacetate after modification by enzymes naturally and/or artificially present in the microorganism producing the oxaloacetate according to the invention, in particular in the yeast producing the oxaloacetate according to the invention.

Examples of such oxaloacetate derivatives can for example be selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine, and ethyl-homoserine.

A pyruvate derivative according to the invention is a metabolite that can be obtained from pyruvate after modification by enzymes naturally and/or artificially present in the microorganism producing the pyruvate according to the invention, in particular in the yeast producing the pyruvate according to the invention.

An acetyl CoA derivative according to the invention is a metabolite that can be obtained from acetyl CoA after modification by enzymes naturally and/or artificially present in the microorganism producing the acetyl CoA according to the invention, in particular in the yeast producing the acetyl CoA according to the invention.

Examples of such pyruvate derivatives or acetyl CoA derivatives can for example be selected from the group consisting of valine; alanine; lactate; components of the krebs cycles or derivatives; fatty acids; flavonoids; polyketides; mevalonate pathway derivatives, such as farnesyl-pp, geranyl-pp and geranyl-geranyl-pp; terpenoids; terpens; squalene; sequiterpenes; sterols; dolichols; lanosterol and sterol and their derivatives; carotens; carotenoids; and ubiquinones.

The term "microorganism", as used herein, refers to a yeast which is not modified artificially. The microorganism may be "donor" if it provides genetic element to be integrated in the microorganism "acceptor" which will express this foreign genetic element or if it used as tool for genetic constructions or protein expressions. The microorganism of the invention is chosen among yeast which expresses genes for the biosynthesis of oxaloacetate and oxaloaectate derivatives.

The term "recombinant microorganism" or "genetically modified microorganism" or "recombinant yeast" or "genetically modified yeast", as used herein, refers to a yeast genetically modified or genetically engineered. It means, according to the usual meaning of these terms, that the microorganism of the invention is not found in nature and is modified either by introduction or by deletion or by modification of genetic elements from equivalent microorganism found in nature. It can also be modified by forcing the development and evolution of new metabolic pathways by combining directed mutagenesis and evolution under specific selection pressure (see for instance WO 2004/076659).

A microorganism may be modified to express exogenous genes if these genes are introduced into the microorganism with all the elements allowing their expression in the host microorganism. A microorganism may be modified to modulate the expression level of an endogenous gene. The modification or "transformation" of microorganism, like yeast, with exogenous DNA is a routine task for those skilled in the art. In particular, a genetic modification of a microorganism according to the invention, more particularly the genetic modification(s) herein defined, may be carried out by using CRISPR-Cas systems, as described in DiCarlo et al. (Nucl. Acids Res., vol. 41, No. 7, 2013: 4336-4343).

The term "endogenous gene" means that the gene was present in the microorganism before any genetic modification, in the wild-type strain. Endogenous genes may be overexpressed by introducing heterologous sequences in addition to, or to replace endogenous regulatory elements, or by introducing one or more supplementary copies of the gene into the chromosome or a plasmid. Endogenous genes may also be modified to modulate their expression and/or activity. For example, mutations may be introduced into the coding sequence to modify the gene product or heterologous sequences may be introduced in addition to or to replace endogenous regulatory elements. Modulation of an endogenous gene may result in the up-regulation and/or enhancement of the activity of the gene product, or alternatively, in the down-regulation and/or attenuation of the activity of the endogenous gene product. Another way to enhance expression of endogenous genes is to introduce one or more supplementary copies of the gene onto the chromosome or a plasmid.

The term "exogenous gene" means that the gene was introduced into a microorganism, by means well known by the man skilled in the art, whereas this gene is not naturally occurring in the wild-type microorganism. Microorganism can express exogenous genes if these genes are introduced into the microorganism with all the elements allowing their expression in the host microorganism. Transforming microorganisms with exogenous DNA is a routine task for the man skilled in the art. Exogenous genes may be integrated into the host chromosome, or be expressed extra-chromosomally from plasmids or vectors. A variety of plasmids, which differ with respect to their origin of replication and their copy number in the cell, are all known in the art. The sequence of exogenous genes may be adapted for its expression in the host microorganism. Indeed, the man skilled in the art knows the notion of codon usage bias and how to adapt nucleic sequences for a particular codon usage bias without modifying the deduced protein.

The term "heterologous gene" means that the gene is derived from a species of microorganism different from the recipient microorganism that expresses it. It refers to a gene which is not naturally occurring in the microorganism.

In the present application, all genes are referenced with their common names and with references to their nucleotide sequences and, the case arising, to their amino acid sequences. Using the references given in accession number for known genes, those skilled in the art are able to determine the equivalent genes in other organisms, bacterial strains, yeast, fungi, mammals, plants, etc. This routine work is advantageously done using consensus sequences that can be determined by carrying out sequence alignments with genes derived from other microorganisms and designing degenerated probes to clone the corresponding gene in another organism.

The man skilled in the art knows different means to modulate, and in particular up-regulate or down-regulate, the expression of endogenous genes. For example, a way to enhance expression of endogenous genes is to introduce one or more supplementary copies of the gene onto the chromosome or a plasmid.

Another way is to replace the endogenous promoter of a gene with a stronger promoter. These promoters may be homologous or heterologous. Promoters particularly interesting in the present invention are described in more detail elsewhere in the present specification.

The nucleic acid expression construct may further comprise 5' and/or 3' recognition sequences and/or selection markers.

The term "overexpression" means that the expression of a gene or of an enzyme is increased as compared to the non-modified microorganism. Increasing the expression of an enzyme is obtained by increasing the expression of a gene encoding said enzyme. Increasing the expression of a gene may be carried out by all techniques known by the one skilled in the art. In this regard, it may be notably cited the implementation of a strong promoter upstream the nucleic acid intended to be overexpressed or the introduction of a plurality of copies of the said nucleic acid between a promoter, especially a strong promoter, and a terminator.

The term "underexpression" means that the expression of a gene or of an enzyme is decreased as compared to the non-modified microorganism. Decreasing the expression of an enzyme is obtained by decreasing the expression of a gene encoding said enzyme. Decreasing the expression of a gene may be carried out by all techniques known by the one skilled in the art. In this regard, it may be notably cited the implementation of a weak promoter upstream the nucleic acid intended to be underexpressed. It may be also cited the implementation of a nucleic acid encoding a variant of the said enzyme that is less active than the parent enzyme or a variant of the said enzyme that is more rapidly degraded in the cell than the parent enzyme. Variants of a parent enzyme that is more rapidly degraded that the said parent enzyme encompass degron-tagged enzymes. It may also be cited the decrease of the expression of a transcription activator of the gene of interest.

The term "inducible promoter" is used to qualify a promoter whose activity is induced, i.e. increased:
  in the presence of one or more particular metabolite(s). The higher the metabolite concentration in the medium, the stronger the promoter activity; or
  in the presence of a low concentration, or in the absence, of one or more metabolite(s). These metabolites are different from those whose increasing presence induces the activity of the promoter. The lower the metabolite concentration in the medium, the stronger the promoter activity.

The term "repressible promoter" is used to qualify a promoter whose activity is repressed, i.e. reduced:
  in the presence of one or more particular metabolite(s). The higher the metabolite concentration in the medium, the weaker the promoter activity; or in the presence of a low concentration, or in the absence, of one or more metabolite(s). These metabolites are different from those whose increasing presence represses the activity of the promoter. The lower the metabolite concentration in the medium, the weaker the promoter activity.

A used herein, a "degron-tagged" enzyme means an enzyme comprising an added protein-degradation signal amino acid sequence that serves as a destruction signal that will cause the said enzyme to be the subject of a degradation, which may be either (i) a ubiquitin-independent degradation or (ii) an ubiquitin-dependent degradation. The said added protein-degradation signal, that is also termed "degron" in the art, encompasses an amino acid sequence that serves as a destruction signal, the said amino acid sequence consisting of a transferrable degradation signal causing a targeted protein degradation. Degrons encompass "N-degrons", which are transferrable N-terminal amino acids that cause the target protein degradation following the well-known N-end rule (Bachmair et al., 1986, Science, Vol. 234 (4773): 179-186). The unstable nature of the N-degron is attributed to its first amino acids, which are prone to acetylation or arginylation modifications and ultimately lead to ubiquitination and degradation. Generally, a degron requires at least two components to ensure targeted protein degradation: (i) a target degradation recognition tag, such as a poly-ubiquitin tag and (ii) an unstructured amino acid sequence in close proximity to the degradation recognition tag. For degron-tagging a protein, and especially herein for degron-tagging an enzyme, the one skilled in the art may refer to Yu et al. (2015, Current Opinion in Biotechnology, Vol. 36: 199-204), Cho et al. (2010, Genes & Development, Vol. 24: 438-442), or to Fortmann et al. (2015, J Mol Biol, Vol. 427 (17): 2748-2756), Ravid et al. (2008, Nat Rev Mol Cell Biol, Vol. 9(9): 679-690) and Hochstrasser (1996, Annu Rev Genet, Vol. 30: 405-439).

The "activity" of an enzyme is used interchangeably with the term "function" and designates, in the context of the invention, the capacity of an enzyme to catalyze a desired reaction.

The terms "reduced activity" or "attenuated activity" of an enzyme mean either a reduced specific catalytic activity of the protein obtained by mutation in the amino acids sequence and/or decreased concentrations of the protein in the cell obtained by mutation of the nucleotide sequence or by deletion of the cognate corresponding gene or also by degron-tagging of the protein.

The term "enhanced activity" of an enzyme designates either an increased specific catalytic activity of the enzyme, and/or an increased quantity/availability of the enzyme in the cell, obtained for example by overexpression of the gene encoding the enzyme.

The terms "encoding" or "coding" refer to the process by which a polynucleotide, through the mechanisms of transcription and translation, produces an amino-acid sequence.

The gene(s) encoding the enzyme(s) considered in the present invention can be exogenous or endogenous.

"Attenuation" of genes means that genes are expressed at an inferior rate than in the non-modified microorganism. The attenuation may be achieved by means and methods known to the man skilled in the art and contains gene deletion obtained by homologous recombination, gene attenuation by insertion of an external element into the gene or gene expression under a weak promoter. The man skilled in the art knows a variety of promoters which exhibit different strengths and which promoter to use for a weak genetic expression.

The methods implemented in the present invention preferably require the use of one or more chromosomal integration constructs for the stable introduction of a heterologous nucleotide sequence into a specific location on a chromosome or for the functional disruption of one or more target genes in a genetically modified microbial cell. In some embodiments, disruption of the target gene prevents the expression of the related functional protein. In some embodiments, disruption of the target gene results in the expression of a non-functional protein from the disrupted gene.

Parameters of chromosomal integration constructs that may be varied in the practice of the present invention include, but are not limited to, the lengths of the homologous sequences; the nucleotide sequence of the homologous sequences; the length of the integrating sequence; the nucleotide sequence of the integrating sequence; and the nucleotide sequence of the target locus. In some embodiments, an effective range for the length of each homologous sequence is 20 to 5,000 base pairs, preferentially 50 to 100 base pairs. In particular embodiments, the length of each homologous sequence is about 50 base pairs. For more information on the length of homology required for gene targeting, see D. Burke et al., Methods in yeast Genetics—A cold spring harbor laboratory course Manual (2000).

In some embodiments, (a) disrupted gene(s) in which the above-mentioned DNA construct(s) is/are intended to be inserted may advantageously comprises one or more selectable markers useful for the selection of transformed microbial cells. Preferably, said selectable marker(s) are comprised in the DNA construct(s) according to the present invention.

In some embodiments, the selectable marker is an antibiotic resistance marker. Illustrative examples of antibiotic resistance markers include, but are not limited to the, NAT1, AUR1-C, HPH, DSDA, KAN<R>, and SH BLE gene products. The NAT 1 gene product from *S. noursei* confers resistance to nourseothricin; the AUR1-C gene product from *Saccharomyces cerevisiae* confers resistance to Auerobasidin A (AbA); the HPH gene product of *Klebsiella pneumonia* confers resistance to Hygromycin B; the DSDA gene product of *E. coli* allows cells to grow on plates with D-serine as the sole nitrogen source; the KAN<R> gene of the Tn903 transposon confers resistance to G418; and the SH BLE gene product from *Streptoalloteichus hindustanus* confers resistance to Zeocin (bleomycin).

In some embodiments, the antibiotic resistance marker is deleted after the genetically modified microbial cell of the invention is isolated. The man skilled in the art is able to choose suitable marker in specific genetic context.

In some embodiments, the selectable marker rescues an auxotrophy (e.g., a nutritional auxotrophy) in the genetically modified microbial cell. In such embodiments, a parent microbial cell comprises a functional disruption in one or more gene products that function in an amino acid or nucleotide biosynthetic pathway, such as, for example, the HIS3, LEU2, LYS1, LYS2, MET 15, TRP1, ADE2, and URA3 gene products in yeast, which renders the parent microbial cell incapable of growing in media without supplementation with one or more nutrients (auxotrophic phenotype). The auxotrophic phenotype can then be rescued by transforming the parent microbial cell with a chromosomal integration encoding a functional copy of the disrupted gene product (NB: the functional copy of the gene can originate from close species, such as *Kluveromyces, Candida* etc.), and the genetically modified microbial cell generated can be selected for based on the loss of the auxotrophic phenotype of the parent microbial cell.

For each of the nucleic acid sequences comprising a promoter sequence, a coding sequence (e.g. an enzyme coding sequence), or a terminator sequence, reference sequences are described herein. The present description also encompasses nucleic acid sequences having specific percentages of nucleic acid identity, with a reference nucleic acid sequence.

For each or the amino acid sequences of interest, reference sequences are described herein. The present description also encompasses amino acid sequences (e.g. enzyme amino acid sequences), having specific percentages of amino acid identity, with a reference amino acid sequence.

For obvious reasons, in all the present description, a specific nucleic acid sequence or a specific amino acid sequence which complies with, respectively, the considered nucleotide or amino acid identity, should further lead to obtaining a protein (or enzyme) which displays the desired biological activity. As used herein, the "percentage of identity" between two nucleic acid sequences or between two amino acid sequences is determined by comparing both optimally aligned sequences through a comparison window.

The portion of the nucleotide or amino-acid sequence in the comparison window may thus include additions or deletions (for example "gaps") as compared to the reference sequence (which does not include these additions or these deletions) so as to obtain an optimal alignment between both sequences.

The identity percentage is calculated by determining the number of positions at which an identical nucleic base, or an identical amino-acid residue, can be noted for both compared sequences, then by dividing the number of positions at which identity can be observed between both nucleic bases, or between both amino-acid residues, by the total number of positions in the comparison window, then by multiplying the result by hundred to obtain the percentage of nucleotide identity between the two sequences or the percentage of amino acid identity between the two sequences.

The comparison of the sequence optimal alignment may be performed by a computer using known algorithms.

Most preferably, the sequence identity percentage is determined using the CLUSTAL W software (version 1.82) the parameters being set as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAP DISTANCES="hide".

The "fermentation" or "culture" is generally conducted in fermenters with an appropriate culture medium adapted to the microorganism being cultivated, containing at least one simple carbon source, and if necessary co-substrates.

Microorganisms disclosed herein may be grown in fermentation media for the production of a product from oxaloacetate. For maximal production of oxaloacetate derivatives, the microorganism strains used as production hosts preferably have a high rate of carbohydrate utilization. These characteristics may be conferred by mutagenesis and selection, genetic engineering, or may be natural. Fermentation media, or "culture medium", for the present cells may contain at least about 10 g/L of glucose. Additional carbon substrates may include but are not limited to monosaccharides such as fructose, mannose, xylose and arabinose; oligosaccharides such as lactose maltose, galactose, or sucrose; polysaccharides such as starch or cellulose or mixtures thereof and unpurified mixtures from renewable feedstocks such as cheese whey permeate cornsteep liquor, sugar beet molasses, and barley malt. Other carbon substrates may include glycerol.

Hence, it is contemplated that the source of carbon utilized in the present invention may encompass a wide variety of carbon containing substrates and will only be limited by the choice of organism.

Although it is contemplated that all of the above-mentioned carbon substrates and mixtures thereof are suitable in the present invention, preferred carbon substrates are glucose, fructose, and sucrose, or mixtures of these with C5 sugars such as xylose and/or arabinose for microorganisms modified to use C5 sugars, and more particularly glucose.

A preferred carbon substrate is glucose.

In addition to an appropriate carbon source, fermentation media may contain suitable minerals, salts, cofactors, buffers and other components, known to those skilled in the art, suitable for the growth of the cultures and promotion of the enzymatic pathway necessary for the production of the desired product.

Besides, additional genetic modifications suitable for the growth of recombinant microorganisms according to the invention may be considered.

The terms "Aerobic conditions" refers to concentrations of oxygen in the culture medium that are sufficient for an aerobic or facultative anaerobic microorganism to use di-oxygene as a terminal electron acceptor.

"Microaerobic condition" refers to a culture medium in which the concentration of oxygen is less than that in air, i.e. oxygen concentration up to 6% O2.

An "appropriate culture medium" designates a medium (e.g. a sterile, liquid medium) comprising nutrients essential or beneficial to the maintenance and/or growth of the cell such as carbon sources or carbon substrate, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids, vitamins, growth promoters, and the like. The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, cellulose, hemicelluloses and combinations thereof.

General Features of Genetic Modifications Introduced According to the Invention

Genes are over expressed by two kinds of non mutually exclusive modifications:
  Placing them under the control of a strong promoter; and/or
  Inserting a plurality of copies of the considered gene.
All the genome modifications are inserted in yeast according to known genetic engineering techniques:

The successive genes included in a gene construct that is introduced in the yeast genome according to the invention are of the following structure:

Prom$_1$-ORF$_1$-term$_1$-ORF$_2$-gene$_2$-term$_2$- . . . / . . . -Prom$_n$-ORF$_n$-term$_n$, wherein:

Prom1 is a sequence regulating the expression of the coding sequence ORF1,

ORF1 is a nucleic acid sequence encoding a desired protein PROT1, and especially a desired enzyme PROT1, Term1 is a transcription terminator sequence that mediates transcriptional termination by providing signals in the newly synthesized mRNA that trigger processes which release the mRNA from the transcriptional complex, and "1", "2", . . . / . . . "n" may or may not describe the same ORF (Open Reading Frame), promoter or terminator. The order of the genes does not matter. "n" is an integer usually ranging from 5 and 20. These constructs are inserted in one of the yeast chromosome at a controlled location. In some embodiments, the insertion site is not essential for the functionality of the inserted construct, nor for the viability of the resulting genetically modified yeast.

When the yeast is for example *Saccharomyces cerevisiae*, genes introduced in the yeast genome and originating from other organisms than *Saccharomyces cerevisiae* are generally "transcoded" (generally codon-optimized"), meaning that these genes are synthesized with an optimal codon usage for expression *S. cerevisiae*. The nucleotide sequence (and not the protein sequence) of some genes from *S. cerevisiae* has also been modified ("transcoded") to minimize recombination with an endogenous copy of the said gene.

Genes may be deleted through standard procedures used in yeast genetic engineering. In some embodiments, the genes targeted for deletion may be interrupted by insertion of one of the above described gene constructs, or alternatively the genes targeted for deletion are replaced by a short stretch of nucleotide.

Down regulating gene expression may be obtained by disrupting the endogenous copy of the gene and replacing it with a copy of the ORF under the control of a weak promoter. A list and sequences of weak promoters is described elsewhere in the present specification.

A gene may be rendered "inducible or repressible" by deleting the endogenous copy of the gene (if necessary) and placing a new copy of the ORF under the control of an inducible or repressible promoter. An inducible or repressible promoter is a promoter which activity is modulated and controlled, i.e. either increased or decreased, upon a change in the environmental conditions or external stimuli. Induction or repression may be artificially controlled, which encompasses induction or repression by abiotic factors such as chemical compounds not found naturally in the organism of interest, light, oxygen levels, heat or cold. A list and sequence of inducible or repressible promoters is described elsewhere in the present specification.

As already specified elsewhere herein, a protein may be underexpressed by destabilization by using "the degron" technology which is described in Yu et al. 2015, (Current Opinion in Biotechnology, Vol. 36: 199-204). In brief this technology consists in introducing in the protein sequence a modification that targets it for degradation. It can consist only in the two first amino acids following the principle known as the N-end rule, or a larger sequence targeting the whole protein to the ubiquitin-preoteasome degradation pathway.

Recombinant Yeast According to the Invention

The inventors have conceived recombinant microorganisms, and especially recombinant yeasts, having an increased ability of producing oxaloacetate, and NADPH, and in particular oxaloacetate derivatives.

The present invention relates to recombinant yeasts having an increased oxaloacetate, pyruvate and/or acetyl-CoA derivatives production, and in particular an increased oxaloacetate derivatives production, and wherein said increased production is obtained through a plurality of alterations that have been introduced in the genome thereof, by genetic engineering methods.

This invention pertains to a recombinant yeast, in particular an oxaloacetate derivatives-producing recombinant yeast, in the genome of which:

(A) (i) at least one nucleic acid encoding a malate dehydrogenase MDH3 is overexpressed and/or is under the control of an inducible or repressible promoter, and (ii) at least one, preferably all, the nucleic acid encoding a malate dehydrogenase MDH3 does not contain the Peroxisome Targeting Sequence thereof;

(B) at least one nucleic acid encoding a NADP-dependent malic enzyme ME3 is overexpressed and/or is under the control of an inducible or repressible promoter;

(C) (i) at least one nucleic acid encoding a phosphoenolpyruvate carboxylase PEPC that converts phosphoenol pyruvate into oxaloacetate is overexpressed and/or is under the control of an inducible or repressible promoter; and/or (ii) at least one nucleic acid encoding a phosphoenolpyruvate carboxykinase PEPCK that converts phosphoenol pyruvate into oxaloacetate is overexpressed and/or is under the control of an inducible or repressible promoter;

(D) at least one nucleic acid encoding an acetaldehyde-CoA dehydrogenase MHPF is overexpressed and/or is under the control of an inducible or repressible promoter; and (E) (i) at least one, preferably all, nucleic acid encoding a pyruvate kinase 1 PYK1 has been deleted, and/or (ii) at least one, preferably all, nucleic acid encoding a pyruvate kinase 1 PYK1 is independently under the control of an inducible or repressible promoter, under the control of a weak promoter, and/or in a destabilized form.

The inventors have found that an increased production of oxaloacetate, pyruvate and/or acetyl-coA derivatives, and in particular an increased production of oxaloacetate derivatives, by yeast cells may be reached by introducing in the genome of these yeast cells a plurality of genetic alterations. As it is fully described herein, the said plurality of genetic alterations encompass an overexpression of certain genes, a controlled expression of certain other genes, as well as repression or deletion of further other genes.

The controlled, and in particular increased, oxaloacetate, pyruvate and/or acetyl-coA derivatives production, and in particular an increased production of oxaloacetate derivatives, by yeast cells has been reached by the inventors by optimizing the metabolism of glucose, so as to direct the subsequent artificially modified metabolic pathway mainly towards oxaloacetate, pyruvate and/or acetyl-CoA production, in particular oxaloacetate, pyruvate and acetyl-CoA production, whereas in the same time maintaining an optimal viability of the resulting genetically modified yeast cells.

After a lengthy research time period, the present inventors have determined that a high oxaloacetate derivatives production by yeast cells is obtained by increasing the conversion of phosphoenolpyruvate into oxaloacetate but also into the successive intermediate metabolites malate, pyruvate, acetaldehyde, and acetyl-CoA while, notably, maintaining a redox status allowing a good viability of the resulting recombinant yeast cells. The increased availability of these metabolites allows a high oxaloacetate derivatives production, which can further be improved by additional modifications described here-after.

Maintaining a redox status allowing a good viability of the resulting recombinant yeast cells is obviously essential and represented a significant challenge for the inventors throughout their research work.

The proposed solution according to the invention unexpectedly allows maintaining a viable NADH/NADPH equilibrium in the yeast cells throughout the metabolite-production pathway through the consumption of less reducing power, the consumption of reducing power in the form of NADH rather than NADPH, and/or the production of NADH instead of NADPH.

As disclosed in detail in the present specification, the resulting recombinant yeast cells are genetically modified so as to effect an over expression and/or a controlled expression of (i) at least one malate dehydrogenase-encoding gene (MDH3) in particular that does not contain the Peroxisome Targeting Sequence thereof, (ii) at least one NADP-dependent malic enzyme-encoding gene (ME3) and (iii) at least one acetaldehyde-CoA dehydrogenase-encoding gene (MHPF).

Further, a recombinant yeast according to the invention is also genetically modified so as to effect an over expression and/or a controlled expression of (i) at least one phosphoenolpyruvate carboxylase-encoding gene (PEPC) that converts phosphoenol pyruvate into oxaloacetate and/or (ii) at least one phosphoenolpyruvate carboxykinase-encoding gene (PEPCK) that converts phosphoenol pyruvate into oxaloacetate.

Moreover, a recombinant yeast according to the invention is also genetically modified so as to (i) delete at least one pyruvate kinase 1-encoding gene (PYK1), (ii) effect a repressible expression of at least one pyruvate kinase 1-encoding gene (PYK1), (iii) effect a weak expression of at least one pyruvate kinase 1-encoding gene (PYK1) and/or (iv) effect the expression of of at least one pyruvate kinase 1-encoding gene (PYK1) destabilized form.

A recombinant yeast according to the invention produces oxaloacetate derivatives with a higher yield than the parent yeast which does not contain the genetic modifications described above.

In some embodiments of a recombinant yeast according to the invention, (i) at least one, preferably all, nucleic acid encoding a pyruvate kinase 2 PYK2 has been deleted, and/or (ii) at least one, preferably all, nucleic acid encoding a pyruvate kinase 2 PYK2 is under the control of an inducible or repressible promoter and/or is in a destabilized form.

In some embodiments, the genome of a recombinant yeast of the invention is such that (i) at least one, preferably all, nucleic acid encoding an alcohol dehydrogenase 1 ADH1 has been deleted, and/or (ii) at least one, preferably all, nucleic acid encoding an alcohol dehydrogenase 1 ADH1 is under the control of an inducible or repressible promoter and/or is in a destabilized form.

In some embodiments, the genome of a recombinant yeast of the invention is such that:

(A) (i) at least one, preferably all, nucleic acid encoding a pyruvate carboxylase 1 PYC1 has been deleted, and/or (ii) at least one, preferably all, nucleic acid encoding a pyruvate carboxylase PYC1 is under the control of an inducible or repressible promoter and/or is in a destabilized form; and/or (B) (i) at least one, preferably all, nucleic acid encoding a pyruvate carboxylase 2 PYC2 has been deleted, and/or (ii) at least one, preferably all, nucleic acid encoding a pyruvate carboxylase 2 PYC2 is under the control of an inducible or repressible promoter and/or is in a destabilized form.

In some embodiments, the genome of a recombinant yeast of the invention is such that:

(A) (i) at least one, preferably all, nucleic acid encoding an alcohol dehydrogenase 3 ADH3 has been deleted, and/or (ii) at least one, preferably all, nucleic acid encoding an alcohol dehydrogenase 3 ADH3 is under the control of an inducible or repressible promoter and/or is in a destabilized form;

(B) (i) at least one, preferably all, nucleic acid encoding an alcohol dehydrogenase 4 ADH4 has been deleted, and/or (ii) at least one, preferably all, nucleic acid encoding an alcohol dehydrogenase 4 ADH4 is under the control of an inducible or repressible promoter and/or is in a destabilized form; and/or (C) (i) at least one, preferably all, nucleic acid encoding an alcohol dehydrogenase 5 ADH5 has been deleted, and/or (ii) at least one, preferably all, nucleic acid encoding an alcohol dehydrogenase 5 ADH5 is under the control of an inducible or repressible promoter and/or is in a destabilized form.

In some embodiments, the malate dehydrogenase nucleic (MDH3) acid is preferably from a yeast, in particular from *Saccharomyces cerevisiae*.

In some embodiments, the NADP-dependent malic enzyme is encoded by a nucleic acid selected, independently, from the group consisting of bacteria, plants, fungi, protists or animals, in particular from the group consisting of nucleic acid from *Arabidopsis thaliana, Escherichia coli, Aloe arborescens, Aspergillus niger, Flaveria species, Corynebacterium glutamicum, Oryza sativa, Streptomyces coelicolor, Rattus norvegicus, Zea mays* and *Trypanosoma cruzi*, and is more preferably encoded by the *Arabidopsis thaliana* ME3.At gene or by the *Escherichia coli* ME3.Ec gene, and most preferably encoded by the *Arabidopsis thaliana* ME3.At gene.

In some embodiments, the nucleic acid encoding a phosphoenolpyruvate carboxykinase that converts phosphoenol pyruvate PEP into oxaloacetate are nucleic acid from a prokaryote or an eukaryote, in particular from the group consisting of *Escherichia coli, Pseudomonas fluorescens, Mycobacterium tuberculosis, Anaerobiospirillum succiniciproducens, Succinatimoras hippie, Bacteroides salyersiae, Trypanosoma cruzi* and *Clostridium thermocellum*, and is more preferably the *Escherichia coli* PEPCK.Ec gene.

In some embodiments, the nucleic acid encoding an acetaldehyde-CoA dehydrogenase is selected, independently, from bacteria or eukarya, in particular from the group consisting of nucleic acid from *Escherichia coli, Giardia intestinalis*, bacteria of the genus *Pseudomonas, Clostridium kluyveri, Klebsiella pneumoniae, Leuconostoc mesenteroides, Pectobacterium atrosepticum, Shigella sonnei* and *Serratia proteamaculans*, and is more preferably encoded by the *E. coli* MHPF.Ec gene.

In some embodiments, the at least one nucleic acid encoding a pyruvate kinase 1 (PYK1) are nucleic acid from a yeast, in particular from *Saccharomyces cerevisiae*.

Malate Dehydrogenase-Encoding Gene Over Expression and/or Controlled Expression

In preferred embodiments of a recombinant yeast according to the invention, over expression of a malate dehydrogenase-encoding gene is obtained by inserting, at selected location(s) of the yeast genome, one or more copies of an expression cassette comprising a malate dehydrogenase coding sequence. Malate dehydrogenase and a malate dehydrogenase-encoding gene that are encompassed by the invention are detailed elsewhere in the present specification.

In some of these embodiments, the said one or more copies of an expression cassette comprising a malate dehydrogenase (MDH3) coding sequence comprise(s) regulatory sequences allowing a strong expression of the malate dehydrogenase, such as a strong promoter that is functional in yeast cells.

In addition to or as an alternative to these embodiments of a recombinant yeast according to the invention, at least one malate dehydrogenase-encoding gene can be under the control of an inducible or repressible promoter that is functional in yeast cells.

Without wishing to be bound by any particular theory, the inventors believe that over expression of a malate dehydrogenase may enhance the conversion of the intermediate oxaloacetate into malate. The same applies when at least one malate dehydrogenase coding sequence is under the control of an inducible or repressible promoter.

In some preferred embodiments, the said malate dehydrogenase-encoding gene is the MDH3 gene from *Saccharomyces cerevisiae* as shown in the examples herein and discussed previously.

In preferred embodiments, the said malate dehydrogenase-encoding gene is placed under the control of the strong promoter pTEF3 or of the strong promoter pPDC1.

Illustratively, the malate dehydrogenase gene may be inserted within the GNP1 gene and/or within the MUP3 gene, as it is shown in the examples herein.

NADP-Dependent Malic Enzyme-Encoding Gene Over Expression and/or Controlled Expression In preferred embodiments of a recombinant yeast according to the invention, over expression of an NADP-dependent malic enzyme-encoding gene is obtained by inserting, at selected location(s) of the yeast genome, one or more copies of an expression cassette comprising an NADP-dependent malic enzyme coding sequence. NADP-dependent malic enzyme and an NADP-dependent malic enzyme-encoding gene that are encompassed by the invention are detailed elsewhere in the present specification.

In some of these embodiments, the said one or more copies of an expression cassette comprising an NADP-dependent malic enzyme coding sequence comprise(s) regulatory sequences allowing a strong expression of the NADP-dependent malic enzyme, such as a strong promoter that is functional in yeast cells.

In addition to or as an alternative to these embodiments of a recombinant yeast according to the invention, at least one NADP-dependent malic enzyme-encoding gene can be under the control of an inducible or repressible promoter that is functional in yeast cells.

Without wishing to be bound by any particular theory, the inventors believe that over expression of an NADP-dependent malic enzyme may enhance the conversion of the intermediate malate into pyruvate. The same applies when at least one NADP-dependent malic enzyme coding sequence is under the control of an inducible or repressible promoter.

In some preferred embodiments, the said NADP-dependent malic enzyme-encoding gene is the ME3 gene from *Arabidopsis thaliana* as shown in the examples herein and discussed previously.

In preferred embodiments, the said NADP-dependent malic enzyme-encoding gene is placed under the control of the strong promoter pCCW12.

Illustratively, the NADP-dependent malic enzyme gene may be inserted within the GNP1 gene and/or within the MUP3 gene and/or within the URA3 gene, as it is shown in the examples herein.

Phosphoenolpyruvate Carboxylase-Encoding Gene Over Expression and/or Controlled Expression In preferred embodiments of a recombinant yeast according to the invention, over expression of a phosphoenolpyruvate carboxylase-encoding gene that that converts phosphoenol pyruvate into oxaloacetate is obtained by inserting, at selected location(s) of the yeast genome, one or more copies of an expression cassette comprising a phosphoenolpyruvate carboxylase coding sequence, this phosphoenolpyruvate carboxylase converting phosphoenol pyruvate into oxaloacetate. Phosphoenolpyruvate carboxylase and a phosphoenolpyruvate carboxylase-encoding gene that are encompassed by the invention, and that converts phosphoenol pyruvate into oxaloacetate are detailed elsewhere in the present specification.

In some of these embodiments, the said one or more copies of an expression cassette comprising a phosphoenolpyruvate carboxylase coding sequence comprise(s) regulatory sequences allowing a strong expression of the phosphoenolpyruvate carboxylase, such as a strong promoter that is functional in yeast cells.

In addition to or as an alternative to these embodiments of a recombinant yeast according to the invention, at least one phosphoenolpyruvate carboxylase-encoding gene can be under the control of an inducible or repressible promoter that is functional in yeast cells.

Without wishing to be bound by any particular theory, the inventors believe that over expression of a phosphoenolpyruvate carboxylase may enhance the conversion of the intermediate metabolite phosphoenolpyruvate (PEP) into oxaloacetate. The same applies when at least one phosphoenolpyruvate carboxylase coding sequence is under the control of an inducible or repressible promoter.

In some preferred embodiments, the said phosphoenolpyruvate carboxylase-encoding gene is the PEPC or PPC gene from *Escherichia coli*.

In preferred embodiments, the said phosphoenolpyruvate carboxylase-encoding gene that converts phosphoenol pyruvate into oxaloacetate is placed under the control of the strong promoter pTDH3 or of the inducible or repressible promoter pACU3p.

Illustratively, the phosphoenolpyruvate carboxylase gene may be inserted within the URA3 gene and/or within the TRP1 gene.

Phosphoenolpyruvate Carboxykinase-Encoding Gene Over Expression and/or Controlled Expression In preferred embodiments of a recombinant yeast according to the invention, over expression of a phosphoenolpyruvate carboxykinase-encoding gene that converts phosphoenol pyruvate into oxaloacetate is obtained by inserting, at selected location(s) of the yeast genome, one or more copies of an expression cassette comprising a phosphoenolpyruvate carboxykinase (PEPCK) coding sequence that converts phosphoenol pyruvate into oxaloacetate. Phosphoenolpyruvate carboxykinase and a phosphoenolpyruvate carboxykinase-encoding gene that are encompassed by the invention convert phosphoenol pyruvate into oxaloacetate and are detailed elsewhere in the present specification.

In some of these embodiments, the said one or more copies of an expression cassette comprising a phosphoenolpyruvate carboxykinase coding sequence comprise(s) regulatory sequences allowing a strong expression of the phosphoenolpyruvate carboxykinase, such as a strong promoter that is functional in yeast cells.

In addition to or as an alternative to these embodiments of a recombinant yeast according to the invention, at least one phosphoenolpyruvate carboxykinase-encoding gene can be under the control of an inducible or repressible promoter that is functional in yeast cells.

Without wishing to be bound by any particular theory, the inventors believe that over expression of a phosphoenolpyruvate carboxykinase may enhance the conversion of the intermediate metabolite phosphoenolpyruvate (PEP) into oxaloacetate. The same applies when at least one phosphoenolpyruvate carboxykinase coding sequence is under the control of an inducible or repressible promoter.

In some preferred embodiments, the said phosphoenolpyruvate carboxykinase-encoding gene is the PEPCK gene from *Escherichia coli*.

In preferred embodiments, the said phosphoenolpyruvate carboxylase-encoding gene is placed under the control of the strong promoter pPDC1, of the strong promoter pTDH3 or of the inducible or repressible promoter pACU1.

Illustratively, the phosphoenolpyruvate carboxykinase gene may be inserted within the GNP1 gene and/or within the MUP3 gene and/or within the PYK1 gene.

Acetaldehyde-CoA Dehydrogenase-Encoding Gene Over Expression and/or Controlled Expression In preferred embodiments of a recombinant yeast according to the invention, over expression of an acetaldehyde-CoA dehydrogenase-encoding gene is obtained by inserting, at selected location(s) of the yeast genome, one or more copies of an expression cassette comprising an acetaldehyde-CoA dehydrogenase coding sequence. Acetaldehyde-CoA dehydrogenase and an acetaldehyde-CoA dehydrogenase-encoding gene that are encompassed by the invention are detailed elsewhere in the present specification.

In some of these embodiments, the said one or more copies of an expression cassette comprising an acetaldehyde-CoA dehydrogenase (MHPF) coding sequence comprise(s) regulatory sequences allowing a strong expression of the acetaldehyde-CoA dehydrogenase, such as a strong promoter that is functional in yeast cells.

In addition to or as an alternative to these embodiments of a recombinant yeast according to the invention, at least one acetaldehyde-CoA dehydrogenase-encoding gene can be under the control of an inducible or repressible promoter that is functional in yeast cells.

Without wishing to be bound by any particular theory, the inventors believe that over expression of an acetaldehyde-CoA dehydrogenase may enhance the conversion of the intermediate metabolite acetaldehyde into acetyl-CoA. The same applies when at least one acetaldehyde-CoA dehydrogenase coding sequence is under the control of an inducible or repressible promoter.

In some preferred embodiments, the said acetaldehyde-CoA dehydrogenase-encoding gene is the MHPF gene from *Escherichia coli* as shown in the examples herein and discussed previously.

In preferred embodiments, the said acetaldehyde-CoA dehydrogenase-encoding gene is placed under the control of the strong promoter pTDH3 or of the strong promoter pPDC1.

Illustratively, the acetaldehyde-CoA dehydrogenase gene may be inserted within the HIS3 gene and/or within the GNP1 gene and/or within the TRP1 gene and/or within the MUP3 gene, as it is shown in the examples herein.

Deletion or Under Expression of Pyruvate Kinase 1

A recombinant yeast according to the invention is further defined as having a genome in which:
(i) at least one, preferably all, endogenous nucleic acid encoding a pyruvate kinase 1 PYK1 has been deleted, and/or
(ii) at least one, preferably all, nucleic acid encoding a pyruvate kinase 1 PYK1 is independently under the control of an inducible or repressible promoter, under the control of a weak promoter, and/or in a destabilized form.

Without wishing to be bound by any particular theory, the inventors believe that an under expression of a pyruvate kinase 1 gene shall increase oxaloacetate production by the recombinant yeast by reducing the consumption of the produced phosphoenolpyruvate (PEP) by its conversion into pyruvate.

The absence or at least reduced expression of pyruvate kinase 1 leads to the production of pyruvate through another pathway, i.e. through the increased conversion of phosphoenol pyruvate into oxaloacetate, followed by increased oxaloacetate conversion into malate, itself being converted into pyruvate in an increased manner. The use of this particular pathway in order to produce pyruvate advantageously allows the consumption of NADH and the production of NADPH.

In some embodiments, under expression of pyruvate kinase 1 may be rendered conditional, for example by placing the expression of this gene under the control of repressible regulatory sequences, such as an inducible or repressible promoters.

Methods for repressing gene expression are well known from the one skilled in the art.

Pyruvate kinase 1 under expression also encompasses the insertion of a nucleic acid encoding a destabilized pyruvate kinase 1. A destabilized pyruvate kinase 1 is a variant of pyruvate kinase 1 that is more rapidly degraded within the yeast cell than the parent pyruvate kinase 1.

In preferred embodiments, a destabilized pyruvate kinase 1 consists of a degron-tagged pyruvate kinase 1 protein.

For example, the pyruvate kinase 1 gene can be interrupted by loxP, or for example by URA3.Kl-loxP, and is thus deleted.

It can alternatively be interrupted by a cassette comprising genes of interest, as illustrated in the examples as filed.

Malate Dehydrogenase (MDH3)

The malate dehydrogenase is a protein which is known in the art to catalyze the NADH-dependent formation of malate from oxaloacetate. The malate dehydrogenase encoded by the genome of *Saccharomyces cerevisiae* may be termed MDH3.

More particularly, a malate dehydrogenase of the invention does not contain the Peroxisome Targeting Sequence thereof. Without wishing to be bound by any particular theory, the inventors believe that the deletion of this sequence from the malate dehydrogenase sequence allows for the enzyme to be expressed in the cytoplasm of the yeast and not be exported to the peroxisome. Said deletion simply consists in the deletion of the three C-terminal amino acids SKL (Serine-Lysine-Leucine) from the coding sequence thorough a method very well known from the man skilled in the art.

A method implemented to measure the activity level of malate dehydrogenase belongs to the general knowledge of the one skilled in the art. Mention can for example be made of the commercial kit sold by Sigma entitled "Malate dehydrogenase assay kit" under the reference MAK196-1KT.

Preferred malate dehydrogenase in the present specification is an enzyme having an EC number 1.1.1.37.

According to a preferred embodiment, the nucleic acid(s) encoding a malate dehydrogenase may be nucleic acid(s) originating from organisms preferably selected in a group comprising prokaryotic organisms and eukaryotic organisms. In some embodiments, the nucleic acid(s) encoding a malate dehydrogenase may be nucleic acid(s) originating from archaebacteria. In some preferred embodiments, the nucleic acid(s) encoding a malate dehydrogenase may be nucleic acid(s) originating from yeast, and especially from *Saccharomyces cerevisiae*.

According to a yet preferred embodiment, the nucleic acid(s) encoding a malate dehydrogenase may be nucleic acid(s) selected from the group consisting of sequences having at least 20%, advantageously at least 65%, preferably at least 80%, nucleic acid identity with a nucleic acid selected in a group consisting of the reference nucleic acid sequences of SEQ ID NO: 1 and also a biological activity of the same nature. The nucleic acids of SEQ ID NO: 1 encode a malate dehydrogenase originating from *Saccharomyces cerevisiae*, that may also be collectively termed MDH3 or MDH3.Sc herein.

A biological activity of the same nature regarding this sequence is the capacity to code for an enzyme that catalyzes the NADH-dependent formation of malate from oxaloacetate.

As described herein, a nucleic acid sequence having at least 20% nucleotide identity with a reference nucleic acid sequence encompasses nucleic acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequences, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the malate dehydrogenase from *Saccharomyces cerevisiae*, the one skilled in the art may refer to the accession number NP010205 in the UniProt database, or to SEQ ID NO. 2 described herein.

According to another particular embodiment, the nucleic acid(s) encoding a malate dehydrogenase may be nucleic acid(s) encoding an amino acid sequence selected from the group consisting of sequences having at least 20%, advantageously at least 65%, preferably at least 80%, amino acid identity with the amino acid sequence of SEQ ID NO: 2, and also a biological activity of the same nature. Illustratively, the malate dehydrogenase originating from *Thecamonas trahens* has 23% amino acid identity with the malate dehydrogenase of SEQ ID NO. 2.

A biological activity of the same nature regarding this sequence is as described previously, i.e. the capacity to catalyze the NADH-dependent formation of malate from oxaloacetate.

As described herein, an amino acid sequence having at least 20% amino acid identity with a reference nucleic acid sequence encompasses amino acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence, and also a biological activity of the same nature.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence, and also a biological activity of the same nature.

As above-mentioned, the expression level of the malate dehydrogenase in the present invention is regulated by at least one promoter and at least one terminator, such as hereinafter defined more in details, which are present in 5' and 3' position respectively of the nucleic acid sequence encoding the said malate dehydrogenase.

As it is specified elsewhere in the present description, the malate dehydrogenase is overexpressed and/or under the control of an inducible or repressible promoter in a recombinant yeast according to the invention.

In some embodiments, overexpression of the malate dehydrogenase may result from the control of the corresponding gene by a strong promoter within the said recombinant yeast.

In some other embodiments, overexpression of the malate dehydrogenase may result from the presence of a plurality of copies of a malate dehydrogenase-encoding sequence within the genome of the said recombinant yeast.

In still further embodiments, overexpression of the malate dehydrogenase may result from both (i) the control of the corresponding gene by a strong promoter within the said recombinant yeast and (ii) the presence of a plurality of copies of a malate dehydrogenase-encoding sequence within the genome the said recombinant yeast.

NADP-Dependent Malic Enzyme (ME3)

The NADP-dependent malic enzyme is a protein which is described in the art for catalyzing the conversion of malate into pyruvate while freeing one NADPH. It is also known as Malate Dehydrogenase NADP dependent. The NADP-dependent malic enzyme encoded by the genome of *Arabidopsis thaliana* may be termed ME3.

A method implemented to measure the activity level of NADP-dependent malic enzyme belongs to the general knowledge of the one skilled in the art.

In this regard, the one skilled in the art may advantageously refer to the method described by Gerrard-Wheeler et al. FEBS Journal 276 (2009) 5665-5677.

Preferred NADP-dependent malic enzyme in the present specification is an enzyme having an EC number of n° EC 1.1.1.40.

According to a preferred embodiment, the nucleic acid(s) encoding an NADP-dependent malic enzyme may be nucleic acid(s) originating from organisms preferably selected in a group comprising prokaryotic organisms and eukaryotic organisms. In some embodiments, the nucleic acid(s) encoding an NADP-dependent malic enzyme may be nucleic acid(s) originating from archaebacteria. In some embodiments, the nucleic acid(s) encoding an NADP-dependent malic enzyme may be nucleic acid(s) originating from organisms preferably selected from plants and bacteria. In some other preferred embodiments, the nucleic acid(s) encoding an NADP-dependent malic enzyme may be nucleic acid(s) originating from *Arabidopsis thaliana*.

According to a yet preferred embodiment, the nucleic acid(s) encoding an NADP-dependent malic enzyme may be nucleic acid(s) selected from the group consisting of sequences having at least 45%, advantageously at least 65%, preferably at least 80%, nucleic acid identity with a nucleic acid of SEQ ID NO: 3, and also a biological activity of the same nature. The nucleic acid of SEQ ID NO: 3 encodes an NADP-dependent malic enzyme originating from *Arabidopsis thaliana*, that may also be termed ME3.

A biological activity of the same nature regarding this sequence is the capacity to code for an enzyme that catalyzes the conversion of malate into pyruvate while freeing one NADPH.

As described herein, a nucleic acid sequence having at least 45% nucleotide identity with a reference nucleic acid sequence encompasses nucleic acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the NADP-dependent malic enzyme from *Saccharomyces cerevisiae*, the one skilled in the art may refer to the accession number NP197960.1 in the UniProt database, or to SEQ ID NO. 4 described herein.

According to another particular embodiment, the nucleic acid(s) encoding aspartokinase may be nucleic acid(s) encoding an amino acid sequence selected from the group consisting of sequences having at least 45%, advantageously at least 65%, preferably at least 80%, amino acid identity with the amino acid sequence of SEQ ID NO: 4, and also a biological activity of the same nature. Illustratively, the NADP-dependent malic enzyme originating from *Chlamydomonas reihnarditii* has 48% amino acid identity with the NADP-dependent malic enzyme of SEQ ID NO. 4.

A biological activity of the same nature regarding this sequence is as described previously, i.e. the capacity to catalyze the conversion of malate into pyruvate while freeing one NADPH.

As described herein, an amino acid sequence having at least 45% amino acid identity with a reference nucleic acid sequence encompasses amino acid sequences having at least 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the NADP-dependent malic enzyme in the present invention is regulated by at least one promoter and at least one terminator, such as herein after defined more in details, which are present in 5' and 3' position respectively of the nucleic acid sequence encoding the said NADP-dependent malic enzyme.

As it is specified elsewhere in the present description, the strong NADP-dependent malic enzyme expression shall be controlled in a recombinant yeast according to the invention.

In preferred embodiments, the controlled strong expression of the NADP-dependent malic enzyme is performed by placing the NADP-dependent malic enzyme-encoding nucleic acid sequence under the control of an appropriate inducible or repressible promoter, preferably a strong inducible or repressible promoter.

Phosphoenolpyruvate Carboxylase (PEPC)

The phosphoenolpyruvate carboxylase is a protein which is described in the art for catalyzing the conversion of phosphoenolpyruvate into oxaloacetate. The phosphoenolpyruvate carboxylase encoded by the genome of *E. coli* may be termed PEPC or PPC.

A method implemented to measure the activity level of phosphoenolpyruvate carboxylase belongs to the general knowledge of the one skilled in the art.

In this regard, the one skilled in the art may advantageously refer to the method described by Bazaes S. et al. (2007) The Protein Journal, 26, 265-269 and Mariët J. Van der Werf et al. (1997) Arch Microbiol 167: 332-342.

Preferred phosphoenolpyruvate carboxylase in the present specification is an enzyme having an EC number of n° 4.1.1.31.

According to a preferred embodiment, the nucleic acid(s) encoding a phosphoenolpyruvate carboxylase may be nucleic acid(s) originating from organisms preferably selected in a group comprising prokaryotic organisms and eukaryotic organisms. In some embodiments, the nucleic acid(s) encoding a phosphoenolpyruvate carboxylase may be nucleic acid(s) originating from archaebacteria. In some embodiments, the nucleic acid(s) encoding a phosphoenolpyruvate carboxylase may be nucleic acid(s) originating from organisms preferably selected from bacteria. In some other preferred embodiments, the nucleic acid(s) encoding a phosphoenolpyruvate carboxylase may be nucleic acid(s) originating from *Escherichia coli*.

According to a yet preferred embodiment, the nucleic acid(s) encoding a phosphoenolpyruvate carboxylase may be nucleic acid(s) selected from the group consisting of sequences having at least 25%, advantageously at least 65%, preferably at least 80%, nucleic acid identity with a nucleic acid of SEQ ID NO: 5, and also a biological activity of the same nature.

A biological activity of the same nature regarding this sequence is the capacity to code for an enzyme that catalyzes the conversion of phosphoenolpyruvate into oxaloacetate.

As described herein, a nucleic acid sequence having at least 25% nucleotide identity with a reference nucleic acid sequence encompasses nucleic acid sequences having at least 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the phosphoenolpyruvate carboxylase from *E. coli*, the one skilled in the art may refer to the accession number WP 032179661 in the UniProt database, or to SEQ ID NO. 6 described herein.

According to another particular embodiment, the nucleic acid(s) encoding phosphoenolpyruvate carboxylase may be nucleic acid(s) encoding an amino acid sequence selected from the group consisting of sequences having at least 25%, advantageously at least 65%, preferably at least 80%, amino acid identity with the amino acid sequence of SEQ ID NO: 6, and also a biological activity of the same nature. Illustratively, the phosphoenolpyruvate carboxylase originating from *Cyanothece* sp. PCC782 has 29% amino acid identity with the phosphoenolpyruvate carboxylase of SEQ ID NO. 6.

A biological activity of the same nature regarding this sequence is as described previously, i.e. the capacity to catalyze the conversion of phosphoenolpyruvate into oxaloacetate.

As described herein, an amino acid sequence having at least 25% amino acid identity with a reference nucleic acid sequence encompasses amino acid sequences having at least 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the phosphoenolpyruvate carboxylase in the present invention is regulated by at least one promoter and at least one terminator, such as herein after defined more in details, which are present in 5' and 3' position respectively of the nucleic acid sequence encoding the said phosphoenolpyruvate carboxylase.

As it is specified elsewhere in the present description, the strong phosphoenolpyruvate carboxylase expression shall be controlled in a recombinant yeast according to the invention.

In preferred embodiments, the controlled strong expression of the phosphoenolpyruvate carboxylase is performed by placing the phosphoenolpyruvate carboxylase-encoding nucleic acid sequence under the control of an appropriate inducible or repressible promoter, preferably a strong inducible or repressible promoter.

Phosphoenolpyruvate Carboxykinase (PEPCK)

The phosphoenolpyruvate carboxykinase is a protein which is described in the art for catalyzing the conversion of phosphoenolpyruvate into oxaloacetate. The phosphoenolpyruvate carboxykinase encoded by the genome of *E. coli* may be termed PEPCK.

A method implemented to measure the activity level of phosphoenolpyruvate carboxykinase belongs to the general knowledge of the one skilled in the art.

In this regard, the one skilled in the art may advantageously refer to the method described by Bazaes S. et al. (2007) The Protein Journal, 26, 265-269 and Mariët J. Van der Werf et al. (1997) Arch Microbiol 167: 332-342.

Preferred phosphoenolpyruvate carboxykinase in the present specification is an enzyme having an EC number of n° 4.1.1.49.

According to a preferred embodiment, the nucleic acid(s) encoding a phosphoenolpyruvate carboxykinase may be nucleic acid(s) originating from organisms preferably selected in a group comprising prokaryotic organisms and eukaryotic organisms. In some embodiments, the nucleic acid(s) encoding a phosphoenolpyruvate carboxykinase may be nucleic acid(s) originating from archaebacteria. In some embodiments, the nucleic acid(s) encoding a phosphoenolpyruvate carboxykinase may be nucleic acid(s) originating from organisms preferably selected from bacteria. In some other preferred embodiments, the nucleic acid(s) encoding a phosphoenolpyruvate carboxykinase may be nucleic acid(s) originating from *Escherichia coll*.

According to a yet preferred embodiment, the nucleic acid(s) encoding a phosphoenolpyruvate carboxykinase may be nucleic acid(s) selected from the group consisting of sequences having at least 20%, advantageously at least 65%, preferably at least 80%, nucleic acid identity with a nucleic acid of SEQ ID NO: 7, and also a biological activity of the same nature.

A biological activity of the same nature regarding this sequence is the capacity to code for an enzyme that catalyzes the conversion of phosphoenolpyruvate into oxaloacetate while phosphorylating an ADP into ATP.

As described herein, a nucleic acid sequence having at least 20% nucleotide identity with a reference nucleic acid sequence encompasses nucleic acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the phosphoenolpyruvate carboxykinase from *E. coli*, the one skilled in the art may refer to the accession number NP013023.3 in the UniProt database, or to SEQ ID NO. 8 described herein.

According to another particular embodiment, the nucleic acid(s) encoding phosphoenolpyruvate carboxykinase may be nucleic acid(s) encoding an amino acid sequence selected from the group consisting of sequences having at least 20%, advantageously at least 65%, preferably at least 80%, amino acid identity with the amino acid sequence of SEQ ID NO: 8, and also a biological activity of the same nature. Illus-tratively, the phosphoenolpyruvate carboxykinase originating from *Streptococcus gorgonii* has 22% amino acid identity with the phosphoenolpyruvate carboxykinase of SEQ ID NO. 8.

A biological activity of the same nature regarding this sequence is as described previously, i.e. the capacity to catalyze the conversion of phosphoenolpyruvate into oxaloacetate.

As described herein, an amino acid sequence having at least 20% amino acid identity with a reference nucleic acid sequence encompasses amino acid sequences having at least 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the phosphoenolpyruvate carboxykinase in the present invention is regulated by at least one promoter and at least one terminator, such as herein after defined more in details, which are present in 5' and 3' position respectively of the nucleic acid sequence encoding the said phosphoenolpyruvate carboxykinase.

As it is specified elsewhere in the present description, the strong phosphoenolpyruvate carboxykinase expression shall be controlled in a recombinant yeast according to the invention.

In preferred embodiments, the controlled strong expression of the phosphoenolpyruvate carboxykinase is performed by placing the phosphoenolpyruvate carboxykinase-encoding nucleic acid sequence under the control of an appropriate inducible or repressible promoter, preferably a strong inducible or repressible promoter.

Acetaldehyde-CoA Dehydrogenase (MHPF)

The acetaldehyde-CoA dehydrogenase enzyme is a protein which is described in the art for catalyzing the conversion of acetaldehyde into acetyl-CoA while freeing one NADH. The acetaldehyde-CoA dehydrogenase encoded by the genome of *E. coli* may be termed MHPF.

A method implemented to measure the activity level of acetaldehyde-CoA dehydrogenase belongs to the general knowledge of the one skilled in the art.

In this regard, the one skilled in the art may advantageously refer to the method described by Fischer et al. (2013) Chemi. Biol. Interact. 202 70-77.

Preferred acetaldehyde-CoA dehydrogenase in the present specification is an enzyme having an EC number of n° EC 1.2.1.10.

According to a preferred embodiment, the nucleic acid(s) encoding an acetaldehyde-CoA dehydrogenase may be nucleic acid(s) originating from organisms preferably selected in a group comprising prokaryotic organisms and eukaryotic organisms. In some embodiments, the nucleic acid(s) encoding an acetaldehyde-CoA dehydrogenase may be nucleic acid(s) originating from archaebacteria. In some embodiments, the nucleic acid(s) encoding an acetaldehyde-CoA dehydrogenase may be nucleic acid(s) originating from organisms preferably selected from bacteria. In some other preferred embodiments, the nucleic acid(s) encoding an acetaldehyde-CoA dehydrogenase may be nucleic acid(s) originating from *Escherichia coli*.

According to a yet preferred embodiment, the nucleic acid(s) encoding an acetaldehyde-CoA dehydrogenase may be nucleic acid(s) selected from the group consisting of sequences having at least 30%, advantageously at least 65%, preferably at least 80%, nucleic acid identity with a nucleic acid of SEQ ID NO: 9, and also a biological activity of the same nature. The nucleic acid of SEQ ID NO: 9 encodes an acetaldehyde-CoA dehydrogenase originating from *Escherichia coli*, that may also be termed MHPF.

A biological activity of the same nature regarding this sequence is the capacity to code for an enzyme that catalyzes the conversion of acetaldehyde into acetyl-CoA while freeing one NADH.

As described herein, a nucleic acid sequence having at least 30% nucleotide identity with a reference nucleic acid sequence encompasses nucleic acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 65% nucleotide identity with a reference nucleic acid sequence encompasses nucleic acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

As described herein, a nucleic acid sequence having at least 80% nucleotide identity with a reference nucleic acid sequence encompasses nucleic acid sequences having at least 81%, 82%, 83%, 84%, 85%, 86%, 87%, 88%, 89%, 90%, 91%, 92%, 93%, 94%, 95%, 96%, 97%, 98% and 99% nucleotide identity with the said reference nucleic acid sequence, and also a biological activity of the same nature.

For the amino acid sequence of the acetaldehyde-CoA dehydrogenase from *Escherichia coli*, the one skilled in the art may refer to the accession number NP414885 in the UniProt database, or to SEQ ID NO. 10 described herein.

According to another particular embodiment, the nucleic acid(s) encoding acetaldehyde-CoA dehydrogenase may be nucleic acid(s) encoding an amino acid sequence selected from the group consisting of sequences having at least 30%, advantageously at least 65%, preferably at least 80%, amino acid identity with the amino acid sequence of SEQ ID NO: 10, and also a biological activity of the same nature. Illustratively, the acetaldehyde-CoA dehydrogenase originating from *Streptomyces niveiscabiei* has 32% amino acid identity with the acetaldehyde-CoA dehydrogenase of SEQ ID NO. 10.

A biological activity of the same nature regarding this sequence is as described previously, i.e. the capacity to catalyze the conversion of acetaldehyde into acetyl-CoA while freeing one NADH.

As described herein, an amino acid sequence having at least 30% amino acid identity with a reference nucleic acid sequence encompasses amino acid sequences having at least 31%, 32%, 33%, 34%, 35%, 36%, 37%, 38%, 39%, 40% 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference nucleic acid sequence.

As described herein, an amino acid sequence having at least 65% amino acid identity with a reference amino acid sequence encompasses amino acid sequences having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As described herein, an amino acid sequence having at least 80% amino acid identity with a reference amino acid sequence encompasses amino acid sequences having at least 81%, 82%, 83%, 84%, 85%, 86%, 87%, 88%, 89%, 90%, 91%, 92%, 93%, 94%, 95%, 96%, 97%, 98% and 99% amino acid identity with the said reference amino acid sequence.

As above-mentioned, the expression level of the acetaldehyde-CoA dehydrogenase in the present invention is regulated by at least one promoter and at least one terminator, such as herein after defined more in details, which are present in 5' and 3' position respectively of the nucleic acid sequence encoding the said acetaldehyde-CoA dehydrogenase.

As it is specified elsewhere in the present description, the strong acetaldehyde-CoA dehydrogenase expression shall be controlled in a recombinant yeast according to the invention.

In preferred embodiments, the controlled strong expression of the acetaldehyde-CoA dehydrogenase is performed by placing the acetaldehyde-CoA dehydrogenase-encoding nucleic acid sequence under the control of an appropriate inducible or repressible promoter, preferably a strong inducible or repressible promoter.

Pyruvate Kinase 1 (PYK1)

The pyruvate kinase 1 is a protein which is described in the art for catalyzing the conversion of phosphoenolpyruvate (PEP) into pyruvate. The pyruvate kinase 1 encoded by the genome of *Saccharomyces cerevisiae* may be termed PYK1.

A method implemented to measure the activity level of pyruvate kinase 1 belongs to the general knowledge of the one skilled in the art.

In this regard, the one skilled in the art may advantageously refer to the method described by Susan-resiga and Nowak (2004) Biochemistry 43, 15230-15245).

Preferred pyruvate kinase 1 in the present specification is an enzyme having an EC number of n° 2.7.1.40.

According to a preferred embodiment, the nucleic acid(s) encoding a pyruvate kinase 1 may be nucleic acid(s) originating from organisms preferably selected in a group comprising prokaryotic organisms and eukaryotic organisms. In some preferred embodiments, the nucleic acid(s) encoding a pyruvate kinase 1 may be nucleic acid(s) originating from a yeast, and especially from *Saccharomyces cerevisiae*.

According to a particular embodiment, the nucleic acid(s) encoding a pyruvate kinase 1 may be nucleic acid of SEQ ID NO: 11. The nucleic acid of SEQ ID NO: 11 encodes a pyruvate kinase 1 originating from *Saccharomyces*, that may also be termed PYK1.

For the amino acid sequence of the pyruvate kinase 1 from *Saccharomyces cerevisiae*, the one skilled in the art may refer to the accession number NP009362.1 in the UniProt database, or to SEQ ID NO. 12 described herein.

As above-mentioned, the expression level of the pyruvate kinase 1 in the present invention is regulated by at least one promoter and at least one terminator, such as herein after defined more in details, which are present in 5' and 3' position respectively of the nucleic acid sequence encoding the said pyruvate kinase 1.

As it is specified elsewhere in the present description, in some embodiments of the invention, the pyruvate kinase 1 is (a) fully or partially deleted, and/or (b) under the control of an inducible or repressible promoter; under the control of a weak promoter; and/or in a destabilized form, in a recombinant yeast according to the invention.

In a preferred embodiment, the pyruvate kinase 1 PYK1 is independently under the control of an inducible or repressible promoter; under the control of a weak promoter; and/or in a destabilized form.

Preferably, the pyruvate kinase 1 PYK1 is not fully deleted from the recombinant yeast of the invention.

Specific Embodiments of an Oxaloacetate Derivative-Producing Recombinant Yeast

Deletion or Under Expression of Pyruvate Kinase 2

In preferred embodiments of a recombinant yeast according to the invention, the recombinant yeast is furthermore defined as having a genome in which:
(i) at least one, preferably all, nucleic acid encoding a pyruvate kinase 2 PYK2 has been deleted, and/or
(ii) at least one, preferably all, nucleic acid encoding a pyruvate kinase 2 PYK2 is under the control of an inducible or repressible promoter and/or is in a destabilized form.

Without wishing to be bound by any particular theory, the inventors believe that an under expression of a pyruvate kinase 2 gene shall increase oxaloacetate production by the recombinant yeast by reducing the consumption of the produced phosphoenolpyruvate (PEP) by its conversion into pyruvate.

In some embodiments, under expression of pyruvate kinase 2 may be rendered conditional, for example by placing the expression of this gene under the control of repressible regulatory sequences, such as an inducible or repressible promoters.

Methods for repressing gene expression, for interrupting target genes or for deleting target genes, are well known from the one skilled in the art.

Pyruvate kinase 2 under expression also encompasses the insertion of a nucleic acid encoding a destabilized pyruvate kinase 2. A destabilized pyruvate kinase 2 is a variant of pyruvate kinase 2 that is more rapidly degraded within the yeast cell than the parent pyruvate kinase 2.

In preferred embodiments, a destabilized pyruvate kinase 2 consists of a degron-tagged pyruvate kinase 2 protein.

For example, the pyruvate kinase 2 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of pyruvate kinase 2 belongs to the general knowledge of the one skilled in the art.

In this regard, the one skilled in the art may advantageously refer to the method described by Susan-resiga and Nowak (2004) Biochemistry 43, 15230-15245).

Preferred pyruvate kinase 2 in the present specification is an enzyme having an EC number of n° 2.7.1.40.

According to a preferred embodiment, the nucleic acid(s) encoding a pyruvate kinase 2 may be nucleic acid(s) originating from organisms preferably selected in a group comprising prokaryotic organisms and eukaryotic organisms. In some preferred embodiments, the nucleic acid(s) encoding a pyruvate kinase 2 may be nucleic acid(s) originating from a yeast, and especially from *Saccharomyces cerevisiae*.

According to a particular embodiment, the nucleic acid(s) encoding a pyruvate kinase 2 may be nucleic acid of SEQ ID NO: 13. The nucleic acid of SEQ ID NO: 13 encodes a pyruvate kinase 2 originating from *Saccharomyces*, that may also be termed PYK2.

For the amino acid sequence of the pyruvate kinase 2 from *Saccharomyces cerevisiae*, the one skilled in the art may refer to the accession number NP014992.3 in the UniProt database, or to SEQ ID NO. 14 described herein.

As above-mentioned, the expression level of the pyruvate kinase 2 in the present invention is regulated by at least one promoter and at least one terminator, such as herein after defined more in details, which are present in 5' and 3' position respectively of the nucleic acid sequence encoding the said pyruvate kinase 2.

As it is specified elsewhere in the present description, in some embodiments of the invention, the pyruvate kinase 2 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 1

In preferred embodiments of a recombinant yeast according to the invention, the recombinant yeast is furthermore defined as having a genome in which:
(i) at least one, preferably all, nucleic acid encoding an alcohol dehydrogenase 1 ADH1 has been deleted, and/or
(ii) at least one, preferably all, nucleic acid encoding an alcohol dehydrogenase 1 ADH1 is under the control of an inducible or repressible promoter and/or is in a destabilized form.

Without wishing to be bound by any particular theory, the inventors believe that an under expression of an alcohol dehydrogenase 1 gene shall increase Acetyl-CoA production by the recombinant yeast by reducing the consumption of the produced acetaldehyde by its conversion into ethanol.

In some embodiments, under expression of alcohol dehydrogenase 1 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 1 under expression also encompasses the insertion of a nucleic acid encoding a destabilized alcohol dehydrogenase 1. A destabilized alcohol dehydrogenase 1 is a variant of alcohol dehydrogenase 1 that is more rapidly degraded within the yeast cell than the parent alcohol dehydrogenase 1.

In preferred embodiments, a destabilized alcohol dehydrogenase 1 consists of a degron-tagged alcohol dehydrogenase 1 protein.

For example, the alcohol dehydrogenase 1 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 1 belongs to the general knowledge of the one skilled in the art.

In this regard, the one skilled in the art may advantageously refer to the method described by Ganzhorn A. J, Green D. W, Hershey A. D, Gould R. M, Plapp B. V (1987) The Journal of Biological Chemistry 262, p 3754-3761.

Preferred alcohol dehydrogenase 1 in the present specification is an enzyme having an EC number of n° 1.1.1.1.

According to a preferred embodiment, the nucleic acid(s) encoding an alcohol dehydrogenase 1 may be nucleic acid(s) originating from organisms preferably selected in a group comprising prokaryotic organisms and eukaryotic organisms. In some preferred embodiments, the nucleic acid(s) encoding an alcohol dehydrogenase 1 may be nucleic acid(s) originating from a yeast, and especially from *Saccharomyces cerevisiae*.

According to a particular embodiment, the nucleic acid(s) encoding an alcohol dehydrogenase 1 may be nucleic acid of SEQ ID NO: 15. The nucleic acid of SEQ ID NO: 15 encodes an alcohol dehydrogenase 1 originating from *Saccharomyces*, that may also be termed ADH1.

For the amino acid sequence of the alcohol dehydrogenase 1 from *Saccharomyces cerevisiae*, the one skilled in the art may refer to the accession number NP014555.1 in the UniProt database, or to SEQ ID NO. 16 described herein.

As above-mentioned, the expression level of the alcohol dehydrogenase 1 in the present invention is regulated by at least one promoter and at least one terminator, such as herein after defined more in details, which are present in 5' and 3' position respectively of the nucleic acid sequence encoding the said alcohol dehydrogenase 1.

As it is specified elsewhere in the present description, in some embodiments of the invention, the alcohol dehydrogenase 1 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Carboxylase 1 (PYC1)

In preferred embodiments of a recombinant yeast according to the invention, the recombinant yeast is furthermore defined as having a genome in which:

(i) at least one, preferably all, nucleic acid encoding a pyruvate carboxylase 1 PYC1 has been deleted, and/or (ii) at least one, preferably all, nucleic acid encoding a pyruvate carboxylase 1 PYC1 is under the control of an inducible or repressible promoter and/or is in a destabilized form.

Without wishing to be bound by any particular theory, the inventors believe that an under expression of a pyruvate carboxylase 1 gene shall increase pyruvate production by the recombinant yeast by reducing the consumption of the produced pyruvate by its conversion into oxaloacetate.

In some embodiments, under expression of pyruvate carboxylase 1 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate carboxylase 1 under expression also encompasses the insertion of a nucleic acid encoding a destabilized pyruvate carboxylase 1. A destabilized pyruvate carboxylase 1 is a variant of pyruvate carboxylase 1 that is more rapidly degraded within the yeast cell than the parent pyruvate carboxylase 1.

In preferred embodiments, a destabilized pyruvate carboxylase 1 consists of a degron-tagged pyruvate carboxylase 1 protein.

For example, the pyruvate carboxylase 1 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of pyruvate carboxylase 1 belongs to the general knowledge of the one skilled in the art.

In this regard, the one skilled in the art may advantageously refer to the method described by Branson, Nezic, Wallace, and Atwood (2002) biochemistry (13) 4459-66.

Preferred pyruvate carboxylase 1 in the present specification is an enzyme having an EC number of n° 6.4.1.1.

According to a preferred embodiment, the nucleic acid(s) encoding a pyruvate carboxylase 1 may be nucleic acid(s) originating from organisms preferably selected in a group comprising prokaryotic organisms and eukaryotic organisms. In some preferred embodiments, the nucleic acid(s) encoding a pyruvate carboxylase 1 may be nucleic acid(s) originating from a yeast, and especially from *Saccharomyces cerevisiae*.

According to a particular embodiment, the nucleic acid(s) encoding a pyruvate carboxylase 1 may be nucleic acid of SEQ ID NO: 17. The nucleic acid of SEQ ID NO: 17 encodes a pyruvate carboxylase 1 originating from *Saccharomyces*, that may also be termed PYC1.

For the amino acid sequence of the pyruvate carboxylase 1 from *Saccharomyces cerevisiae*, the one skilled in the art may refer to the accession number NP011453.1 in the UniProt database, or to SEQ ID NO. 18 described herein.

As above-mentioned, the expression level of the pyruvate carboxylase 1 in the present invention is regulated by at least one promoter and at least one terminator, such as herein after defined more in details, which are present in 5' and 3' position respectively of the nucleic acid sequence encoding the said pyruvate carboxylase 1.

As it is specified elsewhere in the present description, in some embodiments of the invention, the pyruvate carboxylase 1 is (a) fully or partially deleted, and/or (b) under the control of an inducible or repressible promoter; under the control of a weak promoter; and/or in a destabilized form, in a recombinant yeast according to the invention.

Deletion or Under Expression of Pyruvate Carboxylase 2

In preferred embodiments of a recombinant yeast according to the invention, the recombinant yeast is furthermore defined as having a genome in which:

(i) at least one, preferably all, nucleic acid encoding a pyruvate carboxylase 2 PYC2 has been deleted, and/or (ii) at least one, preferably all, nucleic acid encoding a pyruvate carboxylase 2 PYC2 is under the control of an inducible or repressible promoter and/or is in a destabilized form.

Without wishing to be bound by any particular theory, the inventors believe that an under expression of a pyruvate carboxylase 2 gene shall increase pyruvate production by the recombinant yeast by reducing the consumption of the produced pyruvate by its conversion into oxaloacetate.

In some embodiments, under expression of pyruvate carboxylase 2 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Pyruvate carboxylase 2 under expression also encompasses the insertion of a nucleic acid encoding a destabilized pyruvate carboxylase 2. A destabilized pyruvate carboxylase 2 is a variant of pyruvate carboxylase 2 that is more rapidly degraded within the yeast cell than the parent pyruvate carboxylase 2.

In preferred embodiments, a destabilized pyruvate carboxylase 2 consists of a degron-tagged pyruvate carboxylase 2 protein.

For example, the pyruvate carboxylase 2 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of pyruvate carboxylase 2 belongs to the general knowledge of the one skilled in the art.

In this regard, the one skilled in the art may advantageously refer to the method described by Branson, Nezic, Wallace, and Atwood (2002) Biochemistry (13) 4459-66.

Preferred pyruvate kinase 2 in the present specification is an enzyme having an EC number of n° 6.4.1.1.

According to a preferred embodiment, the nucleic acid(s) encoding a pyruvate carboxylase 2 may be nucleic acid(s) originating from organisms preferably selected in a group comprising prokaryotic organisms and eukaryotic organisms. In some preferred embodiments, the nucleic acid(s) encoding a pyruvate carboxylase 2 may be nucleic acid(s) originating from a yeast, and especially from *Saccharomyces cerevisiae*.

According to a particular embodiment, the nucleic acid(s) encoding a pyruvate carboxylase 2 may be nucleic acid of SEQ ID NO: 19. The nucleic acid of SEQ ID NO: 19 encodes a pyruvate carboxylase 2 originating from *Saccharomyces*. For the amino acid sequence of the pyruvate carboxylase 2 from *Saccharomyces cerevisiae*, the one skilled in the art may refer to the accession number NP009777.1 in the UniProt database, or to SEQ ID NO. 20 described herein.

As above-mentioned, the expression level of the pyruvate carboxylase 2 in the present invention is regulated by at least one promoter and at least one terminator, such as herein after defined more in details, which are present in 5' and 3' position respectively of the nucleic acid sequence encoding the said pyruvate carboxylase 2.

As it is specified elsewhere in the present description, in some embodiments of the invention, the pyruvate carboxylase 2 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 3

In preferred embodiments of a recombinant yeast according to the invention, the recombinant yeast is furthermore defined as having a genome in which:

(i) at least one, preferably all, nucleic acid encoding an alcohol dehydrogenase 3 ADH3 has been deleted, and/or (ii) at least one, preferably all, nucleic acid encoding an alcohol dehydrogenase 3 ADH3 is under the control of an inducible or repressible promoter and/or is in a destabilized form.

Without wishing to be bound by any particular theory, the inventors believe that an under expression of an alcohol dehydrogenase 3 gene shall increase Acetyl-CoA production by the recombinant yeast by reducing the consumption of the produced acetaldehyde by its conversion into ethanol.

In some embodiments, under expression of alcohol dehydrogenase 3 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 3 under expression also encompasses the insertion of a nucleic acid encoding a destabilized alcohol dehydrogenase 3. A destabilized alcohol dehydrogenase 3 is a variant of alcohol dehydrogenase 3 that is more rapidly degraded within the yeast cell than the parent alcohol dehydrogenase 3.

In preferred embodiments, a destabilized alcohol dehydrogenase 3 consists of a degron-tagged alcohol dehydrogenase 3 protein.

For example, the alcohol dehydrogenase 3 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 3 belongs to the general knowledge of the one skilled in the art. In this regard, the one skilled in the art may advantageously refer to the method described by Ganzhorn A. J, Green D. W, Hershey A. D, Gould R. M, Plapp B. V (1987) The Journal of Biological Chemistry 262, p 3754-3761

Preferred alcohol dehydrogenase 3 in the present specification is an enzyme having an EC number of n° 1.1.1.1.

According to a preferred embodiment, the nucleic acid(s) encoding an alcohol dehydrogenase 3 may be nucleic acid(s) originating from organisms preferably selected in a group comprising prokaryotic organisms and eukaryotic organisms. In some preferred embodiments, the nucleic acid(s) encoding an alcohol dehydrogenase 3 may be nucleic acid(s) originating from a yeast, and especially from *Saccharomyces cerevisiae*.

According to a particular embodiment, the nucleic acid(s) encoding an alcohol dehydrogenase 3 may be nucleic acid of SEQ ID NO: 21. The nucleic acid of SEQ ID NO: 21 encodes an alcohol dehydrogenase 3 originating from *Saccharomyces*, that may also be termed ADH3.

For the amino acid sequence of the alcohol dehydrogenase 3 from *Saccharomyces cerevisiae*, the one skilled in the art may refer to the accession number NP013800.1 in the UniProt database, or to SEQ ID NO. 22 described herein. As above-mentioned, the expression level of the alcohol dehydrogenase 3 in the present invention is regulated by at least one promoter and at least one terminator, such as herein after defined more in details, which are present in 5' and 3' position respectively of the nucleic acid sequence encoding the said alcohol dehydrogenase 3.

As it is specified elsewhere in the present description, in some embodiments of the invention, the alcohol dehydrogenase 3 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 4

In preferred embodiments of a recombinant yeast according to the invention, the recombinant yeast is furthermore defined as having a genome in which:

(i) at least one, preferably all, nucleic acid encoding an alcohol dehydrogenase 4 ADH4 has been deleted, and/or (ii) at least one, preferably all, nucleic acid encoding an alcohol dehydrogenase 4 ADH4 is under the control of an inducible or repressible promoter and/or is in a destabilized form.

Without wishing to be bound by any particular theory, the inventors believe that an under expression of an alcohol dehydrogenase 4 gene shall increase Acetyl-CoA production by the recombinant yeast by reducing the consumption of the produced acetaldehyde by its conversion into ethanol.

In some embodiments, under expression of alcohol dehydrogenase 4 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 4 under expression also encompasses the insertion of a nucleic acid encoding a destabilized alcohol dehydrogenase 4. A destabilized alcohol dehydrogenase 4 is a variant of alcohol dehydrogenase 4 that is more rapidly degraded within the yeast cell than the parent alcohol dehydrogenase 4.

In preferred embodiments, a destabilized alcohol dehydrogenase 4 consists of a degron-tagged alcohol dehydrogenase 4 protein.

For example, the alcohol dehydrogenase 4 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 4 belongs to the general knowledge of the one skilled in the art.

In this regard, the one skilled in the art may advantageously refer to the method described by Ganzhorn A. J, Green D. W, Hershey A. D, Gould R. M, Plapp B. V (1987) The Journal of Biological Chemistry 262, p 3754-3761.

Preferred alcohol dehydrogenase 4 in the present specification is an enzyme having an EC number of n° 1.1.1.1.

According to a preferred embodiment, the nucleic acid(s) encoding an alcohol dehydrogenase 4 may be nucleic acid(s) originating from organisms preferably selected in a group comprising prokaryotic organisms and eukaryotic organisms. In some preferred embodiments, the nucleic acid(s) encoding an alcohol dehydrogenase 4 may be nucleic acid(s) originating from a yeast, and especially from *Saccharomyces cerevisiae*.

According to a particular embodiment, the nucleic acid(s) encoding an alcohol dehydrogenase 4 may be nucleic acid of SEQ ID NO: 23. The nucleic acid of SEQ ID NO: 23 encodes an alcohol dehydrogenase 4 originating from *Saccharomyces*, that may also be termed ADH4.

For the amino acid sequence of the alcohol dehydrogenase 4 from *Saccharomyces cerevisiae*, the one skilled in the art may refer to the accession number NP011258.2 in the UniProt database, or to SEQ ID NO. 24 described herein.

As above-mentioned, the expression level of the alcohol dehydrogenase 4 in the present invention is regulated by at least one promoter and at least one terminator, such as herein after defined more in details, which are present in 5' and 3' position respectively of the nucleic acid sequence encoding the said alcohol dehydrogenase 4.

As it is specified elsewhere in the present description, in some embodiments of the invention, the alcohol dehydrogenase 4 is (a) fully or partially deleted, and/or (b) under the control of an inducible or repressible promoter; under the control of a weak promoter; and/or in a destabilized form, in a recombinant yeast according to the invention.

Deletion or Under Expression of Alcohol Dehydrogenase 5

In preferred embodiments of a recombinant yeast according to the invention, the recombinant yeast is furthermore defined as having a genome in which:

(i) at least one, preferably all, nucleic acid encoding an alcohol dehydrogenase 5 ADH5 has been deleted, and/or (ii) at least one, preferably all, nucleic acid encoding an alcohol dehydrogenase 5 ADH5 is under the control of an inducible or repressible promoter and/or is in a destabilized form.

Without wishing to be bound by any particular theory, the inventors believe that an under expression of an alcohol dehydrogenase 5 gene shall increase Acetyl-CoA production by the recombinant yeast by reducing the consumption of the produced acetaldehyde by its conversion into ethanol.

In some embodiments, under expression of alcohol dehydrogenase 5 may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

Alcohol dehydrogenase 5 under expression also encompasses the insertion of a nucleic acid encoding a destabilized alcohol dehydrogenase 5. A destabilized alcohol dehydrogenase 5 is a variant of ADH5 that is more rapidly degraded within the yeast cell than the parent alcohol dehydrogenase 5.

In preferred embodiments, a destabilized alcohol dehydrogenase 5 consists of a degron-tagged alcohol dehydrogenase 5 protein.

For example, the alcohol dehydrogenase 5 gene can be interrupted by loxP, or for example by URA3.Kl-loxP, and is thus deleted (which can also be termed inactivated).

It can alternatively be interrupted by a cassette comprising genes of interest, as illustrated in the examples as filed.

A method implemented to measure the activity level of alcohol dehydrogenase 5 belongs to the general knowledge of the one skilled in the art.

In this regard, the one skilled in the art may advantageously refer to the method described by Ganzhorn A. J, Green D. W, Hershey A. D, Gould R. M, Plapp B. V (1987) The Journal of Biological Chemistry 262, p 3754-3761.

Preferred alcohol dehydrogenase 5 in the present specification is an enzyme having an EC number of n° 1.1.1.1.

According to a preferred embodiment, the nucleic acid(s) encoding an alcohol dehydrogenase 5 may be nucleic acid(s) originating from organisms preferably selected in a group comprising prokaryotic organisms and eukaryotic organisms. In some preferred embodiments, the nucleic acid(s)

encoding an alcohol dehydrogenase 5 may be nucleic acid(s) originating from a yeast, and especially from *Saccharomyces cerevisiae*.

According to a particular embodiment, the nucleic acid(s) encoding an alcohol dehydrogenase 5 may be nucleic acid of SEQ ID NO: 25. The nucleic acid of SEQ ID NO: 25 encodes an alcohol dehydrogenase 5 originating from *Saccharomyces*, that may also be termed ADH5.

For the amino acid sequence of the alcohol dehydrogenase 5 from *Saccharomyces cerevisiae*, the one skilled in the art may refer to the accession number NP009703.3 in the UniProt database, or to SEQ ID NO. 26 described herein.

As above-mentioned, the expression level of the alcohol dehydrogenase 5 in the present invention is regulated by at least one promoter and at least one terminator, such as herein after defined more in details, which are present in 5' and 3' position respectively of the nucleic acid sequence encoding the said alcohol dehydrogenase 5.

As it is specified elsewhere in the present description, in some embodiments of the invention, the alcohol dehydrogenase 5 is (a) fully or partially deleted, and/or (b) under the control of an inducible or repressible promoter; under the control of a weak promoter; and/or in a destabilized form, in a recombinant yeast according to the invention.

Export of the Compounds of Interest

In further embodiments of a recombinant yeast according to the invention, the export of the produced oxaloacetate derivatives outside of the yeast cell may be enhanced by (i) under expression of genes encoding yeast permeases, by (ii) over expression of genes encoding amino acid exporter proteins, or by (iii) both under expression of genes encoding yeast permeases and over expression of genes encoding amino acid exporter proteins.

Under Expression of Permease-Encoding Gene(s)

As it is described below, permease-encoding genes that may be under expressed in a recombinant yeast according to the invention encompass AGP1, AGP3, BAP3, BAP2, GAP1, GNP1, MUP3 and MUP1.

AGP1 is the general amino acid permease 1 from *Saccharomyces cerevisiae*. *For the amino acid sequence of AGP1* it may be referred to the access number NP_009905 in the UniProt database. For the nucleic acid sequence, it may be referred to the access number NM_001178671 in the NCBI database.

AGP3 is the general amino acid permease 3 from *Saccharomyces cerevisiae*. For the amino acid sequence of AGP3 it may be referred to the access number NP_116600 in the UniProt database. For the nucleic acid sequence, it may be referred to the access number NM_001179912 in the NCBI database.

BAP3 is the valine amino acid permease from *Saccharomyces cerevisiae*. For the amino acid sequence of BAP3 it may be referred to the access number NP_010331 in the UniProt database. For the nucleic acid sequence, it may be referred to the access number NM_001180354 in the NCBI database.

BAP2 is the Leu/Val/Ile amino acid permease from *Saccharomyces cerevisiae*. For the amino acid sequence of BAP2 it may be referred to the access number NP_009624 in the UniProt database. For the nucleic acid sequence, it may be referred to the access number NM_001178416 in the NCBI database.

GAP1 is the general amino-acid permease from *Saccharomyces cerevisiae*. For the amino acid sequence of GAP1 it may be referred to the access number NP_012965.3 in the UniProt database. For the nucleic acid sequence, it may be referred to the access number NM_001179829 in the NCBI database.

GNP1 is the high-affinity glutamine permease from *Saccharomyces cerevisiae*. For the amino acid sequence of GNP1 it may be referred to the access number NP_010796 in the UniProt database. For the nucleic acid sequence, it may be referred to the access number NM_001180816 in the NCBI database.

MUP3 is the low-affinity methionine permease from *Saccharomyces cerevisiae*. For the amino acid sequence of MUP3 it may be referred to the access number NP_011827 in the UniProt database. For the nucleic acid sequence, it may be referred to the access number NM_001179116 in the NCBI database.

MUP1 is the low-affinity methionine permease from *Saccharomyces cerevisiae*. For the amino acid sequence of MUP it may be referred to the access number NP_011569 in the UniProt database. For the nucleic acid sequence, it may be referred to the access number NM_001181184 in the NCBI database.

In some embodiments of a recombinant yeast according to the invention, the said recombinant yeast is further defined as having an under expression one or more genes encoding a permease, that encompasses AGP1, AGP3, BAP3, BAP2, GAP1, GNP1, MUP3 and MUP1 permeases.

Without wishing to be bound by any particular theory, the inventors believe that an under expression of any of the permease genes shall increase the excretion of the produced oxaloacetate derivatives outside the yeast cell, e.g. in the culture medium.

As regards permeases under expression of one or more of these genes encompasses a complete repression of their expression, e.g. by interruption or deletion of the said one or more permease genes.

In some embodiments, under expression of a permease-encoding gene may be rendered conditional, for example by placing the expression of this gene under the control of repressible regulatory sequences, such as inducible or repressible promoters.

Methods for repressing gene expression, for interrupting target genes or for deleting target genes, are well known from the one skilled in the art.

As regards a permease gene, under expression also encompasses the insertion of a nucleic acid encoding a destabilized permease protein or the insertion of a nucleic acid encoding a destabilized permease protein, or both.

A destabilized permease is a variant of a permease that is more rapidly degraded within the yeast cell than the parent permease.

In preferred embodiments, a destabilized permease consists of a degron-tagged permease protein.

As illustrated in the examples, the AGP3 gene, the BAP3 gene, the GAP1 gene, the GNP1 gene and the MUP3 gene can be interrupted by loxP and are thus deleted.

Over Expression of Amino Acid Exporter Protein-Encoding Gene(s)

As it is described below, exporter protein-encoding genes that may be over expressed in a recombinant yeast according to the invention encompass AQR1 and TPO1.

AQR1 is a transporter from *Saccharomyces cerevisiae*. For the amino acid sequence of AQR1 it may be referred to the access number NP_014334 in the UniProt database. For the nucleic acid sequence, it may be referred to the access number NM_001182903 in the NCBI database.

TPO1 is a polyamine transporter from *Saccharomyces cerevisiae*. For the amino acid sequence of TPO1 it may be referred to the access number NP_013072 in the UniProt database. For the nucleic acid sequence, it may be referred to the access number NM_001181848 in the NCBI database.

In preferred embodiments of a recombinant yeast according to the invention, over expression of a transporter-encoding gene is obtained by inserting, at selected location(s) of the yeast genome, one or more additional copies of an expression cassette comprising the said transporter coding sequence.

Without wishing to be bound by any particular theory, the inventors believe that an over expression of a transporter-encoding gene shall increase the excretion of the produced oxaloacetate derivatives outside the yeast cell, e.g. in the culture medium.

In some embodiments, over expression of a transporter-encoding gene is obtained by inserting, at selected location(s) of the yeast genome, one or more additional copies of an expression cassette comprising a transporter gene coding sequence. In some of these embodiments, the said one or more copies of an expression cassette comprising a transporter coding sequence comprise regulatory sequences allowing a strong expression of the said transporter, such as a strong promoter that is functional in yeast cells.

In some other embodiments, one copy of a transporter-encoding gene is inserted at a selected location of the yeast genome. In these other embodiments, the said one or more copies of an expression cassette comprising a transporter coding sequence comprise regulatory sequences allowing a strong expression of the said transporter, such as a strong promoter that is functional in yeast cells.

In preferred embodiments, the said amino acid exporter protein-encoding gene AQR1 is placed under the control of the strong promoter pTEF3.

Illustratively, the AQR1 gene may be inserted within the HOM3 gene.

In preferred embodiments, the said amino acid exporter protein-encoding gene_TPO1 is placed under the control of the strong inducible or repressible promoter pSAM4 or the strong constitutive promoter pTEF1.

TPO1-1 can be used instead of TPO1. TPO1-1 is an artificial allele in which the lysines 10, 49, 86, 143, 144 and 145 are replaced by arginines.

It is believed by the inventors that these modifications protect TPO1 from degradation through the ubiquitin-proteasome pathway, thus stabilizing it.

Illustratively, the TPO1 gene may be inserted within the MAE1 gene and/or within the TRP1 gene.

Further Embodiments of an Oxaloacetate Derivatives-Producing Recombinant Yeast

According to some embodiments of a recombinant yeast according to the invention, production of oxaloacetate derivatives may be further increased by placing the said recombinant yeast in conditions leading to a further increase in the production of the intermediates downstream oxaloacetate in the biosynthesis pathway of said oxaloacetate derivatives.

Placing the said recombinant yeast in conditions leading to an increased production of the intermediates downstream oxaloacetate in the biosynthesis pathway of said oxaloacetate derivatives may be performed by introducing further genetic modifications in the yeast genome.

The present inventors have found that an optimally increased oxaloacetate derivatives production may be reached by introducing further genetic changes to the oxaloacetate derivatives-producing recombinant yeast, that are described below.

First Further Embodiments of Oxaloacetate Derivatives-Producing Recombinant Yeast According to these first further embodiments of an oxaloacetate derivatives-producing recombinant yeast according to the invention, further genetic engineering of the recombinant yeast is performed with the aim of increasing the production of methionine and/or of methionine derivatives.

Methionine derivatives can for example be selected from the group consisting of 2-hydroxy-4-(methylthio) butanoic acid (HMB) and 2-keto-4-methylthiobutyric acid (KMB).

According to these embodiments, genetic changes are introduced so as to:

(A) over express and/or put under the control of an inducible or repressible promoter at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP;

(B) put under the control of an inducible or repressible promoter at least one nucleic acid encoding an aspartokinase HOM3; and (C) (i) over express and/or put under the control of an inducible or repressible promoter (a) at least one nucleic acid encoding an homoserine-O-acetyltransferase MET2 and/or at least one nucleic acid encoding an homoserine-O-acetyltransferase METX, and (b) at least one nucleic acid encoding a methionine synthase MET17; and/or (ii) over express and/or put under the control of an inducible or repressible promoter (a) at least one nucleic acid encoding an homoserine kinase THR1, and (b) at least one nucleic acid encoding a cystathionine gamma-synthase CGS1 that has an improved O-phospho-L-homoserine (OHPS) dependent methionine synthase activity.

According to these embodiments, at least one nucleic acid encoding an aspartate transaminase AAT2 can optionally be overexpressed and/or is under the control of an inducible or repressible promoter.

According to these embodiments, at least one nucleic acid encoding a glutamate dehydrogenase GDH that converts oxo-glutarate to glutamate can optionally be overexpressed and/or is under the control of an inducible or repressible promoter.

According to these embodiments, at least one nucleic acid encoding an homoserine dehydrogenase HOME can also optionally be overexpressed.

According to these embodiments, the genome of a recombinant yeast of the invention can optionally further be such that, independently: (i) at least one, preferably all, endogenous nucleic acid encoding a S-adenosyl methionine synthase SAM1 and/or SAM2 is deleted, or (ii) at least one, preferably all, nucleic acid encoding a S-adenosyl methionine synthase SAM1 and/or SAM2 is under the control of an inducible or repressible promoter and/or is in a destabilized form.

According to a first embodiment, the genome of a recombinant yeast of the invention can optionally further be such that, independently: (i) at least one, preferably all, endogenous nucleic acid encoding an Aromatic aminotransferase I ARO8 and/or a Cytosolic branched-chain amino acid (BCAA) aminotransferase gene BAT2 has been deleted, or (ii) at least one, preferably all, nucleic acid encoding an Aromatic aminotransferase I ARO8 and/or a Cytosolic branched-chain amino acid (BCAA) aminotransferase gene BAT2 is under the control of an inducible or repressible promoter and/or is in a destabilized form.

According to a second embodiment, the genome of a recombinant yeast of the invention can optionally further be such that, independently: (i) at least one, preferably all, nucleic acid encoding an Aromatic aminotransferase I ARO8, and/or (ii) at least one, preferably all, nucleic acid encoding a Cytosolic branched-chain amino acid (BCAA) aminotransferase gene BAT2, is overexpressed and/or is under the control of an inducible or repressible promoter.

According to this second embodiment, the genome of a recombinant yeast of the invention can optionally further be characterized by an under expression of the phenylpyruvate decarboxylase gene (ARO10).

Furthermore, according to this embodiment, the genome of a recombinant yeast of the invention can optionally further be characterized by a non-expression of the 2-hydroxyacide dehydrogenase gene (KDH) or as being such that at least one nucleic acid encoding 2-hydroxyacide dehydrogenase (KDH) is overexpressed and/or under the control of an inducible or repressible promoter.

According to these embodiments, at least one nucleic acid encoding a cystathionine gamma-lyase CYS3 can, independently, be under the control of a weak promoter or of an inducible or repressible promoter and/or be in a destabilized form.

According to these embodiments, at least one nucleic acid encoding a cystathionine beta-synthase CYS4 can, independently, be under the control of a weak promoter or of an inducible or repressible promoter and/or be in a destabilized form.

According to these embodiments, at least one nucleic acid encoding a homoserine kinase THR1 can optionally, independently, be under the control of an inducible or repressible promoter and/or be in a destabilized form.

Aspartate Semi-Aldehyde Dehydrogenase

The aspartate-semialdehyde dehydrogenase is a protein which is known in the art to catalyze the NADPH-dependent formation of L-aspartate-semialdehyde by the reductive dephosphorylation of L-aspartyl-4-phosphate. The aspartate-semialdehyde dehydrogenase encoded by the genome of Saccharomyces cerevisiae may be termed HOM2.

A method implemented to measure the activity level of aspartate-semialdehyde dehydrogenase belongs to the general knowledge of the one skilled in the art.

Preferred aspartate-semialdehyde dehydrogenase in the present specification is an enzyme having an EC number 1.2.1.11.

For the amino acid sequence of the aspartate-semialdehyde dehydrogenase from Saccharomyces cerevisiae, the one skilled in the art may refer to the accession number NP010442 in the UniProt database. For the nucleic acid sequence, it may be referred to the access number NM_001180465.3 in the UniProt database.

Aspartokinase

The aspartokinase enzyme is a protein which is described in the art for catalyzing the conversion of L-aspartate in the presence of ATP into 4-phospho-L-aspartate. The aspartokinase encoded by the genome of Saccharomyces cerevisiae may be termed HOM3.

A method implemented to measure the activity level of aspartokinase belongs to the general knowledge of the one skilled in the art.

In this regard, the one skilled in the art may advantageously refer to the method described by Stadtman et al. (1961, J Biol Chem, Vol. 236 (7): 2033-2038).

Preferred aspartokinase in the present specification is an enzyme having an EC number of n° EC 2.7.2.4.

For the amino acid sequence of the aspartokinase from Saccharomyces cerevisiae, the one skilled in the art may refer to the accession number NP010972 in the UniProt database. For the nucleic acid sequence, it may be referred to the access number NM_001178943.1 in the UniProt database.

Homoserine-O-Acetyltransferase

The homoserine 0-acetyl transferase enzyme is a protein which is described in the art for catalyzing the reaction between Acetyl-CoA and L-homoserine into CoA and O-acetyl-L-homoserine. The homoserine 0-acetyl transferase encoded by the genome of Saccharomyces cerevisiae may be termed MET2. The homoserine 0-acetyl transferase originating from Corynebacterium glutamicum is usually termed METX.

A method implemented to measure the activity level of homoserine 0-acetyl transferase belongs to the general knowledge of the one skilled in the art.

In this regard, the one skilled in the art may advantageously refer to the method described by Shuzo Yamagata (1987, The Journal of Bacteriology, Vol. 169(8): 3458-3463.

Preferred homoserine 0-acetyl transferase in the present specification is an enzyme having an EC number of n° EC 2.3.1.31.

For the amino acid sequence of the homoserine 0-acetyl transferase from Saccharomyces cerevisiae, the one skilled in the art may refer to the accession number NP014122 in the UniProt database. For the nucleic acid sequence, it may be referred to the access number NM_001183115.1 in the UniProt database.

Methionine Synthase

The methionine synthase is a protein which is described in the art for catalyzing the conversion of O-acetyl-L-homoserine (OAH) in the presence of methanthiol into methionine and acetate. The methionine synthase is also described in the art for catalyzing the conversion of OAH into homocysteine or the conversion of O-acetylserine (OAS) into cysteine. The methionine synthase encoded by the genome of Saccharomyces cerevisiae may be termed MET17. The methionine synthase encoded by the genome of Saccharomyces cerevisiae may also be termed MET25 or MET15 in the art.

A method implemented to measure the activity level of methionine synthase belongs to the general knowledge of the one skilled in the art.

In this regard, the one skilled in the art may advantageously refer to the method described by Ravanel (1995, Archives of Biochemistry and Biophysics, Vol. 316: 572-584).

Preferred methionine synthase in the present specification is an enzyme having an EC number of n° 2.5.1.49.

For the amino acid sequence of the methionine synthase from Saccharomyces cerevisiae, the one skilled in the art may refer to the accession number NP013406 in the UniProt database. For the nucleic acid sequence, it may be referred to the access number NM_001182191.1 in the UniProt database.

Homoserine Kinase

Homoserine kinase enzyme is a protein which is described in the art for catalyzing the ATP-dependent phosphorylation of L-homoserine to L-homoserine phosphate. Homoserine kinase encoded by the genome of Saccharomyces cerevisiae may be termed THR1.

A method implemented to measure the activity level of homoserine kinase belongs to the general knowledge of the one skilled in the art.

In this regard, the one skilled in the art may advantageously refer to the method described by Mannhaupt and Feldmann (1990, Eur J Biochem, Vol. 191: 115-122).

Preferred homoserine kinase in the present specification is an enzyme having an EC number of n° EC 2.7.1.39.

For the amino acid sequence of the homoserine kinase from *Saccharomyces cerevisiae*, the one skilled in the art may refer to the accession number NP011890 in the UniProt database. For the nucleic acid sequence, it may be referred to the access number NM_001179155.1 in the UniProt database.

Cystathionine Gamma-Synthase

The cystathionine gamma synthase 1 enzyme is a protein which is described in the art for catalyzing the formation of L-cystathionine from homoserine esters and L-cysteine, via a gamma-replacement reaction. The cystathionine gamma synthase 1 encoded by the genome of *Arabidopsis thaliana* may be termed CGS1.

A method implemented to measure the activity level of cystathionine gamma synthase belongs to the general knowledge of the one skilled in the art.

In this regard, the one skilled in the art may advantageously refer to the method described by Loizeau et al. (2007, Plant Physiology, Vol. 145: 491-503).

Preferred cystathionine gamma synthase 1 in the present specification is an enzyme having an EC number of n° EC 2.5.1.48.

For the amino acid sequence of the cystathionine gamma synthase 1 from *Arabidopsis thaliana*, the one skilled in the art may refer to the accession number NP186761 in the UniProt database. For the nucleic acid sequence, it may be referred to the access number NM_110977.3 in the UniProt database.

Aspartate Transaminase

The aspartate transaminase enzyme (also known as aspartate aminotransferase) is a protein which is described in the art for catalyzing the reaction of L-aspartate and 2-oxoglutarate for producing oxaloacetate and L-glutamate. The aspartate transaminase enzyme encoded by the genome *Saccharomyces cerevisiae* may be termed AAT2.

A method implemented to measure the activity level of an aspartate transaminase belongs to the general knowledge of the one skilled in the art.

In this regard, the one skilled in the art may advantageously refer to the method described in Yagi et al. (1982, Biochem, Vol. 92: 35-43).

For the amino acid sequence of the aspartate transaminase AAT2 from *Saccharomyces cerevisiae*, the one skilled in the art may refer to the accession number NP013127 in the UniProt database. For the nucleic acid sequence, it may be referred to the access number NM_001181914.1 in the UniProt database.

Glutamate Dehydrogenase

The glutamate dehydrogenase enzyme (also known as NAD-specific glutamate dehydrogenase) is a protein which is described in the art for catalyzing the transformation of 2-oxoglutarate for producing L-glutamate. Thus, glutamate dehydrogenase is an enzyme specifically involved in the chemical reaction involving the conversion of 2-oxoglutarate to L-glutamate, in the presence of NADH.

A method implemented to measure the activity level of glutamate dehydrogenase belongs to the general knowledge of the one skilled in the art.

In this regard, the one skilled in the art may advantageously refer to the method described in Noor and Punekar (2005, Microbiology, Vol. 151: 1409-1419).

In preferred embodiments, the said glutamate dehydrogenase-encoding gene encodes for a glutamate dehydrogenase which uses NADH instead of NADPH, and is more particularly the GDH gene from *Entodinium caudatum* (GDH.eCa).

Preferred glutamate dehydrogenase in the present specification can in particular be the enzyme having the EC number n° EC 1.4.1.2.

For the amino acid sequence of the glutamate dehydrogenase from *Entodinium caudatum*, the one skilled in the art may refer to the accession number AAF15393 in the UniProt database. For the nucleic acid sequence, it may be referred to the access number AF109176 in the UniProt database.

Homoserine Dehydrogenase

The homoserine dehydrogenase enzyme is a protein which is described in the art for catalyzing the conversion of L-homoserine into L-aspartate 4-semialdehyde, in the presence of NAD or NADP. The homoserine dehydrogenase encoded by the genome of *Saccharomyces cerevisiae* may be termed HOM6.

A method implemented to measure the activity level of homoserine dehydrogenase belongs to the general knowledge of the one skilled in the art.

In this regard, the one skilled in the art may advantageously refer to the method described by Calnyanto et al. (2006, Microbiology, Vol. 152: 105-112).

Preferred homoserine dehydrogenase in the present specification is an enzyme having an EC number of n° 1.1.1.3.

For the amino acid sequence of the homoserine dehydrogenase from *Saccharomyces cerevisiae*, the one skilled in the art may refer to the accession number NP012673 in the UniProt database. For the nucleic acid sequence, it may be referred to the access number NM_001181797.3 in the UniProt database.

S-adenosyl methionine synthase SAM1 is the S-adenosylmethionine synthase 1 from *Saccharomyces cerevisiae*. For the amino acid sequence of SAM1, it may be referred to the access number NP_010790 in the UniProt database. For the nucleic acid sequence, it may be referred to the access number NM_001180810 in the NCBI database.

SAM2 is the S-adenosylmethionine synthase 2 from *Saccharomyces cerevisiae*. For the amino acid sequence of SAM1, it may be referred to the access number NP_013281 in the UniProt database. For the nucleic acid sequence, it may be referred to the access number NM_00118082067 in the NCBI database.

Aromatic Aminotransferase I

ARO8 is the aromatic aminotransferase I from *Saccharomyces cerevisiae*. For the nucleic acid sequence, it may be referred to the access number NM_001181067.1 in the NCBI database. For the amino acid sequence of ARO8, it may be referred to the access number NP_011313.1 in the UniProt database.

A method implemented to measure the activity level of an aromatic aminotransferase I belongs to the general knowledge of the one skilled in the art.

Cytosolic Branched-Chain Amino Acid (BCAA) Aminotransferase Gene

BAT2 is the cytosolic branched-chain amino acid (BCAA) amino transferase from *Saccharomyces cerevisiae*. For the nucleic acid sequence, it may be referred to the access number NM_001181806.1 in the NCBI database. For the amino acid sequence of BAT2, it may be referred to the access number NP_012682.1 in the UniProt database.

A method implemented to measure the activity level of a cytosolic branched-chain amino acid (BCAA) amino transferase belongs to the general knowledge of the one skilled in the art.

Phenylpyruvate Decarboxylase

ARO10 is the phenylpyruvate decarboxylase from *Saccharomyces cerevisiae*. For the nucleic acid sequence, it may be referred to the access number NM_001180688.3 in the NCBI database.

For the amino acid sequence of ARO10, it may be referred to the access number NP_010668.3 in the UniProt database.

2-Hydroxyacide Dehydrogenase

KDH is the 2-hydroxyacide dehydrogenase from *Lactococcus lactis*. For the nucleic acid sequence, it may be referred to the Enzyme Commission number E.C. 1.1.1.145.

For the amino acid sequence of KDH, it may be referred to the access number WP_011835036.1. in the UniProt database and/or to the access number WP_010905887.1 in the UniProt database.

Cystathionine Gamma-Lyase

CYS3 is the cystathionine gamma-lyase from *Saccharomyces cerevisiae*. For the amino acid sequence of CYS3, it may be referred to the access number NP_009390 in the UniProt database. For the nucleic acid sequence, it may be referred to the access number NM_001178157 in the NCBI database.

Cystathionine Beta-Synthase

CYS4 is the cystathionine beta-synthase from *Saccharomyces cerevisiae*. For the amino acid sequence of CYS4, it may be referred to the access number NP_011671 in the UniProt database. For the nucleic acid sequence, it may be referred to the access number NM_001181284 in the NCBI database.

Second Further Embodiments of Oxaloacetate Derivatives-Producing Recombinant Yeast According to these second further embodiments of an oxaloacetate derivatives-producing recombinant yeast according to the invention, further genetic engineering of the recombinant yeast is performed with the aim of increasing the production of threonine.

According to these embodiments, genetic changes are introduced so as to:

(A) over express and/or put under the control of an inducible or repressible promoter at least one nucleic acid encoding an aspartate semi-aldehyde dehydrogenase HOM2 and/or at least one nucleic acid encoding an aspartate semi-aldehyde dehydrogenase HOM2 that can use as coenzyme both NAD and NADP;

(B) over express and/or put under the control of an inducible or repressible promoter at least one nucleic acid encoding an homoserine kinase THR1;

(C) over express and/or put under the control of an inducible or repressible promoter at least one nucleic acid encoding a threonine synthase THR4; and (D) (i) put under the control of an inducible or repressible promoter at least one nucleic acid encoding an aspartokinase HOM3; and/or (ii) over express and/or put under the control of an inducible or repressible promoter at least one nucleic acid encoding an aspartate kinase AK.

to these embodiments, at least one nucleic acid encoding an aspartate transaminase AAT2 can optionally be overexpressed and/or is under the control of an inducible or repressible promoter.

According to these embodiments, at least one nucleic acid encoding a glutamate dehydrogenase GDH that converts oxo-glutarate to glutamate can optionally be overexpressed and/or is under the control of an inducible or repressible promoter.

According to these embodiments, at least one nucleic acid encoding an homoserine dehydrogenase HOME can also optionally be overexpressed.

According to these embodiments, (a) at least one, preferably all, endogenous nucleic acid encoding an homoserine-O-acetyltransferase MET2 can be deleted, or (b) at least one, preferably all, nucleic acid encoding an homoserine-O-acetyltransferase MET2 can be under the control of an inducible or repressible promoter and/or be in a destabilized form.

According to these embodiments, (a) at least one, preferably all, endogenous nucleic acid encoding a methionine synthase MET17 can be deleted, or (b) at least one, preferably all, nucleic acid encoding a methionine synthase MET17 can be under the control of an inducible or repressible promoter and/or be in a destabilized form.

According to these embodiments, at least one nucleic acid encoding a probable transporter AQR1 can optionally be overexpressed.

Threonine Synthase THR4

Threonine synthase enzyme is a protein which is described in the art for catalyzing the $H_2O$-dependent dephosphorylation of O-phospho-L-homoserine to L-threonine. Threonine synthase encoded by the genome of *Saccharomyces cerevisiae* may be termed THR4.

A method implemented to measure the activity level of threonine synthase belongs to the general knowledge of the one skilled in the art.

In this regard, the one skilled in the art may advantageously refer to the method described by in Schildkraut and Greer Journal of Bacteriology, (1973), Vol. 115, p. 777-785.

Preferred threonine synthase in the present specification is an enzyme having an EC number of n° EC 4.2.3.1.

For the amino acid sequence of the threonine synthase from *Saccharomyces cerevisiae*, the one skilled in the art may refer to the accession number NP_009982.1 in the UniProt database. For the nucleic acid sequence, it may be referred to the access number NM_001178767.1 in the UniProt database.

Aspartate Kinase AK

The aspartate kinase enzyme is a protein which is described in the art for catalyzing the conversion of L-aspartate in the presence of ATP into 4-phospho-L-aspartate. The aspartate kinase encoded by the genome of *Bacillus subtilis* may be termed AK.

A method implemented to measure the activity level of aspartate kinase belongs to the general knowledge of the one skilled in the art and is the same as the one indicated previously for aspartokinase.

For the amino acid sequence of the aspartate kinase from *Bacillus substilis*, the one skilled in the art may refer to the accession number NP_389558.2 in the UniProt database. For the nucleic acid sequence, it may be referred to the one disclosed in the access number NC_000964.3 in the NCBI database.

Probable Transporter AQR1

AQR1 is a transporter from *Saccharomyces cerevisiae*. For the amino acid sequence of AQR1 it may be referred to the access number NP_014334 in the UniProt database. For the nucleic acid sequence, it may be referred to the access number NM_001182903 in the NCBI database.

Promoters

As it is disclosed herein, the expression of the genes of interest that have been genetically engineered for obtaining a recombinant yeast according to the invention comprise appropriate regulatory sequences that are functional in yeast cells, including in *Saccharomyces cerevisiae*.

As disclosed in the present specification, various promoters may be used for the desired expression of the coding sequences of interest, which include (i) constitutive strong promoters (also called strong promoters in the present text), (ii) constitutive weak promoters (also called weak promoters in the present text) and (iii) inducible or repressible promoters. A list of yeast promoter with their relative activities in different media can be found in Keren et al. (2013) Molecular Systems Biology 9:701.

Promoters allowing the constitutive over-expression of a given gene, may be found in literature (Velculescu et al. (1997) Cell 88, 243-251).

Strong promoters more particularly interesting in the present invention may be selected from the group comprising:
  pTDH3 (SEQ ID N° 27),
  pENO2 (SEQ ID N° 28),
  pTEF KI (SEQ ID N° 29),
  pTEF3 (SEQ ID N° 30),
  pTEF1 (SEQ ID N° 31),
  pADH1 (SEQ ID N° 32),
  pGMP1 (SEQ ID N° 33),
  pFBA1 (SEQ ID N° 34),
  pPDC1 (SEQ ID N° 35),
  pCCW12 (SEQ ID N° 36), and
  pGK1 (SEQ ID N° 37).

According to a particular embodiment, the strong promoter according to the invention is, independently, selected from the group consisting of pTDH3, pENO2, pTEF-KI, pTEF3, pTEF1, pADH1, pGMP1, pFBA1, pPDC1, pCCW12 and pGK1.

Weak promoters more particularly interesting in the present invention may be selected from the group comprising:
  pURA3 (SEQ ID N° 39),
  pRPLA1 (SEQ ID N° 40),
  pNUP57 (SEQ ID N° 119), and
  pGAP1 (SEQ ID N° 120).

According to a particular embodiment, the weak promoter according to the invention is, independently, selected from the group consisting of pURA3, pRPLA1, pNUP57 and pGAP1.

As previously mentioned, inducible or repressible promoters are promoters whose activity is controlled by the presence or absence of biotic or abiotic factors and also by the quantity of said factor. Accordingly, for some promoters, their activity will in particular be induced and thus increased when the quantity of a given factor increases or is increased, and, accordingly, the activity of these same promoters can be repressed and thus reduced when the quantity of said factor diminishes or is reduced. The quantity of said factor(s) in the culture medium of a recombinant yeast of the invention comprising inducible or repressible promoters can be decided and thus controlled by the man skilled in the art.

For example, increasing the quantity of methionine in a culture medium of a recombinant yeast according to the invention comprising a pSAM4 promoter will induce and thus increase transcription of the gene under the control of this promoter. On the contrary, reducing the quantity of methionine in said culture medium will lead to a repression, and thus a reduced, transcription of the gene under the control of this promoter.

In another example, increasing the quantity of copper in a culture medium of a recombinant yeast according to the invention comprising a pCTR1 promoter will repress and thus decrease transcription of the gene under the control of this promoter. On the contrary, reducing the quantity of copper in said culture medium will lead to an induced, and thus an increased, transcription of the gene under the control of this promoter.

For this reason, the following promoters are referred to in the present text as being "inducible or repressible promoters".

According to a first embodiment, inducible or repressible promoters according to the invention may be selected from the group comprising promoters inducible or repressible with copper, promoters inducible or repressible with methionine and promoters inducible or repressible with threonine, and are in particular selected from the group consisting of:
  pSAM4—methionine inducible or repressible (SEQ ID N° 41),
  pCUP1-1—copper inducible or repressible (SEQ ID N° 42),
  pCUP1.cgla—copper inducible or repressible (SEQ ID N° 43),
  pCUP1.sba—copper inducible or repressible (SEQ ID N° 44),
  pACU1—copper inducible or repressible (SEQ ID N° 45),
  pACU2—copper inducible or repressible (SEQ ID N° 46),
  pACU3p—copper inducible or repressible (SEQ ID N° 47),
  pACU4p—copper inducible or repressible (SEQ ID N° 48),
  pACU5—copper inducible or repressible (SEQ ID N° 49),
  pACU6—copper inducible or repressible (SEQ ID N° 50),
  pACU7—copper inducible or repressible (SEQ ID N° 51),
  pACU8—copper inducible or repressible (SEQ ID N° 52),
  pACU9—copper inducible or repressible (SEQ ID N° 53),
  pACU10p—copper inducible or repressible (SEQ ID N° 54),
  pACU11—copper inducible or repressible (SEQ ID N° 55),
  pACU12—copper inducible or repressible (SEQ ID N° 56),
  pACU13—copper inducible or repressible (SEQ ID N° 57),
  pACU14—copper inducible or repressible (SEQ ID N° 58),
  pACU15—copper inducible or repressible (SEQ ID N° 59),
  pGAL/CUP1p—copper inducible or repressible (SEQ ID N° 60),
  pCRS5—copper inducible or repressible (SEQ ID N° 61), and
  pCHA1—threonine inducible or repressible (SEQ ID N° 62).

According to this embodiment, the inducible or repressible promoter according to the invention can in particular, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

The activity of these promoters is thus induced by the increasing presence of methionine, copper or threonine as indicated above, and their activity diminishes, i.e. is repressed, when the quantity of methionine, copper or threonine is reduced.

According to a second embodiment, inducible or repressible promoters according to the invention may be selected from the group comprising promoters inducible or repressible with copper, promoters inducible or repressible with glucose, promoters inducible or repressible with lysine and promoters inducible or repressible with methionine, and in particular selected from the group consisting of:

pCTR1—copper inducible or repressible (SEQ ID N° 63),
pCTR3—copper inducible or repressible (SEQ ID N° 64),
pCUR1—copper inducible or repressible (SEQ ID N° 65),
pCUR2—copper inducible or repressible (SEQ ID N° 66),
pCUR3—copper inducible or repressible (SEQ ID N° 67),
pCUR4—copper inducible or repressible (SEQ ID N° 68),
pCUR5p—copper inducible or repressible (SEQ ID N° 69),
pCUR6—copper inducible or repressible (SEQ ID N° 70),
pCUR7—copper inducible or repressible (SEQ ID N° 71),
pCUR8—copper inducible or repressible (SEQ ID N° 72),
pCUR9—copper inducible or repressible (SEQ ID N° 73),
pCUR10—copper inducible or repressible (SEQ ID N° 74),
pCUR11—copper inducible or repressible (SEQ ID N° 75),
pCUR12—copper inducible or repressible (SEQ ID N° 76),
pCUR13—copper inducible or repressible (SEQ ID N° 77),
pCUR14—copper inducible or repressible (SEQ ID N° 78),
pCUR15—copper inducible or repressible (SEQ ID N° 79),
pCUR16—copper inducible or repressible (SEQ ID N° 80),
pCUR17—copper inducible or repressible (SEQ ID N° 81),
pLYS1—lysine inducible or repressible (SEQ ID N° 82),
pLYS4—lysine inducible or repressible (SEQ ID N° 83),
pLYS9—lysine inducible or repressible (SEQ ID N° 84),
pLYR1p—lysine inducible or repressible (SEQ ID N° 85),
pLYR2p—lysine inducible or repressible (SEQ ID N° 86),
pLYR3p—lysine inducible or repressible (SEQ ID N° 87),
pLYR4p—lysine inducible or repressible (SEQ ID N° 88),
pLYR5p—lysine inducible or repressible (SEQ ID N° 89),
pLYR6p—lysine inducible or repressible (SEQ ID N° 90),
pLYR7p—lysine inducible or repressible (SEQ ID N° 91),
pLYR8—lysine inducible or repressible (SEQ ID N° 92),
pLYR9—lysine inducible or repressible (SEQ ID N° 93),
pLYR10—lysine inducible or repressible (SEQ ID N° 94),
pLYR11—lysine inducible or repressible (SEQ ID N° 95),
pMET17—methionine inducible or repressible (SEQ ID N° 96),
pMET6—methionine inducible or repressible (SEQ ID N° 97),
pMET14—methionine inducible or repressible (SEQ ID N° 98),
pMET3—methionine inducible or repressible (SEQ ID N° 99),
pSAM1—methionine inducible or repressible (SEQ ID N° 100),
pSAM2—methionine inducible or repressible (SEQ ID N° 101),
pMDH2—glucose inducible or repressible (SEQ ID N° 38),
pJEN1—glucose inducible or repressible (SEQ ID N° 121),
pICL1—glucose inducible or repressible (SEQ ID N° 122),
pADH2—glucose inducible or repressible (SEQ ID N° 123), and
pMLS1—glucose inducible or repressible (SEQ ID N° 124).

According to this embodiment, the inducible or repressible promoter according to the invention can, independently, be selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

The activity of these promoters is thus repressed by the increasing presence of methionine, copper, lysine or glucose as indicated above, and their activity increases, i.e. is induced, when the quantity of methionine, copper, lysine or glucose is reduced.

In a particular embodiment, inducible or repressible promoters according to the invention may be selected from the group comprising promoters inducible or repressible with copper, promoters inducible or repressible with glucose, promoters inducible or repressible with lysine, promoters inducible or repressible with methionine and promoters inducible or repressible with threonine.

In a more particular embodiment, the inducible or repressible promoter according to the invention can, independently, be selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, pCHA1, pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

More particularly, said promoters, identical or different, may be preferably characterized by a sequence of nucleic acid selected from the group consisting of sequences having at least 80% identity with sequences SEQ ID NO: 27 to 101 and 119 to 124.

Synthetic promoters as described in Blazeck & Alper (2013) Biotechnol. J. 8 46-58 can also be used.

The strong, weak and inductible or repressible promoters of the invention can originate from any organism from the Saccharomycetes class and can in particular originate, independently, from an organism selected from the group consisting of *Saccharomyces cerevisiae, Saccharomyces boulardii, Saccharomyces castelii, Saccharomyces bayanus, Saccharomyces arboricola, Saccharomyces kudriavzevii, Ashbya gossypii, Kluveromyces lactis, Pichia pastoris, Candida glabrata, Candida tropicalis, Debaryomyces castelii, Yarrowia lipolitica* and *Cyberlindnera jadinii*.

The strong, weak and inductible or repressible promoters of the invention can preferably originate from an organism selected from the group consisting of *Saccharomyces cerevisiae, Saccharomyces castelii, Saccharomyces bayanus, Saccharomyces arboricola, Saccharomyces kudriavzevii* and *Kluveromyces lactis*.

Terminators

As it is disclosed herein, the expression of the genes of interest that have been genetically engineered for obtaining a recombinant yeast according to the invention comprise appropriate transcription terminator sequences that are functional in yeast cells, including in *Saccharomyces cerevisiae*.

Said transcription terminators, identical or different, may be found in literature Yamanishi et al., (2013) ACS synthetic biology 2, 337-347.

Terminators more particularly interesting in the present invention may be selected from the group comprising:
- tTDH2 from the gene coding for Glyceraldehyde-3-phosphate dehydrogenase, isozyme 2 (TDH2 gene=Sequence SEQ ID N° 102),
- tCYC1 (=Sequence SEQ ID N° 103),
- tTDH3 (=Sequence SEQ ID N° 104), and
- tADH1 from gene coding for the alcohol dehydrogenase (ADH1 gene=Sequence SEQ ID N° 105),
- tADH2 from gene coding for the alcohol dehydrogenase (ADH2 gene=Sequence SEQ ID N° 106),
- tTPI1 from the gene encoding for the Triose Phosphate Isomerase (TPI1 gene=Sequence SEQ ID N° 107),
- tMET17 from the gene encoding for the O-acetyl homoserine-O-acetyl serine sulfhydrylase (Met17 gene=Sequence SEQ ID N° 108),
- tENO2 from the gene coding for Enolase II (ENO2 gene=Sequence SEQ ID N° 109),
- tMET3 (=Sequence SEQ ID N° 110), and
- tPGK1 from the gene encoding for the 3-phosphoglycerate kinase (PGK1 gene=Sequence SEQ ID N° 111),
- tDIT1 (=Sequence SEQ ID N° 112)
- tRPL3 (=Sequence SEQ ID N° 113)
- tRPL41B (=Sequence SEQ ID N° 114)
- tRPL15A (=Sequence SEQ ID N° 115)
- tIDP1 (=Sequence SEQ ID N° 116)

More particularly, said terminator, identical or different, may be preferably characterized by a sequence of nucleic acid selected from the group consisting of sequences having at least 80% identity with sequences SEQ ID NO: 102 to 118.

Recombinant Yeast

Generally, yeast can grow rapidly and can be cultivated at higher density as compared with bacteria, and does not require an aseptic environment in the industrial setting. Furthermore, yeast cells can be more easily separated from the culture medium compared to bacterial cells, greatly simplifying the process for product extraction and purification.

Preferentially, the yeast of the invention may be selected from the group consisting of the genus *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia*. In particular, the yeast of the invention may be selected from the group consisting of the genus *Saccharomyces, Pichia, Candida* or *Yarrowia*.

In a particular embodiment, the yeast may be Crabtree positive yeast selected from the group consisting of the genus *Saccharomyces, Dekkera, Schizosaccharomyces, Kluyveromyces, Torulaspora Zigosaccharomyces* and *Brettanomycces*.

More preferentially, the yeast may be selected from the group consisting of the species *Saccharomyces cerevisiae, Saccharomyces boulardii, Saccharomyces douglasii, Saccharomyces bayanus, Candida sorensis, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*.

In particular, the yeast may be selected from the group consisting of the species *Saccharomyces cerevisiae, Saccharomyces boulardii, Saccharomyces douglasii, Saccharomyces bayanus* and *Candida sorensis*.

More preferentially, the recombinant yeast may belong to the *Saccharomyces* genus, and preferably be the *Saccharomyces cerevisiae* species.

As above-mentioned, a recombinant yeast according to the invention has a pyruvate decarboxylase activity which is reduced by insertion of at least one DNA construct(s) selected from those disclosed in the present specification.

Methods implemented to insert a specific DNA construct within a gene belong to the general knowledge of a man skilled in the art. A related method is described in more details in the herein after examples.

Culture Conditions

The present invention also relates to the use of a recombinant yeast such as above-defined, for the production of oxaloacetate derivatives.

The present invention further relates to a method of production of oxaloacetate derivatives comprising the following steps:
- providing a recombinant microorganism as previously described, cultivating the recombinant microorganism in a culture medium containing a source of carbon, and recovering the oxaloacetate derivatives.

Typically, microorganisms of the invention are grown at a temperature in the range of about 20° C. to about 37° C., preferably at a temperature ranging from 27 to 34° C., in an appropriate culture medium.

When the recombinant yeast according to the invention belongs to the *S. cerevisiae* species, the temperature may advantageously range from 27 to 34° C., in an appropriate culture medium.

Suitable growth media for yeast are common commercially prepared media such as broth that includes yeast nitrogen base, ammonium sulfate, and dextrose as the carbon/energy source) or YPD Medium, a blend of peptone, yeast extract, and dextrose in optimal proportions for growing most. Other defined or synthetic growth media may also be used and the appropriate medium for growth of the particular microorganism will be known by one skilled in the art of microbiology or fermentation science.

The term "appropriate culture medium" is above-defined.

Examples of known culture media for a recombinant yeast according to the present invention are known to the person skilled in the art, and are presented in the following publication D. Burke et al., Methods in yeast Genetics—A cold spring harbor laboratory course Manual (2000).

Suitable pH ranges for the fermentation may be between pH 3.0 to pH 7.5, where pH 4.5 to pH 6.5 is preferred as the initial condition.

Fermentations may be performed under aerobic conditions or micro-aerobic conditions.

The amount of product in the fermentation medium can be determined using a number of methods known in the art, for example, high performance liquid chromatography (HPLC) or gas chromatography (GC).

The present process may employ a batch method of fermentation. A classical batch fermentation is a closed system where the composition of the medium is set at the beginning of the fermentation and not subject to artificial alterations during the fermentation. Thus, at the beginning of the fermentation, the medium is inoculated with the desired organism or organisms, and fermentation is permitted to occur without adding anything to the system. Typically, however, a "batch" fermentation is batch with respect to the addition of carbon source and attempts are often made at controlling factors such as temperature, pH and oxygen concentration. In batch systems, the metabolite and biomass compositions of the system change constantly up to the time when the fermentation is stopped. Within batch cultures cells progress through a static lag phase to a high growth log phase and finally to a stationary phase where growth rate is diminished or halted. If untreated, cells in the stationary phase will eventually die. Cells in log phase generally are responsible for the bulk of production of end product or intermediate.

A Fed-Batch system may also be used in the present invention. A Fed-Batch system is similar to a typical batch system with the exception that the carbon source substrate is added in increments as the fermentation progresses. Fed-Batch systems are useful when catabolite repression (e.g. glucose repression) is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$.

Fermentations are common and well known in the art and examples may be found in Sunderland et al., (1992), herein incorporated by reference. Although the present invention is performed in batch mode it is contemplated that the method would be adaptable to continuous fermentation.

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to vary. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for production.

In order to still improve the oxaloacetate derivatives production, a particular embodiment may consist of culturing the recombinant yeast cells in an appropriate culture medium, such as above-mentioned, wherein the said culture medium comprises an optimal amount of carbon source, especially glucose.

Preferably, the cells are cultured in such an optimal culture medium during only a part of the whole culture duration. In some embodiments, the yeast cells are incubated in the said optimal culture medium 10 hours or more after initiation of the culture, which encompasses 11, 12, 13, 14, 15 or 16 hours or more after initiation of the culture.

Preferably, the cells are cultured in such an optimal culture medium during a time period ranging from 5 hours to 15 hours, which includes from 6 hours to 10 hours, e.g. 8 hours after initiation of the culture.

In preferred embodiments, the carbon source comprised in said optimal culture medium consists of glucose. In preferred embodiments, the said optimal culture medium comprises 12% w/w or more glucose, including 15% w/w or more glucose. In preferred embodiments, the said optimal culture medium comprises at most 40% w/w glucose, which includes at most 35% w/w glucose.

Thus, in the preferred embodiments described above, a method for producing oxaloacetate derivatives according to the invention may further comprise, between steps (a) and (c), an intermediate step (b) consisting of cultivating the yeast cells in the said optimal culture medium.

Purification of Oxaloacetate Derivatives

According to a specific aspect of the invention, the fermentative production of oxaloacetate derivatives comprises a step of isolation of the oxaloacetate derivatives from the culture medium. Recovering the oxaloacetate derivatives from the culture medium is a routine task for a man skilled in the art. It may be achieved by a number of techniques well known in the art including but not limiting to distillation, gas-stripping, pervaporation, selective precipitation or liquid extraction. The expert in the field knows how to adapt parameters of each technique dependant on the characteristics of the material to be separated.

The yeast as model of microorganism in the present invention has been retained in that the synthesized oxaloacetate derivatives is/are entirely exported outside the cells, thus simplifying the purification process.

The synthesized oxaloacetate derivatives may be collected by distillation. Distillation may involve an optional component different from the culture medium in order to facilitate the isolation of oxaloacetate derivatives by forming azeotrope and notably with water. This optional component is an organic solvent such as cyclohexane, pentane, butanol, benzene, toluene, trichloroethylene, octane, diethylether or a mixture thereof.

Gas stripping is achieved with a stripping gas chosen among helium, argon, carbon dioxide, hydrogen, nitrogen or mixture thereof.

Liquid extraction is achieved with organic solvent as the hydrophobic phase such as pentane, hexane, heptane or dodecane.

Oxaloacetate Derivatives

Oxaloacetate derivatives according to the invention are compounds that can be produced by a microorganism, in particular a yeast, using oxaloacetate as substrate or co-substrate upstream in the biosynthesis pathway after modification by at least one enzyme naturally and/or artificially present in the microorganism producing the oxaloacetate according to the invention, in particular in the yeast producing the oxaloacetate according to the invention.

Examples of such oxaloacetate derivatives can for example be selected from the group consisting of methionine, 2-hydroxy-4-(methylthio) butanoic acid (HMB), 2-keto-4-methylthiobutyric acid (KMB), threonine and 2,4-dihydroxybutyrate (2,4-DHB), lysine, isoleucine, homoserine, O-acetyl-L-homoserine and ethyl-homoserine.

Throughout the description, including the claims, the expression "comprising a" should be understood as being synonymous with "comprising at least one", unless otherwise specified.

The terms "between . . . and . . . " and "ranging from . . . to . . . " should be understood as being inclusive of the limits, unless otherwise specified.

The examples and figures which follow are presented by way of illustration and without implied limitation of the invention.

EXAMPLES

Example 1: Protocol for Making a Recombinant *Saccharomyces cerevisiae* Strain According to the Invention All the hereinafter implemented recombinant *Saccharomyces cerevisiae* strains were constructed from standard strains using standard yeast molecular genetics procedure (Methods in yeast Genetics—A cold spring harbor laboratory course Manual (2000) by D. Burke, D. Dawson, T. Stearns CSHL Press).

Cluster of the following-mentioned genes were integrated in recombinant yeast at once using the ability of yeast to efficiently recombine free DNA ends which have sequence homology.

In addition, for a better comprehension of following genotypes;
- ade2, his3, leu2, trp1 and ura3 are auxotrophy marker genes.
- Lowercase letters mean that the considered gene is inactive, uppercase letters reflect an active gene.
- "::": following a gene name means that the gene is interrupted by what follows (if more than one gene are inserted, they are noted in brackets [ ]). The interruption of the gene is concomitant with an entire deletion of the coding sequence but preserves the promoter. In consequence the gene followed by "::" is inactive and is noted in lowercase. If not specified the transcription of the gene inserted is controlled by the promoter of the disrupted gene.
- "gene.Kl" means that the gene originates from *Kluyveromyces lactis*.

More particularly, the coding sequences to be cloned were artificially synthetized. For heterologous sequences (non-yeast), the nucleic sequences were modified in order to obtain a synonymous coding sequence using the yeast codon usage. Using restriction enzyme and classical cloning technology, each synthetic sequence was cloned in between a transcription promoter and a transcription terminator. Each promoter sequence is preceded by a 50 to 200 nucleotide sequence homologous to the sequence of the terminator of the upstream gene. Similarly, the terminator of each gene (a gene comprising the promoter-coding sequence-terminator) is followed by sequences homologous to the gene immediately following. So that each of the unit to be integrated have a 50-200 nucleotide overlap with both the unit upstream and the unit downstream. For the first unit, the promoter is preceded by 50-200 nucleotides homologous to the yeast chromosome nucleotide for the locus in which it will be integrated. Similarly, for the last unit, the terminator is followed by 50-200 nucleotides homologous to the yeast chromosome nucleotide for the locus in which it will be integrated.

Each unit are then PCR amplified from the plasmids constructs, yielding X unit of linear DNA having overlapping sequences. At least one of this gene is an auxotrophic marker, in order to select for recombination event. All the linear fragments are transformed in the yeast at once, and recombinant yeast are selected for the auxotrophy related to the marker used. The integrity of the sequence is then verified by PCR and sequencing.

Example 2: Comparative Examples for the Production of Oxaloacetate Derivatives A. Firstly, two recombinant strains according to the invention are obtained: YA2679-28 and YA2687-142.

Accordingly, these two strains are as follows:

YA2679-28: MAT-α, gnp1::[LEU2.Kl, pENO2-ADH2-tIDP1, pADH1-AAT2-tRPL15A, pTEF3-MDH3-tRPL3, pPDC1-PEPCK.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[LEU2.Kl, pPGK1-AAT2-tTDH2, pENO2-TPO1-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK.Ec-tIDP1, pTEF1-HOM2-tTDH3, pPDC1-MDH3-tRPL15A, pADH1-HOME-tENO2], pyk1::[HIS5.Sp-pCUR3-PYK1-4], sam3::[pTDH3-GDH-2.Eca-tRPL3-pSAM4-HOM3-tTPI1]x9, trp1::[pTDH3-MHPF.Ec-tRPL3-pCUP1-1-HOM3-tIDP1-TRP1.Sc]x5, ura3::[pCCW12-ME3.At-tRPL3-pTEF3-MET17-tRPL15A-URA3.Sc]x11

YA2687-142: MAT-α, gnp1::[LEU2.Kl, pENO2-ADH2-tIDP1, pADH1-AAT2-tRPL15A, pTEF3-MDH3-tRPL3, pPDC1-PEPCK.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[LEU2.Kl, pPGK1-AAT2-tTDH2, pENO2-TPO1-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK.Ec-tIDP1, pTEF1-HOM2-tTDH3, pPDC1-MDH3-tRPL15A, pADH1-HOME-tENO2], pyk1::[HIS5.Sp-pCUR3-PYK1-6], sam3::[pTDH3-GDH-2.Eca-tRPL3-pSAM4-HOM3-tTPI1].

PYK1-4 and PYK1-6 are destabilized forms of PYK1, destabilized according to the N-end rule, well known to the man skilled in the art (Gibbs et al. (2014) Trends in Cell Biology, 10, 603-610).

PEPCK-1 is a form of PEPCK stabilized by modification of the Arginine amino acid in position 2 by a Glycine. The two strains were grown for 48 hours in YE (Yeast Extract) 2%, Glucose 8%, $(NH_4)_2SO_4$ 50 mM, and MeSNa 1 g/L. 500 μM of $CuSO_4$ was added after 8 hours. The content of methionine in the medium was assayed after 26 hours using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of methionine, the strain YA2679-28 produced 2 g·L$^{-1}$ of methionine in 24 hours and the strain YA2687-142 produced in the same amount of time 2.2 g·L$^{-1}$ of methionine.

B. Two further recombinant strains according to the invention, illustrated here-after, have also been assayed for methionine.

Strain YA3984-2: MAT-α, gap1::HIS5.Sp-loxP, gnp1::[RS-pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOME-tENO2], pyk1::[pCUR3-PYK1-7-tCYC1, HIS5.Sp-loxP], sam3::[pCUP1-1-MET17.Rp-tRPL15A-pACU6-METX.Cg-tTPI1]x4, trp1::[pTDH3-MHPF.Ec-tRPL3-pCUP1-1-HOM3-tIDP1-TRP1]x5, ura3::[pCCW12-ME3.At tRPL3-pTEF3-MET17-tRPL15A-URA3]x4

Strain YA4178: MAT-α, gap1::loxP, gnp1::[pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3, leu2, mup3::[pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOME-tENO2], pyk1::[pCUR3-PYK1-7-tCYC1, HIS5.Sp-loxP], pyk1::[pCUR3-PYK1-7-tCYC1, HIS5.Sp-loxP], sam3::[pCUP1-1-MET17.Rp-tRPL15A-pACU6-METX.Cg-tTPI1]x10, trp1::[pTDH3-MHPF.Ec-tRPL3-pCUP1-1-HOM3-tIDP1-TRP1]x5, ura3::[pCCW12-ME3.At tRPL3-pTEF3-MET17-tRPL15A-URA3]x4

PYK1-7 is an artificial allele of PYK1 that is tagged with a degron.

These two strains were grown in 25 ml of Yeast extract 2%, Glucose 10%, Urea 50 mM, and Cu(SO$_4$) 500 μM for seven hours, then a final concentration of 500 μM Cu(SO$_4$)$_2$ was added and 4 ml of CH$_3$SNa (23 g/l) were slowly added (0.25 ml/h). The content of methionine in the medium was assayed after 25 h 30 hours using the AccQ-Tag precolumn derivatization method for amino acid determination using a AccQ-Tag Ultra Derivatization Kit from Waters as advised by the manufacturer.

While the non-recombined corresponding yeasts do not produce a detectable quantity of methionine, the strain YA3984-2 produced 1.32 g·L-1 of methionine in 25 h 30, the strain YA4178 produced in the same amount of time 1.26 g·L-1 of methionine.

C. Two further recombinant strains according to the invention are obtained as follows and were assayed for ethyl-homoserine production:

DA1303-1: MAT-a/MAT-α, GAP1/gap1::HIS5.Sp-loxP, gnp1::[LEU2.Kl-RS-pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3 At-tRPL3, pTDH3-MHPF.Ec-tIDP1, pCCW12-ME3.At-tRPL3]/gnp1::[LEU2.Kl-RS-pENO2-ADH2-tIDP1, pADH1-AAT2-tRPL15A, pTEF3-MDH3-1-tRPL3, pPDC1-PEPCK-1.Ec-tMET17, pTDH3-MHPF.Ec-tTPI1, pCCW12-ME3.At-tRPL3, pTDH3-MHPF.Ec-tIDP1, pCCW12-ME3.At-tRPL3, pTDH3-MHPF.Ec-tTPI1, pCCW12-ME3.At-tRPL3, pTDH3-MHPF.Ec-tIDP1, pCCW12-ME3.At-tRPL3], his3/his3, leu2/leu2, LYP1/lyp1::[pCUP1-1-HOM3.Sc-tDIT1-lyp1]x13, mup3::[LEU2.Kl-RS-pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOM6-tENO2]/mup3::[LEU2.Kl-RS-pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOME-tENO2], pyk1::[pCUR3-PYK1-7-tCYC1, HIS5.Sp-loxP]/pyk1::[pCUR3-PYK1-7-tCYC1, HIS5.Sp-loxP], sam3::[pCUP1-1-NCE103-tRPL15A-pCUP1-1-MET2-tMET17-sam3]x15/sam3::[pCUP1-1-MET17.Rp-tRPL15A, pACU6-METX.Cg-tTPI1-sam3]x4, trp1::[pTDH3-MHPF.Ec-tRPL3-pCUP1-1-HOM3-tIDP1-TRP1]x5/trp1::[pTDH3-MHPF.Ec-tRPL3-pCUP1-1-HOM3-tIDP1-TRP1]x5, ura3::[pCCW12-ME3.At tRPL3-pTEF3-MET17-tRPL15A]x4/ura3::[pCCW12-ME3.At tRPL3-pTEF3-MET17-tRPL15A-URA3]x4 MDH3-1 is an artificial allele of MDH3 in which the three last amino acids (SKL) have been deleted. NCE103 is an endogenous yeast gene that catalyzes $CO_2$ hydration to bicarbonate.

YA3604-38: MAT-a, gnp1::[LEU2.Kl-RS-ADH2-AAT2-MDH3-1-PEPCK-1.Ec-MHPF.Ec-ME3.At-MHPF.Ec-ME3.At-MHPF.Ec-ME3.At-MHPF.Ec-ME3.At], his3, leu2, lyp1::[pCUP1-1-HOM3.Sc-tDIT1-lyp1]x12, mup3::[LEU2.Kl-RS-pPGK1-AAT2-tTDH2, pENO2-TPO1-3-tMET17, pCCW12-MET17-tRPL41B, pTDH3-MET2-tRPL3, pCUP1-1-HOM3-tDIT1, pTDH3-MHPF.Ec-tTPI1, pCCW12-ME3.At-tRPL3, pTDH3-PEPCK-1.Ec-tIDP1, pTEF1-HOM2-tTDH3, pPDC1-MDH3-1-tRPL15A, pADH1-HOM6-tENO2], pyk1::[pCUR3-PYK1-7-tCYC1, HIS5.Sp-loxP], sam3::[pCUP1-1-MET17.Rp-tRPL15A, pACU6-METX.Cg-tTPI1-sam3]x3, trp1::[pTDH3-MHPF.Ec-tRPL3-pCUP1-1-HOM3-tIDP1-TRP1]x5, ura3::[pCCW12-ME3.At tRPL3-pTEF3-MET17-tRPL15A-URA3]x4

These two strains were grown in 2% Yeast extract, 8% Glucose, 0.65 mM Histidine, 1.5 mM Adenine, 0.9 mM Uracil, 0.5 mM Tryptophane, 7.5 mM leucine, 50 mM (NH$_4$)$_2$SO$_4$ and 500 μM CuSO$_4$ for 7 hours, then 500 μM CuSO$_4$ was added and the yeast were grown for 18 hours.

The content of ethyl-homoserine in the medium was then assayed using the AccQ-Tag precolumn derivatization method for amino acid determination using an AccQ-Tag Ultra Derivatization Kit from Waters as advised by the manufacturer.

While the non-recombined corresponding yeasts do not produce a detectable quantity of ethyl-homoserine, the strain DA1303 produced 1.6 g·L$^{-1}$ of ethyl-homoserine in 25 h, the strain YA3604-38 produced in the same amount of time 1.7 g·L$^{-1}$ of ethyl-homoserine.

The invention claimed is:

1. A recombinant yeast, in the genome of which:

(A) (i) at least one nucleic acid encoding a malate dehydrogenase is overexpressed and/or is under the control of an inducible or repressible promoter, and (ii) at least one nucleic acid encoding a malate dehydrogenase does not contain the Peroxisome Targeting Sequence thereof;

(B) at least one nucleic acid encoding a NADP-dependent malic enzyme is overexpressed and/or is under the control of an inducible or repressible promoter;

(C) (i) at least one nucleic acid encoding a phosphoenolpyruvate carboxylase that converts phosphoenol pyruvate into oxaloacetate is overexpressed and/or is under the control of an inducible or repressible promoter; and/or (ii) at least one nucleic acid encoding a phosphoenolpyruvate carboxykinase that converts phosphoenol pyruvate into oxaloacetate is overexpressed and/or is under the control of an inducible or repressible promoter;

(D) at least one nucleic acid encoding an acetaldehyde-CoA dehydrogenase is overexpressed and/or is under the control of an inducible or repressible promoter; and (E) (i) at least one nucleic acid encoding a pyruvate kinase 1 has been deleted, and/or (ii) at least one nucleic acid encoding a pyruvate kinase 1 is independently under the control of an inducible or repressible promoter, under the control of a weak promoter, and/or in a destabilized form.

2. The recombinant yeast according to claim 1, in the genome of which:

(i) at least one nucleic acid encoding a pyruvate kinase 2 has been deleted, and/or (ii) at least one nucleic acid encoding a pyruvate kinase 2 is under the control of an inducible or repressible promoter and/or is in a destabilized form.

3. The recombinant yeast according to claim 1, in the genome of which:

(i) at least one nucleic acid encoding an alcohol dehydrogenase 1 has been deleted, and/or (ii) at least one nucleic acid encoding an alcohol dehydrogenase 1 is under the control of an inducible or repressible promoter and/or is in a destabilized form.

4. The recombinant yeast according to claim 1, in the genome of which:

(A) (i) at least one nucleic acid encoding a pyruvate carboxylase 1 has been deleted, and/or (ii) at least one nucleic acid encoding a pyruvate carboxylase 1 is under the control of an inducible or repressible promoter and/or is in a destabilized form;

and/or (B) (i) at least one nucleic acid encoding a pyruvate carboxylase 2 has been deleted, and/or (ii) at least one nucleic acid encoding a pyruvate carboxylase 2 is under the control of an inducible or repressible promoter and/or is in a destabilized form.

5. The recombinant yeast according to claim 1, in the genome of which:

(A) (i) at least one nucleic acid encoding an alcohol dehydrogenase 3 has been deleted, and/or (ii) at least one nucleic acid encoding an alcohol dehydrogenase 3 is under the control of an inducible or repressible promoter and/or is in a destabilized form;

(B) (i) at least one nucleic acid encoding an alcohol dehydrogenase 4 has been deleted, and/or (ii) at least one nucleic acid encoding an alcohol dehydrogenase 4 is under the control of an inducible or repressible promoter and/or is in a destabilized form;

and/or (C) (i) at least one nucleic acid encoding an alcohol dehydrogenase 5 has been deleted, and/or (ii) at least one nucleic acid encoding an alcohol dehydrogenase 5 is under the control of an inducible or repressible promoter and/or is in a destabilized form.

6. The recombinant yeast according to claim 1, wherein the at least one nucleic acid encoding a malate dehydrogenase is nucleic acid from a yeast.

7. The recombinant yeast according to claim 1, wherein the nucleic acid encoding a NADP-dependent malic enzyme is selected, independently, from the group consisting of nucleic acid from *Arabidopsis thaliana, Escherichia coli, Aloe arborescens, Aspergillus niger, Flaveria species, Corynebacterium glutamicum, Oryza sativa, Streptomyces coelicolor, Rattus norvegicus, Zea mays* and *Trypanosoma cruzi*.

8. The recombinant yeast according to claim 1, wherein the nucleic acid encoding a phosphoenolpyruvate carboxylase that converts phosphoenol pyruvate PEP into oxaloacetate is nucleic acid from a prokaryote or an eukaryote, from the group consisting of *Escherichia coli, Pseudomonas fluorescens, Mycobacterium tuberculosis, Anaerobiospirillum succiniciproducens, Succinatimoras hippie, Bacteroides salyersiae, Trypanosoma cruzi* and *Clostridium thermocellum*.

9. The recombinant yeast according to claim 1, wherein the nucleic acid encoding an acetaldehyde-CoA dehydrogenase is selected, independently, from bacteria or eukarya, from the group consisting of nucleic acid from *Escherichia coli, Giardia intestinalis*, bacteria of the genus *Pseudomonas, Clostridium kluyveri, Klebsiella pneumoniae, Leuconostoc mesenteroides, Pectobacterium atrosepticum, Shigella sonnei* and *Serratia proteamaculans*.

10. The recombinant yeast according to claim 1, wherein the at least one nucleic acid encoding a pyruvate kinase 1 is nucleic acid from a yeast.

11. The recombinant yeast according to claim 1, wherein the recombinant yeast is selected from the group consisting of the genus *Saccharomyces, Candida*, Ashbya, Dekkera, *Pichia (Hansenula)*, Debaryomyces, *Clavispora, Lodderomyces, Yarrowia, Zigosaccharomyces, Schizosaccharomyces, Torulaspora, Kluyveromyces, Brettanomycces, Cryptococcus* and *Malassezia*.

12. The recombinant yeast according to claim 1, wherein the inducible or repressible promoter is, independently, selected from the group consisting of promoters inducible or repressible with copper, promoters inducible or repressible with methionine and promoters inducible or repressible with threonine.

13. The recombinant yeast according to claim 1, wherein the weak promoter is, independently, selected from the group consisting of pURA3, pRPLA1, pNUP57 and pGAP1.

14. The recombinant yeast according to claim 1, wherein the inducible or repressible promoter is, independently, selected from the group consisting of promoters inducible or repressible with copper, promoters inducible or repressible with lysine and promoters inducible or repressible with methionine.

15. A method for producing at least one oxaloacetate derivative, pyruvate derivative and/or acetyl-CoA derivative, the method comprising the steps of:

(a) culturing a recombinant yeast as defined in claim 1 in a culture medium; and (b) recovering the oxaloacetate derivative, pyruvate derivative and/or acetyl-CoA derivative from the culture medium.

16. The method according to claim 15, wherein the at least one oxaloacetate derivative is selected from the group consisting of methionine, 2-hydroxy-4-(methylthio) butanoic acid (HMB), 2-keto-4-methylthiobutyric acid (KMB), threonine, 2,4-dihydroxybutyrate (2,4-BDH), lysine, isoleucine, homoserine, O-acetyl-L-homoserine and ethyl-homoserine.

17. The method according to claim 15, wherein the at least one pyruvate derivative and/or acetyl-CoA derivative is selected from the group consisting of valine; alanine; lactate; components of the Krebs cycle or derivatives of those components; fatty acids; flavonoids; polyketides; and mevalonate pathway derivatives.

18. The method according to claim 15, wherein the culture medium comprises at least a carbon source.

19. The recombinant yeast according to claim 1, wherein the recombinant yeast is selected from the group consisting of the genus *Saccharomyces, Pichia, Candida* and *Yarrowia*.

20. The recombinant yeast according to claim 1, wherein the inducible or repressible promoter is, independently, selected from the group consisting of pSAM4, pCUP1-1, pCUP1.Cgla, pCUP1.Sba, pACU1, pACU2, pACU3p, pACU4p, pACU5, pACU6, pACU7, pACU8, pACU9, pACU10p, pACU11, pACU12, pACU13, pACU14, pACU15, pGAL/CUP1p, pCRS5, and pCHA1.

21. The recombinant yeast according to claim 1, wherein the inducible or repressible promoter is, independently, selected from the group consisting of pCTR1, pCTR3, pCUR1, pCUR2, pCUR3, pCUR4, pCUR5p, pCUR6, pCUR7, pCUR8, pCUR9, pCUR10, pCUR11, pCUR12, pCUR13, pCUR14, pCUR15, pCUR16, pCUR17, pLYS1, pLYS4, pLYS9, pLYR1p, pLYR2p, pLYR3p, pLYR4p, pLYR5p, pLYR6p, pLYR7p, pLYR8, pLYR9, pLYR10, pLYR11, pMET17, pMET6, pMET14, pMET3, pSAM1, pSAM2, pMDH2, pJEN1, pICL1, pADH2 and pMLS1.

* * * * *